(12) United States Patent
Furumoto et al.

(10) Patent No.: US 9,365,514 B2
(45) Date of Patent: Jun. 14, 2016

(54) COMPOSITION COMPRISING TETRACYCLIC COMPOUND

(75) Inventors: Kentaro Furumoto, Gotemba (JP); Koji Shiraki, Gotemba (JP); Tomoaki Hirayama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 198 days.

(21) Appl. No.: 13/816,804

(22) PCT Filed: Aug. 19, 2011

(86) PCT No.: PCT/JP2011/068735
§ 371 (c)(1),
(2), (4) Date: Feb. 13, 2013

(87) PCT Pub. No.: WO2012/023597
PCT Pub. Date: Feb. 23, 2012

(65) Prior Publication Data
US 2013/0143877 A1    Jun. 6, 2013

(30) Foreign Application Priority Data

Aug. 20, 2010    (JP) ................. 2010-185385

(51) Int. Cl.
| | |
|---|---|
| C07D 209/56 | (2006.01) |
| A61K 31/407 | (2006.01) |
| C07D 401/10 | (2006.01) |
| A61K 31/475 | (2006.01) |
| C07D 405/12 | (2006.01) |
| A61K 9/16 | (2006.01) |
| A61K 9/19 | (2006.01) |
| A61K 31/343 | (2006.01) |
| A61K 31/381 | (2006.01) |
| A61K 31/403 | (2006.01) |
| A61K 31/4439 | (2006.01) |
| A61K 31/454 | (2006.01) |
| A61K 31/4545 | (2006.01) |
| A61K 31/496 | (2006.01) |
| A61K 31/5377 | (2006.01) |
| C07D 405/14 | (2006.01) |

(52) U.S. Cl.
CPC ............ *C07D 209/56* (2013.01); *A61K 9/1641* (2013.01); *A61K 9/19* (2013.01); *A61K 31/343* (2013.01); *A61K 31/381* (2013.01); *A61K 31/403* (2013.01); *A61K 31/4439* (2013.01); *A61K 31/454* (2013.01); *A61K 31/4545* (2013.01); *A61K 31/496* (2013.01); *A61K 31/5377* (2013.01); *C07D 401/10* (2013.01); *C07D 405/12* (2013.01); *C07D 405/14* (2013.01)

(58) Field of Classification Search
CPC ..... A61K 9/19; A61K 31/343; A61K 31/381; A61K 31/403; A61K 31/4439; A61K 31/4545; A61K 31/496; A61K 31/5377; A61K 31/454; C07D 405/14; C07D 209/56; C07D 401/10; C07D 405/12
USPC .............. 514/232.08, 254.08, 323, 339, 410
See application file for complete search history.

(56) References Cited

U.S. PATENT DOCUMENTS

| | | | |
|---|---|---|---|
| 7,125,565 B2 | 10/2006 | Sugishita et al. | |
| 7,799,860 B2 * | 9/2010 | Sugishita ............... | A61K 9/145 524/489 |
| 2004/0076675 A1 | 4/2004 | Sugishita et al. | |
| 2007/0060595 A1 * | 3/2007 | Yoshizawa et al. ........ | 514/259.3 |
| 2007/0065516 A1 | 3/2007 | Sugishita et al. | |
| 2008/0090776 A1 | 4/2008 | Mano et al. | |
| 2009/0099193 A1 | 4/2009 | Mano et al. | |
| 2009/0221555 A1 | 9/2009 | Ahmed et al. | |
| 2010/0240673 A1 | 9/2010 | Mano et al. | |
| 2011/0230545 A1 | 9/2011 | Mano et al. | |
| 2012/0083488 A1 | 4/2012 | Kinoshita et al. | |

FOREIGN PATENT DOCUMENTS

| | | |
|---|---|---|
| JP | 08-092090 A | 4/1996 |
| JP | 2008-280352 A | 11/2008 |
| JP | 2009-100783 A | 5/2009 |
| RU | 2387650 C2 | 4/2010 |
| WO | WO 02/43704 A1 | 6/2002 |
| WO | WO 2007/066185 A2 | 6/2007 |
| WO | WO 2008/051547 A1 | 5/2008 |

(Continued)

OTHER PUBLICATIONS

Dorwald, F. A. Side Reactions in Organic Synthesis, 2005, Wiley: VCH, Weinheim p. IX of Preface.*

(Continued)

*Primary Examiner* — Uma Ramachandran
(74) *Attorney, Agent, or Firm* — Foley & Lardner LLP

(57) ABSTRACT

A composition which comprises substance represented by Formula (I), (I)

[Meanings of the symbols that are included in the formula are given in the specification as definitions]
a pharmaceutically acceptable carrier, and a dissolution aid is useful for improving solubility, oral absorbability and/or absorbability in blood of a poorly water-soluble or water insoluble tetracyclic compounds having an ALK inhibitory activity that are useful as a prophylactic and/or therapeutic agent for cancer, depression, and cognitive function disorder.

4 Claims, 15 Drawing Sheets

(56) References Cited

FOREIGN PATENT DOCUMENTS

WO   WO 2009/073620 A2   6/2009
WO   WO 2010/143664 A1   12/2010

OTHER PUBLICATIONS

Bilsland et al,. "Behavioral and Neurochemical Alterations in Mice Deficient in Anaplastic Lymphoma Kinase Suggest Therapeutic Potential for Psychiatric Indications," Neuropsychopharmacology, 2008, 33:685-700.

Garbett et al., "Extending Nature's Leads: The Anticancer Agent Ellipticine," Curr. Med. Chem.—Anti-Cancer Agents, 2004, 4:149-172.

Soda et al., "Identification of the transforming EML4-ALK fusion gene in non-small-cell lung cancer," Nature, Aug. 2, 2007, 448:561-566.

Kinoshita et al., "Discovery of novel tetracyclic compounds as anaplastic lymphoma kinase inhibitors," Bioorganic & Medicinal Chemistry Letters, Apr. 8, 2011, 21(12):3788-3793.

Kinoshita et al., "9-Substituted 6,6-Dimethyl-11-oxo-6,11-dihydro-5H-benzo[b]carbazoles as Highly Selective and Potent Anaplastic Lymphoma Kinase Inhibitors," J. Med. Chem., Sep. 22, 2011, 54(18):6286-6294.

Sakamoto et al., "CH5424802, a Selective ALK Inhibitor Capable of Blocking the Resistant Gatekeeper Mutant," Cancer Cell, May 17, 2011, 19:679-690.

Wanner et al., "Inter- and Intramolecular Addition of Ester Anions to Nicotinium Salts, A Facile Approach to Nauclefine and Ellipticine Derivatives," Tetrahedron, Jan. 1, 1983, 3673-3681.

* cited by examiner

COMPOSITION COMPRISING TETRACYCLIC COMPOUND

CROSS-REFERENCE TO RELATED APPLICATIONS

This application is a National Stage application of PCT/JP2011/068735, filed Aug. 19, 2011, which claims priority from Japanese application JP 2010-185385, filed Aug. 20, 2010.

TECHNICAL FIELD

The present invention relates to a composition of a tetracyclic compound having an ALK inhibitory activity, and in particular to a composition for oral administration.

BACKGROUND ART

Anaplastic Lymphoma Kinase (ALK) is one of the receptor type tyrosine kinases belonging to an insulin receptor family (Non-Patent Document Nos. 1 and 2). It is reported that gene alteration of ALK causes production of abnormal kinase fused with other gene.

Examples of the disorders accompanied with ALK abnormality include cancer and cancer metastasis (Non-Patent Document 1 and Patent Document 1), depression and cognitive function disorder (Non-Patent Document 2). Thus, an inhibitor for ALK will provide pharmaceuticals that are effective for treatment and prevention of the disorders.

Such pharmaceuticals are required to be developed in the form of orally administrable formulation. However, propriety of development of an orally administrable formulation depends on the level of bioavailability of a pharmaceutical compound. As a factor which affects bioavailability, water solubility of a pharmaceutical compound can be considered. In general, when a compound which is poorly water-soluble or insoluble in water is orally administered, it shows poor bioavailability. Improving an oral absorbability by increasing the bioavailability of an active ingredient is also important in terms of obtaining stable exhibition of pharmaceutical effect of the active ingredient. Patent Document 2 discloses a composition which comprises a poorly water-soluble ingredient such as steroids, sodium lauryl sulfate and an organic polymer for improving solubility and oral absorbability of a poorly water-soluble ingredient, that is obtained by wet granulation in the presence of water.

Until now, for example, tricyclic compounds (Patent Document 2) or the like have been reported as an ALK inhibiting substance.

However, the tetracyclic compounds that are represented by the following Formula (I) or salts thereof are not described in any document.

Meanwhile, ellipticine derivatives are known as tetracyclic compound (Non-Patent Document 3).

Although the tetracyclic compounds used in the present invention have an excellent ALK inhibitory activity, due to their poorly water-soluble or insoluble property in water, further studies have been needed to develop them in the form of orally administrable formulation.

DOCUMENT LIST

Patent Document

[Patent Document 1] JP2009100783 (A)
[Patent Document 2] Japanese Patent Application Laid-Open (JP-A) No. 2008-280352

Non-Patent Document

[Non-Patent Document 1] Nature, Vol. 448, pages 561-566, 2007
[Non-Patent Document 2] Neuropsychopharmacology, Vol. 33, pages 685-700, 2008
[Non-Patent Document 3] Current Medicinal Chemistry: Anti-Cancer Agents, Vol. 4, Issue No. 2, pages 149-172, 2004

SUMMARY OF THE PRESENT INVENTION

Problems to be Solved by the Present Invention

The inventors of the present invention extensively studied to solve the problems described above, and as a result, unexpectedly found that, by allowing a dissolution aid to co-exist with a poorly water-soluble or insoluble substance represented by the Formula (I), solubility of the substance can be significantly improved. The inventors carried out further studies based on these findings, and completed the present invention accordingly.

Means for Solving the Problems

Specifically, the present invention relates to the followings.
[1] A composition comprising a substance represented by the Formula (I), a pharmaceutically acceptable carrier, and a dissolution aid,

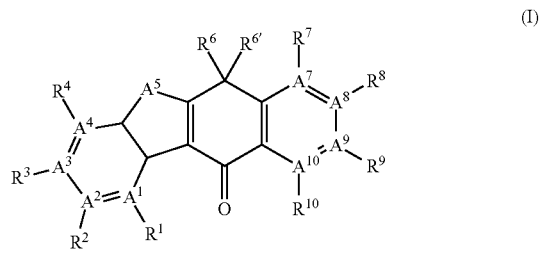

[wherein,
$A^1$, $A^2$, $A^3$, $A^4$, $A^7$, $A^8$, $A^9$ and $A^{10}$ all represent C, or any one of $A^2$, $A^3$, $A^4$, $A^7$, $A^8$ and $A^9$ represents N (with the proviso that, when it represents N, no substituent group exists therefor) and the remainings represent C;

$A^5$ is selected from $NR^5$, O and S;

$R^1$ and $R^{10}$ each independently represent [1] a hydrogen atom, [2] a cyano group, [3] a halogen atom or [4] a 4- to 10-membered heterocycloalkyl group which may be substituted by 4- to 10-membered heterocycloalkyl group(s);

$R^2$ is selected from the group consisting of:
(1) a hydrogen atom,
(2) a $C_{1-8}$ alkyl group,
(3) a $C_{2-8}$ alkenyl group,
(4) a $C_{2-8}$ alkynyl group,
(5) a cyano group,
(6) a halogen atom,
(7) a $(C_{1-8}$ alkyl$)_{m2}$-amino group which may be substituted by $C_{1-8}$ alkylsulfonyl group(s),
m2: 0~2, and
(8) a nitro group;

$R^3$ is selected from the group consisting of:
(1) a hydrogen atom,
(2) a $C_{1-8}$ alkyl group which may be substituted by [1] halogen atom(s), [2] hydroxy group(s) or [3] $C_{1-8}$ alkoxy group(s), (3) a $C_{6-10}$ aryl group,
(4) a cyano group,
(5) a $C_{1-8}$ alkanoyl group which may be substituted by $C_{6-10}$ aryl group(s),
(6) a $(C_{1-8}$ alkyl$)_{m3a}$-aminocarbonyl group which may be substituted by one or more $R^{3A}$,
  $R^{3A}$: [1] a $C_{6-10}$ aryl group, [2] a $C_{1-8}$ alkoxy group, [3] a 5- to 14-membered heteroaryl group, or [4] a $C_{6-10}$ arylsulfonyl group,
  m3a: 0~2,
(7) a hydroxycarbonyl group,
(8) a $C_{1-8}$ alkoxycarbonyl group which may be substituted by [1] hydroxy group(s) or [2] $C_{1-8}$ alkoxy group(s),
(9) a halogen atom,
(10) a $(C_{1-8}$ alkyl$)_{m3b}$-amino group which may be substituted by $C_{6-10}$ aryl group(s),
  m3b: 0~2,
(11) a $C_{1-8}$ alkylcarbonyl($C_{0-8}$ alkyl)amino group which may be substituted by [1] $C_{6-10}$ aryl group(s) or [2] $C_{6-10}$ aryloxy group(s),
(12) a $C_{6-10}$ arylcarbonyl($C_{0-8}$ alkyl)amino group which may be substituted by $C_{1-8}$ alkyl group(s) which may be substituted by halogen atom(s),
(13) a $(C_{1-8}$ alkyl$)_{m3c}$-aminocarbonyl($C_{0-8}$ alkyl)amino group which may be substituted by $C_{6-10}$ aryl group(s),
  m3c: 0~2,
(14) a nitro group,
(15) a hydroxy group,
(16) a $C_{1-8}$ alkoxy group which may be substituted by one or more $R^{3B}$,
  $R^{3B}$: [1] a hydroxy group, [2] a $C_{1-8}$ alkoxy group, [3] a $C_{6-10}$ aryl($C_{0-8}$ alkyl)aminocarbonyl group, [4] a $(C_{1-8}$ alkyl$)_{m3d}$-amino group, or [5] a halogen atom,
  m3 d: 0~2,
(17) a 4- to 10-membered heterocycloalkyloxy group,
(18) a 5- to 14-membered heteroaryloxy group,
(19) a $(C_{1-8}$ alkyl$)_{m3e}$-aminocarbonyloxy group which may be substituted by $C_{6-10}$ aryl group(s)
  m3e: 0~2,
(20) a 4- to 10-membered nitrogen-containing heterocycloalkylcarbonyl group,
(21) a $C_{1-8}$ alkylsulfonyloxy group which may be substituted by halogen atom(s),
(22) a $C_{1-8}$ alkylthio group,
(23) a $C_{1-8}$ alkylsulfonyl group which may be substituted by $C_{6-10}$ aryl group(s),
(24) a 5- to 14-membered heteroaryl group which may be substituted by $C_{1-8}$ alkyl group(s) which may be substituted by $C_{1-8}$ alkoxy group(s),
(25) a $C_{1-8}$ alkoxycarbonyl($C_{0-8}$ alkyl)amino group which may be substituted by $C_{1-8}$ alkoxy group(s),
(26) a $C_{6-10}$ aryloxycarbonyl($C_{0-8}$ alkyl)amino group which may be substituted by $C_{1-8}$ alkyl group(s) which may be substituted by halogen atom(s),
(27) a $C_{6-10}$ aryl($C_{0-8}$ alkyl)aminocarbonyl($C_{0-8}$ alkyl)amino group which may be substituted by one or more $R^{3C}$,
  $R^{3C}$: [1] a $C_{1-8}$ alkyl group which may be substituted by halogen atom(s), or [2] a $C_{1-8}$ alkoxy group,
(28) a $C_{3-8}$ cycloalkyl($C_{0-8}$ alkyl)aminocarbonyloxy group, and
(29) a $C_{6-10}$ aryl($C_{0-8}$ alkyl)aminocarbonyloxy group which may be substituted by substituent group(s) selected from the group consisting of [1] a $C_{1-8}$ alkyl group and [2] a $C_{1-8}$ alkoxy group;

$R^4$ is selected from the group consisting of:
(1) a hydrogen atom,
(2) a $C_{1-8}$ alkyl group which may be substituted by halogen atom(s),
(3) a $C_2$ alkenyl group,
(4) a $C_2$ alkynyl group,
(5) a $C_{3-8}$ cycloalkyl group,
(6) a cyano group,
(7) an aminocarbonyl group,
(8) a $(C_{1-8}$ alkyl$)_{m4a}$-aminocarbonyl group,
  m4a: 1~2,
(9) a hydroxycarbonyl group,
(10) a $C_{1-8}$ alkoxycarbonyl group,
(11) a halogen atom,
(12) a $(C_{1-8}$ alkyl$)_{m4b}$-amino group,
  m4b: 0~2,
(13) a hydroxy group, and
(14) a $C_{1-8}$ alkoxy group which may be substituted by hydroxy group(s);

$R^5$ is selected from the group consisting of:
(1) a hydrogen atom,
(2) a $C_{1-8}$ alkyl group which may be substituted by one or more $R^{5A}$,
  $R^{5A}$: [1] a hydroxycarbonyl group, [2] a $C_{1-8}$ alkoxycarbonyl group, [3] a hydroxy group, [4] a $C_{1-8}$ alkoxy group, [5] a $(C_{1-8}$ alkyl$)_{m5}$-amino group, [6] a $C_{6-10}$ aryl group, or [7] a $C_{1-8}$ alkylthio group,
  m5: 0~2,
(3) a $C_{2-8}$ alkenyl group,
(4) a $C_{2-8}$ alkynyl group,
(5) a $C_{3-8}$ cycloalkyl group, and
(6) a $C_{1-8}$ alkylsulfonyl group;

$R^6$ and $R^{6'}$ are each independently selected from the group consisting of:
(1) a $C_{1-8}$ alkyl group which may be substituted by halogen atom(s),
(2) a $C_{2-8}$ alkenyl group, and
(3) a $C_{2-8}$ alkynyl group; or $R^6$ and $R^{6'}$ are taken together with the carbon atoms to which they are bound to form:
(4) a $C_{3-8}$ cycloalkyl group, or
(5) a 4- to 10-membered heterocycloalkyl group which may be substituted by $C_{1-8}$ alkyl $C_{6-10}$ aryl sulfonyl group(s) which may be substituted by $C_{1-8}$ alkyl group(s);

$R^7$ is selected from the group consisting of:
(1) a hydrogen atom,
(2) a halogen atom,
(3) a $C_{1-8}$ alkoxy group which may be substituted by one or more $R^{7A}$,
  $R^{7A}$: [1] a $(C_{1-8}$ alkyl$)_{m7a}$-amino group, [2] a hydroxy, [3] a 4- to 10-membered heterocycloalkyl group which may be substituted by $C_{1-8}$ alkyl group(s),
  m7a: 0~2,
(4) a $C_{1-8}$ alkylsulfonyl group,
(5) a nitro group, and
(6) a hydroxyl group;

$R^8$ is selected from the group consisting of:
(1) a hydrogen atom,
(2) a $C_{1-8}$ alkyl group which may be substituted by one or more $R^{8A}$,
  $R^{8A}$: [1] a 4- to 10-membered heterocycloalkyl group which may be substituted by one or more $R^{8A1}$, [2] a $(C_{1-8}$ alkyl$)_{m8a}$-amino group which may be substituted by a halogen atom, or [3] a hydroxy group,
  m8a: 0~2, $R^{8A1}$: [1] a $C_{1-8}$ alkyl group, [2] a $C_{1-8}$ alkylsulfonyl group, [3] a $(C_{1-8}$ alkyl$)_{m8b}$-aminosulfonyl group, [4] an oxo group, [5] a $C_{1-8}$ alkoxycarbonyl, or [6] a $C_{1-8}$ alkoxycarbonyl$(C_{0-8}$ alkyl)aminosulfonyl,
　m8b: 0~2,
　(3) a $C_{2-8}$ alkenyl group,
　(4) a 4- to 10-membered heterocycloalkyl group which may be substituted by one or more $R^{8B}$,
　$R^{8B}$:
<1> a $C_{1-8}$ alkyl group which may be substituted by one or more $R^{8B1}$,
<2> a $C_{2-8}$ alkeynyl group,
<3> a $C_{2-8}$ alkynyl group,
<4> a $C_{3-8}$ cycloalkyl group which may be substituted by [1] cyano group(s) or [2] $C_{1-8}$ alkyl group(s),
<5> a 4- to 10-membered heterocycloalkyl group which may be substituted by one or more $R^{8B2}$
<6> a $C_{1-8}$ alkoxy group which may be substituted by substituent group(s) selected from the group consisting of [1] a $C_{1-8}$ alkoxy group and [2] a $C_{3-8}$ cycloalkyl group,
<7> a $C_{1-8}$ alkoxycarbonyl group,
<8> a $C_{1-8}$ alkylsulfonyl group,
<9> a 5- to 14-membered heteroarylsulfonyl group,
<10> an oxo group,
<11> a cyano group,
<12> a $C_{1-8}$ alkanoyl group which may be substituted by one or more $R^{8133}$,
<13> a $C_{1-8}$ cycloalkylcarbonyl group,
<14> a $(C_{1-8}$ alkyl$)_{m8c}$-aminosulfonyl group,
<15> a $C_{1-8}$ alkylsulfonyl$(C_{0-8}$ alkyl)amino group,
<16> a $(C_{1-8}$ alkyl$)_{m8d}$-amino group which may be substituted by one or more $R^{8B4}$,
<17> a hydroxy group,
<18> a $(C_{1-8}$ alkyl$)_{m8e}$-aminocarbonyl group, or
<19> a $C_{1-8}$ alkoxycarbonyl$(C_{0-8}$ alkyl)amino group
　m8c: 0~2
　m8 d: 0~2
　m8e: 0~2
　$R^{8B1}$: [1] a $C_{3-8}$ cycloalkyl group, [2] a hydroxy group, or [3] a $C_{1-8}$ alkoxy group(s),
　$R^{8B2}$: [1] a halogen atom, [2] a $C_{1-8}$ alkyl group, [3] an oxo group, [4] a hydroxy group, or [5] a deuterium atom,
　$R^{8B3}$: a $(C_{1-8}$ alkyl$)_{m8f}$-amino group,
　m8f: 0~2,
　$R^{8B4}$: [1] a $C_{3-8}$ cycloalkyl group, or [2] a hydroxy group,
　(5) a 5- to 14-membered heteroaryl group which may be substituted by a $C_{1-8}$ alkyl group,
　(6) a $(C_{1-8}$ alkyl$)_{m8g}$-aminocarbonyl group which may be substituted by one or more $R^{8C}$,
　m8g: 0~2,
　$R^{8C}$: [1] a hydroxy group, [2] a $(C_{1-8}$ alkyl$)_{m8h}$-amino group which may be substituted by substituent group(s) selected from the group consisting of <1> a $(C_{1-8}$ alkyl$)_{m8i}$-aminosulfonyl group, <2> a $C_{1-8}$ alkylsulfonyl group, <3> a $C_{1-8}$ alkoxycarbonyl group and <4> a $C_{1-8}$ alkoxycarbonyl$(C_{0-8}$ alkyl)aminosulfonyl group, [3] a $C_{1-8}$ alkylsulfonyl group, or [4] a $C_{1-8}$ alkoxy group which may be substituted by a hydroxy group,
　m8h: 0~2,
　m8i: 0~2,
　(7) a 4- to 10-membered heterocycloalkyl$(C_{0-8}$ alkyl)aminocarbonyl group which may be substituted by oxo group(s),
　(8) a 4- to 10-membered nitrogen-containing heterocycloalkylcarbonyl group which may be substituted by one or more $R^{8D}$, $R^{8D}$: [1] a $C_{1-8}$ alkyl group which may be substituted by one or more $R^{8D1}$, [2] a hydroxy group, [3] a $C_{1-8}$ alkylsulfonyl group, or [4] a $C_{1-8}$ alkoxycarbonyl group,
　$R^{8D1}$: [1] a hydroxy group, or [2] a $C_{1-8}$ alkoxy group,
　(9) a hydroxycarbonyl group,
　(10) a $C_{0-8}$ alkoxy$(C_{0-8}$ alkyl)aminocarbonyl group which may be substituted by hydroxy group(s),
　(11) a halogen atom,
　(12) a $(C_{1-8}$ alkyl$)_{m8j}$-amino group which may be substituted by one or more $R^{8H}$,
　m8j: 0~2,
　$R^{8H}$: [1] a hydroxy group, or [2] a 4- to 10-membered heterocycloalkyl group,
　(13) a hydroxyl group,
　(14) a $C_{1-8}$ alkoxy group which may be substituted by one or more $R^{8E}$,
　$R^{8E}$:
<1> a hydroxy group,
<2> halogen atom,
<3> a hydroxycarbonyl group,
<4> a $C_{1-8}$ alkoxycarbonyl group,
<5> a 4- to 10-membered nitrogen-containing heterocycloalkylcarbonyl group which may be substituted by one or more $R^{8E1}$,
<6> a $(C_{1-8}$ alkyl$)_{m8k1}$-amino group which may be substituted by one or more $R^{8E2}$,
　m8k1: 0~2,
<7> a 4- to 10-membered heterocycloalkyl group which may be substituted by one or more $R^{8E3}$,
<8> a 5- to 14-membered heteroaryl group,
<9> a $(C_{1-8}$ alkyl$)_{m8k2}$-aminocarbonyl group which may be substituted by one or more $R^{8E6}$,
　m8k2: 0~2,
<10> a $C_{1-8}$ alkoxy group which may be substituted by one or more $R^{8E7}$,
<11> a $C_{1-8}$ alkylthio group,
<12> a $C_{1-8}$ alkylsulfinyl group,
<13> a $C_{1-8}$ alkylsulfonyl group,
　$R^{8E1}$;
<1> a $C_{1-8}$ alkoxycarbonyl group,
<2> a $C_{1-8}$ alkanoyl group,
<3> a $C_{1-8}$ alkylsulfonyl group,
<4> a $(C_{1-8}$ alkyl$)_{m8k3}$-aminosulfonyl group,
　m8k3: 0~2, or
<5> a 4- to 10-membered heterocycloalkyl group,
　m8k3: 0~2, or
<1> a hydroxy group,
<2> a $C_{1-8}$ alkoxycarbonyl group which may be substituted by halogen atom(s),
<3> a $C_{3-8}$ cycloalkyl group which may be substituted by $C_{1-8}$ alkyl group(s) which may be substituted by hydroxy group(s),
<4> a $C_{1-8}$ alkanoyl group which may be substituted by substituent group(s) selected from the group consisting of [1] a $(C_{1-8}$ alkyl$)_{m8k4}$-amino group and [2] a halogen atom(s),
　m8k4: 0~2,
<5> a $(C_{1-8}$ alkyl$)_{m8k5}$-aminocarbonyl group,
　m8 k5: 0~2,
<6> a $C_{1-8}$ alkylsulfonyl group,
<7> a 4- to 10-membered nitrogen-containing heterocycloalkylsulfonyl group which may be substituted by $C_{1-8}$ alkyl group(s),
<8> a $(C_{1-8}$ alkyl$)_{m8k6}$-aminosulfonyl group which may be substituted by $C_{1-8}$alkoxycarbonyl group(s),
　m8k6: 0~2, or $R^{8E3}$:
<1> a $C_{1-8}$ alkyl group which may be substituted by substituent group(s) selected from the group consisting of [1] a hydroxy group and [2] a $C_{1-8}$ alkylcarbonyloxy group,
<2> a $C_{1-8}$ alkylcarbonyloxy group,
<3> a hydroxy group,
<4> a $C_{1-8}$ cycloalkyl group,
<5> a $C_{1-8}$ alkoxy group,
<6> a $C_{1-8}$ alkoxycarbonyl group,
<7> a $C_{1-8}$ alkylsulfonyl group,
<8> a $(C_{1-8}$ alkyl$)_{m8k8}$-aminocarbonyl group
   m8k8: 0~2,
<9> a $C_{1-8}$ alkanoyl group which may be substituted by hydroxy group(s),
<10> an oxo group, or
<11> a 4- to 10-membered heterocycloalkyl group which may be substituted by substituent group(s) selected from the group consisting of [1] a $C_{1-8}$ alkanoyl group, [2] a $C_{1-8}$ alkoxycarbonyl group and [3] a $C_{1-8}$ alkylsulfonyl group,
$R^{8E6}$:
<1> a $C_{2-8}$ alkenylcarbonyloxy group,
<2> a hydroxy group,
<3> a cyano group,
<4> a $(C_{1-8}$ alkyl$)_{m8k9}$-amino group which may be substituted by hydroxy group(s)
   m8k9: 0~2
<5> a $C_{1-8}$ alkoxy group which may be substituted by hydroxy group(s),
<6> a $C_{1-8}$ alkylcarbonyloxy group,
<7> a 4- to 10-membered heterocycloalkyl group which may be substituted by $C_{1-8}$ alkyl group(s), or
<8> a 5- to 14-membered heteroaryl group,
$R^{8E7}$:
<1> a hydroxy group, or
<2> a $C_{1-8}$ alkoxy group which may be substituted by hydroxy group(s),
   (15) a 4- to 10-membered heterocycloalkyloxy group which may be substituted by one
or more $R^{8F}$,
$R^{8F}$:
<1> a $C_{1-8}$ alkyl group which may be substituted by one or more $R^{8F1}$,
<2> a $C_{3-8}$ cycloalkyl group,
<3> a $C_{1-8}$ alkanoyl group which may be substituted by halogen atom(s),
<4> a $C_{1-8}$ alkylcarbonyloxy group,
<5> a $C_{1-8}$ alkoxycarbonyl group,
<6> a 4- to 10-membered heterocycloalkyl group which may be substituted by one or more $R^{8F2}$
<7> a $C_{1-8}$ alkyl sulfonyl group,
<8> a hydroxy group, or
<9> a $C_{6-10}$ aryl group,
   $R^{8F1}$: [1] a hydroxy group, [2] a $C_{1-8}$ alkoxy group, or [3] a halogen atom,
   $R^{8F2}$: [1] a 4- to 10-membered heterocycloalkyl group, [2] a $C_{1-8}$ alkoxycarbonyl group, or [3] a $C_{1-8}$ alkylsulfonyl group,
   (16) a 5- to 14-membered heteroaryloxy group,
   (17) a 4- to 10-membered heterocycloalkylcarbonyloxy group,
   (18) a $(C_{1-8}$ alkyl$)_{m8l1}$-aminosulfonyloxy group, m8l1: 0~2,
   (19) a $C_{1-8}$ alkyl thio group which may be substituted by [1] $(C_{1-8}$ alkyl$)_{m8l2}$-amino group(s), [2] hydroxy group(s) or [3] hydroxycarbonyl group(s),
   m8l2: 0~2,
   (20) a $C_{1-8}$ alkylsulfonyl group which may be substituted by one or more $R^{8G}$,
$R^{8G}$: [1] a hydroxycarbonyl group, [2] a hydroxy group, or [3] a $(C_{1-8}$ alkyl$)_{m8l3}$-amino group,
   m8l3: 0~2,
   (21) a 4- to 10-membered nitrogen-containing heterocycloalkylsulfonyloxy group which may be substituted by $C_{1-8}$ alkyl group(s),
   (22) a $C_{2-8}$ alkenyloxy group, and
   (23) a $C_{1-8}$ alkylsulfonyloxy group which may be substituted by halogen atom(s);
$R^9$ is selected from the group consisting of:
   (1) a hydrogen atom,
   (2) a $C_{1-8}$ alkyl group which may be substituted by one or more $R^{9A}$,
$R^{9A}$: [1] a $C_{3-8}$ cycloalkyl group, [2] a 4- to 10-membered heterocycloalkyl group which may be substituted by one or more $R^{9A1}$, [3] a hydroxy group, [4] a $C_{1-8}$ alkoxy group, or [5] a hydroxycarbonyl group,
   $R^{9A1}$: [1] a $C_{1-8}$ alkyl group, [2] a $C_{3-8}$ cycloalkyl group, or [3] a 4- to 10-membered heterocycloalkyl group,
   (3) a $C_{2-8}$ alkenyl group which may be substituted by one or more $R^{9B}$,
$R^{9B}$: [1] a $(C_{1-8}$ alkyl$)_{m9a}$-amino group, [2] a 4- to 10-membered heterocycloalkyl group which may be substituted by one or more $R^{9B1}$,
$R^{9B1}$: [1] a $C_{3-8}$ cycloalkyl group, or [2] a 4- to 10-membered heterocycloalkyl group,
   m9a: 0~2,
   (4) a $C_{7-8}$ alkynyl group which may be substituted by one or more $R^{9C}$,
$R^{9C}$: [1] a $C_{1-8}$ alkoxy group, [2] a $(C_{1-8}$ alkyl$)_{m9b}$-amino group which may be substituted by $C_{6-10}$ aryl group(s), [3] a 4- to 10-membered heterocycloalkyl group which may be substituted by one or more $R^{9C1}$, [4] a $C_{3-8}$ cycloalkyl group, [5] a hydroxy group, [6] a hydroxycarbonyl group, or [7] a $C_{1-8}$ alkyloxycarbonyl group,
   m9b: 0~2,
$R^{9C1}$: [1] a $C_{3-8}$ cycloalkyl group, [2] a 4- to 10-membered heterocycloalkyl group, or [3] an oxo group,
   (5) a $C_{3-8}$ cycloalkyl group,
   (6) a 4- to 10-membered heterocycloalkyl group which may be substituted by one or more $R^{9D}$,
$R^{9D}$: [1] a $C_{1-8}$ alkyl group which may be substituted by 4- to 10-membered heterocycloalkyl group(s), [2] a $C_{3-8}$ cycloalkyl group, [3] a 4- to 10-membered heterocycloalkyl group, or [4] a $C_{1-6}$ alkylsulfonyl group, or [5] a $C_{1-8}$ alkoxycarbonyl group,
   (7) a $C_{6-10}$ aryl group which may be substituted by one or more $R^{9E}$,
$R^{9E}$: [1] a halogen atom, [2] a hydroxy group, [3] a hydroxycarbonyl group, or [4] a $C_{1-8}$ alkyl group which may be substituted by hydroxy group(s), or [5] a $C_{1-8}$ alkoxy group,
   (8) a 5- to 14-membered heteroaryl group which may be substituted by $C_{1-8}$ alkyl group(s),
   (9) a cyano group,
   (10) a $C_{1-8}$ alkanoyl group,
   (11) a 4- to 10-membered nitrogen-containing heterocycloalkylcarbonyl group which may be substituted by $C_{1-8}$ alkyl group(s),
   (12) a halogen atom,
   (13) a $(C_{1-8}$ alkyl$)_{m9c}$-amino group which may be substituted by one or more $R^{9F}$,
   m9c: 0~2,
   (14) a $C_{1-8}$ alkylcarbonyl$(C_{0-8}$ alkyl)amino group which may be substituted by $(C_{1-8}$ alkyl$)_{m9d}$-amino group(s), m9d: 0~2,

(15) a $C_{1-8}$ alkylsulfonyl($C_{0-8}$ alkyl)amino group,

(16) a $(C_{1-8}$ alkyl$)_{m9e}$-aminosulfonyl($C_{0-8}$ alkyl)amino group, m9e: 0~2,

(17) a nitro group,

(18) a hydroxy group,

(19) a $C_{1-8}$ alkoxy group which may be substituted by one or more $R^{9G}$, $R^{9G}$: [1] a hydroxy group, [2] a hydroxycarbonyl group, [3] a $C_{6-10}$ aryl group which may be substituted by $C_{1-8}$ alkoxy group(s), [4] a $(C_{1-8}$ alkyl$)_{m9g1}$-amino group, [5] a $C_{1-8}$ alkoxy group which may be substituted by one or more $R^{9G1}$, [6] a 5- to 14-membered heteroaryl group, or [7] a 4- to 10-membered heterocycloalkyloxy group which may be substituted by $C_{1-8}$ alkyl group(s), m9g1: 0~2, $R^{9G1}$: [1] a $C_{1-8}$ alkoxy group, or [2] a hydroxycarbonyl group,

(20) a 4- to 10-membered heterocycloalkyloxy group which may be substituted by [1] 4- to 10-membered heterocycloalkyl group(s), or [2] $C_{1-8}$ alkoxycarbonyl group(s),

(21) a $C_{1-8}$ alkylsulfonyloxy group which may be substituted by halogen atom(s),

(22) a $C_{1-8}$ alkylthio group which may be substituted by $(C_{1-8}$ alkyl$)_{m9f}$-amino group(s), m9f: 0~2,

(23) a $C_{1-8}$ alkylsulfonyl group which may be substituted by $(C_{1-8}$ alkyl$)_{m9g}$-amino group(s), m9g: 0~2,

(24) a $(C_{1-8}$ alkyl$)_{m9h}$-aminosulfonyl group, m9h: 0~2,

(25) a 4- to 10-membered nitrogen-containing heterocycloalkylsulfonyl group which may be substituted by $C_{1-8}$ alkyl group(s), and

(26) a hydroxycarbonyl group].

[2] The composition according to [1] above, wherein the dissolution aid is a surfactant,

[3] The composition according to [2] above, wherein the surfactant is a non-ionic or an anionic surfactant,

[4] The composition according to [2] or [3] above, wherein the surfactant is selected from a group consisting of monoalkyl sulfate, polyoxyl 40 stearate, sorbitan trioleate, polyoxyethylene (105) polyoxypropylene (5) glycol, polyoxyethylene hydrogenated castor oil 60, polyoxyl 35 castor oil, lauromacrogol, dioctyl sodium sulfosuccinate, sodium lauroylsarcosine, sodium dodecylbenzene sulfonate, and a mixture thereof, [4-1] The composition according to [2] or [3] above, wherein the surfactant is selected from a group consisting of monoalkyl sulfate, sorbitan trioleate, polyoxyethylene (105) polyoxypropylene (5) glycol, polyoxyethylene hydrogenated castor oil 60, polyoxyl 35 castor oil, dioctyl sodium sulfosuccinate, sodium lauroylsarcosine, sodium dodecylbenzene sulfonate and a mixture thereof,

[4-2] The composition according to [2] to [4] above, wherein the surfactant is selected from a group consisting of sodium lauryl sulfate, sodium tetradecyl sulfate, sodium hexadecyl sulfate, sodium octadecyl sulfate, and a mixture thereof,

[4-3] The composition according to [2] to [4] above, wherein the surfactant is a mixture of sodium lauryl sulfate and polyoxyethylene (105) polyoxypropylene (5) glycol,

[4-4] The composition according to [2] to [4] above, wherein the surfactant is sodium lauryl sulfate,

[4-5] The composition according to [2] to [4-4] above, wherein content of the surfactant is 0.5 to 25 parts by weight,

[4-6] The composition according to [2] to [4-4] above, wherein content of the surfactant is 1.5 to 15 parts by weight,

[5] The composition according to [2] to [4-6] above, wherein the composition further comprises an organic polymer,

[6] The composition according to [5] above, wherein the organic polymer is selected from a group consisting of a synthetic resin, a water soluble polymer, a gastric-soluble polymer, an enteric-soluble polymer, and a mixture thereof,

[7] The composition according to [5] above, wherein the organic polymer is a synthetic resin,

[7-1] The composition according to [6] above, wherein the water soluble polymer is hydroxypropyl cellulose, hydroxypropylmethyl cellulose, methyl cellulose, propylene glycol alginate ester, sodium caseinate, a carboxyvinyl polymer, powdered agar, guar gum, copolyvidone, hydroxyethylmethyl cellulose, or polyvinyl alcohol, the gastric-soluble polymer is amino alkylmethacrylate copolymer E, or polyvinylacetal diethylaminoacetate, and the enteric-soluble polymer is methacrylic acid copolymer LD, purified shellac, carboxymethylethyl cellulose, cellulose acetate phthalate, hydroxypropylmethyl cellulose acetate succinate, methacrylic acid copolymer S, casein, or zein,

[7-2] The composition according to [6] above, wherein the water soluble polymer is, propylene glycol alginate ester, sodium caseinate, a carboxyvinyl polymer, powdered agar, guar gum, copolyvidone, hydroxyethylmethyl cellulose, or polyvinyl alcohol, the gastric-soluble polymer is amino alkylmethacrylate copolymer E or polyvinylacetal diethylaminoacetate, and the enteric-soluble polymer is methacrylic acid copolymer LD, carboxymethylethyl cellulose, cellulose acetate phthalate, hydroxypropylmethyl cellulose acetate succinate, methacrylic acid copolymer S, casein, or zein,

[7-3] The composition according to [6] above, wherein the organic polymer is selected from a group consisting of casein, sodium caseinate, sodium polystyrene sulfonate, polyvinylacetal diethylaminoacetate, carboxymethylethyl cellulose, cellulose acetate phthalate, hydroxypropylmethyl cellulose acetate succinate, methacrylic acid copolymer S, and a mixture thereof,

[7-4] The composition according to [5] to [7-3] above, wherein the surfactant is selected from sodium lauryl sulfate and the organic polymer is selected from sodium polystyrene sulfonate,

[7-5] The composition according to [5] to [7-3] above, wherein the surfactant is a mixture of sodium lauryl sulfate and polyoxyethylene (105) polyoxypropylene (5) glycol and the organic polymer is selected from sodium polystyrene sulfonate,

[7-6] The composition according to [7] above, wherein the synthetic resin is sodium polystyrene sulfonate or a vinyl acetate resin,

[7-7] The composition according to [5] to [7-6] above, wherein the content of the organic polymer is 1 to 20 parts by weight,

[7-8] The composition according to [5] to [7-6] above, wherein the content of the organic polymer is 2 to 10 parts by weight,

[8] The composition according to [2] to [7-5] above, wherein the composition comprises further one or more additives which are selected from the following additive group A: additive A: citric acid, fumaric acid, DL-malic acid, adipic acid, succinic acid, tartaric acid, lactic acid, maleic acid, sulfuric acid, phosphoric acid, sodium dehydroacetate, sodium stearyl fumarate, stearic L-ascorbate ester, L-aspartic acid, skimmed milk powder, aluminum lactate, ascorbic acid palmitate, aluminum sulfate, monobasic calcium phosphate, or acetyl tryptophan.

[8-2] The composition according to [8] above, wherein the additive group A is citric acid, fumaric acid, DL-malic acid, adipic acid, succinic acid, tartaric acid, lactic acid, maleic acid, phosphoric acid, sodium dehydroacetate, sodium stearyl fumarate, stearic L-ascorbate ester, L-aspartic acid, skimmed milk powder, or monobasic calcium phosphate,

[8-3] The composition according to [8] above, wherein the additive selected from the additive group A is sodium dehydroacetate, or skimmed milk powder,

[8-4] The composition according to [8] to [8-3] above, wherein the total content of one or more additives that are selected from the additive group A is 1 to 20 parts by weight,

[9] The composition according to [1] to [8-4] above, wherein the water solubility of the substance is less than 100 μg/mL at 25° C.,

[9-1] The composition according to [1], characterized in that the dissolution aid is selected from the following group
Group:
citric acid, sodium stearyl fumarate, methacrylic acid copolymer LD, sodium lauryl sulfate, sodium dehydroacetate, fumaric acid, DL-malic acid, stearic L-ascorbate ester, L-aspartic acid, adipic acid, amino alkylmethacrylate copolymer E, propylene glycol alginate ester, casein, sodium caseinate, a carboxyvinyl polymer, carboxymethylethyl cellulose, powdered agar, guar gum, succinic acid, copolyvidone, cellulose acetate phthalate, tartaric acid, dioctyl sodium sulfosuccinate, zein, skimmed milk powder, sorbitan trioleate, lactic acid, aluminum lactate, ascorbic acid palmitate, hydroxyethylmethyl cellulose, hydroxypropylmethyl cellulose acetate succinate, polyoxyethylene (105) polyoxypropylene (5) glycol, polyoxyethylene hydrogenated castor oil 60, polyoxyl 35 castor oil, sodium polystyrene sulfonate, polyvinylacetal diethylaminoacetate, polyvinyl alcohol, maleic acid, methacrylic acid copolymer S, sulfuric acid, aluminum sulfate, phosphoric acid, monobasic calcium phosphate, sodium dodecylbenzene sulfonate, a vinyl pyrrolidone.vinyl acetate copolymer, sodium lauroylsarcosine, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate, and sodium octadecyl sulfate.

[9-2] The composition according to [1], characterized in that the dissolution aid is selected from the following group
Group:
citric acid, methacrylic acid copolymer LD, sodium lauryl sulfate, sodium dehydroacetate, fumaric acid, DL-malic acid, stearic L-ascorbate ester, L-aspartic acid, adipic acid, propylene glycol alginate ester, casein, sodium caseinate, carboxymethylethyl cellulose, succinic acid, copolyvidone, dioctyl sodium sulfosuccinate, lactic acid, aluminum lactate, ascorbic acid palmitate, hydroxyethylmethyl cellulose, hydroxypropylmethyl cellulose acetate succinate, polyoxyethylene hydrogenated castor oil 60, polyoxyl 35 castor oil, sodium polystyrene sulfonate, polyvinylacetal diethylaminoacetate, polyvinyl alcohol, methacrylic acid copolymer S, sulfuric acid, aluminum sulfate, sodium dodecylbenzene sulfonate, a vinyl pyrrolidone.vinyl acetate copolymer, acetyl tryptophan, sodium decyl sulfate, sodium tetradecyl sulfate, and sodium octadecyl sulfate.

[9-3] The composition according to [1], characterized in that the dissolution aid is selected from the following group
Group:
citric acid, methacrylic acid copolymer LD, sodium lauryl sulfate, sodium dehydroacetate, fumaric acid, DL-malic acid, L-aspartic acid, adipic acid, propylene glycol alginate ester, sodium caseinate, carboxymethylethyl cellulose, succinic acid, copolyvidone, dioctyl sodium sulfosuccinate, lactic acid, aluminum lactate, hydroxyethylmethyl cellulose, hydroxypropylmethyl cellulose acetate succinate, sodium polystyrene sulfonate, polyvinylacetal diethylaminoacetate, methacrylic acid copolymer S, sulfuric acid, aluminum sulfate, a vinyl pyrrolidone.vinyl acetate copolymer, and sodium decyl sulfate.

[9-4] The composition according to [1], wherein the dissolution aid which is selected from the following group is used for improving a solubility of a substance of the formula (I).
Group:
citric acid, hydroxypropyl cellulose, hydroxypropylmethyl cellulose, sodium stearyl fumarate, methacrylic acid copolymer LD, methyl cellulose, sodium lauryl sulfate, purified shellac, sodium dehydroacetate, fumaric acid, DL-malic acid, stearic L-ascorbate ester, L-aspartic acid, adipic acid, amino alkylmethacrylate copolymer E, propylene glycol alginate ester, casein, sodium caseinate, a carboxyvinyl polymer, carboxymethylethyl cellulose, powdered agar, guar gum, succinic acid, copolyvidone, cellulose acetate phthalate, tartaric acid, dioctyl sodium sulfosuccinate, zein, skimmed milk powder, sorbitan trioleate, lactic acid, aluminum lactate, ascorbic acid palmitate, hydroxyethylmethyl cellulose, hydroxypropylmethyl cellulose acetate succinate, polyoxyethylene (105) polyoxypropylene (5) glycol, polyoxyethylene hydrogenated castor oil 60, polyoxyl 35 castor oil, sodium polystyrene sulfonate, polyvinylacetal diethylaminoacetate, polyvinyl alcohol, maleic acid, methacrylic acid copolymer S, sulfuric acid, aluminum sulfate, phosphoric acid, monobasic calcium phosphate, sodium dodecylbenzene sulfonate, a vinyl pyrrolidone.vinyl acetate copolymer, sodium lauroylsarcosine, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate, and sodium octadecyl sulfate,

[9-5] The composition according to [1], wherein the dissolution aid which is selected from the following group is used for improving a solubility of a substance of the formula (I).
Group:
citric acid, hydroxypropyl cellulose, hydroxypropylmethyl cellulose, methacrylic acid copolymer LD, methyl cellulose, sodium lauryl sulfate, purified shellac, sodium dehydroacetate, fumaric acid, DL-malic acid, stearic L-ascorbate ester, L-aspartic acid, adipic acid, propylene glycol alginate ester, casein, sodium caseinate, carboxymethylethyl cellulose, succinic acid, copolyvidone, dioctyl sodium sulfosuccinate, lactic acid, aluminum lactate, ascorbic acid palmitate, hydroxyethylmethyl cellulose, hydroxypropylmethyl cellulose acetate succinate, polyoxyethylene hydrogenated castor oil 60, polyoxyl 35 castor oil, sodium polystyrene sulfonate, polyvinylacetal diethylaminoacetate, polyvinyl alcohol, methacrylic acid copolymer S, sulfuric acid, aluminum sulfate, sodium dodecylbenzene sulfonate, a vinyl pyrrolidone.vinyl acetate copolymer, acetyl tryptophan, sodium decyl sulfate, sodium tetradecyl sulfate, and sodium octadecyl sulfate,

[9-6] The composition according to [1], wherein the dissolution aid which is selected from the following group is used for improving a solubility of a substance of the formula (I).
Group:
citric acid, hydroxypropyl cellulose, hydroxypropylmethyl cellulose, methacrylic acid copolymer LD, methyl cellulose, sodium lauryl sulfate, purified shellac, sodium dehydroacetate, fumaric acid, DL-malic acid, L-aspartic acid, adipic acid, propylene glycol alginate ester, sodium caseinate, carboxymethylethyl cellulose, succinic acid, copolyvidone, dioctyl sodium sulfosuccinate, lactic acid, aluminum lactate, hydroxyethylmethyl cellulose, hydroxypropylmethyl cellulose acetate succinate, sodium polystyrene sulfonate, polyvinylacetal diethylaminoacetate, methacrylic acid copolymer S, sulfuric acid, aluminum sulfate, a vinyl pyrrolidone.vinyl acetate copolymer, and sodium decyl sulfate,

[10] The composition according to [1] to [9-3] above, wherein $A^1$ to $A^4$, $A^6$, and $A^7$ are a carbon atom, $A^5$ is NH, $R^3$ is cyano, $R^6$ and $R^{6'}$ are both methyl for the substance,

[10-1] The composition according to [1] to [10] above, wherein $A^1$ to $A^4$, $A^6$, and $A^7$ are a carbon atom, $A^5$ is NH, $R^3$ is cyano, $R^8$ is a 4- to 10-membered heterocycloalkyl group or a 4- to 10-membered heterocycloalkyl group which may be substituted by a $C_{3-8}$ cycloalkyl group for the substance,

[11] The composition according to any one of [1] to [9-6], wherein the substance is selected from a group consisting of 9-(4-isopropyl-piperazin-1-yl)-6,6-dimethyl-11 oxo-6,11-dihydro-5H-benzo[b]carbazole-3-carbonitrile;

6,6-dimethyl-8-(4-oxetan-3-yl-piperazin-1-yl)-11-oxo-9-prop-1-ynyl-6,11-dihydro-5H-benzo[b]carbazole-3-carbonitrile;

9-cyclopropylethynyl-6,6-dimethyl-8-(4-oxetan-3-yl-piperazin-1-yl)-11-oxo-6,11-dihydro-5H-benzo[b]carbazole-3-carbonitrile;

6,6-dimethyl-8-(1-oxetan-3-yl-piperidin-4-yl)-11-oxo-6,11-dihydro-5H-benzo[b]carbazole-3-carbonitrile;

9-bromo-6,6-dimethyl-8-(4-oxetan-3-yl-piperazin-1-yl)-11-oxo-6,11-dihydro-5H-benzo[b]carbazole-3-carbonitrile;

9-bromo-8-(4-cyclopropyl-piperazin-1-yl)-6,6-dimethyl-11-oxo-6,11-dihydro-5H-benzo[b]carbazole-3-carbonitrile;

9-chloro-6,6-dimethyl-8-(4-morpholin-4-yl-piperidin-1-yl)-11-oxo-6,11-dihydro-5H-benzo[b]carbazole-3-carbonitrile;

8-(4-cyclobutyl-piperazin-1-yl)-6,6-dimethyl-11-oxo-9-prop-1-ynyl-6,11-dihydro-5H-benzo[b]carbazole-3-carbonitrile;

6,6,9-trimethyl-8-(4-morpholin-4-yl-piperidin-1-yl)-11-oxo-6,11-dihydro-5H-benzo[b]carbazole-3-carbonitrile;

9-ethyl-6,6-dimethyl-8-(4-oxetan-3-yl-piperazin-1-yl)-11-oxo-6,11-dihydro-5H-benzo[b]carbazole-3-carbonitrile;

9-ethyl-6,6-dimethyl-8-(4-morpholin-4-yl-piperidin-1-yl)-11-oxo-6,11-dihydro-5H-benzo[b]carbazole-3-carbonitrile;

9-ethyl-6,6-dimethyl-8-(4-oxetan-3-yl-piperazin-1-yl)-11-oxo-6,11-dihydro-5H-benzo[b]carbazole-3-carbonitrile;

8-(4-cyclobutyl-piperazin-1-yl)-9-ethyl-6,6-dimethyl-11-oxo-6,11-dihydro-5H-benzo[b]carbazole-3-carbonitrile;

9-ethynyl-6,6-dimethyl-11-oxo-8-(4-pyrrolidin-1-yl-piperidin-1-yl)-6,11-dihydro-5H-benzo[b]carbazole-3-carbonitrile;

6,6-dimethyl-11-oxo-8-(4-pyrrolidin-1-yl-piperidin-1-yl)-6,11-dihydro-5H-benzo[b]carbazole-3-carbonitrile;

8-(4-cyclobutyl-piperazin-1-yl)-9-ethynyl-6,6-dimethyl-11-oxo-6,11-dihydro-5H-benzo[b]carbazole-3-carbonitrile;

8-(4-cyclobutyl-piperazin-1-yl)-6,6-dimethyl-1'-oxo-9-propyl-6,11-dihydro-5H-benzo[b]carbazole-3-carbonitrile;

8-(1-isopropyl-piperidin-4-yl)-6,6-dimethyl-11-oxo-6,11-dihydro-5H-benzo[b]carbazole-3-carbonitrile;

8-(4-isopropyl-piperazin-1-yl)-6,6-dimethyl-11-oxo-6,11-dihydro-5H-benzo[b]carbazole-3-carbonitrile;

8-(4-cyclobutyl-piperazin-1-yl)-9-cyclopropyl-6,6-dimethyl-11-oxo-6,11-dihydro-5H-benzo[b]carbazole-3-carbonitrile;

8-(2-tert-butylamino-ethoxy)-6,6-dimethyl-11-oxo-6,11-dihydro-5H-benzo[b]carbazole-3-carbonitrile;

9-ethynyl-8-(4-methanesulfonyl-piperazin-1-yl)-6,6-dimethyl-1'-oxo-6,11-dihydro-5H-benzo[b]carbazole-3-carbonitrile;

9-bromo-8-(4-cyclobutyl-piperazin-1-yl)-6,6-dimethyl-11-oxo-6,11-dihydro-5,4-benzo[b]carbazole-3-carbonitrile;

6,6-dimethyl-8-(4-oxetan-3-yl-piperazin-1-yl)-11-oxo-9-propyl-6,11-dihydro-5H-benzo[b]carbazole-3-carbonitrile; and 9-ethynyl-6,6-dimethyl-8-morpholin-4-yl-11-oxo-6,11-dihydro-5H-benzo[b]carbazole-3-carbonitrile.

[11-1] The composition according to any one of [1] to [8], wherein the substance is selected from a group consisting of (i) 6,6-dimethyl-8-(1-oxetan-3-yl-piperidin-4-yl)-11-oxo-6,11-dihydro-5H-benzo[b]carbazole-3-carbonitrile, (ii) 8-(4-cyclobutyl-piperazin-1-yl)-9-cyclopropyl-6,6-dimethyl-11-oxo-6,11-dihydro-5H-benzo[b]carbazole-3-carbonitrile, (iii) 8-(4-cyclobutyl-piperazin-1-yl)-9-ethyl-6,6-dimethyl-11-oxo-6,11-dihydro-5H-benzo[b]carbazole-3-carbonitrile, and (iv) 9-ethyl-6,6-dimethyl-8-(4-morpholin-4-yl-piperidin-1-yl)-11-oxo-6,11-dihydro-5H-benzo[b]carbazole-3-carbonitrile.

[11-2] The composition according to [1] to [11-1] above, characterized in that the content of the substance is 1 to 50 parts by weight.

[11-3] The composition according to [1] to [11-1] above, characterized in that the content of the substance is 3 to 30 parts by weight.

[11-4] The composition according to [2] to [8] above, wherein the weight ratio between the substance and the surfactant is 1:0.01 to 1:25,

[11-5] The composition according to [2] to [8] above, wherein the weight ratio between the substance and the surfactant is 1:0.05 to 1:1,

[11-6] The composition according to [9] to [11-5] above, wherein the weight ratio between the substance and the organic polymer is 1:0.02 to 1:20,

[11-7] The composition according to [9] to [11-6] above, wherein the weight ratio between the substance and the organic polymer is 1:0.25 to 1:1,

[11-8] The composition according to [8] to [11-7] above, wherein the weight ratio between the substance and the total amount of one or more additives selected from the additive group A is 1:0.02 to 1:20.

The present invention further includes the aspects as follows.

[12] A pharmaceutical formulation comprising the composition according to [1] to [11-8],

[13] The pharmaceutical formulation according to [12] above, which is an orally administrable formulation,

[14] The pharmaceutical formulation according to [12] above, wherein the orally administrable formulation is a solid formulation, and

[15] The pharmaceutical formulation according to [13] above, wherein the orally administrable formulation is a tablet, a capsule, a granule, powder, a pill, a water soluble or insoluble liquid or a suspension for oral administration.

[16-1] A dissolution aid consisting of a substance selected from the following group for use in the improvement of a solubility of a substance of the formula (I).

Group:

citric acid, hydroxypropyl cellulose, hydroxypropylmethyl cellulose, sodium stearyl fumarate, methacrylic acid copolymer LD, methyl cellulose, sodium lauryl sulfate, purified shellac, sodium dehydroacetate, fumaric acid, DL-malic acid, stearic L-ascorbate ester, L-aspartic acid, adipic acid, amino alkylmethacrylate copolymer E, propylene glycol alginate ester, casein, sodium caseinate, a carboxyvinyl polymer, carboxymethylethyl cellulose, powdered agar, guar gum, succinic acid, copolyvidone, cellulose acetate phthalate, tartaric acid, dioctyl sodium sulfosuccinate, zein, skimmed milk powder, sorbitan trioleate, lactic acid, aluminum lactate, ascorbic acid palmitate, hydroxyethylmethyl cellulose, hydroxypropylmethyl cellulose acetate succinate, polyoxyethylene (105) polyoxypropylene (5) glycol, polyoxyethylene hydrogenated castor oil 60, polyoxyl 35 castor oil, sodium polystyrene sulfonate, polyvinylacetal diethylaminoacetate, polyvinyl alcohol, maleic acid, methacrylic acid copolymer S, sulfuric acid, aluminum sulfate, phosphoric acid, monobasic calcium phosphate, sodium dodecylbenzene sulfonate, a vinyl pyrrolidone.vinyl acetate copolymer, sodium lauroylsarcosine, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate, and sodium octadecyl sulfate,

[16-2] A dissolution aid consisting of a substance selected from the following group for use in the improvement of a solubility of a substance of the formula (I).
Group:
citric acid, hydroxypropyl cellulose, hydroxypropylmethyl cellulose, methacrylic acid copolymer LD, methyl cellulose, sodium lauryl sulfate, purified shellac, sodium dehydroacetate, fumaric acid, DL-malic acid, stearic L-ascorbate ester, L-aspartic acid, adipic acid, propylene glycol alginate ester, casein, sodium caseinate, carboxymethylethyl cellulose, succinic acid, copolyvidone, dioctyl sodium sulfosuccinate, lactic acid, aluminum lactate, ascorbic acid palmitate, hydroxyethylmethyl cellulose, hydroxypropylmethyl cellulose acetate succinate, polyoxyethylene hydrogenated castor oil 60, polyoxyl 35 castor oil, sodium polystyrene sulfonate, polyvinylacetal diethylaminoacetate, polyvinyl alcohol, methacrylic acid copolymer S, sulfuric acid, aluminum sulfate, sodium dodecylbenzene sulfonate, a vinyl pyrrolidone.vinyl acetate copolymer, acetyl tryptophan, sodium decyl sulfate, sodium tetradecyl sulfate, and sodium octadecyl sulfate,

[16-3] A dissolution aid consisting of a substance selected from the following group for use in the improvement of a solubility of a substance of the formula (I).
Group:
citric acid, hydroxypropyl cellulose, hydroxypropylmethyl cellulose, methacrylic acid copolymer LD, methyl cellulose, sodium lauryl sulfate, purified shellac, sodium dehydroacetate, fumaric acid, DL-malic acid, L-aspartic acid, adipic acid, propylene glycol alginate ester, sodium caseinate, carboxymethylethyl cellulose, succinic acid, copolyvidone, dioctyl sodium sulfosuccinate, lactic acid, aluminum lactate, hydroxyethylmethyl cellulose, hydroxypropylmethyl cellulose acetate succinate, sodium polystyrene sulfonate, polyvinylacetal diethylaminoacetate, methacrylic acid copolymer S, sulfuric acid, aluminum sulfate, a vinyl pyrrolidone vinyl acetate copolymer, and sodium decyl sulfate.

Effect of the Invention

The composition of the present invention improves solubility, oral absorbability and/or absorbability in blood of the poorly water-soluble or water insoluble tetracyclic compounds having an ALK inhibitory activity which are useful as a prophylactic and/or therapeutic agent for cancer, depression, and cognitive function disorder.

BRIEF DESCRIPTION OF THE DRAWINGS

FIG. 4 It is a graph to illustrate the solubility of the Compound F6-20 hydrochloride salt when sodium lauryl sulfate and hydroxypropyl cellulose are blended in.

FIG. 7 It is a graph to illustrate the solubility of the Compound F6-20 mesylate salt when sodium lauryl sulfate and hydroxypropyl cellulose are blended in.

MODE FOR CARRYING OUT THE INVENTION

Figure 1:
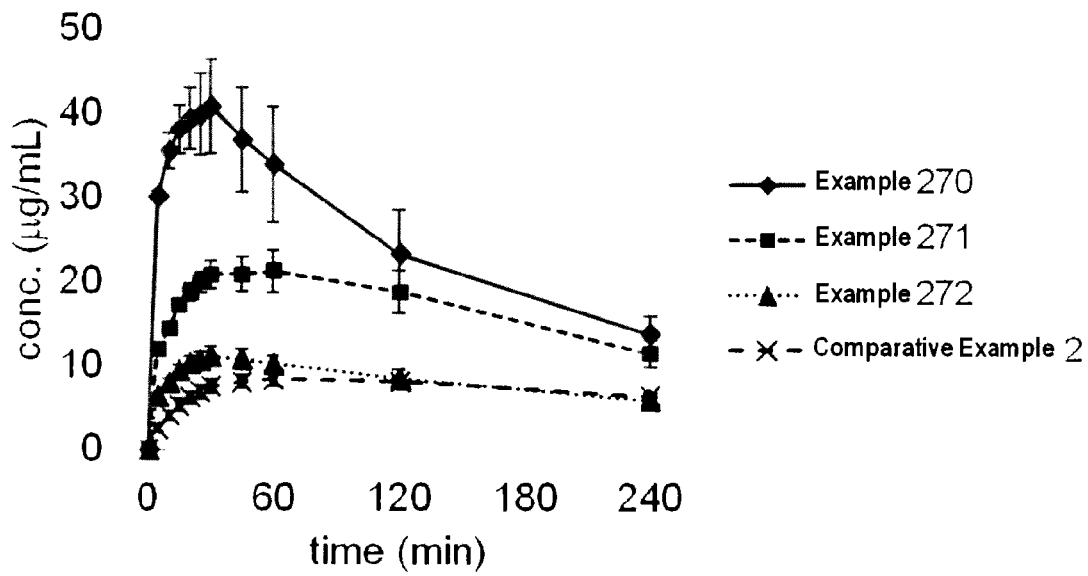
FIG. 1 It is a graph to compare the effect of the additive amount of sodium lauryl sulfate on the solubility of the Compound F6-20.

The term "pharmaceutically acceptable carrier", as used in the present specification, means one or more acceptable solid or liquid filler/diluents or encapsulating substances which are suitable for administration to a mammal. The term "acceptable", as used herein, means that the ingredients of the composition are capable of being miscible with the subject compound, and with each other, in a manner such that there is no interaction which would substantially reduce the pharmaceutical efficacy of the composition under ordinary use situations. Pharmaceutically acceptable carriers should, of course, be of sufficiently high purity and sufficiently low toxicity to render them suitable for administration preferably to an animal, more preferably mammal being treated.

The "dissolution aid" used in the present invention includes a surfactant, an organic polymer, and a pH adjusting agent, etc., and specific examples thereof are the substances given in Table 2 below. Preferred examples thereof include casein, sodium caseinate, skimmed milk powder, sodium lauryl sulfate (herein below, also referred to as SLS), dioctyl sodium sulfosuccinate, polyoxyl 40 stearate, sorbitan trioleate, polyoxyethylene (105) polyoxypropylene (5) glycol, polyoxyethylene hydrogenated castor oil 60, polyoxyl 35 castor oil, lauromacrogol, sodium lauroylsarcosine, sodium tetradecyl sulfate, sodium hexadecyl sulfate, sodium octadecyl sulfate, sodium methyl sulfate, sodium ethyl sulfate, sodium butyl sulfate, sodium octyl sulfate, sodium decyl sulfate, and sodium dodecylbenzene sulfonate.

According to the present invention, the dissolution aid may be used in combination of two or more types that are mixed at an appropriate ratio.

Particularly preferred is a surfactant.

In the present invention, when two or more dissolution aids are used as a combination, preferred examples of the combination of dissolution aids include a combination of sodium lauryl sulfate and polyoxyethylene (105) polyoxypropylene (5) glycol and a combination of sodium lauryl sulfate and sodium polystyrene sulfonate. More preferred examples include a combination of sodium lauryl sulfate, sodium polystyrene sulfonate, and polyoxyethylene (105) polyoxypropylene (5) glycol.

Examples of sodium polystyrene sulfonate include CAS (Chemical Abstract) registration number of 9080-79-9 (a cationic exchange resin wherein a sulfonic acid group attached to a copolymer of styrene and divinyl benzene is present in the form of a sodium, as defined in Pharmacopoeia of Japan, 15th revised edition) and poly(sodium 4-styrene sulfonate) [CAS registration number of 25704-18-1, a homopolymer obtained by polymerization of 4-ethenylbenzene sodium sulfonate], and poly(sodium 4-styrene sulfonate) is preferable.

The term "surfactant" indicates a substance which has both a hydrophilic group and a hydrophobic group in a molecule. The surfactant includes an ionic surfactant and a non-ionic surfactant.

The ionic surfactant means an ionic surfactant which dissociates to give an ion (i.e., an atom or an atomic group having a charge) when it is dissolved in water. Depending on the charge of generated ion, the ionic surfactant is further classified into an anionic surfactant, a cationic surfactant, and an amphoteric surfactant. According to the present invention, a non-ionic surfactant and an anionic surfactant are preferable.

Examples of the non-ionic surfactant include sugar ester type surfactant such as sorbitan fatty acid ester ($C_{12-18}$), POE sorbitan fatty acid ester ($C_{12-18}$), and sucrose fatty acid ester; fatty acid ester type such as POE fatty acid ester ($C_{12-18}$), POE resin acid ester, and POE fatty acid diester ($C_{12-18}$); alcohol type such as POE alkyl ether ($C_{12-18}$); alkyl phenol type surfactant such as POE alkyl($C_{8-12}$)phenyl ether, POE dialkyl ($C_{8-12}$)phenyl ether, and POE alkyl($C_{8-12}$)phenyl ether formalin condensate; polyoxyethylene.polyoxypropylene block polymer type surfactant such as polyoxyethylene polyoxypropylene block polymer and alkyl($C_{12-18}$) polyoxyethylene.polyoxypropylene block polymer ether; alkylamine type such as POE alkylamine ($C_{12-18}$) and POE fatty acid amide ($C_{12-18}$); bisphenol type surfactant such as POE fatty acid bisphenyl ether; polyaromatic type surfactant such as POA benzylphenyl (or phenylphenyl)ether and POA styrylphenyl (or phenylphenyl)ether; POE ether and ester type silicon and fluorine-based surfactant, and; plant oil type surfactant such as POE castor oil and POE hydrogenated castor oil. Preferred examples include polyoxyl 40 stearate, sorbitan trioleate, polyoxyethylene (105) polyoxypropylene (5) glycol, polyoxyethylene hydrogenated castor oil 60, polyoxyl 35 castor oil, and lauromacrogol.

Examples of the anionic surfactant include sulfate type surfactant such as alkyl sulfate ($C_{12-18}$, Na, $NH_4$, alkanolamine), POE alkyl ether sulfate ($C_{12-18}$, Na, $NH_4$, alkanolamine), POE alkylphenyl ether sulfate ($C_{12-18}$, $NH_4$, alkanolamine, Ca), POE benzyl (or styryl)phenyl (or phenylphenyl) ether sulfate (Na, $NH_4$, alkanolamine), polyoxyethylene.polyoxypropylene block polymer sulfate (Na, $NH_4$, alkanolamine); sulfonate type surfactant such as paraffin (alkane) sulfonate ($C_{12-22}$, Na, Ca, alkanolamine), AOS ($C_{14-16}$, Na, alkanolamine), dialkylsulfosuccinate ($C_{8-12}$, Na, Ca, Mg), alkylbenzene sulfonate ($C_{12}$, Na, Ca, Mg, $NH_4$, alkylamine, alkanol, amine, cyclohexylamine), mono or dialkyl($C_{3-6}$) naphthalene sulfonate (Na, $NH_4$, alkanolamine, Ca, Mg), naphthalene sulfonate.formalin condensate (Na, $NH_4$), alkyl ($C_{8-12}$)diphenyl ether disulfonate (Na, $NH_4$), lignin sulfonate (Na, Ca), POE alkyl($C_{8-12}$)phenyl ether sulfonate (Na), and POE alkyl($C_{12-18}$)ether sulfosuccinic acid half ester (Na); carboxylic acid type surfactant such as fatty acid salt ($C_{12-18}$, Na, K, $NH_4$, alkanolamine), N-methyl-fatty acid sarcocinate ($C_{12-18}$, Na), and resin acid salt (Na, K); and phosphate type surfactant like POE alkyl($C_{12-18}$)ether phosphate (Na, alkanolamine), POE mono or dialkyl($C_{8-12}$)phenyl ether phosphate (Na, alkanolamine), POE benzyl (or styryl)ated phenyl (or phenylphenyl)ether phosphate (Na, alkanolamine), polyoxyethylene.polyoxypropylene block polymer (Na, alkanolamine), phosphatidylcholine.phosphatidyl ethanolamine (lecithine), and alkyl($C_{8-12}$) phosphate. Preferred examples include monoalkyl sulfate such as sodium lauryl sulfate, sodium tetradecyl sulfate, sodium hexadecyl sulfate, and sodium octadecyl sulfate, dioctyl sodium sulfosuccinate, sodium lauroylsarcosine, and sodium dodecylbenzene sulfonate.

The organic polymer indicates a substance having molecular weight of at least 10,000 and the skeleton mainly composed of a carbon. The organic polymer includes a protein derived from an animal or a plant, polysaccharides, synthetic resin, and the like.

Specific examples of the organic polymer include polysaccharides such as hydroxypropyl cellulose (herein below, also referred to as HPC), hydroxypropylmethyl cellulose, methyl cellulose, propylene glycol alginate ester, powdered agar, guar gum, zein, and hydroxyethylmethyl cellulose, a synthetic resin such as a carboxyvinyl polymer, polyvinyl alcohol, or a vinyl acetate resin, and sodium polystyrene sulfonate, and phosphorus protein such as casein and sodium caseinate.

Among the organic polymers, those having water solubility of 1 g/100 g or higher are called water soluble polymer. Specific examples thereof include hydroxypropyl cellulose, hydroxypropylmethyl cellulose, methyl cellulose, propylene glycol alginate ester, sodium caseinate, a carboxyvinyl polymer, powdered agar, guar gum, copolyvidone, hydroxyethylmethyl cellulose, and polyvinyl alcohol.

Among the organic polymers, those soluble under acidic condition of pH 1.2 to 3.5, which is the pH of gastric juice, are called gastric-soluble polymer, while those quickly soluble at enteric pH of 6 to 8 are called enteric-soluble polymer. Examples of the gastric soluble polymer include amino alkylmethacrylate copolymer E and polyvinylacetal diethylaminoacetate, and examples of the enteric-soluble polymer include methacrylic acid copolymer LD (emulsion), methacrylic acid copolymer 5, purified shellac, carboxymethylethyl cellulose, cellulose acetate phthalate (cellaphate), hydroxypropylmethyl cellulose acetate succinate, casein, and zein.

The pH adjusting agent indicates a substance which controls the pH of a solution with addition of an acid agent or an alkali agent so as to improve the solubility of a poorly water-soluble substance. The pH adjusting agent is appropriately selected according to the property of a substance to be dissolved. For example, in case of a basic poorly water-soluble substance, an acid agent is added to adjust the pH to be acidic and to improve the solubility.

Examples of the pH adjusting agent include adipic acid, citric acid, trisodium citrate, gluconic acid, sodium gluconate, glucono deltalactone, potassium gluconate, succinic acid, monosodium succinate, disodium succinate, sodium acetate, L-tartaric acid, potassium hydrogen L-tartrate, sodium L-tartrate, DL-tartaric acid, potassium hydrogen DL-tartrate, sodium DL-tartrate, sodium hydrogencarbonate, potassium carbonate (anhydrous), sodium carbonate, carbon dioxide, lactic acid, sodium lactate, glacial acetic acid, disodium dihydrogen pyrophosphate, fumaric acid, monosodium fumarate, DL-malic acid, sodium DL-malate, phosphoric acid, monobasic potassium phosphate, sodium dihydrogen phosphate, dipotassium hydrogen phosphate, and disodium hydrogen phosphate.

Preferred examples include an acid agent such as adipic acid, citric acid, gluconic acid, glucono deltalactone, succinic acid, L-tartaric acid, DL-tartaric acid, carbon dioxide, lactic acid, glacial acetic acid, fumaric acid, DL-malic acid, and phosphoric acid.

It is particularly preferable that the formulation of the present invention comprises a dissolution aid that is selected from casein, sodium caseinate, skimmed milk powder, sodium lauryl sulfate, sodium tetradecyl sulfate, sodium hexadecyl sulfate, and sodium octadecyl sulfate.

The term "orally administrable formulation" indicates a formulation which can be administered orally. The oral administration means that the formulation is swallowed to enter a gastrointestinal tract, and the active ingredient is absorbed mainly in an intestinal tract.

Specific examples of the orally administrable formulation include a solid formulation such as a tablet, a capsule, a liquid, powder, a troche, a chewing formulation, granules, a gel formulation, a film formulation, and a spray formulation as well as a liquid formulation. Examples of the liquid formulation include a suspension, a liquid, a syrup, and an elixir. These formulations can be used as a filler for a soft or hard capsule, and as a carrier, water, ethanol, polyethylene glycol, propylene glycol, methyl cellulose, or suitable oil, and one or more emulsifying agent and/or a suspending agent are generally used. Furthermore, the liquid formulation can be prepared, for example, by dissolving solid state pharmaceutical formulation, for example, an individually packaged pharmaceutical formulation, in water, etc.

In the present specification, the term "poorly water-soluble or insoluble in water" indicates that the solubility in water is less than 100 μg/mL, preferably less than 10 μg/mL at 25° C., for example. The solubility can be determined according to a method well known in the art.

In the present specification, the expression "water solubility is improved" indicates that the solubility in FaSSIF, which is fasted state simulated intestinal fluid of human, is improved. Specifically, it indicates that the solubility is increased in significant sense ($p<0.05$) when a T-test is carried out for a comparative example. Similarly, the expression "water solubility is improved in significant sense" indicates that the solubility is increased in significant sense ($p<0.01$) when a significant difference test is carried out. Similarly, the expression "water solubility is improved in particularly significant sense" indicates that the solubility is increased in significant sense ($p<0.001$) when a significant difference test is carried out.

In the present specification, the term "ALK" indicates "a receptor type tyrosine kinase which means anaplastic lymphoma kinase and belongs to an insulin receptor family."

In the present specification, the "substance" represented by the Formula (I) or specific chemical name means a compound represented by a certain structure, the salts, or solvates or prodrugs thereof.

In the present specification, the term "halogen atom" means a fluorine atom, a chlorine atom, a bromine atom, an iodine atom and the like. According to the present invention, when the halogen atom is a substituent group for an aromatic carbon ring, an aromatic heterocycle and the like, the preferred halogen atom includes a fluorine atom, a chlorine atom and a bromine atom. According to the present invention, when the halogen atom is a substituent group for an alkyl group or a group which comprises the alkyl as at least a part of the group (e.g., alkoxy, alkenyl, unsaturated carbocycle, unsaturated heterocycle and the like), the preferred halogen atom includes a fluorine atom. Specific examples thereof include a trifluoromethyl group, a pentafluoroethyl group, a heptafluoropropyl group, a nonafluorobutyl group, a trifluoromethoxy group, a pentafluoroethoxy group, a heptafluoropropoxy group, a nonafluorobutoxy group, a trifluoroacetyl group, a pentafluoropropionyl group, a heptafluorobutyryl group and a nonafluoropentanoyl group.

The "$C_{1-8}$ alkyl group" means a monovalent group which is derived by removing any one of hydrogen atoms from a linear or branched aliphatic hydrocarbon having 1 to 8 carbon atoms. Specific examples thereof include a methyl group, an ethyl group, an isopropyl group, a butyl group, an n-butyl group, an isobutyl group, a sec-butyl group, a t-butyl group, a pentyl group, an isopentyl group, a 2,3-dimethyl propyl group, a hexyl group, a 2,3-dimethyl hexyl group, a 1,1-dimethyl pentyl group, a heptyl group and an octyl group. Preferably, it is a $C_{1-6}$ alkyl group, more preferably a $C_{1-5}$ alkyl group, still more preferably a $C_{1-4}$ alkyl group, and even still more preferably a $C_{1-3}$ alkyl group.

The "$C_{1-8}$ alkyl group which may be substituted" means an unsubstituted $C_{1-8}$ g alkyl group or a $C_{1-8}$ alkyl group of which at least one hydrogen atom on the alkyl group is substituted by a certain substituent group. When two or more substituent groups are present, each substituent group may be the same or different from each other. In addition, the alkyl group may be substituted by a cyclic substituent group through a spiro bond. Preferably, it is a $C_{1-8}$ alkyl group which may be substituted by certain 1 to 3 substituent group(s).

The "$C_{2-8}$ alkenyl group" means a monovalent group wherein at least one double bond (two adjacent SP2 carbon atoms) is comprised in a linear or branched aliphatic hydrocarbon group having 2 to 8 carbon atoms. Specific examples of the $C_{2-8}$ alkenyl group include a vinyl group, an allyl group, a 1-propenyl group, a 2-propenyl group, a 1-butenyl group, a 2-butenyl group (including both cis and trans), a 3-butenyl group, a pentenyl group and a hexenyl group. Preferably, it is a $C_{2-6}$ alkenyl group, more preferably a $C_{2-5}$ alkenyl group, still more preferably a $C_{2-4}$ alkenyl group, and even still more preferably a $C_{2-3}$ alkenyl group.

The "$C_{2-8}$ alkenyl group which may be substituted" means the unsubstituted $C_{2-8}$ alkenyl group as defined above or a $C_{2-8}$ alkenyl group of which at least one hydrogen atom on the alkenyl group is substituted by a certain substituent group. When two or more substituent groups are present, each substituent group may be the same or different from each other. In addition, the single-bonded carbon atom may be substituted by a cyclic substituent group through a spiro bond. Preferably, it is a $C_{2-8}$ alkenyl group which may be substituted by 1 to 3 certain substituent group(s). More preferably, there are 1 to 3 substituent groups for a $C_{2-6}$ alkenyl group and a $C_{2-5}$ alkenyl group and 1 to 2 substituent groups for a $C_{2-3}$ alkenyl group.

The "$C_{2-8}$ alkynyl group" means a monovalent group wherein at least one triple bond (two adjacent SP carbon atoms) is comprised in a linear or branched aliphatic hydrocarbon group having 2 to 8 carbon atoms. Specific examples of the $C_{2-8}$ alkynyl group include an ethynyl group, a 1-propynyl group, a propargyl group and a 3-butynyl group. Preferably, it is a $C_{2-6}$ alkynyl group, more preferably a $C_{2-5}$ alkynyl group, still more preferably a $C_{2-4}$ alkynyl group, and even still more preferably a $C_{2-3}$ alkynyl group.

The "$C_{2-8}$ alkynyl group which may be substituted" means the unsubstituted $C_{2-8}$ alkynyl group as defined above or a $C_{2-8}$ alkynyl group of which at least one hydrogen atom on the alkynyl group is substituted by a certain substituent group. When two or more substituent groups are present, each substituent group may be the same or different from each other. In addition, the single-bonded carbon atom may be substituted by a cyclic substituent group through a spiro bond. Preferably, it is a $C_{2-8}$ alkynyl group which may be substituted by certain 1 to 3 substituent group(s). More preferably, there are 1 to 3 substituent groups for a $C_{2-6}$ alkynyl group and a $C_{2-5}$ alkynyl group and 1 to 2 substituent groups for a $C_{2-3}$ alkynyl group.

The "$C_{3-8}$ cycloalkyl group" means an aliphatic hydrocarbon group in cyclic form. Preferably, it includes a $C_{3-6}$ cycloalkyl group. Specific examples thereof include a cyclopropyl group, a cyclobutyl group, a cyclopentyl group, a cyclohexyl group, a cycloheptyl group and a cyclooctyl group. Preferably, it is a $C_{3-6}$ cycloalkyl group.

The "$C_{3-8}$ cycloalkyl group which may be substituted" means the unsubstituted $C_{3-8}$ cycloalkyl group as defined above or the $C_{3-8}$ cycloalkyl group in which one or more hydrogen atoms are substituted by a certain substituent group. When there are two or more substituent groups, each substituent group may be the same or different from each other. Preferably, it is a $C_3$ cycloalkyl group which may be substituted by certain 1 to 3 substituent group(s).

The "4- to 10-membered heterocycloalkyl group" means a saturated or partially unsaturated heterocyclic group which consists of 4 to 10 ring-constituting atoms and comprises 1 to 3 hetero atoms that are selected from O, S and N. The heterocycloalkyl group can be a monocyclic, a bicyclic or a spirocyclic type heterocycloalkyl group. Specific examples thereof include an oxetanyl group, a tetrahydrofuryl group, a tetrahydrothienyl group, a tetrahydropyranyl group, a pyrrolidino group, a pyrrolidinyl group, a piperidino group, a piperidinyl group, a piperazino group, a piperazinyl group, a morpholino group, a morpholinyl group, a tetrahydrothiopyranyl group, a thiomorpholino group, an imidazolidinyl group, a 1,3-dioxadinyl group, a tetrahydropyranyl group, a 1,3-dioxadinyl group, a 1,2,3,6-tetrahydropyridinyl group, a 1-oxa-8-aza-spiro[4.5]decanyl group, and a 1,4-dioxa-8-aza-spiro[4.5]decanyl group. Preferably, it is a 4- to 8-membered heterocycloalkyl group, more preferably, 4- to 6-membered heterocycloalkyl group.

The "4- to 10-membered heterocycloalkyl group which may be substituted" means the unsubstituted 4- to 10-membered heterocycloalkyl group as defined above or a 4- to 10-membered heterocycloalkyl group of which at least one hydrogen atom on the heterocycloalkyl group is substituted by a certain substituent group. When two or more substituent groups are present, each substituent group may be the same or different from each other. In addition, the alkyl moiety which may be substituted by a cyclic substituent group through a spiro bond. Preferably, it is a 4- to 10-membered heterocycloalkyl group which may be substituted by 1 to 4 certain substituent group(s). More preferably, there are 1 to 4 substituent groups for a 4- to 8-membered heterocycloalkyl group and 1 to 3 substituent group(s) for a 4- to 6-membered heterocycloalkyl group. When the substituent group is an oxo group, two oxo groups may bind to the same sulfur atom. When a quaternary ammonium salt is formed, two alkyl groups may bind to the nitrogen atom.

The "$C_{6-10}$ aryl group" means a monovalent aromatic hydrocarbon ring. Specific examples of the $C_{6-10}$ aryl group include a phenyl group, a 1-naphthyl group and a 2-naphthyl group.

The "$C_{6-10}$ aryl group which may be substituted" means the unsubstituted $C_{6-10}$ aryl group as defined above or a $C_{6-10}$ aryl group of which at least one hydrogen atom is substituted by a certain substituent group. When two or more substituent groups are present, each substituent group may be the same or different from each other. Preferably, it is a $C_{6-10}$ aryl group which may be substituted by certain 1 to 3 substituent group(s).

The "5- to 14-membered heteroaryl group" means an aromatic cyclic group comprising one or more hetero atoms among 5 to 14 ring-constituting atoms. The cycle can be a monocyclic or bicyclic heteroaryl group fused to a benzene ring or a monocyclic heteroaryl ring. Specific examples thereof include a furyl group, a thienyl group, a pyrrolyl group, an imidazolyl group, a pyrazolyl group, a thiazolyl group, an isothiazolyl group, an oxazolyl group, an isooxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzoxazolyl group, a benzoxadiazolyl group, a benzoimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolizinyl group, an imidazopyridyl group and the like. Preferably, it is a 5- to 6-membered heteroaryl group.

The "5- to 14-membered heteroaryl group which may be substituted" means the unsubstituted 5- to 14-membered heteroaryl group as defined above or a 5- to 14-membered heteroaryl group of which at least one hydrogen atom on the heteroaryl group is substituted by a certain substituent group. When two or more substituent groups are present, each substituent group may be the same or different from each other. Preferably, it is a 5- to 14-membered heteroaryl group which may be substituted by certain 1 to 3 substituent group(s). More preferably, there are 1 to 3 substituent group(s) or 1 to 2 substituent group(s) for a 5- to 6-membered heteroaryl group.

The "$C_{1-8}$ alkanoyl group" means a $C_{1-8}$ alkyl-C(O)— group, wherein the $C_{1-8}$ alkyl group is as defined above. Specific examples thereof include acetyl, propionyl, butyryl, isobutyryl, pentanoyl, tert-butylcarbonyl and a hexanoyl group. Preferably, it is a $C_{1-6}$ alkanoyl group, and more preferably a $C_{1-3}$ alkanoyl group.

The "$C_{1-8}$ alkanoyl group which may be substituted" means the unsubstituted $C_{1-8}$ alkanoyl group as defined above or a $C_{1-8}$ alkanoyl group of which at least one hydrogen atom on the alkanoyl group is substituted by a certain substituent group. When two or more substituent groups are present, each substituent group may be the same or different from each other. Preferably, it is a $C_{1-8}$ alkanoyl group which may be substituted by certain 1 to 3 substituent group(s). More preferably, there are 1 to 2 substituent group(s) for a $C_{1-6}$ alkanoyl group and a $C_{1-3}$ alkanoyl group.

The "$C_{3-8}$ cycloalkylcarbonyl group" means a $C_{3-8}$ cycloalkyl-C(O)— group, wherein the $C_{3-8}$ cycloalkyl group is as defined above. Specific examples thereof include a cyclopropylcarbonyl group, a cyclobutylcarbonyl group, a cyclopentylcarbonyl group, a cyclohexylcarbonyl group, a cycloheptylcarbonyl group and a cyclooctylcarbonyl group.

The "4- to 10-membered heterocycloalkylcarbonyl group" means a 4- to 10-membered heterocycloalkyl-CO— group, and it contains the 4- to 10-membered heterocycloalkyl as defined above.

The "$C_{3-8}$ cycloalkyl($C_{0-8}$ alkyl)aminocarbonyloxy group" means a $C_{3-8}$ cycloalkyl-NHC(O)O— group or a $C_{3-8}$ cycloalkyl-N($C_{1-8}$ alkyl)C(O)O— group, wherein the $C_{3-8}$ cycloalkyl group is as defined above. Specific examples thereof include a cyclopropylaminocarbonyloxy group, a cyclobutylaminocarbonyloxy group, a cyclopentylaminocarbonyloxy group, a cyclohexylaminocarbonyloxy group, a cyclopropyl(N-methyl)aminocarbonyloxy group, and a cyclobutyl(N-methyl)aminocarbonyloxy group.

The "($C_{1-8}$ alkyl)$_x$-aminocarbonyl group" (wherein, x represents the symbol as defined in the claims) means a NH$_2$—C(O)— group, a ($C_{1-8}$ alkyl)-N—C(O)— group or a ($C_{1-8}$ alkyl)$_2$-N—C(O)— group. Specific examples thereof include an N-methylamino carbonyl group, an N-ethylaminocarbonyl group, an N-n-butyl-aminocarbonyl group, and a N,N-dimethylaminocarbonyl group.

The "($C_{1-8}$ alkyl)$_x$-aminocarbonyl group which may be substituted" means the unsubstituted ($C_{1-8}$ alkyl)$_x$ aminocarbonyl group or the group in which at least one hydrogen atom of the nitrogen atom or the alkyl moiety is substituted by a certain substituent group. When there are two or more substituent groups, each substituent group may be the same or different from each other.

The "$C_{6-10}$ aryl($C_{0-8}$ alkyl)aminocarbonyl group" means a $C_{6-10}$ aryl NHC(O)— group or a $C_{6-10}$ aryl N($C_{1-8}$ alkyl)C(O)— group. Specific examples thereof include a phenyl-NHC(O)— group and a phenyl-(N-methyl)-aminocarbonyl group. The $C_{6-10}$ aryl and $C_{1-8}$ alkyl are as defined above. Specific examples thereof include a phenylaminocarbonyl group and a phenyl(N-methyl)aminocarbonyl group.

The "nitrogen-containing 4- to 10-membered heterocycloalkylcarbonyl group" means a carbonyl group to which a nitrogen-containing 4- to 10-membered heterocycloalkyl group is bonded. Herein, the a nitrogen-containing 4- to 10-membered heterocycloalkyl group (a nitrogen-containing 4- to 10-membered heterocycloalkyl group) means a heterocycloalkyl group which consists of 4 to 10 ring-constituting atoms and comprises at least one nitrogen atom as a hetero atom. Preferably, it is bonded to the carbonyl group via nitrogen atom that is comprised in the heterocycloalkyl ring. Specific examples of the heterocycloalkyl group include a pyrrolidinyl group, an imidazolidinyl group, a morpholino group, a piperazino group and a piperidino group. As for the nitrogen-containing 4- to 10-membered heterocycloalkylcarbonyl group, examples thereof include a pyrrolidinocarbonyl group, a piperidinocarbonyl group, a piperazinocarbonyl group and a morpholinocarbonyl group.

The "nitrogen-containing 4- to 10-membered heterocycloalkylcarbonyl group which may be substituted" means the unsubstituted nitrogen-containing 4- to 10-membered heterocycloalkylcarbonyl group or the group in which at least one hydrogen atom of the heterocycloalkyl moiety is substituted by a certain substituent group. When two or more substituent groups are present, each substituent group may be the same or different from each other. Further, the heterocycloalkyl moiety may be substituted by a cyclic substituent group through a spiro bond. Preferably, it is a nitrogen-containing 4- to 10-membered heterocycloalkylcarbonyl group which may be substituted by certain 1 to 3 substituent group(s).

The "4- to 10-membered heterocycloalkyl($C_{0-8}$ alkyl)aminocarbonyl group" means a 4- to 10-membered heterocycloalkyl NHC(O)— group or a 4- to 10-membered heterocycloalkyl N($C_{1-8}$ alkyl) C(O)— group. Specific examples thereof include oxetan-3-yl-amide group and a (1,1-dioxotetrahydrothiophen-3-yl)amide group.

The "4- to 10-membered heterocycloalkylaminocarbonyl group which may be substituted by one or more oxo group" means the unsubstituted 4- to 10-membered heterocycloalkylaminocarbonyl group or the group in which the heterocycloalkyl moiety is substituted by at least one oxo group.

The "$C_{6-10}$ arylsulfonyl group" means a $C_{6-10}$ aryl-S(O)$_2$— group, wherein the $C_{6-10}$ aryl group is as defined above. Specific examples thereof include a phenylsulfonyl group.

The "5- to 14-membered heteroarylsulfonyl group" means a 5- to 14-membered heteroaryl-S(O)$_2$— group, wherein the 5- to 14-membered heteroaryl group is as defined above. Specific examples thereof include an imidazole sulfonyl group.

The "$C_{1-8}$ alkyl$C_{6-10}$ arylsulfonyl group" means a $C_{1-8}$ alkyl-$C_{6-10}$ aryl-S(O)$_2$— group, wherein the $C_{1-8}$ alkyl and $C_{6-10}$ aryl group are as defined above. Specific examples thereof include a 4-methyl-phenylsulfonyl group.

The "($C_{1-8}$ alkyl)$_x$-amino group" (wherein, x represents the symbol as defined in the claims) means an amino group, a NH($C_{1-8}$ alkyl) group, or a NH($C_{1-8}$ alkyl)$_2$ group. Specific examples thereof include amino, methylamino, ethylamino, butylamino, isopropylamino, dimethylamino, and diethylamino. Preferably, it is a $C_{1-3}$ alkylamino group.

The "$(C_{1-8}$ alkyl$)_x$-amino group which may be substituted" means the unsubstituted ($C_{1-8}$ alkyl), amino group or the group in which at least one hydrogen atom of the nitrogen atom or the alkyl moiety is substituted by a certain substituent group. When two or more substituent groups are present, each substituent group may be the same or different from each other.

The "$C_{1-8}$ alkylcarbonyl($C_{0-8}$ alkyl)amino group" means a $C_{1-8}$ alkyl-C(O)—NH— group, or a $C_{1-8}$ alkyl-C(O)—N($C_{1-8}$ alkyl)- group, wherein the $C_{1-8}$ alkyl is as defined above. Specific examples thereof include a methylcarbonylamino group, an ethylcarbonylamino group, a propylcarbonylamino group, and a butylcarbonylamino group.

The "$C_{1-8}$ alkylcarbonyl($C_{0-8}$ alkyl)amino group which may be substituted" means the unsubstituted $C_{1-8}$ alkylcarbonyl($C_{0-8}$ alkyl)amino group or the group in which at least one hydrogen atom on the terminal alkyl moiety of the $C_{1-8}$ alkylcarbonyl($C_{0-8}$ alkyl)amino group is substituted by a certain substituent group. When two or more substituent groups are present, each substituent group may be the same or different from each other. Further, the alkyl group may be substituted by a cyclic substituent group through a spiro bond. Preferably, it is a $C_{1-8}$ alkylcarbonyl($C_{0-8}$ alkyl)amino group which may be substituted by certain 1 to 3 substituent group(s).

The "$C_{6-10}$ arylcarbonyl($C_{0-8}$ alkyl)amino group" means a $C_{6-10}$ aryl-C(O)—NH— group, or a $C_{6-10}$ aryl-C(O)—N($C_{1-8}$ alkyl)- group, wherein the $C_{6-10}$ aryl group and $C_{1-8}$ alkyl group are as defined above. Specific examples thereof include a phenylcarbonylamino group.

The "$C_{6-10}$ arylcarbonyl($C_{0-8}$ alkyl)amino group which may be substituted" means the unsubstituted $C_{6-10}$ arylcarbonyl($C_{0-8}$ alkyl)amino group or the group in which at least one hydrogen atom of the aryl moiety of the $C_{6-10}$ arylcarbonyl($C_{0-8}$ alkyl)amino group is substituted by a certain substituent group. When two or more substituent groups are present, each substituent group may be the same or different from each other. Preferably, it is a $C_{6-10}$ arylcarbonyl($C_{0-8}$ alkyl)amino group which may be substituted by certain 1 to 3 substituent group(s).

The "($C_{1-8}$ alkyl$)_x$-aminocarbonyl($C_{0-8}$ alkyl)amino group" (wherein, x represents the symbol as defined in the claims) means a $NH_2C(O)NH$— group, a ($C_{1-8}$ alkyl)NHC(O)NH— group, a $NH_2C(O)N(C_{1-8}$ alkyl)- group, or a ($C_{1-8}$ alkyl)NHC(O)N($C_{1-8}$ alkyl)- group, wherein the $C_{1-8}$ alkyl group is as defined above. Specific examples thereof include aminocarbonyl-(N-methyl)amino and (N-methyl)aminocarbonyl-(N'-methyl)amino.

The "($C_{1-8}$ alkyl$)_x$-aminocarbonyl($C_{0-8}$ alkyl)amino group which may be substituted" means the unsubstituted ($C_{1-8}$ alkyl$)_x$-aminocarbonyl($C_{0-8}$ alkyl)amino group or the ($C_{1-8}$ alkyl$)_x$-aminocarbonyl($C_{0-8}$ alkyl)amino group in which at least one hydrogen atom of the nitrogen atom or the alkyl moiety of the ($C_{1-8}$ alkyl$)_x$-aminocarbonyl($C_{0-8}$ alkyl)amino group is substituted by a certain substituent group. Preferably, it is a ($C_{1-8}$ alkyl$)_x$-aminocarbonyl($C_{0-8}$ alkyl)amino group which may be substituted by a phenyl group.

The "($C_{1-8}$ alkyl$)_x$ aminosulfonyl($C_{0-8}$ alkyl)amino group" (wherein, x represents the symbol as defined in the claims) means a $NH_2S(O)_2NH$ group, a $NH(C_{1-8}$ alkyl)-$S(O)_2NH$ group, a $N(C_{1-8}$ alkyl$)_2$-$S(O)_2NH$ group, a $NH_2S(O)_2N(C_{1-8}$ alkyl)N— group, a $NH(C_{1-8}$ alkyl)-$S(O)_2(C_{1-8}$ alkyl)N— group, or a $N(C_{1-8}$ alkyl$)_2$-$S(O)_2(C_{1-8}$alkyl)N— group wherein the $C_{1-8}$ alkyl is as defined above. Specific examples thereof include a methylaminosulfonylamino group and a dimethylaminomethylsulfonylamino group.

The "$C_{1-8}$ alkoxy group" means a $C_{1-8}$ alkyl-O— group. Specific examples thereof include a methoxy group, an ethoxy group, a 1-propoxy group, a 2-propoxy group, an n-butoxy group, an i-butoxy group, a sec-butoxy group, a t-butoxy group, pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group and a 1-methylcyclopropylmethoxy group. Preferably, it is a $C_{1-6}$ alkoxy group. More preferably, it is a $C_{1-5}$ alkoxy group. Still more preferably, it is a $C_{1-4}$ alkoxy group, and even still more preferably it is a $C_{1-3}$ alkoxy group.

The "$C_{1-8}$ alkoxy group which may be substituted" means the unsubstituted $C_{1-8}$ alkoxy group or the group in which at least one hydrogen atom of the alkyl moiety is substituted by a certain substituent group. When two or more substituent groups are present, each substituent group may be the same or different from each other. In addition, the alkyl moiety may be substituted by a cyclic substituent group through a spiro bond. Preferably, it is a $C_{1-8}$ alkoxy group which may be substituted by certain 1 to 3 substituent group(s). More preferably, there are 1 to 3 substituent group(s) for the $C_{1-6}$ alkoxy group and a $C_{1-4}$ alkoxy group or 1 to 2 substituent group(s) for a $C_{1-3}$ alkoxy group.

The "$C_{1-8}$ alkoxycarbonyl group" means a $C_{1-8}$ alkyl-O—C(O)— group, wherein the $C_{1-8}$ alkyl group is as defined above. Specific examples thereof include a methoxycarbonyl group, an ethoxycarbonyl group, an n-propoxycarbonyl group and an i-propoxycarbonyl group. Preferably, it is a $C_{1-6}$ alkoxycarbonyl group, and more preferably a $C_{1-3}$ alkoxycarbonyl group.

The "$C_{1-8}$ alkoxycarbonyl group which may be substituted" means the unsubstituted $C_{1-8}$ alkoxycarbonyl group or the group in which at least one hydrogen atom of the $C_{1-8}$ alkoxycarbonyl group is substituted by a certain substituent group. When two or more substituent groups are present, each substituent group may be the same or different from each other. In addition, the alkyl moiety of the alkoxycarbonyl group may be substituted by a cyclic substituent group through a spiro bond. Preferably, it is a $C_{1-8}$ alkoxycarbonyl group which may be substituted by certain 1 to 3 substituent group(s).

The "$C_{0-8}$ alkoxy($C_{0-8}$ alkyl)aminocarbonyl group" means a HO—NH—C(O)— group, a $C_{1-8}$ alkyl-NH—C(O)— group, a HO—N($C_{1-8}$ alkyl)-C(O)— group, or a $C_{1-8}$ alkyl-N($C_{1-8}$ alkyl)-C(O)— group, wherein the $C_{1-8}$ alkoxy group and $C_{1-8}$ alkyl group are as defined above. Specific examples thereof include a methoxyaminocarbonyl group, an ethoxyaminocarbonyl group, an n-propoxyaminocarbonyl group, and an i-propoxyaminocarbonyl group. Preferably, it is a $C_{1-6}$ alkoxyaminocarbonyl group. More preferably, it is a $C_{1-3}$ alkoxyaminocarbonyl group.

The "$C_{0-8}$ alkoxy($C_{0-8}$ alkyl)aminocarbonyl group which may be substituted" means the unsubstituted hydroxyaminocarbonyl group, $C_{1-8}$ alkoxyaminocarbonyl group, or a hydroxy($C_{1-8}$ alkyl)aminocarbonyl group or the group in which or at least one hydrogen atom of the alkyl moiety of the $C_{1-8}$ alkoxy($C_{1-8}$ alkyl)aminocarbonyl group is substituted by a certain substituent group. When two or more substituent groups are present, each substituent group may be the same or different from each other. In addition, the alkyl moiety may be substituted by a cyclic substituent group through a spiro bond. Preferably, it is a $C_{1-8}$ alkoxyaminocarbonyl group which may be substituted by certain 1 to 3 substituent group(s).

The "4- to 10-membered heterocycloalkyloxy group" means a 4- to 10-membered heterocycloalkyl-O— group having the 4- to 10-membered heterocycloalkyl defined above.

The "4- to 10-membered heterocycloalkyloxy group which may be substituted" means the unsubstituted 4- to 10-membered heterocycloalkyloxy group as defined above or a 4- to 10-membered heterocycloalkyloxy group in which at least one hydrogen atom of the heterocycloalkyl moiety is substituted by a certain substituent group. When two or more substituent groups are present, each substituent group may be the same or different from each other. In addition, the heterocycloalkyl moiety may be substituted by a cyclic substituent group through a spino bond. Preferably, it is a 4- to 10-membered heterocycloalkyloxy group which may be substituted by 1 to 3 certain substituent group.

The "$C_{6-10}$ aryloxy group" means a $C_{6-10}$ aryl-O— group, wherein the $C_{6-10}$ aryl group is as defined above.

The "5- to 14-membered heteroaryloxy group" means a 5- to 14-membered heteroaryl-O— group having the 5- to 14-membered heteroaryl described above. Specific examples thereof include a pyrimidinyloxy group.

The "$C_{1-8}$ alkylcarbonyloxy group" means a $C_{1-8}$ alkyl-C(O)—O— group having the $C_{1-8}$ alkyl described above. Specific examples thereof include a methylcarbonyloxy group, an ethylcarbonyloxy group and a propylcarbonyloxy group.

The "$C_{2-8}$ alkenylcarbonyloxy group" means a $C_{2-8}$ alkenyl-C(O)—O— group having the $C_{2-8}$ alkenyl described above. Specific examples thereof include a 2-methyl-2-butenoyloxy group.

The "4- to 10-membered heterocycloalkylcarbonyloxy group" means a 4- to 10-membered heterocycloalkyl-C(O)—O— group having the 4- to 10-membered heterocycloalkyl described above.

The "($C_{1-8}$ alkyl)$_x$-aminocarbonyloxy group" (wherein, x represents the symbol as defined in the claims) means a NHC(O)—O— group, a N($C_{1-8}$ alkyl)C(O)—O— group, or a N($C_{1-8}$ alkyl)$_2$C(O)—O— group. Specific examples thereof include a methyl-aminocarbonyloxy group, an ethyl-aminocarbonyloxy group, and a propyl-aminocarbonyloxy group.

The "($C_{1-8}$ alkyl)$_x$-aminocarbonyloxy group which may be substituted" means the unsubstituted ($C_{1-8}$ alkyl)$_x$-aminocarbonyloxy group or the group in which at least one hydrogen atom on the nitrogen atom or the alkyl moiety is substituted by a certain substituent group. When two or more substituent groups are present, each substituent group may be the same or different from each other.

The "nitrogen-containing 4- to 10-membered heterocycloalkylsulfonyl group" means the nitrogen-containing 4- to 10-membered heterocycloalkyl-S(O)$_2$— group. Specific examples thereof include a morpholino-sulfonyl group.

The "nitrogen-containing 4- to 10-membered heterocycloalkylsulfonyl group which may be substituted" means the unsubstituted nitrogen-containing 4- to 10-membered heterocycloalkylsulfonyl group or the group in which at least one hydrogen atom of the nitrogen-containing 4- to 10-membered heterocycloalkyl moiety is substituted by a certain substituent group. When two or more substituent groups are present, each substituent group may be the same or different from each other. Preferably, it is a nitrogen-containing 4- to 10-membered heterocycloalkylsulfonyl group which may be substituted by certain 1 to 3 substituent group(s).

The "nitrogen-containing 4- to 10-membered heterocycloalkylsulfonyloxy group" means a nitrogen-containing 4- to 10-membered heterocycloalkyl-S(O)$_2$—O— group. Specific examples thereof include a morpholino-sulfonyloxy group and a piperazino-sulfonyloxy group.

The "nitrogen-containing 4- to 10-membered heterocycloalkylsulfonyloxy group which may be substituted" means the unsubstituted nitrogen-containing 4- to 10-membered heterocycloalkylsulfonyloxy group or the group in which at least one hydrogen atom of the nitrogen-containing 4- to 10-membered heterocycloalkyl moiety is substituted by a certain substituent group. When two or more substituent groups are present, each substituent group may be the same or different from each other. Preferably, it is a nitrogen-containing 4- to 10-membered heterocycloalkylsulfonyloxy group which may be substituted by certain 1 to 3 substituent group(s).

The "$C_{1-8}$ alkylsulfonyloxy group" means a $C_{1-8}$ alkyl-S(O)$_2$—O— group, wherein the $C_{1-8}$ alkyl is as defined above.

The "$C_{1-8}$ alkylsulfonyloxy group which may be substituted" means the unsubstituted $C_{1-8}$ alkylsulfonyloxy group or the group in which at least one hydrogen atom of the alkyl moiety is substituted by a certain substituent group. When two or more substituent groups are present, each substituent group may be the same or different from each other. In addition, the alkyl moiety may be substituted by a cyclic substituent group through a spiro bond. Preferably, it is a $C_{1-8}$ alkylsulfonyloxy group which may be substituted by certain 1 to 3 substituent group(s). Specific examples thereof include a trifluoromethylsulfonyloxy group.

The "($C_{1-8}$ alkyl)$_x$-aminosulfonyloxy group" (wherein, x represents the symbol as defined in the claims) means a NH$_2$S(O)$_2$O— group, a N($C_{1-8}$ alkyl)S(O)$_2$O— group, or a N($C_{1-8}$ alkyl)$_2$S(O)$_2$O— group. Specific examples thereof include an N-methylaminosulfonyloxy group.

The "$C_{1-8}$ alkylthio group" means a $C_{1-8}$ alkyl-S— group, wherein the $C_{1-8}$ alkyl group is as defined above. Examples thereof include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio and the like. Preferably, it is a $C_{1-6}$ alkylthio group, and more preferably a $C_{1-3}$ alkylthio group.

The "$C_{1-8}$ alkylthio group which may be substituted" means the unsubstituted $C_{1-8}$ alkylthio group or the group in which at least one hydrogen atom of the alkyl moiety is substituted by a certain substituent group. When two or more substituent groups are present, each substituent group may be the same or different from each other. In addition, the alkyl moiety may be substituted by a cyclic substituent group through a spiro bond. Preferably, it is a $C_{1-8}$ alkylthio group which may be substituted by certain 1 to 3 substituent group(s).

The "$C_{1-8}$ alkylsulfonyl group" means a $C_{1-8}$ alkyl-S(O)$_2$— group, wherein the $C_{1-8}$ alkyl group is as defined above. Specific examples thereof include a methylsulfonyl group, an ethylsulfonyl group and an n-propylsulfonyl group. Preferably, it is a $C_{1-6}$ alkylsulfonyl group, and more preferably a $C_{1-3}$ alkylsulfonyl group.

The "$C_{1-8}$ alkylsulfinyl group" means a $C_{1-8}$ alkyl-S(O)— group, wherein the $C_{1-8}$ alkyl group is as defined above. Specific examples thereof include a methylsulfinyl group, an ethylsulfinyl group and an n-propylsulfinyl group. Preferably, it is a $C_{1-6}$ alkylsulfinyl group, and more preferably a $C_{1-3}$ alkylsulfinyl group.

The "$C_{1-8}$ alkylsulfonyl group which may be substituted" means the unsubstituted $C_{1-8}$ alkylsulfonyl group or the group in which at least one hydrogen atom of the alkyl moiety is substituted by a certain substituent group. When two or more substituent groups are present, each substituent group may be the same or different from each other. Preferably, it is a $C_{1-8}$ alkylsulfonyl group which may be substituted by certain 1 to 3 substituent group(s).

The "$C_{1-8}$ alkylsulfinyl group which may be substituted" means the unsubstituted $C_{1-8}$ alkylsulfinyl group or the group in which at least one hydrogen atom of the alkyl moiety is substituted by a certain substituent group. When two or more substituent groups are present, each substituent group may be the same or different from each other. Preferably, it is a $C_{1-8}$ alkylsulfinyl group which may be substituted by certain 1 to 3 substituent group(s).

The "4- to 10-membered heterocycloalkylsulfonyl group" means a 4- to 10-membered heterocycloalkyl-$S(O)_2$— group having the 4- to 10-membered heterocycloalkyl defined above.

The "4- to 10-membered heterocycloalkylsulfonyl group which may be substituted" means the unsubstituted 4- to 10-membered heterocycloalkylsulfonyl group or the group in which at least one hydrogen atom of the heterocycloalkyl moiety is substituted by a certain substituent group. When two or more substituent groups are present, each substituent group may be the same or different from each other. In addition, the heterocycloalkyl moiety may be substituted by a cyclic substituent group through a spiro bond. Preferably, it is a 4- to 10-membered heterocycloalkylsulfonyl group which may be substituted by certain 1 to 3 substituent group(s).

The "$(C_{1-8}$ alkyl$)_x$-aminosulfonyl group" (wherein, x represents the symbol as defined in the claims) means a $NH_2$—$S(O)_2$— group, a $C_{1-8}$ alkylamino-$S(O)_2$— group or a $(C_{1-8}$ alkyl$)_2$amino-$S(O)_2$— group, wherein the $C_{1-8}$ alkyl is as defined above. Specific examples thereof include an aminosulfonyl group, a methylaminosulfonyl group, and a dimethylaminosulfonyl group.

The "$(C_{1-8}$ alkyl$)_x$-aminosulfonyl group which may be substituted" means the unsubstituted aminosulfonyl group or the group in which at least one hydrogen atom on the nitrogen atom or the alkyl moiety is substituted by a certain substituent group. When two or more substituent groups are present, each substituent group may be the same or different from each other.

The "$C_{1-8}$ alkoxycarbonyl($C_{0-8}$ alkyl)amino group" means a $C_{1-8}$ alkoxy-$C(O)$—NH group, or a $C_{1-8}$ alkoxy-$C(O)$—N($C_{1-8}$ alkyl) group, wherein the $C_{1-8}$ alkoxy and $C_{1-8}$ alkyl are as defined above. Specific examples thereof include a methoxycarbamoyl group and an N-ethylcarbonyl-N-methylamino group.

The "$C_{1-8}$ alkoxycarbonyl($C_{0-8}$ alkyl)amino group which may be substituted" means the unsubstituted $C_{1-8}$ alkoxycarbonyl($C_{0-8}$ alkyl)amino group or the $C_{1-8}$ alkoxycarbonyl($C_{0-8}$ alkyl)amino group in which at least one hydrogen atom on the nitrogen atom or the alkyl moiety may be substituted by a certain substituent group. Preferably, it is a $C_{1-8}$ alkoxycarbonyl($C_{0-8}$ alkyl)amino group which is substituted by certain 1 to 3 substituent group(s).

The "$C_{1-8}$ alkoxycarbonyl($C_{0-8}$ alkyl)amino sulfonyl group" means a $C_{1-8}$ alkoxy-$C(O)$—$NHS(O)_2$— group, or $C_{1-8}$ alkoxy-$C(O)$—$N(C_{1-8}$ alkyl$)S(O)_2$— group, wherein the $C_{1-8}$ alkoxy and $C_{1-8}$ alkyl are as defined above. The specific examples thereof include a methoxycarbonylaminosulfonyl group and an ethoxycarbonyl-N-methylaminosulfonyl group.

The "$C_{6-10}$ aryloxycarbonyl($C_{0-8}$ alkyl)amino group" means a $C_{6-10}$ acyl-$O$—$C(O)$—NH group, or $C_{6-10}$ aryl-$O$—$C(O)$—$N(C_{1-8}$ alkyl) group, wherein the $C_{6-10}$ aryl and $C_{1-8}$ alkyl group are as defined above. The specific examples thereof include a phenyloxycarbonylamino group and an N-methyl-N-phenyloxycarbonylamino group.

The "$C_{6-10}$ aryloxycarbonyl($C_{0-8}$ alkyl)amino group which may be substituted" means the unsubstituted $C_{6-10}$ aryloxycarbonyl($C_{0-8}$ alkyl)amino group or the $C_{6-10}$ aryloxycarbonyl($C_{0-8}$ alkyl)amino group in which at least one hydrogen atom on the nitrogen atom or the alkyl moiety is substituted by a certain substituent group. When two or more substituent groups are present, each substituent group may be the same or different from each other. Preferably, it is a $C_{6-10}$ aryloxycarbonyl($C_{0-8}$ alkyl)amino group which may be substituted by certain 1 to 3 substituent group(s).

The "$C_{6-10}$ aryl($C_{0-8}$ alkyl)aminocarbonyl($C_{0-8}$ alkyl)amino group" means a $C_{6-10}$ aryl-NH—$C(O)$—NH group, a $C_{6-10}$ aryl-$N(C_{1-8}$ alkyl)-$C(O)$—NH group, or $C_{6-10}$ aryl-$N(C_{1-8}$ alkyl)-$C(O)$—$N(C_{1-8}$ alkyl) group, wherein the $C_{6-10}$ aryl and $C_{1-8}$ alkyl group are as defined above. Specific examples thereof include a phenylaminocarbonylamino group and a phenylaminocarbonyl(N-methyl)amino group.

The "$C_{6-10}$ aryl($C_{0-8}$ alkyl)aminocarbonyl($C_{0-8}$ alkyl)amino group which may be substituted" means the unsubstituted $C_{6-10}$ aryl($C_{0-8}$ alkyl)aminocarbonyl($C_{0-8}$ alkyl)amino group or the $C_{6-10}$ aryl($C_{0-8}$ alkyl)aminocarbonyl($C_{0-8}$ alkyl)amino group in which at least one hydrogen atom on the nitrogen atom or the alkyl moiety is substituted by a certain substituent group. When two or more substituent groups are present, each substituent group may be the same or different from each other. Preferably, it is a $C_{6-10}$ aryl($C_{0-8}$ alkyl)aminocarbonyl($C_{0-8}$ alkyl)amino group which may be substituted by certain 1 to 3 substituent group(s).

The "$C_{6-10}$ aryl($C_{0-8}$ alkyl)aminocarbonyloxy group" means a $C_{6-10}$ aryl-NH—$C(O)$—$O$— group, or a $C_{6-10}$ aryl-$N(C_{1-8}$ alkyl)-$C(O)$—$O$— group, wherein the $C_{6-10}$ aryl and $C_{1-8}$ alkyl group are as defined above. Specific examples thereof include a phenylaminocarbonyloxy group and a phenyl(N-methyl)aminocarbonyloxy group.

The "$C_{6-10}$ aryl($C_{0-8}$ alkyl)aminocarbonyloxy group which may be substituted" means the unsubstituted $C_{6-10}$ aryl($C_{0-8}$ alkyl)aminocarbonyloxy group or the $C_{6-10}$ aryl($C_{0-8}$ alkyl)aminocarbonyloxy group in which at least one hydrogen atom on the nitrogen atom or the alkyl moiety is substituted by a certain substituent group. When two or more substituent groups are present, each substituent group may be the same or different from each other. Preferably, it is a $C_{6-10}$ aryl($C_{0-8}$ alkyl)aminocarbonyloxy group which may be substituted by certain 1 to 3 substituent group(s).

The "$C_{1-8}$ alkylsulfonyl($C_{0-8}$ alkyl)amino group" means a $C_{1-8}$ alkyl-$S(O)_2$—NH— group or a $C_{1-8}$ alkyl-$S(O)_2$—$N(C_{1-8}$ alkyl)- group, wherein the $C_{1-8}$ alkyl group is as defined above. Specific examples thereof include a methylsulfonylamino group, an ethylsulfonylamino group, and a methylsulfonyl(N-methyl)amino group.

The "$C_{2-8}$ alkenyloxy group" means a $C_{2-8}$ alkenyl-$O$— group, wherein the $C_{2-8}$ alkenyl is as defined above. Specific examples of $C_2$ alkenyloxy group include a vinyloxy group and an aryloxy group.

Preferred examples of the substance represented by the Formula (I) include a substance in which $A^1$ to $A^4$ and $A^6$ to $A^7$ are a carbon atom, $R^3$ is cyano, and $A^5$ is NH.

More preferred examples of the substance represented by the Formula (I) include a substance in which $A^1$ to $A^4$ and $A^6$ to $A^7$ are a carbon atom, $R^3$ is cyano, $A^5$ is NH, $R^8$ is a 4- to 10-membered heterocycloalkyl group or a 4- to 10-membered heterocycloalkyl group which may be substituted by a $C_{3-8}$ cycloalkyl group.

Specific examples of the preferred substance represented by the Formula (I) include 9-(4-isopropyl-piperazin-1-yl)-6,6-dimethyl-11-oxo-6,11-dihydro-5H-benzo[b]carbazole-3-carbonitrile;
6,6-dimethyl-8-(4-oxetan-3-yl-piperazin-1-yl)-11-oxo-9-prop-1-ynyl-6,11-dihydro-5H-benzo[b]carbazole-3-carbonitrile;
9-cyclopropylethynyl-6,6-dimethyl-8-(4-oxetan-3-yl-piperazin-1-yl)-11-oxo-6,11-dihydro-5H-benzo[b]carbazole-3-carbonitrile;
6,6-dimethyl-8-(4-oxetan-3-yl-piperidin-4-yl)-11-oxo-6,11-dihydro-5H-benzo[b]carbazole-3-carbonitrile;
9-bromo-6,6-dimethyl-8-(4-oxetan-3-yl-piperazin-1-yl)-11-oxo-6,11-dihydro-5H-benzo[b]carbazole-3-carbonitrile;
9-bromo-8-(4-cyclopropyl-piperazin-1-yl)-6,6-dimethyl-11-oxo-6,11-dihydro-5H-benzo[b]carbazole-3-carbonitrile;
9-chloro-6,6-dimethyl-8-(4-morpholin-4-yl-piperidin-1-yl)-11-oxo-6,11-dihydro-5H-benzo[b]carbazole-3-carbonitrile;
8-(4-cyclobutyl-piperazin-1-yl)-6,6-dimethyl-11-oxo-9-prop-1-ynyl-6,11-dihydro-5H-benzo[b]carbazole-3-carbonitrile;
6,6,9-trimethyl-8-(4-morpholin-4-yl-piperidin-1-yl)-11-oxo-6,11-dihydro-5H-benzo[b]carbazole-3-carbonitrile;
9-ethyl-6,6-dimethyl-8-(4-oxetan-3-yl-piperazin-1-yl)-11-oxo-6,11-dihydro-5H-benzo[b]carbazole-3-carbonitrile;
9-ethyl-6,6-dimethyl-8-(4-morpholin-4-yl-piperidin-1-yl)-11-oxo-6,11-dihydro-5H-benzo[b]carbazole-3-carbonitrile;
9-ethynyl-6,6-dimethyl-8-(4-oxetan-3-yl-piperazin-1-yl)-11-oxo-6,11-dihydro-5H-benzo[b]carbazole-3-carbonitrile;
8-(4-cyclobutyl-piperazin-1-yl)-9-ethyl-6,6-dimethyl-11-oxo-6,11-dihydro-5H-benzo[b]carbazole-3-carbonitrile;
9-ethynyl-6,6-dimethyl-11-oxo-8-(4-pyrrolidin-1-yl-piperidin-1-yl)-6,11-dihydro-5H-benzo[b]carbazole-3-carbonitrile;
6,6-dimethyl-11-oxo-8-(4-pyrrolidin-1-yl-piperidin-1-yl)-6,11-dihydro-5H-benzo[b]carbazole-3-carbonitrile;
8-(4-cyclobutyl-piperazin-1-yl)-9-ethynyl-6,6-dimethyl-11-oxo-6,11-dihydro-5H-benzo[b]carbazole-3-carbonitrile;
8-(4-cyclo butyl-piperazin-1-yl)-6,6-dimethyl-11-oxo-9-propyl-6,11-dihydro-5H-benzo[b]carbazole-3-carbonitrile;
8-(1-isopropyl-piperidin-4-yl)-6,6-dimethyl-11-oxo-6,11-dihydro-5H-benzo[b]carbazole-3-carbonitrile;
8-(4-isopropyl-piperazin-1-yl)-6,6-dimethyl-11-oxo-6,11-dihydro-5H-benzo[b]carbazole-3-carbonitrile;
8-(4-cyclobutyl-piperazin-1-yl)-9-cyclopropyl-6,6-dimethyl-11-oxo-6,11-dihydro-5H-benzo[b]carbazole-3-carbonitrile;
8-(2-tert-butylamino-ethoxy)-6,6-dimethyl-11-oxo-6,11-dihydro-5H-benzo[b]carbazole-3-carbonitrile;
9-ethynyl-8-(4-methanesulfonyl-piperazin-1-yl)-6,6-dimethyl-11-oxo-6,11-dihydro-5H-benzo[b]carbazole-3-carbonitrile;
9-bromo-8-(4-cyclobutyl-piperazin-1-yl)-6,6-dimethyl-11-oxo-6,11-dihydro-5H-benzo[b]carbazole-3-carbonitrile;
6,6-dimethyl-8-(4-oxetan-3-yl-piperazin-1-yl)-11-oxo-9-propyl-6,11-dihydro-5H-benzo[b]carbazole-3-carbonitrile; and
9-ethynyl-6,6-dimethyl-8-morpholin-4-yl-11-oxo-6,11-dihydro-5H-benzo[b]carbazole-3-carbonitrile.

Specific examples of the more preferred substance represented by the Formula (I) include (i) 6,6-dimethyl-8-(1-oxetan-3-yl-piperidin-4-yl)-11-oxo-6,11-dihydro-5H-benzo[b]carbazole-3-carbonitrile, (ii) 8-(4-cyclobutyl-piperazin-1-yl)-9-cyclopropyl-6,6-dimethyl-11-oxo-6,11-dihydro-5H-benzo[b]carbazole-3-carbonitrile, (iii) 8-(4-cyclobutyl-piperazin-1-yl)-9-ethyl-6,6-dimethyl-11-oxo-6,11-dihydro-5H-benzo[b]carbazole-3-carbonitrile, or (iv) 9-ethyl-6,6-dimethyl-8-(4-morpholin-4-yl-piperidin-1-yl)-11-oxo-6,11-dihydro-5H-benzo[b]carbazole-3-carbonitrile or the salts thereof.

(Method for Production of the Substances Used in the Present Invention)

Representative Production Method

The substances represented by the Formula (I) of the present invention can be produced by the method described below, for example. However, method of producing the compounds used in the present invention is not limited thereto. Further, depending on necessity, order of the reaction step such as introduction of a substituent group, etc. can be changed. Although the compounds used in the present invention are novel compounds which have not been described in literatures, the compounds can be produced according to a chemical method that is well known in the art. Still further, as for the reacting compounds that are used for the production, commercially available ones can be used or they can be produced according to a method that is generally known in the art depending on necessity.

In the following reaction schemes showing the reaction step, $A^1$ to $A^{10}$ and $R^1$ to $R^{10}$ are as defined in the Formula (I). $PR^1$ to $PR^{10}$ are the same as $R^1$ to $R^{10}$ that are defined in the Formula (I) or represent a group which can be converted to $R^1$ to $R^{10}$ according to modification or deprotection of a functional group.

Other abbreviated symbols described in the following reaction schemes have the general meanings that can be understood by a skilled person in the art.

Production Method I

This is one of the methods for producing the skeletons of the Formula (I) in which $A^5$ is N and $R^5$ is H.

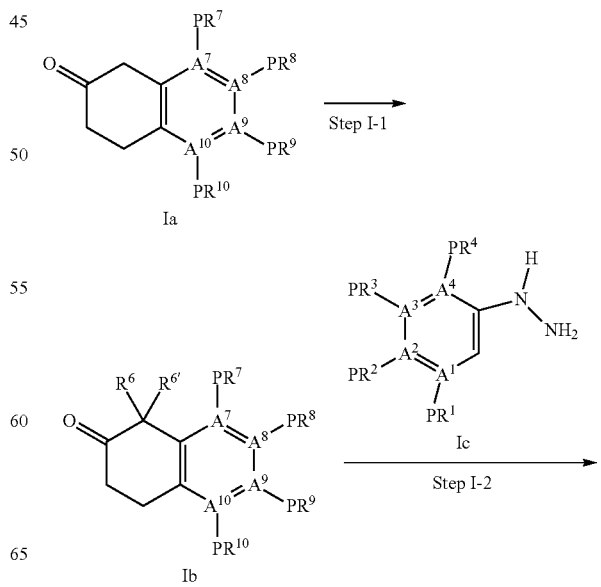

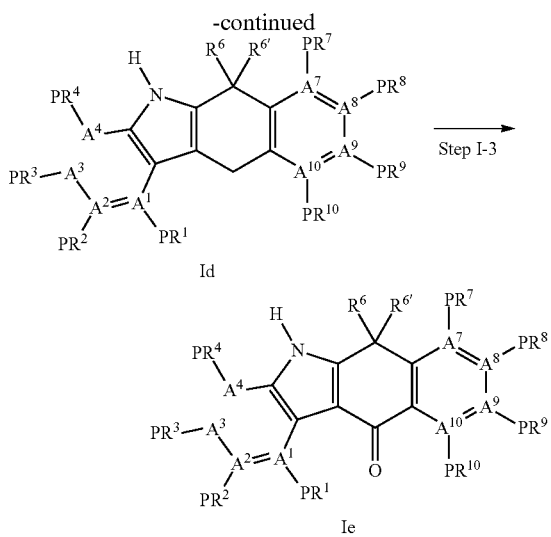

(The symbols that are included in the formula have the meanings as defined above. P represents a protecting group, and for the production methods described below, when a defined group is subjected to undesirable chemical modification under a condition for implementing the method, desired compound can be produced by using means such as protection and deprotection of a functional group, etc. using a suitable protecting group).

Step I-1

It is an alkylation step of a cyclic ketone derivative Ia. The step can be carried out by reacting cyclic ketone derivative Ia with an alkylating agent corresponding to $R^6$ and $R^{6'}$ in the presence of a base. For example, it can be carried out in view of the method described in Journal of the American Chemical Society, 115(23), 10628-36; 1993 and Organic Letters, 9(24), 5027-5029; 2007, etc. The reaction is carried out in a solvent under the condition of a reaction temperature of −20° C. to boiling point of the solvent, in the presence or the absence of a catalyst. When $R^6$ and $R^{6'}$ are atomic groups other than a hydrogen atom, the reaction order can be optionally selected, and separation and purification can be carried out at each step or the reaction can be carried out continuously.

As for the alkylating agent, examples thereof include an alkyl halide such as MeI, ethyl iodide, 2-iodopropane, 1,4-dibromobutane, 1,1'-oxybis(2-bromoethane) and the like, dimethyl sulfate, and sulfonic acid ester such as dimethyl sulfuric acid methylmethane sulfonate, methyl tosylate and methyltrifluoromethane sulfonate. Preferably, it is an alkyl halide such as MeI and the like. As for the catalyst, examples thereof include a phase transfer catalyst such as tetrabutylammonium chloride and tetrabutylammonium hydrogen sulfate. Preferably, it is tetrabutylammonium hydrogen sulfate. As for the base, examples thereof include an inorganic base such as sodium hydroxide, potassium hydroxide, sodium carbonate, potassium carbonate, cesium carbonate, sodium hydride, potassium hydride, calcium hydride and the like or an organic base such as t-BuOK, t-BuONa, pyridine, TEA (trifluoroacetic acid), DIPEA (N,N-diisopropylethylamine), LDA (lithium diisopropylamide), LiHMDS (lithium hexamethyl disilazide) and n-BuLi. Preferably, it is potassium hydroxide, potassium t-butoxy, or sodium t-butoxy. As for the solvent, examples thereof include toluene, xylene, n-hexane, cyclohexane, DMF (N,N-dimethyl formamide), DMA (N,N-dimethyl acetamide), EtOAc, DMSO (dimethyl sulfoxide), dichloromethane, carbon tetrachloride, THF (tetrahydrofuran), dioxane, acetonitrile, water, methanol, ethanol and a mixture thereof. Preferably, it is a mixture solvent of water-THF or THF.

Step I-2

It is the synthesis of carbazole skeleton Id according to Fischer method. This step is generally carried out by using cyclic ketone Ib in the presence of hydrazine compound Ic and an acid in a solvent or by using an acid as a solvent under the condition of a reaction temperature of 0° C. to boiling point of the solvent, and also can be carried out in view of the method described in Journal of Heterocyclic Chemistry, 28(2), 321-3; 1991 and Bioorganic & Medicinal Chemistry Letters (2008), 18(24), 6479-6481. Further, when the reaction proceeds slowly, a zinc chloride catalyst and the like can be also used in view of the reaction condition disclosed in Organic Letters (2006), 8(3), 367-370. The reaction includes a step of producing phenyl hydrazone and a step of sigmatropic rearrangement. Separation and purification can be carried out at each step or the reaction can be carried out continuously. Further, according to the structure of aryl hydrazine, which is a reacting material of this reaction step, mixture of a position isomer can be obtained as a reaction product. Such position isomer can be separated from each other or used as a mixture for the next reaction step.

As for the acid used for the reaction, examples thereof include formic acid, acetic acid, methane sulfonic acid, p-toluene sulfonic acid, benzene sulfonic acid, TFA, hydrochloric acid, sulfuric acid and pyridinium p-toluene sulfonate. Preferably, it is acetic acid, sulfuric acid, or TFA. As for the solvent, examples thereof include toluene, xylene, NMP (N-methylpyrrolidone), DMF, DMA, DMSO, sulfolane, dioxane, DME (dimethoxyethane), TFE (trifluoroethanol), diethylene glycol, triethylene glycol and a mixture thereof.

Step I-3

It is a step of oxidation at benzyl at 11-position of carbazole skeleton Id. This step is carried out by applying an oxidizing agent to a substrate in a solvent in the presence or absence of a catalyst under the condition of a reaction temperature of −20° C. to boiling point of the solvent. As for the reaction condition, the method described in Journal of Medicinal Chemistry, 51(13), 3814-3824; 2008, etc. can be considered.

As for the oxidizing agent and the catalyst used for the reaction, DDQ, peracid such as, mCPBA and the like, cerium ammonium nitrate (IV) (CAN), permanganate such as potassium permanganate, barium permanganate and the like, sodium chlorite, hydrogen peroxide, or N-hydroxyphthalimide and the like can be used alone or in a combination thereof. Preferably, it is DDQ (2,3-dichloro-5,6-dicyano-p-benzoquinone) or N-hydroxyphthalimide. As for the solvent used for the reaction, examples thereof include water, t-butanol, acetonitrile, THF, dichloromethane, ethyl acetate and a mixture thereof. Preferably, it is THF.

According to the present invention, examples of the salts of the compounds that are represented by the Formula (I) include hydrochloric acid salt, hydrobromic acid salt, hydriodic acid salt, phosphoric acid salt, phosphonic acid salt, sulfuric acid salt, sulfonic acid salt such as methane sulfonic acid salt, p-toluene sulfonic acid salt and the like, carboxylic acid salt such as acetic acid salt, citric acid salt, malic acid salt, tartaric acid salt, succinic acid salt, salicylic acid salt and the like, or alkali metal salt such as sodium salt, potassium salt and the like; alkaline earth metal salt such as magnesium salt, calcium salt and the like; ammonium salt such as ammonium salt, alkyl ammonium salt, dialkyl ammonium salt, trialkyl ammonium salt, and tetraalkyl ammonium salt. Preferred examples thereof include hydrochloride salt and methane sulfonate salt. More preferred examples thereof include hydrochloride salt.

These salts are produced by bringing the compounds described above in contact with an acid or a base which can be used for the production of a pharmaceutical product.

According to the present invention, the compounds that are represented by the Formula (I) or salts thereof can be an anhydride or a solvate such as a hydrate and the like. Herein, the term "solvate" indicates a phenomenon by which solute molecules or ions contained in a solution strongly attract neighboring solvent molecules to form a huge group of molecules. When the solvent is water, it is called "hydrate." The solvate can be any one of a hydrate and a non-hydrate. For the non-hydrate, alcohol (for example, methanol, ethanol, n-propanol), dimethylformamide and the like can be used.

The compounds of the present invention and salts thereof may be present in several tautomer forms, for example, enol and imine form, keto and enamine form, and a mixture thereof. In a solution, a tautomer is present as a mixture of tautomeric set. In case of solid form, one type of tautomer is generally present in dominant ratio. In this regard, even if only one type of tautomer is described, the present invention includes all types of tautomer of the compounds of the present invention.

The present invention includes all types of stereoisomer of the compounds represented by the Formula (I) (for example, enantiomer, diastereomer (including cis and trans geometric isomer)), racemate of the isomer and a mixture thereof. For example, the compounds having the Formula (I) of the present invention may have one or more asymmetric center, and the present invention includes a racemic mixture, a diastereomer mixture and enantiomer of such compound.

When the compounds of the present invention are obtained in free form, the compounds can be converted into a salt, a hydrate or solvate thereof which can be formed from the compounds according to a method generally known in the art.

Further, when the compounds of the present invention are obtained in the form of a salt, hydrate or solvate of the compounds, the compounds can be converted to free form according to a method generally known in the art.

Further, the substances used in the present invention can be administered in the form of prodrug of the compounds having the Formula (I). Herein, the term "prodrug" indicates the derivatives of the compounds having the Formula (I) that can be converted to the compounds having the Formula (I) or pharmaceutically acceptable salts thereof after administration by enzymatic or non-enzymatic degradation under a physiological condition. The prodrug can be in an inactive form when it is administered to a patient. However, in living organisms, it converts to the compounds having the Formula (I) and present therein in the active form.

For example, the prodrug converts into a desired drug form at specific pH or by an enzymatic action. Typical prodrug is a compound having a hydrolyzable ester residue which produces a free acid in living organisms. Examples of such hydrolyzable ester residue include a residue having a carboxyl moiety of which free hydrogen (for example, a free hydrogen in a carboxyl group when Y in the Formula has a carboxyl group) is substituted by a $C_{1-4}$ alkyl group, a $C_{2-7}$ alkanoyloxymethyl group, a 1-(alkanoyloxy)ethyl group having 4 to 9 carbon atoms, a 1-methyl-1-(alkanoyloxy)-ethyl group having 5 to 10 carbon atoms, an alkoxycarbonyloxymethyl group having 3 to 6 carbon atoms, a 1-(alkoxycarbonyloxy)ethyl group having 4 to 7 carbon atoms a 1-methyl-1-(alkoxycarbonyloxy)ethyl group having 5 to 8 carbon atoms, an N-(alkoxycarbonyl)aminomethyl having 3 to 9 carbon atoms, a 1-(N-(alkoxycarbonyl)amino)ethyl group having 4 to 10 carbon atoms, a 3-phthalidyl group, a 4-crotonolactonyl group, a γ-butyrolacton-4-yl group, a di-N,N—$(C_{1-2})$alkylamino$(C_{2-3})$alkyl group (for example, N,N-dimethylaminoethyl group), a carbamoyl$(C_{1-2})$alkyl group, a N,N-di$(C_{1-2})$alkylcarbamoyl-$(C_{1-2})$alkyl group, a piperidino$(C_{2-3})$alkyl group, a pyrrolidino$(C_{2-3})$alkyl group, or a morpholino$(C_{2-3})$alkyl group, but not limited thereto.

The formulation of the present invention is produced according to a method well known in the art by using additives such as a filler, a lubricating agent, a coating agent, a binding agent, a disintegrating agent, a stabilizing agent, a flavoring agent, or a diluent.

Examples of the filler include starch such as corn starch, potato starch, wheat starch, rice starch, partially pregelatinized starch, pregelatinized starch, and porous starch; sugars or sugar alcohols such as lactose hydrate, fructose, glucose, mannitol, and sorbitol; and anhydrous dibasic calcium phosphate, microcrystalline cellulose, precipitated calcium carbonate, and calcium silicate. Preferred examples of the filler include starch such as starch, potato starch, and corn starch, lactose hydrate, microcrystalline cellulose, and anhydrous dibasic calcium phosphate.

For the formulation of the present invention, lactose hydrate and microcrystalline cellulose are preferably used as a filler. Herein, the used amount of lactose hydrate is preferably 5 to 60 parts by weight, and more preferably 10 to 50 parts by weight with respect to 100 parts by weight of the formulation. Further, the used amount of microcrystalline cellulose is preferably 5 to 60 parts by weight, and more preferably 10 to 50 parts by weight with respect to 100 parts by weight of the formulation.

Examples of the disintegrating agent include the compounds mentioned above as a filler above, and chemically modified starch and celluloses such as Crosscarmellose sodium, sodium starch glycolate, and crosslinked polyvinyl pyrrolidone. Specific examples of disintegrating agent include sodium starch glycolate, carboxymethyl cellulose, calcium carboxymethyl cellulose, sodium carboxymethyl starch, Crosscarmellose sodium, crospovidone, low-substituted hydroxypropyl cellulose, and hydroxypropyl starch. The used amount of the disintegrating agent is preferably 0.5 to 25 parts by weight, and more preferably 1 to 15 parts by weight with respect to 100 parts by weight of the formulation.

Examples of the binding agent include polyvinyl pyrrolidone, Macrogol, and the compounds mentioned above as a filler above. Specific examples of binding agent include hydroxypropyl cellulose, hydroxypropylmethyl cellulose, methyl cellulose, povidone (polyvinyl pyrrolidone), and gum Arabic powder. The used amount of the binding agent is preferably 0.1 to 50 parts by weight, and more preferably 0.5 to 40 parts by weight with respect to 100 parts by weight of the formulation.

As for the lubricating agent, suitable examples thereof include magnesium stearate, calcium stearate, talc, sucrose fatty acid ester, and sodium stearyl fumarate.

As for the surfactant or an emulsifying agent, examples thereof include polysorbate 80, polyoxyl 40 stearate and lauromacrogol.

As for the coloring agent, any of those allowed to be used in a pharmaceutical can be used. Examples thereof include a dye used for food such as Food Yellow No. 5 (Sunset yellow, US Food Yellow No. 6), Food Red No. 2, and Food Blue No, 2, Food Lake dye, and iron trioxide.

As a stabilizing agent, examples thereof include paraoxy benzoic acid esters such as methyl paraben, propyl paraben and the like; alcohols such as chlorobutanol, benzyl alcohol, phenylethyl alcohol and the like; benzalkonium chloride; phenols such as phenol, cresol and the like; thimerosal; dehydroacetic acid; and sorbic acid.

As a flavoring agent, examples thereof include a sweetener, an acid tasting agent, a flavor and the like that are commonly used in the art.

With respect to the fluidizing agent, it is used for the purpose of improving the fluidity of mixed powder or granules, and representative examples include talc, light anhydrous silicic acid, i.e., silicon dioxide, and hydrated silicon dioxide. Herein, the light anhydrous silicic acid is only required to contain hydrated silicon dioxide ($SiO_2.nH2O$) (n represents an integer) as a main ingredient, and specific examples thereof include SYLYSIA 320 (trade name, manufactured by FUJI SILYSIA CHEMICAL LTD.), and AEROSIL 200 (trade name, manufactured by Nippon Aerosil Co., Ltd.).

Suitable examples of the preservatives include paraoxy benzoic acid esters, chlorobutanol, benzyl alcohol, phenethyl alcohol, dehydroacetic acid, and sorbic acid.

Suitable examples of the anti-oxidant include sulfite salt and ascorbic acid.

These additives may be used in combination of two or more types that are mixed at appropriate ratio.

Further, as a solvent to produce a liquid formulation, examples thereof include ethanol, phenol, chlorocresol, purified water and distilled water.

The solid formulation of the present invention can be produced by mixing the substance used for the present invention with a dissolution aid and a pharmaceutically acceptable carrier, and performing a production method generally carried out in the art. Preferably, it is produced according to the production method described below.

1) The substance used for the present invention is mixed with the ingredients such as additive, filler, disintegrating agent, and lubricating agent that are selected from the additive group A, and then filled in a capsule or subjected to compression molding to produce the solid formulation of the present invention.

2) The substance used for the present invention is mixed with the ingredients such as additive, filler, and binding agent that are selected from the additive group A, and then granulated while adding or spraying a solvent (for example, purified water, ethanol, or their mixture, and the like). To the granulate obtained, a suitable amount of a lubricating agent, and if necessary, a disintegrating agent, etc., are added and mixed, and then the mixture is filled in a capsule or subjected to compression molding to produce the solid formulation of the present invention.

3) The substance used for the present invention is mixed with the ingredients such as additive, and filler that are selected from the additive group A, and then granulated while adding or spraying a liquid that is obtained by dispersing or dissolving a binding agent, and if necessary, other additives to a solvent (for example, purified water, ethanol, or their mixture, and the like). To the granulate obtained, a suitable amount of a lubricating agent, and if necessary, a disintegrating agent, etc., are added and mixed, and then the mixture is filled in a capsule or subjected to compression molding to produce the solid formulation of the present invention.

It is also possible to obtain a sugar-coated pellet or a film-coated pellet using a more appropriate coating agent.

Examples of a base material for sugars include sugars or sugar alcohols such as white sugar and erythritol. In addition, one kind or a combination of two or more kinds that are selected from talc, precipitated calcium carbonate, gelatin, gum Arabic, pullulan, carnauba wax, and the like may be used.

As a coating agent, examples thereof include ethyl cellulose, hydroxypropyl cellulose, hydroxypropylmethyl cellulose, shellac, talc, carnauba wax and paraffin.

Examples of the base material for enteric film coating include cellulose polymers such as hydroxypropylmethyl cellulose phthalate, hydroxypropylmethyl cellulose acetate succinate, carboxymethylethyl cellulose, and cellulose acetate phthalate; acrylic polymers such as methacrylic acid copolymer L [Eudragit L (trade name), Evonik Degussa Co., Ltd.], methacrylic acid copolymer LD [Eudragit L-30 D55 (trade name), Evonik Degussa Co., Ltd.], methacrylic acid copolymer S [Eudragit S (trade name), and Evonik Degussa Co., Ltd.]; and natural products such as shellac.

Examples of the base material for extended-release film coating include cellulose polymers such as ethyl cellulose; acrylate polymers such as amino alkylmethacrylate copolymer RS [Eudragit RS (trade name), Evonik Degussa Co., Ltd.], ethylacrylate methyl methacrylate copolymer suspension [Eudragit NE (trade name), Evonik Degussa Co., Ltd.]; and cellulose acetate.

The base material for coating may be used in combination of two or more types that are mixed at appropriate ratio.

If necessary, a water soluble substance and a plasticizer, etc. may be added to the coating agent for controlling dissolution rate. Examples of the water soluble substance include at least one selected from water soluble polymers such as hydroxypropylmethyl cellulose, sugar alcohols such as mannitol, sugars such as white sugar and anhydrous maltose, and surfactants such as sucrose fatty acid ester, polyoxyethylene polyoxypropylene glycol, polysorbate, and sodium lauryl sulfate. Examples of the plasticizer that can be used include acetylated monoglyceride, trimethyl citrate, triacetin, dibutyl sebacate, dimethyl sebacate, medium chain fatty acid triglyceride, acetyltriethyl citrate, tributyl citrate, acetyltributyl citrate, dibutyl adipate, oleic acid, and oleanolic acid.

Further, as a method for coating a tablet with a coating layer, a method commonly used in the field can be used and the examples thereof include pan coating, fluid coating, tumbling coating, and fluid tumbling coating. Further, the coating liquid used for such method is obtained by mixing the base material for coating as described above with the talc and solvent (preferably, ethanol or a mixture of ethanol and water). Further, the concentration of solid matters in the coating liquid is within the range of 5 to 15% by mass with respect to the total mass of the coating liquid.

The method comprises a step of administering a pharmaceutically effective amount of a pharmaceutical composition containing the substance used in the disclosed present invention to a subject who is in need of treatment or in the state of having a disorder or a symptom.

The substance used in the present invention has an excellent ALK inhibitory activity and has excellent stability in a body and excellent solubility in water, and therefore, it is useful as a prophylactic or therapeutic agent (in particular, a therapeutic agent) for a proliferative disorder. The compounds of the present invention or their pharmaceutically acceptable salts are useful as a prophylactic or therapeutic agent (in particular, a therapeutic agent) for disorders including leukemia (acute myelogenous leukemia, chronic myelogenous leukemia, acute lymphatic leukemia, and chronic lymphatic leukemia, etc.), malignant lymphoma (Hodgkin's lymphoma and Non-Hodgkin's lymphoma, etc.), and various cancers such as brain tumor, neuroblastoma, neuroglioma, thyroid cancer, myelodysplastic syndrome, head and neck cancer, esophageal cancer, stomach cancer, colon cancer, colorectal cancer, breast cancer, ovarian cancer, lung cancer, pancreas cancer, liver cancer, gallbladder cancer, skin cancer, malignant myeloma, kidney cancer, renal pelvis-ureter cancer, urinary bladder cancer, ovarian cancer, uterine cancer, testicular cancer, and prostate cancer. Further, the compounds of the present invention are useful as a prophylactic or therapeutic agent (in particular, a therapeutic agent) for infiltration and metastasis of solid tumors. Further, the substance used in the present invention is effective as a prophylactic or therapeutic agent for other disorders related to ALK, for example, depression and cognitive function disorder.

When the pharmaceutical composition of the present invention is used as an ALK inhibitor, or a prophylactic or therapeutic agent for a proliferative disorder, or depression and cognitive function disorder, the administration method includes oral, rectal, parenteral (intravenous, intramuscular, and subcutaneous), intracisternal, intravaginal, intraperitoneal, intravesical, topical (drops, powder, ointment, gel or cream) administration and inhalation (buccal or nasal spray), etc. Examples of the administration form include a tablet, a capsule, granules, powder, a pill, an aqueous or non-aqueous oral solution and suspension, and a non-oral solution that is filled in a container appropriate for small divided dose. Further, the formulation form can be adapted to various administration methods including a regimen for release control such as subcutaneous implant, etc.

Preferably, it is an oral administration of a tablet, capsule, granule powder, pill, or the like.

The formulation of the present invention is produced according to a method well known in the art by using additives such as a filler, a lubricating agent (i.e. coating agent), a binding agent, a disintegrating agent a stabilizing agent, a flavoring agent, a diluent and the like.

When the pharmaceutical composition of the present invention is used as an ALK inhibitor, or a prophylactic or therapeutic agent for a proliferative disorder, or depression and cognitive function disorder, the used amount of the compounds of the present invention or their pharmaceutically acceptable salts varies depending on the symptoms, age, body weight, relative health condition, presence of other medication, and administration method, etc.

When the pharmaceutical composition of the present invention is used as an ALK inhibitor, or a prophylactic or therapeutic agent for a proliferative disorder, or depression and cognitive function disorder, the used amount of the compounds of the present invention or their pharmaceutically acceptable salts or solvates thereof varies depending on the symptoms, age, body weight, relative health condition, presence of other medication, and administration method, etc. For a patient (i.e., warm blooded animal, in particular, human), the generally effective amount is, in terms of active ingredient (i.e., the compounds of the present invention that are represented by the Formula (I)), preferably 0.001 to 1000 mg per kg of body weight per day, and more preferably 0.01 to 300 mg per kg of body weight per day for an orally administrable formulation, for example. The daily dosage is preferably in the range of 1 to 800 mg for an adult patient with normal body weight. In case of a' parenteral formulation, it is preferably 0.001 to 1000 mg per kg of body weight per day, and more preferably 0.01 to 300 mg per kg of body weight per day. It is preferably administered once or in dose divided several times per day depending on the symptoms.

Further, the pharmaceutical composition of the present invention may be combined with other chemotherapeutic agents, hormonal therapeutic agents, immunotherapeutic agents, molecular targeting agents, or the like.

Examples of the "chemotherapeutic agents" include an alkylating agent, a platinum formulation, a metabolic antagonist, a topoisomerase inhibitor, an anticancer antibiotic substance, and an anticancer agent derived from plant, etc. Examples of the "alkylating agent" include nitrogen mustard, nitrogen mustard-N-oxide hydrochloride, chlorambucil, cyclophosphamide, ifosfamide, thiotepa, carboquone, improsulfan tosylate, busulfan, nimustin hydrochloride, mitobronitol, melphalan, dacarbazine, ranimustin, estramustin sodium phosphate, triethylene melamine, carmustin, lomustin, streptozocin, pipobroman, etoglucid, altretamin, ambamustin, dibrospidium hydrochloride, fotemustin, prednimustin, pumitepa, ribomustin, temozolomid, treosulfan, trophosphamide, zinostatin stimalamer, carboquone, adozelesin, cystemstin, and bizelecin. Examples of the "platinum formulation" include carboplatin, cisplatin, miboplatin, nedaplatin, and oxaliplatin. Examples of the "metabolic antagonist" include mercaptopurine, 6-mercaptopurine riboside, thioinosine, methotrexate, enocitabin, cytarabin, cytarabin ocfosfate, ancitabin hydrochloride, 5-FU based pharmaceuticals (for example, fluorouracil, tegafur, UFT, doxifluridin, carmofur, galocitabin, and emitefur, etc.), aminopterin, calcium leucovorin, tabloid, butocin, calcium folinate, calcium levofolinate, cladribin, emitefur, fludarabin, gemcitabin, hydrocycarbamide, pentostatin, piritrexim, idoxuridin, mitoguazon, tiazofurin, and ambamustin. Topoisomerase I inhibitor (for example, irinotecan and topotecan, etc.), topoisomerase II inhibitor (for example, sobuzoxan, etc.). Examples of the "anticancer antiobiotic material" include anthracycline-based anticancer agent (doxorubicin hydrochloride, daunorubicin hydrochloride, acrarubicin hydrochloride, pirarubicin hydrochloride, and epirubicin hydrochloride, etc.), actinomycin D, actinomycin C, mitomycin C, chromomycin A3, bleomycin hydrochloride, bleomycin sulfate, peplomycin sulfate, neocarzinostatin, mitramycin, sarcomycin, carzinophyllin, mitotam, zorubicin hydrochloride, mitoxantrone hydrochloride, and idarubicin hydrochloride, etc. Examples of the "anticancer agent derived from a plant" include vincalkaloid anticancer agent (vinblatin sulfate, vincristin sulfate, and vindecin sulfate), taxan anticancer agent (paclitaxel and docetaxel, etc), etoposide, etoposide phosphate, teniposide, and vinorelbin.

Examples of the "hormonal therapeutic agents" include adrenocortical hormone-based pharmaceuticals (for example, dexamethasone, prednisolone, betamethasone, and triamcinolone, et Of these, prednisolone is preferable.

Examples of the "immunotherapeutic agents (BRIM)" include picibanil, krestin, sizofuran, lentinan, ubenmex, interferon, interleukin, macrophage colony stimulating factor, granulocyte colony stimulating factor, lymphotoxin, BCG vaccine, *Corynebacterium parvum*, levamisole, polysaccharide K, and procodazole.

The "molecular targeting agents" include a "pharmaceutical which inhibits the function of a cell proliferation factor and its receptor," or the like. Examples of the "cell proliferation factor" can be any substance if only it can promote proliferation of a cell, and the included are a peptide having molecular weight of 20,000 or less which exhibits its activity at low concentration via binding to a receptor. Specific examples thereof include (1) EGF (epidermal growth factor) or a substance which has substantially the same activity [e.g., EGF, heregulin (HER2 ligand) etc.], (2) insulin or a substance which has substantially the same activity [e.g., insulin, IGF (insulin-like growth factor)-1, IGF-2, etc.], (3) FGF (fibroblast growth factor) or a substance which has substantially the same activity [e.g., acidic FGF, basic FGF, KGF (keratinocyte growth factor), FGF-10 etc.], (4) VEGF (vascular endothelial growth factor), (5) other cell proliferation factors [e.g., CSF (colony stimulating factor), EPO (erythropoietin), IL-2 (interleukin-2), NGF (nerve growth factor), PDGF (platelet-derived growth factor), TGFβ (transforming growth factor (3), HGF (hepatocyte growth factor), etc.], etc.

The "receptor for cell proliferation factor" can be any receptor if only it has an ability of binding to the cell proliferation factor described above. Specific examples thereof include EGF receptor, heregulin receptor (HER2), insulin receptor, IGF receptor, FGF receptor-1 or FGF receptor-2, HGF receptor (c-met), VEGF receptor, and SCF receptor (c-kit). Examples of the "pharmaceuticals which inhibit the activity of cell proliferation factor" include herceptin (HER2 antibody), GLEEVEC (c-kit, abl inhibitor), and Iressa (EGF receptor inhibitor).

Further, a pharmaceutical which inhibits the activity of a plurality of cell proliferation factors even as a single formulation, or a pharmaceutical which blocks cellular signal produced by cell proliferation factor are also included.

In addition to the pharmaceuticals described above, L-asparaginase, aceglaon, procarbazine hydrochloride, protoporphyrin.cobalt complex, mercury hematoporphyrin.sodium, differentiation-promoting agent (e.g., retinoid, vitamin D, etc.), angiogenesis inhibitor, and α-blocker (e.g., tamsulosin hydrochloride, etc.), etc. can be also used.

Among the above, preferred examples of a concomitant medicine include a platinum complex (e.g., carboplatin, cisplatin, and oxaliplatin, etc.), taxan-based pharmaceuticals (e.g., paclitaxel and docetaxel), topoisomerase I inhibitor (e.g., irinotecan and topotecan, etc.), vinorelbin, gemcitabin, an anticancer antibiotic material (e.g., mitomycin C), and a molecular targeting agent (e.g., VEGF inhibitor), etc. Further, they can be used in combination of the combination therapy for said pharmaceuticals. For examples, coadministration with combination therapy such as cisplatin and vinblastin and mitonycin C, cisplatin and vinorelbin, cisplatin and paclitaxel, cisplatin and gemcitabin, and carboplatin and paclitaxel, etc. can be mentioned.

The time in which the solid formulation of the present invention and a pharmaceutical for coadministration is not limited. They can be administered to a subject either simultaneously or with time interval. Further, the solid formulation of the present invention and a pharmaceutical for coadministration can be administered to a subject in the form of single formulation comprising both of them. For example, there is multi-drug combination therapy by which a plurality of pharmaceuticals are instilled over a period of 3 to 6 months, and a method of taking an oral formulation over two years approximately.

Further, in order to prevent recurrence caused by metastasis by inhibiting already-propagating cancer cells, or to limit an area for operation, a pre-operative adjuvant therapy such as "chemical therapy" may be carried out before performing operation.

Further, when topical treatment such as operation or radiation is not sufficient, in order to prevent recurrence caused by metastasis by inhibiting the growth of remaining cancer cells, a post-operative adjuvant therapy such as "chemical therapy" may be carried out.

Meanwhile, the anticancer agent used in combination also exhibits its activity on normal cells as well as cancer cells, therefore showing a side effect. Representative examples of the side effect include nausea, vomiting, lack of appetite, stomatitis, diarrhea or constipation, and dysgeusia due to mucosal disease in digestive organ, and reduction in leucocyte.erythrocyte.blood platelet, acomia and reduced immunity due to bone marrow disorder. Thus, a pharmaceutical for reducing a side effect like them can be also used in combination. Examples thereof include an antiemetic pharmaceutical agent which can effectively inhibit nausea (e.g., granisetron hydrochloride salt) or a pharmaceutical agent for promoting recovery from a bone marrow disorder (e.g., erythropoietin, G-CSF and GM-CSF).

Dosage of the pharmaceutical for coadministration can be appropriately selected with reference to the dosage that is clinically used. Further, the mixing ratio between the solid formulation of the present invention and the pharmaceutical for coadministration can be appropriately selected depending on the subject for administration, administration route, disease to be treated, symptoms, and combination, etc. When the subject for administration is a human, the pharmaceutical for coadministration can be used in an amount of 0.01 to 100 parts by weight with respect to 1 part by weight of the solid formulation.

EXAMPLE

Herein below, the present invention will be explained in greater detail in view of the following examples and test examples. However, the present invention is not limited by these.

NMR Analysis

NMR analysis was carried out by using JNM-EX270 (270 MHz, manufactured by JEOL), JNM-GSX400 (400 MHz, manufactured by JEOL), or 400 MR (400 MHz, manufactured by Varian). NMR data was expressed in ppm (parts per million; δ), while it was compared with the deuterium lock signal obtained from a sample solvent.

Mass Spectrometry

The measurement was carried out by using JMS-DX303 or JMS-SX/SX102A (both manufactured by JEOL).

Mass Spectrometry Data Equipped with High Performance Liquid Chromatography (LC-MS)

Measurement was carried out by using Micromass (ZMD, manufactured by Micromass) equipped with 996-600E gradient high performance liquid chromatography (manufactured by Waters) or Micromass (ZQ, manufactured by Micromass) equipped with Waters 2525 (manufactured by Waters) gradient high performance liquid chromatography.

One of the following conditions that are described in the Table 1 below was taken as a condition for high performance liquid chromatography.

TABLE 1

| Analysis condition | Apparatus | Column used | Column temperature | Mobile phase, gradient | Rate (mL/min) | Detection wavelength |
| --- | --- | --- | --- | --- | --- | --- |
| S | ZQ | Sunfire C18 (Waters) 4.5 mml. D. × 50 mm, 5 um | Room Temp. | TFA, MeCN (A/B): 90/10 ⇒ 5/95(3.1 min) ⇒ 90/10(1 min) ⇒ 90/10(0.5 min) A) 0.05% TFA, H2O B) 0.05% | 4.0 | 200-400 nm PDA total |

TABLE 1-continued

| Analysis condition | Apparatus | Column used | Column temperature | Mobile phase, gradient | Rate (mL/min) | Detection wavelength |
|---|---|---|---|---|---|---|
| U | ZQ | WAKOsil 3C18 AR, (WAKO) 4.6 mml. D. × 30 mm | Room Temp. | TFA, MeCN (A/B): 90/10 ⇒ 90/10(0.2 min) ⇒ 5/95 (3.1 min) ⇒ 5/95(1.4 min) A) 0.05% TFA, H2O B) 0.05% | 2.0 | 210-400 nm PDA total |
| W | ZMD | Sunfire C18 (Waters) 4.5 mml. D. × 50 mm, 5 um | Room Temp. | TFA, MeCN (A/B): 90/10 ⇒ 5/95(3.1 min) ⇒ 90/10(1 min) ⇒ 90/10(0.5 min) | 4.0 | 200-400 nm PDA total |

Commercially available reagents were used without any further purification. The room temperature indicates the temperature range of about 20 to 25° C. All the non-aqueous reaction was carried out in anhydrous solvent under nitrogen or argon atmosphere. For concentration under reduced pressure or removal of a solvent by distillation, a rotary evaporator was used.

Herein below, production examples for the substances that are used in the present invention as represented by the Formula (I) are given.

Reference Example 1

Compound J2

6-Methoxy-1,1-dimethyl-3,4-dihydro-1H-naphthalen-2-one

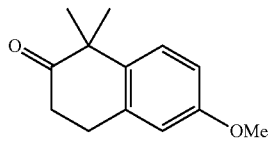

With the same condition as the method for synthesizing the Compound B1 (7-methoxy-3,4-dihydro-1H-naphthalen-2-one (Compound A1, 209 g, 1.18 mol), tetrabutylammonium hydrogen sulfate (40 g, 0.118 mol) and methyl iodide (162 g, 2.60 mol) were suspended in THF (500 ml) at room temperature. Under stirring, the mixture was added with 50% aqueous solution of potassium hydroxide (400 g) over 5 minutes. Reflux occurred as the inner temperature rapidly increases. Once the inner temperature stopped to increase, stirring was continued for 45 minutes. The reaction solution was diluted with distilled water (1 L) and extracted twice with CPME (1.5 L). The combined organic layer was washed (distilled water 1 L×3), dried over anhydrous sodium sulfate, and concentrated under reduced pressure. The resulting crude product was recrystallized with MeOH (1 L) and distilled water (500 ml) to obtain the Compound B1 (7-methoxy-1,1-dimethyl-3,4-dihydro-1H-naphthalen-2-one) as a colorless needle-like crystal (177 g, 73%)), and the title compound was synthesized from 6-methoxy-3,4-dihydro-1H-naphthalen-2-one and iodomethane.

LCMS: m/z 205 [M+H]+

HPLC retention time: 1.54 minutes (analysis condition S)

Reference Example 2

Compound J3-1

9-Methoxy-6,6-dimethyl-6,11-dihydro-5H-benzo[b]carbazole-3-carbonitrile

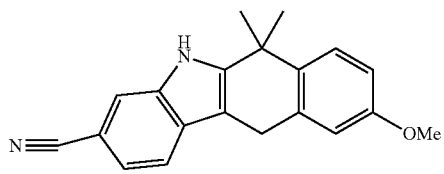 [SMILES: COc1ccc2c(c1)Cc1c([nH]c3cc(C#N)ccc13)C2(C)C]

With the same condition as the synthesis of the Compound E2-1 (6-bromo-7-methoxy-1,1-dimethyl-3,4-dihydro-1H-naphthalen-2-one (7.89 g, 27.85 mmol) and 3-hydrazino-benzonitrile (4.45 g, 1.2 eq.) were dissolved in TFA (250 mL) and stirred at 100° C. for 2 hours. TFA was removed by concentration under reduced pressure. After that, the residues were added with saturated aqueous solution of NaHCO3 (500 mL), and extracted with ethyl acetate. The organic layer was washed with saturated brine and dried over sodium sulfate. After filtering off the drying agent, the residues obtained after concentration under reduced pressure was added with ethyl acetate, stirred at room temperature, and the precipitated solid was filtered. By concentrating the filtrate under reduced pressure, the Compound E2-1 (9-bromo-8-methoxy-6,6-dimethyl-6,11-dihydro-5H-benzo[b]carbazole-3-carbonitrile) (yellowish white powder, 2.65 g) was obtained as a mixture with the Compound E2-2 (9-bromo-8-methoxy-6,6-dimethyl-6,11-dihydro-5H-benzo[b]carbazole-1-carbonitrile)), the title compound was synthesized from the Compound J2 and 3-hydrazino-benzonitrile.

LCMS: m/z 303 [M+H]+

HPLC retention time: 2.73 minutes (analysis condition S)

Reference Example 3

Compound J3-2

9-Methoxy-6,6-dimethyl-6,11-dihydro-5H-benzo[b]carbazole-1-carbonitrile

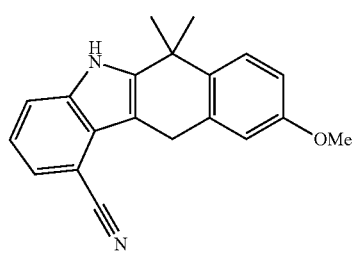 [SMILES: COc1ccc2c(c1)Cc1c([nH]c3cccc(C#N)c13)C2(C)C]

The Compound J3-2 was obtained as a byproduct of the Compound J3-1 synthesis.

LCMS: m/z 303 [M+H]+

HPLC retention time: 2.67 minutes (analysis condition S)

Production Example 1

Compound J4

9-Methoxy-6,6-dimethyl-11-oxo-6,11-dihydro-5H-benzo[b]carbazole-3-carbonitrile

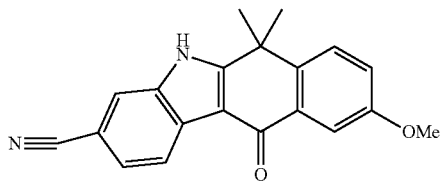 [SMILES: COc1ccc2c(c1)C(=O)c1c([nH]c3cc(C#N)ccc13)C2(C)C]

With the same condition as the method for synthesizing the Compound A4, the title compound was synthesized from the Compound J3-1 and the Compound J3-2 (mixture).

1H-NMR (DMSO-D6) δ: 12.79 (1H, s), 8.33 (1H, d, J=8.2 Hz), 8.02 (1H, s), 7.81 (1H, d, J=8.6 Hz), 7.69 (1H, d, J=3.0 Hz), 7.63 (1H, dd, J=8.3, 1.4 Hz), 7.28 (1H, dd, J=8.7, 3.0 Hz), 3.87 (3H, s), 1.74 (6H, s).

LCMS: m/z 317 [M+H]+

HPLC retention time: 2.25 minutes (analysis condition S)

Production Example 2

Compound J5

9-Hydroxy-6,6-dimethyl-11-oxo-6,11-dihydro-5H-benzo[b]carbazole-3-carbonitrile

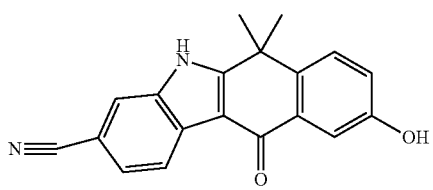 [SMILES: CC1(C)c2ccc(O)cc2C(=O)c2c1[nH]c1cc(C#N)ccc21]

With the same condition as the method for synthesizing the Compound A6, the title compound was synthesized from the Compound J4.

1H-NMR (DMSO-D6) δ: 12.75 (1H, s), 9.77 (1H, s), 8.32 (1H, dd, J=8.2, 0.7 Hz), 8.01 (1H, s), 7.68 (1H, d, 1=8.6 Hz), 7.62 (1H, dd, J=8.2, 1.4 Hz), 7.58 (1H, d, J=2.8 Hz), 7.10 (1H, dd, J=8.6, 2.8 Hz), 1.72 (6H, s).

LCMS: m/z 303 [M+H]+

HPLC retention time: 1.75 minutes (analysis condition S)

Production Example 3

Compound J6

Trifluoro-methane sulfonic acid 3-cyano-6,6-dimethyl-11-oxo-6,11-dihydro-5H-benzo[b]carbazol-9-yl ester

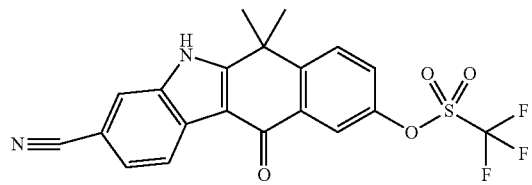 [SMILES: CC1(C)c2ccc(OS(=O)(=O)C(F)(F)F)cc2C(=O)c2c1[nH]c1cc(C#N)ccc21]

With the same condition as the method for synthesizing the Compound B1, the title compound was synthesized from the Compound J5.

1H-NMR (DMSO-D6) δ: 12.95 (1H, s), 8.31 (1H, d, J=8.2 Hz), 8.15 (2H, m), 8.05 (1H, s), 7.87 (1H, dd, J=9.0, 2.7 Hz), 7.65 (1H, d, J=8.2 Hz), 1.80 (6H, s).

LCMS: m/z 435 [M+H]+

HPLC retention time: 2.75 minutes (analysis condition S)

Production Example 4

Compound J7-4

9-(4-Isopropyl-piperazin-1-yl)-6,6-dimethyl-11-oxo-6,11-dihydro-5H-benzo[b]carbazole-3-carbonitrile

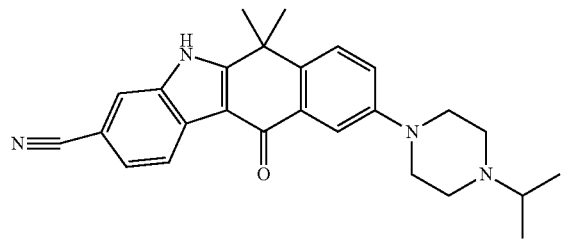 [SMILES: CC(C)N1CCN(c2ccc3c(c2)C(=O)c2c([nH]c4cc(C#N)ccc24)C3(C)C)CC1]

With the same condition as the method for synthesizing the Compound B2-10 (trifluoro-methane sulfonic acid 3-cyano-6,6-dimethyl-11-oxo-6,11-dihydro-5H-benzo[b]carbazol-8-yl ester (Compound B1, 30 mg, 0.069 mmol) was dissolved in 1,4-dioxane (1 mL), added with thiomorpholine 1,1-dioxide (19 mg, 2 eq.), Pd2dba3 (6.3 mg, 0.1 eq.), BINAP (8.6 mg, 0.2 eq.) and K3PO4 (29 mg, 2 eq.), and stirred at 100° C. all night and all day. The reaction solution was poured into water, and then extracted with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain the Compound B2-10 (8-(1,1-dioxothiomorpholino)-6,6-dimethyl-11-oxo-6,11-dihydro-5H-benzo[b]carbazole-3-carbonitrile) (white powder, 2.1 mg, 7%)), the title compound was synthesized from the Compound J6 and 1-isopropyl-piperazine.

1H-NMR (270 MHz, DMSO-d6) δ: 12.80 (1H, s), 8.33 (1H, d, J=7.6 Hz), 8.02 (1H, s), 7.66 (3H, m), 7.33 (1H, d, J=8.2 Hz), 3.21 (4H, br), 2.66 (5H, m), 1.72 (6H, s), 1.02 (6H, d, J=6.3 Hz).

LCMS: m/z 413 [M+H]+
HPLC retention time: 1.38 minutes (analysis condition S)

Reference Example 4

Compound A2

7-Methoxy-1,1-dimethyl-3,4-dihydro-1H-naphthalen-2-one

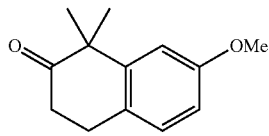

7-Methoxy-3,4-dihydro-1H-naphthalen-2-one (Compound A1, 209 g, 1.18 mol), tetrabutylammonium hydrogen sulfate (40 g, 0.118 mol) and methyl iodide (162 g, 2.60 mol) were suspended in THF (500 ml) at room temperature. Under stirring, the mixture was added with 50% aqueous solution of potassium hydroxide (400 g) over 5 minutes. Reflux occurred as the inner temperature rapidly increases. Once the inner temperature stopped to increase, stirring was continued for 45 minutes. The reaction solution was diluted with distilled water (1 L) and extracted twice with CPME (1.5 L). The combined organic layer was washed (distilled water 1 L×3), dried over anhydrous sodium sulfate, and concentrated under reduced pressure. The resulting crude product was recrystallized with MeOH (1 L) and distilled water (500 ml) to obtain the title compound as a colorless needle-like crystal (177 g, 73%).

$^1$H-NMR (400 MHz, CDCl$_3$) δ: 1.43 (6H, s), 2.65 (2H, t, 12 Hz), 3.02 (2H, t, 12 Hz), 3.79 (3H, s), 6.74 (1H, m), 6.87 (1H, m), 7.24 (1H, m).

LCMS: m/z 205 [M+H]+

Reference Example 5

Compound A3-1, Compound A3-2

3-Bromo-8-methoxy-6,6-dimethyl-6,11-dihydro-5H-benzo[b]carbazole 1-Bromo-8-methoxy-6,6-dimethyl-6,11-dihydro-5H-benzo[b]carbazole

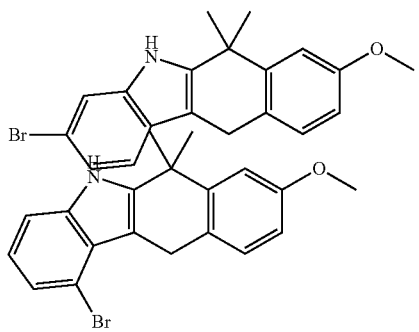

7-Methoxy-1,1-dimethyl-3,4-dihydro-1H-naphthalen-2-one (Compound A2, 66.2 g, 324 mmol) and 3-bromophenylhydrazine hydrochloric acid salt (71.0 g, 318 mmol) were dissolved in AcOH (350 ml) and refluxed under stirring for 6 hours. The reaction solvent was removed by distillation under reduced pressure to obtain the crude product as a mixture of the title compound A3-1 and A3-2.

Production Example 5

Compound A4

3-Bromo-8-methoxy-6,6-dimethyl-5,6-dihydrobenzo[b]carbazol-11-one

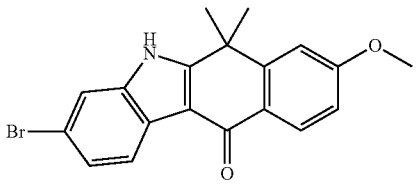 [SMILES: COc1ccc2c(c1)C(C)(C)c1[nH]c3cc(Br)ccc3c1C2=O]

The crude product obtained from the above (i.e., mixture of A3-1 and A3-2) was dissolved in a mixture solvent of THF (450 ml) and distilled water (50 ml), added once with DDQ (115 g, 509 mmol), and then stirred at room temperature for 1 hour. The reaction mixture was diluted with CPME (3 L), and the organic layer was washed three times with 0.5 N aqueous solution of sodium hydroxide (1 L) and twice with distilled water (1 L) in order and dried over anhydrous sodium sulfate. The organic layer was concentrated to 500 ml under reduced pressure. The precipitated product was collected by filtration and washed with a small amount of CPME to obtain the title compound as a yellow crystal (48 g, 40%).

$^1$H-NMR (400 MHz, DMSO-d$_6$) δ: 1.73 (6H, s), 3.90 (3H, s), 7.06-7.09 (1H, m), 7.32-7.38 (2H, m), 7.65-7,66 (1H, m), 8.09-8.17 (2H, m), 12.32 (1H, br. s).

LCMS: m/z 370, 372 [M+H]+

Production Example 6

Compound A5-2

8-Methoxy-6,6-dimethyl-11-oxo-6,11-dihydro-5H-benzo[b]carbazole-3-carbonitrile

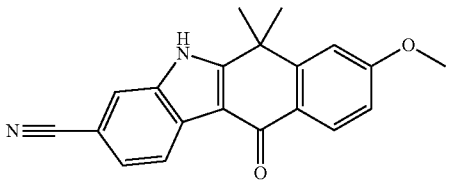 [SMILES: COc1ccc2c(c1)C(C)(C)c1[nH]c3cc(C#N)ccc3c1C2=O]

3-Bromo-8-methoxy-6,6-dimethyl-5,6-dihydrobenzo[b]carbazol-11-one (Compound A4, 10.45 g, 28.2 mmol) and copper cyanide (5.0 g, 50.2 mmol) were dissolved in NMP (100 ml) and stirred at 170° C. for 17 hours. The reaction mixture was suspended in ethyl acetate (500 ml) and distilled water (200 ml). The insoluble matters were filtered off using Celite, and washed with ethyl acetate (300 ml×2). The organic layer was washed once with aqueous solution of disodium EDTA (200 ml) and twice with saturated brine (200 ml) in order, and then dried over anhydrous sodium sulfate. The organic layer was concentrated under reduced pressure, and the resultant was suspended and washed with a small amount of CPME to give the title compound as a colorless crystal (6.58 g, 73%).

$^1$H-NMR (400 MHz, DMSO-d$_6$) δ: 1.71 (6H, s), 3.89 (3H, s), 7.07-7.09 (1H, m), 7.34 (1H, s), 7.58-7.60 (1H, m), 7.99 (1H, s), 8.14-8.16 (1H, m), 8.30-8.32 (1H, m), 12.32 (1H, br.s),

LCMS: m/z 317 [M+H]+
HPLC retention time: 2.56 minutes (analysis condition U)

Production Example 7

Compound A6

8-Hydroxy-6,6-dimethyl-11-oxo-6,11-dihydro-5H-benzo[b]carbazole-3-carbonitrile

8-Methoxy-6,6-dimethyl-11-oxo-6,11-dihydro-5H-benzo[b]carbazole-3-carbonitrile (Compound A5-2, 6.58 g, 20.8 mmol) was dissolved in pyridine hydrochloric acid salt (25.0 g), and stirred at 170° C. for 13 hours. The reaction mixture was partitioned in ethyl acetate (400 mL) and distilled water (400 mL), and the aqueous layer was extracted one more time with ethyl acetate (400 mL). The combined organic layer was washed twice with distilled water (100 mL) and once with saturated brine (100 mL) in order, and dried over anhydrous sodium sulfate. The organic layer was concentrated under reduced pressure to yield a product, which was suspended and washed with a small amount of CPME to obtain the title compound as a colorless crystal (5.91 g, 93%).

$^1$H-NMR (400 MHz, DMSO-d$_6$) δ: 1.73 (6H, s), 6.87-6.90 (1H, m), 7.11 (1H, s), 7.57-7.59 (1H, m), 7.97 (1H, s), 8.04-8.06 (1H), 8.29-8.31 (1H, s), 10.27 (1H, s), 12.66 (1H, br.s),
LCMS: m/z 303 [M+H]+

Production Example 8

Compound B1

Trifluoro-methane sulfonic acid 3-cyano-6,6-dimethyl-11-oxo-6,11-dihydro-5H-benzo[b]carbazol-8-yl ester 8-Hydroxy-6,6-dimethyl-11-oxo-6,11-dihydro-5H-benzo[b]carbazole-3-carbonitrile (Compound A6, 550 mg, 0.189 mmol) was dissolved in pyridine (18 mL), added with anhydrous trifluoromethane sulfonic acid (0.758 ml, 3 eq.), and stirred at room temperature for 30 minutes. The reaction solution was poured into water and then extracted with dichloromethane. The organic layer was dried over magnesium sulfate. The drying agent was removed by filtration and the residues obtained after concentration under reduced pressure were purified by silica gel column chromatography (ethyl acetate/hexane) to obtain the target compound (white powder, 641 mg, 81%).

$^1$H-NMR (400 MHz, DMSO-d$_6$) δ: 12.89 (1H, br. s), 8.36 (1H, d, J=8.8 Hz), 8.31 (1H, dd, J=8.1, 0.7 Hz), 8.11 (1H, d, J=2.3 Hz), 8.04 (1H, dd, J=1.5, 0.7 Hz), 7.65-7.60 (2H, m), 1.76 (6H, s)
LCMS: m/z 435 [M+H]+
HPLC retention time: 3, 10 minutes (analysis condition U)

Production Example 9

Compound B2-22-1

4-(3-Cyano-6,6-dimethyl-11-oxo-6,11-dihydro-5H-benzo[b]carbazol-8-yl)-3,6-dihydro-2H-pyridine-1-carboxylic acid tert-butyl ester To trifluoro-methane sulfonic acid 3-cyano-6,6-dimethyl-11-oxo-6,11-dihydro-5H-benzo[b]carbazol-8-yl ester (Compound B1, 7.80 g, 18.0 mmol), 4-(4,4,5,5-tetramethyl-[1,3,2]dioxaborolan-2-yl)-3,6-dihydro-2H-pyridine-1-carboxylic acid tert-butyl ester (6.11 g, 19.8 mmol, 1.1 eq.), Pd(PPh$_3$)$_2$Cl$_2$ (630 mg, 0.898 mmol, 0.05 eq.), and sodium carbonate (5.71 g, 53.9 mmol, 3.0 eq.), DME (125 ml) and water (25 ml) were added. The mixture was subjected to reduced pressure under ultrasonication treatment, followed by filling with nitrogen. This procedure was repeated five times to remove air. After further stirring at 80° C. for 2 hours under nitrogen atmosphere, the mixture was cooled to room temperature, added with water (250 ml), and further stirred for 30 minutes. The precipitates were filtered and washed with water (50 ml). They were further washed with CH$_3$CN (50 ml) to obtain the target compound as a crude product (gray powder, 7.54 g, 90%).

LCMS: m/z 468 [M+H]+
HPLC retention time: 2.90 minutes (analysis condition S)

Production Example 10

Compound B3-13-1

4-(3-Cyano-6,6-dimethyl-oxo-6,11-dihydro-5H-benzo[b]carbazol-8-yl)-piperidin-1-carboxylic acid tert-butyl ester 4-(3-Cyano-6,6-dimethyl-11-oxo-6,11-dihydro-5H-benzo[1)] carbazol-8-yl)-3,6-dihydro-2H-pyridine-1-carboxylic acid tert-butyl ester (Compound B2-22-1, 16.2 g, 34.6 mmol) was dissolved in THF (800 ml) and methanol (230 ml), added with 10 wt % Pd/C (3.2 g), and stirred under hydrogen atmosphere for 19 hours. The solid was filtered through Celite, eluted with a mixture solvent (400 ml; THF/methanol=4/1), and concentrated under reduced pressure. The residues were dissolved in ethyl acetate (400 ml), and then washed with 1% aqueous solution of N-acetylcysteine, saturated aqueous solution of NaHCO$_3$ and saturated brine. The organic layer was dried over sodium sulfate. The drying agent was removed by filtration and the residues were concentrated under reduced pressure to obtain the title compound as a crude product (white powder, 14.0 g, 86%).

LCMS: m/z 470 [M+H]$^+$

HPLC retention time: 2.88 minutes (analysis condition S)

Production Example 11

Compound B3-13-2

6,6-Dimethyl-11-oxo-8-piperidin-4-yl-6,11-dihydro-5H-benzo[b]carbazole-3-carbonitrile

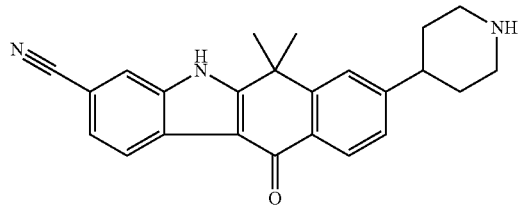 [SMILES: CC1(C)c2cc(C3CCNCC3)ccc2C(=O)c2c1[nH]c1cc(C#N)ccc21]

With the same condition as the method for synthesizing the Compound A8-1 (THF (0.5 mL) and TFA (0.5 mL) were added to 4-(3-cyano-6,6-dimethyl-11-oxo-6,11-dihydro-5H-benzo[b]carbazol-8-yloxy)-piperidine-1-carboxylic acid tert-butyl ester (Compound A7-1, 35 mg, 0.072 mmol), and the mixture was stirred at room temperature until Compound A7-1 disappears. The reaction solution was concentrated under reduced pressure and the residue was desalinated by using anionic exchange resin PL StratoSpheres (trademark) PL-HCO3 MP to obtain the Compound A8-1 (37 mg, 76%)), the title compound was synthesized from the Compound B3-13-1.

LCMS: m/z 370 [M+H]$^+$

HPLC retention time: 1.30 minutes (analysis condition S)

Production Example 12

Compound B4-8

6,6-Dimethyl-8-(1-oxetan-3-yl-piperidin-4-yl)-11-oxo-6,11-dihydro-5H-benzo[b]carbazole-3-carbonitrile

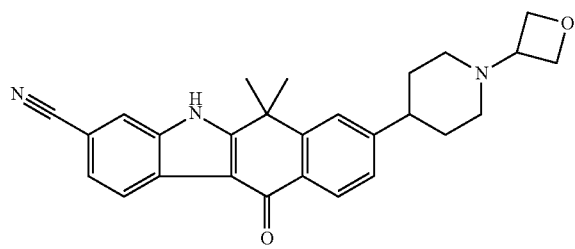 [SMILES: CC1(C)c2cc(C3CCN(C4COC4)CC3)ccc2C(=O)c2c1[nH]c1cc(C#N)ccc21]

With the same condition as the method for synthesizing the Compound B3-32 (morpholine (6 μl, 1.5 eq.) and sodium triacetoxy borohydride (81 mg, 2.0 eq.) were added to THF (1 ml) solution of the Compound B2-29: 8-formyl-6,6-dimethyl-11-oxo-6,11-dihydro-5H-benzo[b]carbazole-3-carbonitrile (30 mg, 0.095 mmol), and stirred at room temperature for 1 hour. The reaction solution was filtered to remove insoluble matters. The residues obtained after concentration under reduced pressure were purified by high performance liquid chromatography to obtain the Compound B3-32 (6,6-dimethyl-8-morpholin-4-yl methyl-11-oxo-6,11-dihydro-5H-benzo carbazole-3-carbonitrile) (19 mg, 50%)), the title compound was synthesized from the Compound B3-13-2 and oxetan-3-one.

$^1$H-NMR (400 MHz, DMSO-d$_6$) δ: 12.74 (1H, s), 8.32 (1H, d, 7.9 Hz), 8.13 (1H, d, 7.9 Hz), 8.00 (1H, s), 7.74 (1H, s), 7.61 (1H, d, 9.8 Hz), 7.40 (1H, d, 7.9 Hz), 4.56 (2H, t, 6.7 Hz), 4.46 (2H, t, 6.1 Hz), 3.46-3.39 (1H, m), 2.85-2.82 (2H, m), 2.71-2.64 (1H, m), 1.92-1.86 (2H, m), 1.82-1.79 (4H, m), 1.77 (6H, s)

LCMS: m/z 426 [M+H]$^+$

HPLC retention time: 1.53 minutes (analysis condition S)

Compound B4-8 sulfate salt 6,6-Dimethyl-8-(1-oxetan-3-yl-piperidin-4-yl)-11-oxo-6,11-dihydro-5H-benzo[b]carbazole-3-carbonitrile was dissolved at 80° C. in a mixture of 5 v/w of DMA and 1.4 v/w of 2 N sulfuric acid. After cooling to room temperature, 15 v/w of acetone were added dropwise, and the precipitated solids were filtered and dried to obtain sulfuric acid salt of 6,6-dimethyl-8-(1-oxetan-3-yl-piperidin-4-yl)-11-oxo-6,11-dihydro-5H-benzo[b]carbazole-3-carbonitrile.

$^1$H-NMR (400 MHz, DMSO-d$_6$) δ: 12.81 (1H, s), 10.26 (1H, br.s), 8.33 (1H, d, 8.3 Hz), 8.21 (1H, d, 8.3 Hz), 8.04 (1H, s), 7.75 (1H, s), 7.63 (1H, d, 8.3 Hz), 7.41 (1H, d, 8.3 Hz), 4.85-4.70 (4H, m), 4.50-4.40 (1H, br.s), 3.60-3.00 (6H, br.m), 2.20-2.10 (2H, m), 2.05-1.90 (2H, m), 1.79 (6H, s)

LCMS: m/z 426 [M+H]$^+$

B4-8 Hydrochloride Salt

B4-8 was dissolved in 5 v/w of dimethyl sulfoxide and 0.41 v/w of aqueous hydrochloric acid solution (6 N), and then the dissolved solution was subjected to freeze-drying. To the freeze-dried product, a mixture of 3.7 v/w of water and 1.3 v/w of acetonitrile was added. After stirring at room temperature all night and all day, the precipitated crystals were filtered and dried to give the B4-8 monohydrochloride salt.

B4-8 Mesylate Salt

B4-8 was dissolved in 4 v/w of dimethyl sulfoxide and 1.2 v/w of aqueous solution of mesylic acid (2 N), and then the dissolved solution was subjected to freeze-drying. To the freeze-dried product, 0.1 v/w of water and 5 v/w of ethyl acetate were added. After stirring at room temperature all night and all day, the precipitated crystals were filtered and dried to give the B4-8 monomesylate salt.

B4-8 L-Tartrate Salt

B4-8 and L-tartaric acid, which is added in an amount of 0.81 times the weight of B4-8, were dissolved in 10 v/w of tetrahydrofuran and 2 v/w of water at 80° C. The dissolved solution was added with 30 v/w of ethanol. The mixture was stirred at room temperature all night and all day, and the precipitated crystals were filtered and dried to give the B4-8 hemi-L-tartrate salt. The B4-8 hemi-L-tartrate salt obtained was pulverized by using a jet mill.

B4-8 Phosphate Salt

B4-8 was dissolved in 14 v/w of N,N-dimethylacetamide and 5.9 v/w of aqueous solution of phosphoric acid (2 N) under reflux with heating. The dissolved solution was added with 43 v/w of ethanol. The mixture was stirred at room temperature all night and all day, and the precipitated crystals were filtered and dried to give the B4-8 monophosphate salt. The B4-8 monophosphate salt obtained was pulverized by using a jet mill.

Production Example 13

Compound F5-22

6,6-Dimethyl-8-(4-oxetan-3-yl-piperazin-1-yl)-11-oxo-9-prop-1-ynyl-6,11-dihydro-5H-benzo[b]carbazole-3-carbonitrile

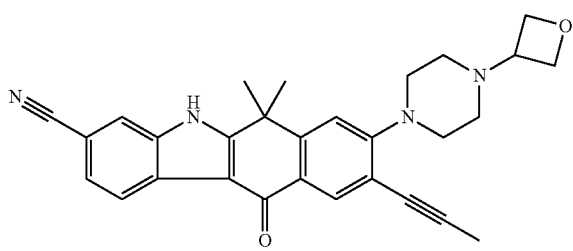 [SMILES: CC#Cc1cc2c(cc1N1CCN(C3COC3)CC1)C(C)(C)c1[nH]c3cc(C#N)ccc3c1C2=O]

The Compound E4-2-1 (9-bromo-8-methoxy-6,6-dimethyl-11-oxo-6,11-dihydro-5H-benzo[b]carbazole-3-carbonitrile (Compound E3-1-1, 50 mg, 0.13 mmol), bis(acetonitrile)dichloropalladium (II) (1.64 mg, 0.05 eq.), XPhos (9.05 mg, 0.15 eq.), cesium carbonate (185 mg, 4.5 eq.) and 3-methyl-1-butyn-1-ol (18.6 μl, 1.5 eq.) were dissolved in acetonitrile and stirred at 85° C. for 2 hours. The reaction solution was poured into water, and then extracted with ethyl acetate. The organic layer was washed with aqueous solution of sodium chloride and dried over sodium sulfate. The drying agent was removed by filtration and the residues obtained after concentration under reduced pressure were purified by HPLC, and under the same condition as the method for synthesizing the Compound E4-2-1 (9-(3-hydroxy-3-methyl-but-1-ynyl)-8-methoxy-6,6-dimethyl-11-oxo-6,11-dihydro-5H-benzo[b]carbazole-3-carbonitrile) (brown solid, 21.3 mg, 42%)), the title compound was synthesized from the Compound F4-3 and propyne.

1H-NMR (400 MHz, CD$_3$OD) δ: 8.37 (1H, d, J=8.2 Hz), 8.18 (1H, s), 7.84 (1H, s), 7.53 (1H, d, J=8.2 Hz), 7.19 (1H, s), 4.70-4.77 (2H, m), 4.62-4.68 (2H, m), 3.57-3.63 (1H, m), 3.38-3.45 (4H, m), 2.54-2.61 (4H, m), 2.10 (3H, s), 1.79 (6H, s)

LCMS: m/z 465 [M+H]$^+$

HPLC retention time: 1.90 minutes (analysis condition U)

Production Example 14

Compound F5-25

9-Cyclopropylethynyl-6,6-dimethyl-8-(4-oxetan-3-yl-piperazin-1-yl)-11-oxo-6,11-dihydro-5H-benzo[b]carbazole-3-carbonitrile

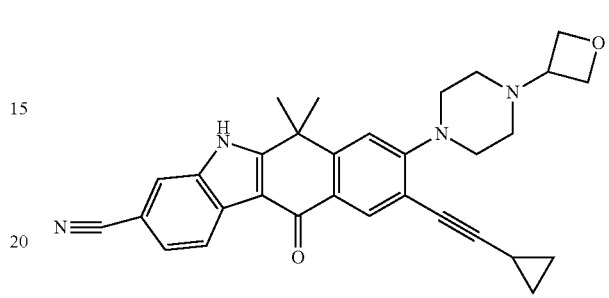

With the same condition as the method for synthesizing the Compound E4-2-1, the title compound was synthesized from the Compound F4-3 and ethynylcyclopropane.

$^1$H-NMR (270 MHz, DMSO-d$_6$) δ: 12.74 (1H, br.s), 8.32-8.29 (1H, d, 8.08 Hz), 8.05 (1H, s), 8.00 (1H, s), 7.62-7.58 (1H, m), 7.21 (1H, s), 4.62-4.57 (2H, m), 4.51-4.47 (2H, m), 3.53-3.48 (1H, m), 3.34 (4H, m), 2.46 (4H, m), 1.76 (6H, s), 1.64-1.58 (1H, m), 0.97-0.89 (2H, m), 0.76-0.70 (2H, m)

LCMS: m/z 491 [M+H]$^+$

Reference Example 6

Compound E1

6-Bromo-7-methoxy-1,1-dimethyl-3,4-dihydro-1H-naphthalen-2-one

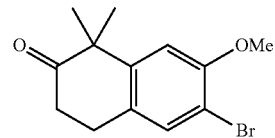 [SMILES: COc1cc2c(cc1Br)CCC(=O)C2(C)C]

7-Methoxy-1,1-dimethyl-3,4-dihydro-1H-naphthalen-2-one (Compound A2, 2.0 g, 9.791 mmol) was dissolved in CH$_3$CN (40 mL), added with NBS (1.92 g, 1.1 eq.), and the mixture was stirred at room temperature for 2.5 hours. The reaction solution was poured into water (40 mL), and the precipitated solid was filtered to obtain the title compound (white powder, 2.55 g, 92%).

$^1$H-NMR (270 MHz, CDCl$_3$) δ: 7.36 (1H, s), 6.84 (1H, s), 3.91 (3H, s), 3.02 (2H, t, J=6.8 Hz), 2.66 (2H, t, J=6.8 Hz), 1.42 (6H, s).

LCMS: m/z 283, 285 [M+H]$^+$

HPLC retention time: 2.67 minutes (analysis condition S)

Reference Example 7

Compound E2-1

9-Bromo-8-methoxy-6,6-dimethyl-6,11-dihydro-5H-benzo[b]carbazole-3-carbonitrile

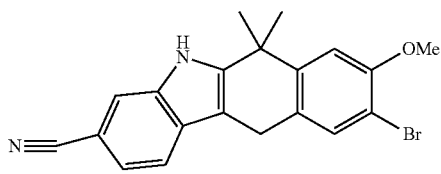 [SMILES: COc1cc2c(cc1Br)Cc1c([nH]c3cc(C#N)ccc13)C2(C)C]

6-Bromo-7-methoxy-1,1-dimethyl-3,4-dihydro-1H-naphthalen-2-one (Compound E1, 7.89 g, 27.85 mmol) and 3-hydrazino-benzonitrile (4.45 g, 1.2 eq.) were dissolved in TFA (250 mL), and stirred at 100° C. for 2 hours. TFA was removed by concentration under reduced pressure and the residues were added with saturated aqueous solution of NaHCO₃ (500 mL), followed by extraction with ethyl acetate. The organic layer was washed with saturated brine and dried over sodium sulfate. The drying agent was removed by filtration and the residues obtained after concentration under reduced pressure were added with ethyl acetate. After stirring at room temperature, the precipitated solid was separated by filtration (Compound E2-2). The filtrate was concentrated under reduced pressure to obtain the title compound as a mixture with E2-2 (yellowish white powder, 2.65 g).

LCMS: m/z 381, 383 [M+H]⁺

HPLC retention time: 3.03 minutes (analysis condition S)

Production Example 15

Compound E3-1-1

9-Bromo-8-methoxy-6,6-dimethyl-11-oxo-6,11-dihydro-5H-benzo[b]carbazole-3-carbonitrile

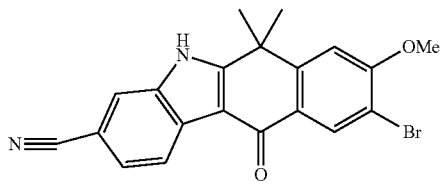 [SMILES: COc1cc2c(cc1Br)C(=O)c1c([nH]c3cc(C#N)ccc13)C2(C)C]

With the same condition as the method for synthesizing the Compound A4, the title compound was synthesized from the Compound E2-1.

¹H-NMR (270 MHz, DMSO-D₆) δ: 12.82 (1H, s), 8.30 (2H, s+d), 8.03 (1H, s), 7.61 (1H, dd, J=8.2, 1.4 Hz), 7.49 (1H, s), 4.04 (3H, s), 1.81 (6H, s).

LCMS: m/z 395, 397 [M+H]⁺

HPLC retention time: 2.77 minutes (analysis condition S)

Production Example 16

Compound E3-2

9-Bromo-8-hydroxy-6,6-dimethyl-11-oxo-6,11-dihydro-5H-benzo[b]carbazole-3-carbonitrile

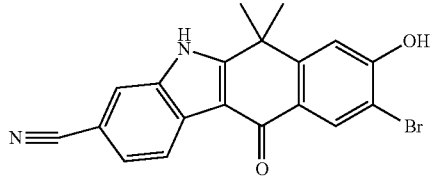 [SMILES: CC1(C)c2cc(O)c(Br)cc2C(=O)c2c1[nH]c1cc(C#N)ccc21]

9-Bromo-8-methoxy-6,6-dimethyl-11-oxo-6,11-dihydro-5H-benzo[b]carbazole-3-carbonitrile (Compound E3-1-1, 1.0 g, 2.53 mmol) was dissolved in NMP (10 mL), added with NaOMe (683 mg, 5 eq.) and 1-dodecanethiol (3.0 mL, 5 eq.), and stirred at 160° C. for 1 hour. The reaction solution was poured into 0.5 N aqueous solution of hydrochloric acid, and then extracted with ethyl acetate. The organic layer was washed with brine and dried over sodium sulfate. The drying agent was removed by filtration and the residues obtained after concentration under reduced pressure were added with MeOH, and the solid remaining after dissolution was filtered to obtain the title compound (yellow powder, 1.88 g, 65%).

¹H-NMR (400 MHz, DMSO-d₆) δ: 12.77 (1H, s), 11.13 (1H, d, J=2.4 Hz), 8.31 (1H, dd, J=7.9, 2.4 Hz), 8.25 (1H, d, J=3.0 Hz), 8.01 (1H, s), 7.61 (1H, d, J=7.9 Hz), 7.28 (1H, d, J=2.4 Hz), 1.74 (6H, s).

LCMS: m/z 381, 383 [M+H]⁺

HPLC retention time: 2.40 minutes (analysis condition S)

Production Example 17

Compound F2

Trifluoro-methane sulfonic acid 9-bromo-3-cyano-6,6-dimethyl-11-oxo-6,11-dihydro-5H-benzo[b]carbazol-8-yl ester

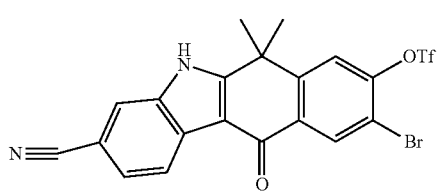 [SMILES: CC1(C)c2cc(OS(=O)(=O)C(F)(F)F)c(Br)cc2C(=O)c2c1[nH]c1cc(C#N)ccc21]

With the same condition as the method for synthesizing the Compound B1, the title compound was synthesized from the Compound E3-2.

¹H-NMR (270 MHz, DMSO-d₆) δ: 12.99 (1H, s), 8.51 (1H, s), 8.31 (1H, dd, J=8.2, 0.7 Hz), 8.17 (1H, s), 8.07 (1H, s), 7.67 (1H, dd, J=8.2, 1.4 Hz), 1.81 (6H, s).

LCMS: m/z 513, 515 [M+H]⁺

HPLC retention time: 3.13 minutes (analysis condition S)

Production Example 18

Compound F3-9

9-Bromo-6,6-dimethyl-11-oxo-8-piperazin-1-yl-6,11-dihydro-5H-benzo[b]carbazole-3-carbonitrile

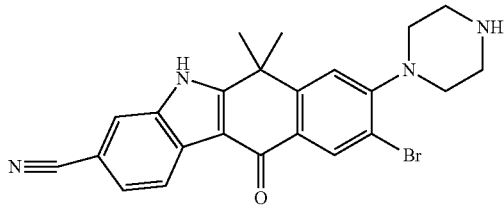 [SMILES: CC1(C)c2cc(N3CCNCC3)c(Br)cc2C(=O)c2c1[nH]c1cc(C#N)ccc21]

With the same condition as the method for synthesizing the Compound B2-1 (trifluoro-methane sulfonic acid 3-cyano-6,6-dimethyl-11-oxo-6,11-dihydro-5H-benzo[b]carbazol-8-yl ester (Compound B1, 40 mg, 0.0921 mmol) was dissolved in NMP (1 ml) and added with 1-isopropylpiperazine (236 mg, 20 eq.). The mixture was stirred at 120° C. for 3 hours. After cooling to room temperature, purification was carried out by HPLC to obtain the Compound B2-1 (8-(4-isopropyl-piperazin-1-yl)-6,6-dimethyl-11-oxo-6,11-dihydro-5H-benzo[b]carbazole-3-carbonitrile) (white powder, 12.8 mg, 34%)), and the title compound was synthesized from the Compound F2 and piperazine.

$^1$H-NMR (DMSO-D$_6$) δ: 8.30-8.24 (2H, m), 8.00 (1H, s), 7.63-7.58 (1H, m), 7.37 (1H, s), 3.10-3.01 (4H, m), 2.91-2.85 (4H, m), 1.76 (6H, s)

LCMS: m/z 449, 451 [M+H]$^+$

HPLC retention time: 1.45 minutes (analysis condition S)

Production Example 19

Compound F4-3

9-Bromo-6,6-dimethyl-8-(4-oxetan-3-yl-piperazin-1-yl)-1'-oxo-6,11-dihydro-5H-benzo[b]carbazole-3-carbonitrile

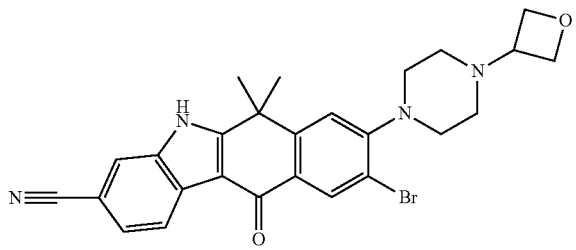 [SMILES: CC1(C)c2cc(N3CCN(C4COC4)CC3)c(Br)cc2C(=O)c2c1[nH]c1cc(C#N)ccc21]

With the same condition as the Compound B3-32, the title compound was synthesized from the Compound F3-9 and 1-oxetan-3-one.

$^1$H-NMR (270 MHz, DMSO-d$_6$) δ: 12.83 (1H, br.s), 8.31-8.32 (1H, m), 8.27-8.29 (1H, m), 8.01-8.04 (1H, m), 7.59-7.64 (1H, m), 7.48 (1H, s), 4.59 (2H, dd, J=6.3, 6.3 Hz), 4.48 (2H, dd, J=6.3, 6.3 Hz), 3.52 (1H, t, J=6.3 Hz), 3.12-3.25 (4H, m), 2.44-2.54 (4H, m), 1.78 (6H, s).

LCMS: m/z 505, 507 [M+H]$^+$

HPLC retention time: 1.45 minutes (analysis condition S)

Compound F4-3 hydrochloride salt

9-Bromo-6,6-dimethyl-8-(4-oxetan-3-yl-piperazin-1-yl)-11-oxo-6,11-dihydro-5H-benzo[b]carbazole-3-carbonitrile was added with 1.05 eq. of 6 N hydrochloric acid and DMSO and dissolved therein. After freeze-drying, the mixture was crystallized from ethanol containing 25% water to give 9-bromo-6,6-dimethyl-8-(4-oxetan-3-yl-piperazin-1-yl)-11-oxo-6,11-dihydro-5H-benzo[b]carbazole-3-carbonitrile monohydrochloride salt.

$^1$H-NMR (270 MHz, DMSO-d$_6$) δ: 12.91 (1H, br.s), 11.70 (1H, br.s), 8.32-8.29 (2H, m), 8.04 (1H, s), 7.64-7.62 (1H, m), 7.52 (1H, s), 4.89-4.62 (4H, br.m), 3.66-3.39 (1H, m), 3.31-3.05 (8H, br.m), 1.81 (6H, s)

LCMS: m/z 505, 507 [M+H]$^+$

Production Example 20

Compound F4-9

9-Bromo-8-(4-cyclopropyl-piperazin-1-yl)-6,6-dimethyl-11-oxo-6,11-dihydro-5H-benzo[b]carbazole-3-carbonitrile

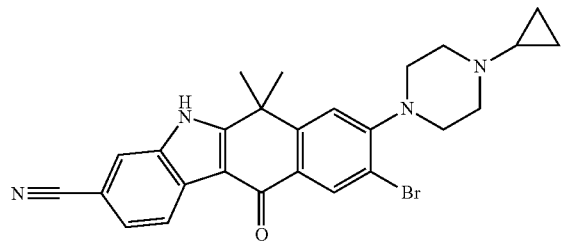 [SMILES: CC1(C)c2cc(N3CCN(C4CC4)CC3)c(Br)cc2C(=O)c2c1[nH]c1cc(C#N)ccc21]

With the same condition as the Compound B3-32, the title compound was synthesized from the Compound F3-9 and (1-ethoxy-cyclopropoxy)-trimethyl-silane.

$^1$H-NMR (270 MHz, DMSO-D$_6$) δ: 8.22-8.30 (2H, m), 8.00 (1H, s), 7.56 (1H, d, J=7.9 Hz), 7.43 (1H, s), 3.30 (1H, d, J=5.8 Hz), 3.11 (4H, s), 2.75 (4H, s), 1.75 (6H, s), 0.47 (2H, d, J=5.8 Hz), 0.34 (2H, d, J=5.8 Hz)

LCMS: m/z 489, 491 [M+H]$^+$

HPLC retention time: 1.68 minutes (analysis condition S)

Reference Example 8

Compound I1-1

6-Chloro-7-methoxy-1,1-dimethyl-3,4-dihydro-1H-naphthalen-2-one

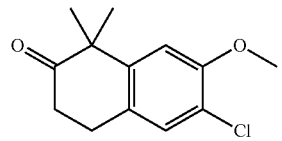 [SMILES: COc1cc2c(cc1Cl)CCC(=O)C2(C)C]

7-Methoxy-1,1-dimethyl-3,4-dihydro-1H-naphthalen-2-one (Compound A2, 3.37 g, 16.5 mmol) was dissolved in CH$_3$CN (82 mL), added with NCS (2.42 g, 1.1 eq.) and stirred at 90° C. for 1.5 hours. The reaction solution was extracted with ethyl acetate. The organic layer was washed with brine and dried over sodium sulfate. The drying agent was removed and the target compound was obtained after concentration under reduced pressure (yellow oily substance, 4.45 g).

¹H-NMR (400 MHz, CDCl₃) δ: 7.16 (1H, s), 6.85 (1H, s), 3.90 (3H, s), 3.00 (2H, t, J=6.8 Hz), 2.65 (2H, t, J=6.8 Hz), 1.42 (6H, s).

LCMS: m/z 239 [M+H]⁺

HPLC retention time: 2.80 minutes (analysis condition U)

Reference Example 9

Compound I1-2

9-Chloro-8-methoxy-6,6-dimethyl-6,11-dihydro-5H-benzo[b]carbazole-3-carbonitrile

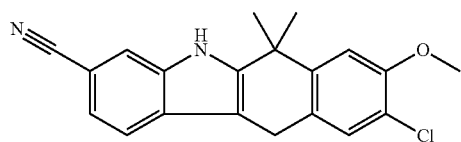 [SMILES: COc1cc2c(cc1Cl)Cc1c([nH]c3cc(C#N)ccc13)C2(C)C]

6-Chloro-7-methoxy-1,1-dimethyl-3,4-dihydro-1H-naphthalen-2-one (Compound I1-1, 4.45 g, 16.5 mmol) and 3-hydrazinobenzonitrile (2.63 g, 1.2 eq.) were dissolved in TFA (91 mL), and stirred at 90° C. for 3 hours. According to the concentration under reduced pressure, TFA was removed and the residues were added with saturated aqueous solution of NaHCO₃, followed by extraction with ethyl acetate. The organic layer was washed with brine and dried over sodium sulfate. The drying agent was removed by filtration and the residues obtained after concentration under reduced pressure were added with ethyl acetate. After stirring at room temperature, the precipitated solid was separated by filtration. The filtrate was concentrated under reduced pressure to obtain the target compound as a mixture with 11-3 (red powder, 6.46 g).

Production Example 21

Compound I3

9-Chloro-8-methyoxy-6,6-dimethyl-11-oxo-6,11-dihydro-5H-benzo[b]carbazole-3-carbonitrile

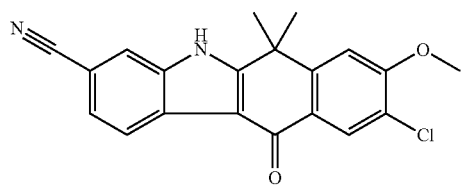 [SMILES: COc1cc2c(cc1Cl)C(=O)c1c([nH]c3cc(C#N)ccc13)C2(C)C]

With the same condition as the method for synthesizing the Compound A4, the title compound was synthesized from the Compound I1-2.

¹H-NMR (400 MHz, DMSO-d₆) δ: 12.79 (1H, s), 8.27-8.31 (1H, m), 8.12 (1H, s), 8.00-8.02 (1H, m), 7.58-7.63 (1H, m), 7.51 (1H, s), 4.03 (3H, s), 1.80 (6H, s).

LCMS: m/z 351 [M+H]⁺

HPLC retention time: 2.87 minutes (analysis condition U)

Production Example 22

Compound I4

9-Chloro-8-hydroxy-6,6-dimethyl-11-oxo-6,11-dihydro-5H-benzo[b]carbazole-3-carbonitrile

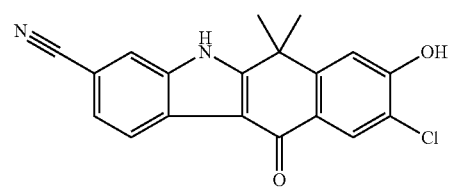 [SMILES: CC1(C)c2cc(O)c(Cl)cc2C(=O)c2c1[nH]c1cc(C#N)ccc21]

With the same condition as the method for synthesizing the Compound E3-2 (9-bromo-8-methoxy-6,6-dimethyl-11-oxo-6,11-dihydro-5H-benzo[b]carbazole-3-carbonitrile (Compound E3-1-1, 1.0 g, 2.53 mmol) was dissolved in NMP (10 mL), added with NaOMe (683 mg, 5 eq.) and 1-dodecanethiol (3.0 mL, 5 eq.), and stirred at 160° C. for 1 hour. The reaction solution was poured into 0.5 N aqueous solution of hydrochloric acid, and then extracted with ethyl acetate. The organic layer was washed with brine and dried over sodium sulfate. The drying agent was removed by filtration and the residues obtained after concentration under reduced pressure were added with MeOH, the solid remaining after dissolution was filtered to obtain the Compound E3-2 (9-bromo-8-hydroxy-6,6-dimethyl-11-oxo-6,11-dihydro-5H-benzo[b]carbazole-3-carbonitrile) (yellow powder, 1.88 g, 65%)), and the title compound was synthesized from the Compound I3.

LCMS: m/z 337 [M+H]⁺

HPLC retention time: 2.47 minutes (analysis condition U)

Production Example 23

Compound I5

Trifluoro-methane sulfonic acid 9-chloro-3-cyano-6,6-dimethyl-11-oxo-6,11-dihydro-5H-benzo[b]carbazol-8-yl ester

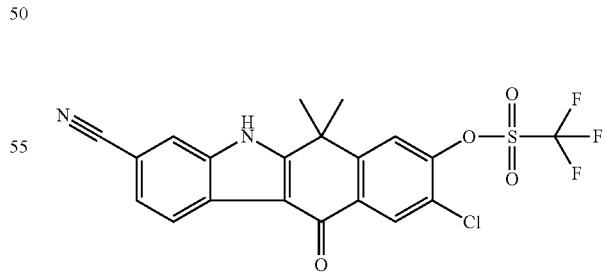

With the same condition as the method for synthesizing the Compound B1, the title compound was synthesized from the Compound I4.

LCMS: m/z 469 [M+H]⁺

HPLC retention time: 3.40 minutes (analysis condition U)

Production Example 24

Compound I6-4

9-Chloro-6,6-dimethyl-8-(4-morpholin-4-yl-piperidin-1-yl)-11-oxo-6,11-dihydro-5H-benzo[b]carbazole-3-carbonitrile

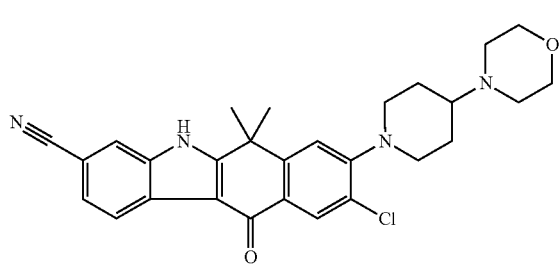 [SMILES: CC1(C)c2cc(N3CCC(N4CCOCC4)CC3)c(Cl)cc2C(=O)c2c1[nH]c1cc(C#N)ccc21]

With the same condition as the method for synthesizing the Compound B2-1, the title compound was synthesized from the Compound I5 and 4-piperidin-4-yl-morpholine.

$^1$H-NMR (400 MHz, DMSO-d$_6$) δ: 12.75 (1H, s), 8.28 (1H, d, 8.0 Hz), 8.07 (1H, s), 8.00 (1H, s), 7.59 (1H, d, 8.0 Hz), 7.41 (1H, s), 3.55-3.62 (4H, m), 3.47-3.56 (4H, m), 2.75-2.86 (2H, m), 2.45-2.55 (4H, m), 2.28-2.39 (11-1, m), 1.86-1.96 (2H, m), 1.76 (6H, s), 1.52-1.66 (2H, m)

LCMS: m/z 489 [M+H]$^+$

HPLC retention time: 1.97 minutes (analysis condition U)

Production Example 25

Compound F5-44

8-(4-Cyclobutyl-piperazin-1-yl)-6,6-dimethyl-11-oxo-9-prop-1-ynyl-6,11-dihydro-5H-benzo[b]carbazole-3-carbonitrile

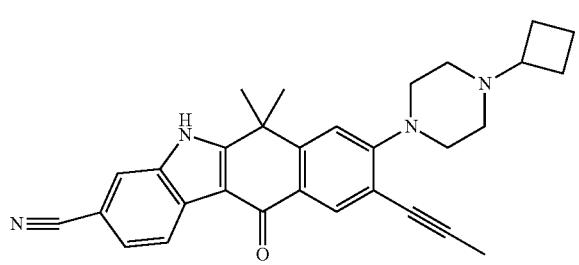 [SMILES: CC#Cc1cc2c(cc1N1CCN(C3CCC3)CC1)C(C)(C)c1[nH]c3cc(C#N)ccc3c1C2=O]

With the same condition as the method for synthesizing the Compound E4-2-1, the title compound was synthesized from the Compound F4-10 under atmosphere of propyne gas.

$^1$H-NMR (400 MHz, DMSO-d$_6$) δ: 12.71 (1H, s), 8.30 (1H, d, 7.9 Hz), 8.06 (1H, s), 8.00 (1H, s), 7.59 (1H, d, 7.9 Hz), 7.20 (1H, s), 2.75-2.83 (1H, m), 2.40-2.48 (4H, m), 2.11 (3H, s), 1.97-2.06 (2H, m), 1.76 (6H, s), 1.62-1.71 (2H, m)

LCMS: m/z 463 [M+H]$^+$

HPLC retention time: 2.80 minutes (analysis condition W)

Example 282

Production Example 26

Compound F3-11

9-Bromo-6,6-dimethyl-8-(4-morpholin-4-yl-piperidin-1-yl)-11-oxo-6,11-dihydro-5H-benzo[b]carbazole-3-carbonitrile

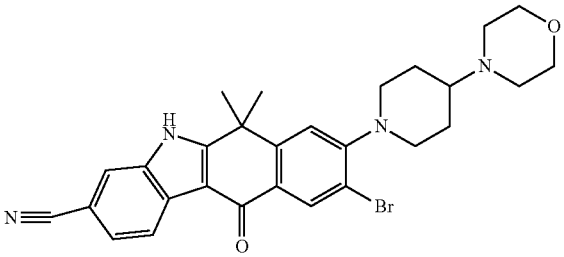 [SMILES: CC1(C)c2cc(N3CCC(N4CCOCC4)CC3)c(Br)cc2C(=O)c2c1[nH]c1cc(C#N)ccc21]

With the same condition as the method for synthesizing the Compound B2-1, the title compound was synthesized from the Compound F2 and 4-piperidin-4-yl morpholine.

1H-NMR (DMSO-D$_6$) δ: 8.30-8.24 (2H, m), 8.00 (1H, s), 7.59 (1H, d, J=8.2 Hz), 7.42 (1H, s), 3.66-3.45 (6H, m), 2.80 (2H, t, J=11.1 Hz), 2.38-2.28 (1H, m), 1.96-1.87 (2H, m), 1.75 (6H, s), 1.66-1.56 (2H, m)

LCMS: m/z 533, 535 [M+H]$^+$

HPLC retention time: 1.53 minutes (analysis condition S)

Production Example 27

Compound F5-51

6,6,9-Trimethyl-8-(4-morpholin-4-yl-piperidin-1-yl)-11-oxo-6,11-dihydro-5H-benzo[b]carbazole-3-carbonitrile

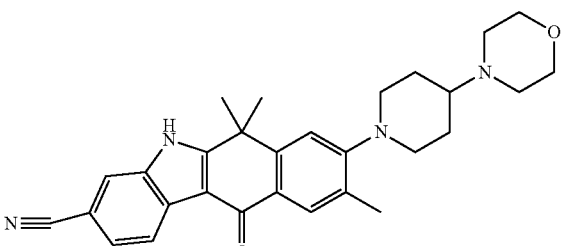

With the same condition as the method for synthesizing the Compound F5-47 (under nitrogen atmosphere, to the N,N-dimethyl formamide (1.5 ml) solution of 9-bromo-8-(4-cyclobutyl-piperazin-1-yl)-6,6-dimethyl-11-oxo-6,11-dihydro-5H-benzo[b]carbazole-3-carbonitrile (Compound F4-10, 50 mg, 0.099 mmol), trimethyl boroxine (12 mg, 0.1 eq.), tetrakis triphenylphosphine palladium (39 mg, 0.2 eq.), and potassium carbonate (41 mg, 3.0 eq.) were added, and the mixture was stirred at 100° C. for 24 hours. Upon the completion of the reaction, distilled water was poured into the reaction solution, which was then extracted with ethyl acetate. The organic layer was washed with aqueous solution of sodium chloride and dried over sodium sulfate. The drying agent was removed by filtration and the residues obtained after concentration under reduced pressure were purified by silica gel column chromatography (ethyl acetate/methanol) to obtain the Compound F5-47 (8-(4-cyclobutyl-piperazin-1-yl)-6,6,9-trimethyl-11-oxo-6,11-dihydro-5H-benzo[b]carbazole-3-carbonitrile) (25 mg, 58%)), the title compound was synthesized from the Compound F3-11.

$^{1}$H-NMR (270 MHz, DMSO-$d_6$) δ: 12.70 (1H, br.s), 8.33-8.30 (1H, d, 8.08 Hz), 8.00 (1H, s), 7.95 (1H, s), 7.61-7.58 (1H, m), 7.28 (1H, s), 3.60 (4H, m), 3.32-3.26 (2H, m), 2.79-2.69 (2H, m), 2.32 (3H, s), 1.95-1.90 (2H, m), 1.74 (6H, s), 1.65-1.52 (2H, m), LCMS: m/z 469 [M+H]$^{+}$

Compound F5-51 methane sulfonic acid salt 6,6,9-Trimethyl-8-(4-morpholin-4-yl-piperidin-1-yl)-11-oxo-6,11-dihydro-5H-benzo[b]carbazole-3-carbonitrile was added with 1.05 eq. of 2 N methane sulfonic acid and DMSO and dissolved therein. After freeze-drying, the mixture was crystallized from ethanol to give 6,6,9-trimethyl-8-(4-morpholin-4-yl-piperidin-1-yl)-11-oxo-6,11-dihydro-5H-benzo[b]carbazole-3-carbonitrile methane sulfonic acid salt.

$^{1}$H-NMR (270 MHz, DMSO-$d_6$) δ: 12.72 (1H, br.s), 9.60 (1H, br.s), 8.33-8.31 (1H, d, 9.8 Hz), 8.01 (1H, s), 7.99 (1H, s), 7.61-7.59 (1H, m), 7.31 (1H, s), 4.07-4.04 (2H, m), 3.73-3.67 (2H, m), 3.55-3.40 (8H, m), 3.32-3.26 (1H, m), 2.70-2.60 (2H, m), 2.34 (3H, s), 2.30 (3H, s), 1.95-1.90 (2H, m), 1.75 (6H, s)

LCMS: m/z 469 [M+H]$^{+}$

F5-51 Hydrochloride Salt

F5-51 was dissolved in 5 v/w of dimethyl sulfoxide and 0.37 v/w of aqueous solution of hydrochloric acid (6 N), and then the dissolved solution was subjected to freeze-drying. To the freeze-dried product, 5 v/w of ethanol was added. The precipitated crystals were filtered and dried to give the F5-51 hydrochloride salt.

Production Example 28

Compound F6-4

9-Ethyl-6,6-dimethyl-8-(4-oxetan-3-yl-piperazin-1-yl)-11-oxo-6,11-dihydro-5H-benzo[b]carbazole-3-carbonitrile

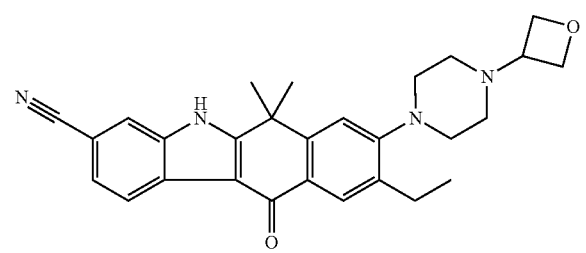 [SMILES: CCc1cc2c(cc1N1CCN(C3COC3)CC1)C(C)(C)c1[nH]c3cc(C#N)ccc3c1C2=O]

With the same condition as the method for synthesizing the Compound B3-13-1, the title compound was synthesized from the Compound F5-16.

$^{1}$H-NMR (400 MHz, DMSO-$d_6$) δ: 12.70 (1H, br. s), 8.29 (1H, d, 8.0 Hz), 8.03-7.94 (2H, m), 7.59-7.55 (1H, m), 7.38 (1H, s), 4.59-4.47 (4H, m), 3.53-5.47 (1H, m), 3.03-2.97 (2H, m), 2.73-2.62 (2H, m), 1.74 (6H, s), 1.29-1.98 (3H, m)

LCMS: m/z 455 [M+H]$^{+}$

HPLC retention time: 1.92 minutes (analysis condition U)

Compound F6-4 Hydrochloride Salt

9-Ethyl-6,6-dimethyl-8-(4-oxetan-3-yl-piperazin-1-yl)-1'-oxo-6,11-dihydro-5H-benzo[b]carbazole-3-carbonitrile was added with 1.05 eq. of 6 N hydrochloric acid and DMSO and dissolved therein. After freeze-drying, the mixture was crystallized from ethanol containing 25% water to give 9-ethyl-6,6-dimethyl-8-(4-oxetan-3-yl-piperazin-1-yl)-11-oxo-6,11-dihydro-5H-benzo[b]carbazole-3-carbonitrile monohydrochloride salt.

$^{1}$H-NMR (270 MHz, DMSO-$d_6$) δ: 12.83 (1H, br.s), 11.59 (1H, br.s), 8.33-8.31 (1H, m), 8.09 (1H, s), 8.02 (1H, s), 7.63-7.61 (1H, m), 7.39 (1H, s), 4.91-4.60 (4H, br.m), 3.58-3.40 (1H, m), 3.31-3.05 (8H, br.m), 2.73 (2H, q, J=7.3), 1.81 (6H, s), 1.29 (3H, t, J=7.3)

LCMS: m/z 455 [M+H]$^{+}$

F6-4 Mesylate Salt

F6-4 was dissolved in 5 v/w of dimethyl sulfoxide and 1.2 v/w of aqueous solution of mesylic acid (2 N), and then the dissolved solution was subjected to freeze-drying. To the freeze-dried product, a mixture of 3.8 v/w of water and 1.3 v/w of ethanol was added. The precipitated crystals were filtered and dried to give the F6-4 mesylate salt.

Production Example 29

Compound F5-49

9-Ethynyl-6,6-dimethyl-8-(4-morpholin-4-yl-piperidin-1-yl)-11-oxo-6,11-dihydro-5H-benzo[b]carbazole-3-carbonitrile

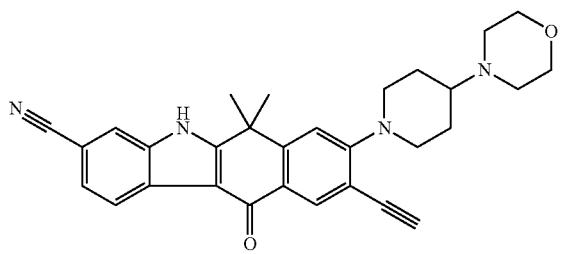 [SMILES: C#Cc1cc2c(cc1N1CCC(N3CCOCC3)CC1)C(C)(C)c1[nH]c3cc(C#N)ccc3c1C2=O]

With the same condition as the method for synthesizing the Compound F5-43, the title compound was synthesized from the Compound F3-11.

LCMS: m/z 479 [M+H]$^{+}$

HPLC retention time: 1.90 minutes (analysis condition U)

Production Example 30

Compound F6-20

9-Ethyl-6,6-dimethyl-8-(4-morpholin-4-yl-piperidin-1-yl)-1'-oxo-6,11-dihydro-5H-benzo[b]carbazole-3-carbonitrile

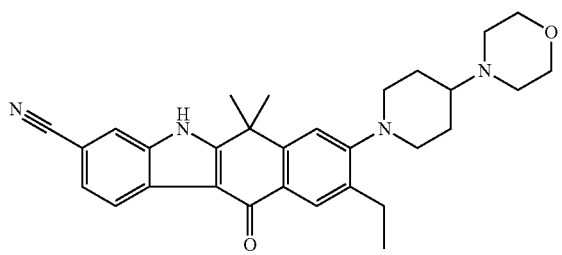 [SMILES: CCc1cc2c(cc1N1CCC(N3CCOCC3)CC1)C(C)(C)c1[nH]c3cc(C#N)ccc3c1C2=O]

With the same condition as the method for synthesizing the Compound B3-13-1, the title compound was synthesized from the Compound F5-49.

¹H-NMR (400 MHz, DMSO-D₆) δ: 12.70 (1H, s), 8.32 (1H, d, J=7.9 Hz), 8.04 (1H, s), 8.00 (1H, s), 7.61 (1H, d, J=8.5 Hz), 7.34 (1H, s), 3.64-3.57 (4H, m), 3.27-3.18 (2H, m), 2.82-2.66 (4H, m), 2.39-2.28 (1H, m), 1.96-1.87 (2H, m), 1.76 (6H, s), 1.69-1.53 (2H, m), 1.29 (3H, t, J=7.3 Hz)

LCMS: m/z 483 [M+H]⁺

HPLC retention time: 1.98 minutes (analysis condition U)

Compound F6-20 Hydrochloride Salt

9-Ethyl-6,6-dimethyl-8-(4-morpholin-4-yl-piperidin-1-yl)-11-oxo-6,11-dihydro-5H-benzo[b]carbazole-3-carbonitrile was dissolved in a mixture of 10 v/w of methyl ethyl ketone, 4 v/w of water, and 3 v/w of acetic acid at 60° C. To the dissolved solution, 1 v/w of hydrochloric acid (2 N) was added dropwise. After stirring at 60° C. for 30 minutes, 25 v/w of ethanol was added dropwise. The precipitated solid was filtered and dried to give 9-ethyl-6,6-dimethyl-8-(4-morpholin-4-yl-piperidin-1-yl)-11-oxo-6,11-dihydro-5H-benzo[b]carbazole-3-carbonitrile monohydrochloride salt. 9-Ethyl-6,6-dimethyl-8-(4-morpholin-4-yl-piperidin-1-yl)-11-oxo-6,11-dihydro-5H-benzo[b]carbazole-3-carbonitrile monohydrochloride salt obtained was pulverized by using a jet mill.

¹H-NMR (400 MHz, DMSO-D₆) δ: 12.78 (1H, s), 10.57 (1H, br.s), 8.30 (1H, J=8.4 Hz), 8.05 (1H, s), 7.99 (1H, s), 7.59 (1H, d, J=7.9 Hz), 7.36 (1H, s), 4.02-3.99 (2H, m), 3.84-3.78 (2H, m), 3.51-3.48 (2H, m), 3.15-3.13 (1H, s), 2.83-2.73 (2H, s), 2.71-2.67 (2H, s), 2.23-2.20 (2H, m), 1.94-1.83 (2H, m), 1.75 (6H, s), 1.27 (3H, t, J=7.5 Hz)

FABMS: m/z 483 [M+H]⁺

F6-20 Mesylate Salt

F6-20 was dissolved in 33 v/w of dimethyl acetamide at 90° C. The dissolved solution was added with 1.2 v/w of aqueous solution of mesylic acid (2 N) and 168 v/w of ethyl acetate followed by stirring for 4 hours. The precipitated crystals were filtered and dried to give the F6-20 monomesylate salt. The F6-20 monomesylate salt obtained was pulverized by using a jet mill.

Production Example 31

Compound F5-16

9-Ethynyl-6,6-dimethyl-8-(4-oxetan-3-yl-piperazin-1-yl)-11-oxo-6,11-dihydro-5H-benzo[b]carbazole-3-carbonitrile

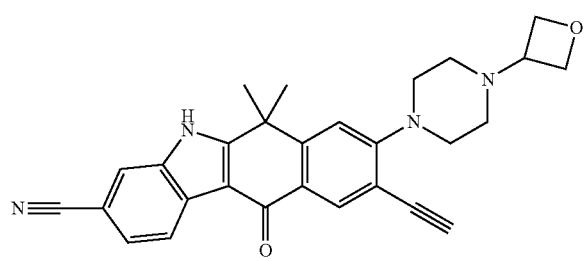 [SMILES: C#Cc1cc2c(cc1N1CCN(C3COC3)CC1)C(C)(C)c1[nH]c3cc(C#N)ccc3c1C2=O]

With the same condition as the method for synthesizing the Compound F5-43, the title compound was synthesized from the Compound F4-3.

¹H-NMR (270 MHz, DMSO-D₆) δ: 12.77 (1H, br.s), 8.31 (1H, d, J=8.2 Hz), 8.16 (1H, s), 8.02 (1H, s), 7.61 (1H, dd, J=8.2, 1.3 Hz), 7.27 (1H, s), 4.59 (2H, dd, J=6.6, 6.6 Hz), 4.51 (1H, s), 4.49 (2H, dd, J=6.6, 6.6 Hz), 3.51 (1H, t, J=6.6 Hz), 3.35-3.43 (4H, m), 2.43-2.50 (4H, s), 1.78 (6H, s).

LCMS: m/z 451 [M+H]⁺

HPLC retention time: 1.40 minutes (analysis condition S)

Production Example 32

Compound F6-17

8-(4-Cyclobutyl-piperazin-1-yl)-9-ethyl-6,6-dimethyl-11-oxo-6,11-dihydro-5H-benzo[b]carbazole-3-carbonitrile

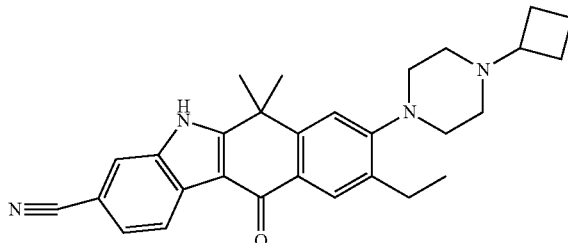

With the same condition as the method for synthesizing the Compound B3-13-1, the title compound was synthesized from the Compound F5-43.

¹H-NMR (400 MHz, DMSO-d₆) δ: 12.80 (1H, s), 8.32 (1H, d, 7.9 Hz), 8.10 (1H, s), 8.02 (1H, s), 7.62 (1H, d, 7.9 Hz), 7.38 (1H, s), 3.78-3.88 (1H, m), 3.79-3.89 (1H, m), 3.48-3.54 (2H, m), 3.40-3.47 (2H, m), 3.30-3.39 (2H, m), 3.02-3.24 (4H, m), 2.73 (2H, q, 7.3 Hz), 2.30-2.41 (2H, m), 2.17-2.26 (2H, m), 1.71-1.86 (8H, m), 1.29 (3H, t, 7.3 Hz)

LCMS: m/z 453 [M+H]⁺

HPLC retention time: 2.76 minutes (analysis condition W)

Compound F6-17 Methane Sulfonic Acid Salt 8-(4-Cyclobutyl-piperazin-1-yl)-9-ethyl-6,6-dimethyl-11-oxo-6,11-dihydro-5H-benzo[b]carbazole-3-carbonitrile was dissolved at room temperature and added with 6 v/w of DMF and added dropwise with 1.05 eq. of an aqueous solution of methane sulfonic acid (2 M). The resulting solution was added dropwise to 60 v/w of acetonitrile. The precipitated solid was filtered and dried to give 8-(4-cyclobutyl-piperazin-1-yl)-9-ethyl-6,6-dimethyl-11-oxo-6,11-dihydro-5H-benzo[b]carbazole-3-carbonitrile monomethane sulfonic acid salt.

¹H-NMR (400 MHz, DMSO-D₆) δ: 12.75 (1H, s), 8.31 (1H, J=8.4 Hz), 8.07 (1H, s), 8.01 (1H, s), 7.59 (1H, d, J=7.9 Hz), 7.38 (1H, s), 3.58-2.84 (10H, m), 2.71 (2, q, J=7.5 Hz), 2.34 (3H, s), 2.20-2.04 (4H, m), 1.76-1.68 (8H, m), 1.26 (3H, t, J=7.5 Hz)

FARMS: m/z 453 [M+H]⁺

F6-17 Hydrochloride Salt

F6-17 was dissolved in 5 v/w of dimethyl sulfoxide and 0.39 v/w of aqueous solution of hydrochloric acid (6 N), and then the dissolved solution was subjected to freeze-drying. To the freeze-dried product, a mixture of 4.0 v/w of water and 1.3 v/w of ethanol was added. The precipitated crystals were filtered and dried to give the F6-17 hydrochloride salt.

F6-17 Maleate Salt

A mixture containing F6-17 and maleic acid, which is added in an amount of 0.38 times the weight of F6-17 was dissolved in 10 v/w of dimethyl acetamide at 80° C. The dissolved solution was cooled to room temperature, and added dropwise with a mixture of 5.8 v/w of acetone and 5.8 v/w of water followed by stirring at room temperature. 3.5 v/w of water was further added dropwise, and the precipitated crystals were filtered and dried to give the F6-17 maleate salt.

F6-17 L-Tartrate Salt

A mixture containing F6-17 and L-tartaric acid, which is added in an amount of 0.51 times the weight of F6-17, was dissolved in 6 v/w of dimethyl acetamide at 80° C. The dissolved solution was cooled to room temperature, and added dropwise with 37 v/w of acetonitrile followed by stirring at room temperature all night and all day. The precipitated crystals were filtered and dried to give the F6-17 tartrate salt. The F6-17 tartrate salt obtained was pulverized by using a jet mill.

F6-17 Citrate Salt

A mixture containing F6-17 and citric acid, which is added in an amount of 0.50 times the weight of F6-17, was dissolved in 6 v/w of dimethyl acetamide at 80° C. The dissolved solution was cooled to room temperature, and added dropwise with 12 v/w of acetonitrile. The precipitated crystals were filtered and dried to give the F6-17 citrate salt. The F6-17 citrate salt obtained was pulverized by using a jet mill.

F6-17 Malate Salt

A mixture containing F6-17 and L-malic acid, which is added in an amount of 0.46 times the weight of F6-17, was dissolved in 8 v/w of dimethyl acetamide at 80° C. The dissolved solution was cooled to room temperature, and added dropwise with 62 v/w of acetonitrile. The precipitated crystals were filtered and dried to give the F6-17 malate salt.

Production Example 33

Compound F3-2

9-Bromo-6,6-dimethyl-11-oxo-8-(4-pyrrolidin-1-yl-piperidin-1-yl)-6,11-dihydro-5H-benzo[b]carbazole-3-carbonitrile

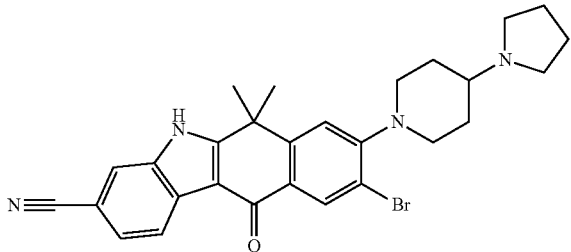 [SMILES: CC1(C)c2cc(N3CCC(N4CCCC4)CC3)c(Br)cc2C(=O)c2c1[nH]c1cc(C#N)ccc21]

With the same condition as the Compound B2-1, the title compound was synthesized from the Compound F2 and 4-pyrrolidin-1-yl-piperidine.

LCMS: m/z 517, 519 [M+H]$^+$
HPLC retention time: 1.70 minutes (analysis condition S)

Production Example 34

Compound F5-4

9-Ethynyl-6,6-dimethyl-11-oxo-8-(4-pyrrolidin-1-yl-piperidin-1-yl)-6,11-dihydro-5H-benzo[b]carbazole-3-carbonitrile

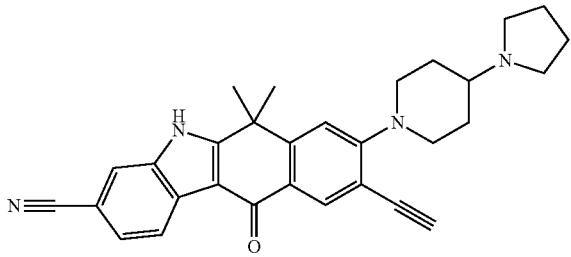 [SMILES: C#Cc1cc2c(cc1N1CCC(N3CCCC3)CC1)C(C)(C)c1[nH]c3cc(C#N)ccc3c1C2=O]

With the same condition as the method for synthesizing the Compound E4-2-1, the Compound E4-2-2 (9-(3-hydroxy-3-methyl-but-1-ynyl)-8-methoxy-6,6-dimethyl-11-oxo-6,11-dihydro-5H-benzo[b]carbazole-3-carbonitrile (Compound E4-2-1, 21.3 mg, 0.05 mmol) and sodium hydride (3.2 mg, 1.5 eq.) were dissolved in THF, and the mixture was stirred overnight at 50° C. Water was added to the reaction solution and the residues obtained after concentration under reduced pressure were purified by HPLC to obtain the Compound E4-2-2 (9-ethynyl-8-methoxy-6,6-dimethyl-11-oxo-6,11-dihydro-5H-benzo[b]carbazole-3-carbonitrile) (brown solid, 9.6 mg, 31%)), the title compound was synthesized from the Compound F3-2.

$^1$H-NMR (270 MHz, DMSO-D$_6$) δ: 8.29 (1H, d, J=8.2 Hz), 8.14 (1H, s), 8.00 (1H, s), 7.58 (1H, dd, J=8.1, 1.3 Hz), 7.24 (1H, s), 4.50 (1H, s), 3.70-3.83 (2H, m), 3.34-3.48 (1H, m), 2.83-2.98 (2H, m), 2.45-2.58 (2H, m), 2.10-2.23 (2H, m), 1.90-2.03 (2H, m), 1.76 (61-1, s), 1.51-1.74 (6H, m).

LCMS: m/z 463 [M+H]$^+$
HPLC retention time: 1.60 minutes (analysis condition S)

Production Example 35

Compound B2-4

6,6-Dimethyl-11-oxo-8-(4-pyrrolidin-1-yl-piperidin-1-yl)-6,11-dihydro-5H-benzo[b]carbazole-3-carbonitrile

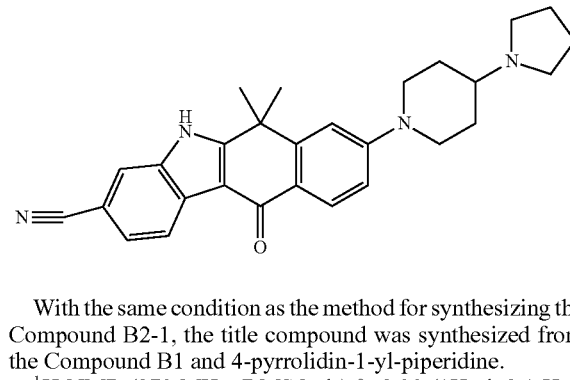

With the same condition as the method for synthesizing the Compound B2-1, the title compound was synthesized from the Compound B1 and 4-pyrrolidin-1-yl-piperidine.

$^1$H-NMR (270 MHz, DMSO-d$_6$) δ: 8.30 (1H, d, 8.1 Hz), 8.01 (1H, d, 8.7 Hz), 7.97 (1H, s), 7.56 (1H, d, 8.6 Hz), 7.20 (1H, s), 3.94-3.90 (2H, m), 3.30-3.28 (4H, m), 2.95 (2H, t, 11.8 Hz), 2.24-2.20 (1H, m), 1.95-1.91 (2H, m), 1.75 (6H, s), 1.70-1.66 (4H, m), 1.54-1.52 (2H, m)

LCMS: m/z 439 [M+H]$^+$

Production Example 36

Compound F5-43

8-(4-Cyclobutyl-piperazin-1-yl)-9-ethynyl-6,6-dimethyl-11-oxo-6,11-dihydro-5H-benzo[b]carbazole-3-carbonitrile

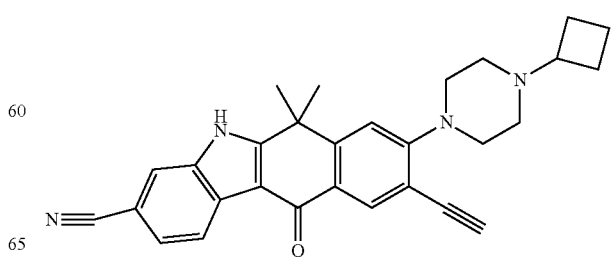

Under nitrogen atmosphere, to the MeCN (8 ml) suspension of 9-bromo-8-(4-cyclobutyl-piperazin-1-yl)-6,6-dimethyl-11-oxo-6,11-dihydro-5H-benzo[b]carbazole-3-carbonitrile (Compound F4-10, 200 mg, 0.397 mmol), ethynyltriisopropylsilane (268 mg, 3.0 eq.), 2-dicyclohexylphosphino-2',4',6'-triisopropylbiphenyl (Xphos) (39 mg, 0.2 eq.), Pd(CH$_3$CN)$_2$Cl$_2$ (11 mg, 0.1 eq.) and cesium carbonate (518 mg, 4.0 eq.) were added and the mixture was stirred and heated under reflux condition until the reaction is completed. Upon the completion of the reaction, distilled water was poured into the reaction solution, which was then extracted with ethyl acetate. The organic layer was washed with aqueous solution of sodium chloride and dried over sodium sulfate. The drying agent was removed by filtration and the residues obtained after concentration under reduced pressure were purified by silica gel column chromatography (ethyl acetate/methanol) to obtain 8-(4-cyclobutyl-piperazin-1-yl)-6,6-dimethyl-1'-oxo-9-[(triisopropylsilanyl)-ethynyl]-6,11-dihydro-5H-benzo[b]carbazole-3-carbonitrile (179 mg, 74%). To the THF (6 ml) solution of the obtained compound (179 mg, 0.295 mmol), 1 M THF solution (710 µl) of tetrabutylammonium fluoride was added and the mixture was stirred until the reaction was completed. Upon the completion of the reaction, ethyl acetate was poured into the reaction solution, which was then washed with distilled water and dried over sodium sulfate. The drying agent was removed by filtration and the residues obtained after concentration under reduced pressure were washed with a mixture solvent of ethanol and distilled water to obtain the title compound (67 mg, 92%).

$^1$H-NMR (400 MHz, DMSO-d$_6$) δ: 12.85 (1H, s), 8.31 (1H, d, 7.9 Hz), 8.20 (1H, s), 8.03 (1H, s), 7.62 (1H, d, 7.9 Hz), 7.35 (1H, s), 4.62 (1H, s), 3.94-4.03 (2H, m), 3.79-3.89 (1H, m), 3.48-3.54 (2H, m), 3.27-3.38 (2H, m), 2.96-3.16 (2H, m), 2.30-2.41 (2H, m), 2.16-2.26 (2H, m), 1.72-1.85 (8H, m)

LCMS: m/z 449 [M+H]$^+$

HPLC retention time: 2.69 minutes (analysis condition W)

Production Example 37

Compound F6-18

8-(4-Cyclobutyl-piperazin-1-yl)-6,6-dimethyl-11-oxo-9-propyl-6,11-dihydro-5H-benzo[b]carbazole-3-carbonitrile

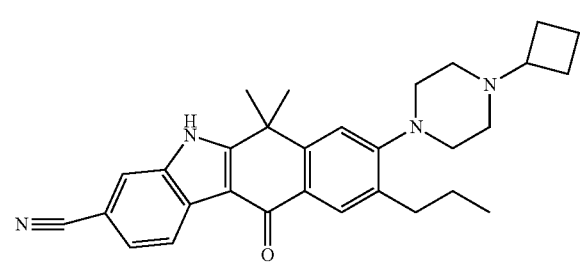 [SMILES: CCCc1cc2c(cc1N1CCN(C3CCC3)CC1)C(C)(C)c1[nH]c3cc(C#N)ccc3c1C2=O]

With the same condition as the method for synthesizing the Compound B3-13-1, the title compound was synthesized from the Compound F5-44.

$^1$H-NMR (400 MHz, DMSO-d$_6$) δ: 12.69 (1H, s), 8.31 (1H, d, 7.9 Hz), 8.01 (1H, s), 7.99 (1H, s), 7.60 (1H, d, 7.9 Hz), 7.39 (1H, s), 2.92-3.02 (4H, m), 2.75-2.84 (1H, m), 2.65 (2H, t, 7.3 Hz), 2.38-2.48 (4H, m), 1.96-2.06 (2H, m), 1.78-1.87 (2H, m), 1.75 (6H, s), 1.62-1.73 (4H, m), 0.97 (3H, t, 7.3 Hz)

LCMS: m/z 467 [M+H]$^+$

HPLC retention time: 2.96 minutes (analysis condition W)

Production Example 38

Compound B4-7

8-(1-Isopropyl-piperidin-4-yl)-6,6-dimethyl-11-oxo-6,11-dihydro-5H-benzo[b]carbazole-3-carbonitrile

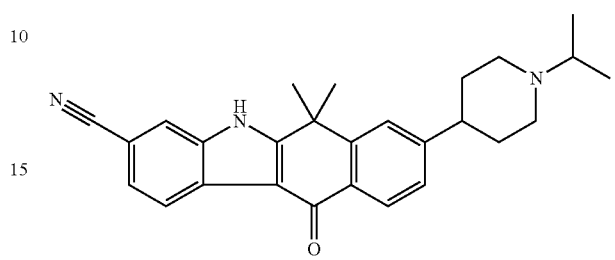

With the same condition as the method for synthesizing the Compound B3-32, the title compound was synthesized from the Compound B3-13-2 and acetone.

$^1$H-NMR (400 MHz, DMSO-d$_6$) δ: 12.77 (1H, s), 8.32 (1H, d, 7.9 Hz), 8.13 (1H, d, 7.9 Hz), 8.01 (1H, s), 7.73 (1H, s), 7.61 (1H, d, 9.1 Hz), 7.39 (1H, d, 9.8 Hz), 2.93 (2H, d, 11.0 Hz), 2.77-2.71 (1H, m), 2.67-2.62 (1H, m), 2.25 (2H, t, 10.1 Hz), 1.80-1.73 (10H, m), 1.02 (6H, d, 6.7 Hz)

LCMS: m/z 412 [M+H]$^+$

HPLC retention time: 1.60 minutes (analysis condition S)

Production Example 39

Compound B2-1

8-(4-Isopropyl-piperazin-1-yl)-6,6-dimethyl-11-oxo-6,11-dihydro-5H-benzo[b]carbazole-3-carbonitrile

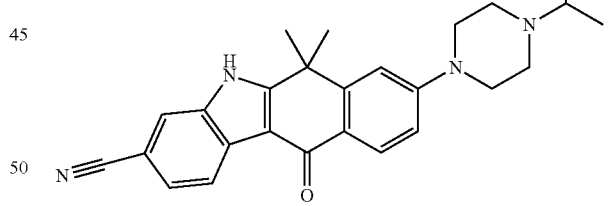

Trifluoro-methane sulfonic acid 3-cyano-6,6-dimethyl-11-oxo-6,11-dihydro-5H-benzo[b]carbazol-8-yl ester (Compound B1, 40 mg, 0.0921 mmol) was dissolved in NMP (1 ml) and added with 1-isopropylpiperazine (236 mg, 20 eq.). The mixture was stirred at 120° C. for 3 hours. After cooling to room temperature, purification was carried out by HPLC to obtain the target compound (white powder, 12.8 mg, 34%).

$^1$H-NMR (270 MHz, DMSO-d$_6$) δ: 8.30 (1H, d, 8.1 Hz), 8.03 (1H, d, 8.6 Hz), 7.98 (1H, s), 7.56 (1H, d, 8.6 Hz), 7.21 (1H, s), 7.04 (1H, d, 9.1 Hz), 3.40-3.37 (4H, m), 2.73-2.65 (1H, m), 2.61-2.58 (4H, m), 1.75 (61-1, s), 1.02 (6H, d, 6.6 Hz)

LCMS: m/z 413 [M+H]$^+$

Production Example 40

Compound F3-10

4-(9-Bromo-3-cyano-6,6-dimethyl-11-oxo-6,11-dihydro-5H-benzo[b]carbazol-8-yl)-piperazine-1-carboxylic acid tert-butyl ester

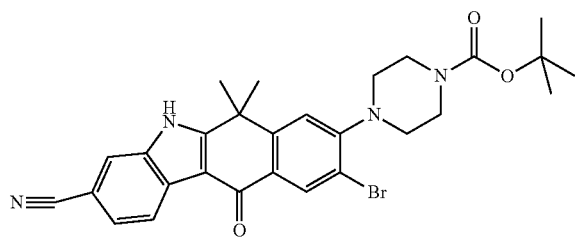 [SMILES: CC(C)(C)OC(=O)N1CCN(c2cc3c(cc2Br)C(=O)c2c([nH]c4cc(C#N)ccc24)C3(C)C)CC1]

With the same condition as the method for synthesizing the Compound B2-1, the title compound was synthesized from the Compound F2 and piperazine-1-carboxylic acid tert-butyl ester.

LCMS: m/z 549, 551 [M+H]$^+$
HPLC retention time: 4.61 minutes (analysis condition W)

Production Example 41

Compound F5-15-1

4-(3-Cyano-9-cyclopropyl-6,6-dimethyl-11-oxo-6,11-dihydro-5H-benzo[b]carbazol-8-yl)-piperazine-1-carboxylic acid tert-butyl ester

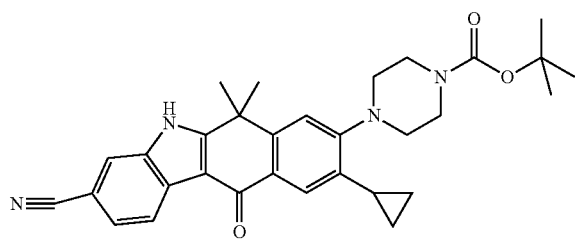 [SMILES: CC(C)(C)OC(=O)N1CCN(c2cc3c(cc2C2CC2)C(=O)c2c([nH]c4cc(C#N)ccc24)C3(C)C)CC1]

With the same condition as the method for synthesizing the Compound E4-7-1 (to 9-bromo-8-methoxy-6,6-dimethyl-11-oxo-6,11-dihydro-5H-benzo[b]carbazole-3-carbonitrile (Compound E3-1-1, 300 mg, 0.759 mmol), 4-(4,4,5,5-tetramethyl-[1,3,2]dioxaborolan-2-yl)-3,6-dihydro-2H-pyridine-1-carboxylic acid tert-butyl ester (282 mg, 0.911 mmol, 1.2 eq.), Pd(PPh$_3$)$_2$Cl$_2$ (26.6 mg, 0.0379 mmol, 0.05 eq.) and sodium carbonate (241 mg, 2.28 mmol, 3.0 eq.), DME (5 ml) and water (1 ml) were added. The mixture was subjected to reduced pressure under ultrasonication treatment, followed by filling with nitrogen. This procedure was repeated five times to remove air. The mixture was stirred at 80° C. for 80 minutes under nitrogen atmosphere. Pd(PPh$_3$)$_2$Cl$_2$ (26.6 mg, 0.0379 mmol, 0.05 eq.) was added and the mixture was further stirred at 80° C. for 20 minutes. Then, the mixture was cooled to room temperature, and added with water and ethyl acetate. The insoluble matters were filtered through Celite. The organic layer was dried over sodium sulfate. The drying agent was removed by filtration, followed by concentration under reduced pressure to obtain the Compound E4-7-1 (4-(3-cyano-8-methoxy-6,6-dimethyl-11-oxo-6,11-dihydro-5H-benzo[b]carbazole-9-yl)-3,6-dihydro-2H-pyridine-1-carboxylic acid tert-butyl ester) as a crude product (gray powder)), the title compound was synthesized from the Compound F3-10 and potassium cyclopropyltrifluoroborate.

$^1$H-NMR (400 MHz, DMSO-d$_6$) δ: 8.55 (1H, s), 8.28-8.25 (1H, m), 7.98-7.95 (1H, m), 7.62 (1H, s), 7.32 (1H, s), 3.56-3.53 (4H, m), 3.09-3.07 (4H, m), 2.22-2.18 (1H, m), 1.73 (6H, br s), 1.44 (9H, s), 1.08-1.05 (2H, m), 0.77-0.76 (2H, m)
LCMS: m/z 511 [M+H]$^+$
HPLC retention time: 4.50 minutes (analysis condition W)

Production Example 42

Compound F5-15-2

9-Cyclopropyl-6,6-dimethyl-11-oxo-8-piperazin-1-yl-6,11-dihydro-5H-benzo[b]carbazole-3-carbonitrile

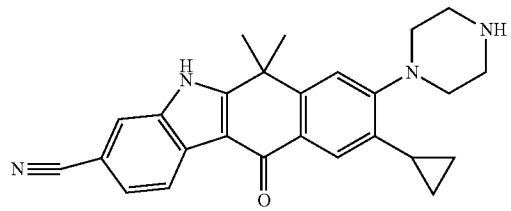 [SMILES: CC1(C)c2cc(N3CCNCC3)c(C3CC3)cc2C(=O)c2c1[nH]c1cc(C#N)ccc21]

With the same condition as the method for synthesizing the Compound A8-1, the title compound was synthesized from the Compound F5-15-1.
LCMS: m/z 411 [M+H]$^+$
HPLC retention time: 2.67 minutes (analysis condition W)

Production Example 43

Compound F5-46

8-(4-Cyclobutyl-piperazin-1-yl)-9-cyclopropyl-6,6-dimethyl-11-oxo-6,11-dihydro-5H-benzo[b]carbazole-3-carbonitrile

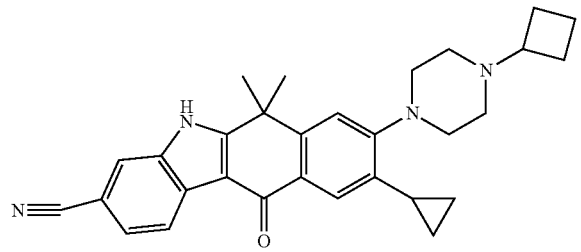 [SMILES: CC1(C)c2cc(N3CCN(C4CCC4)CC3)c(C3CC3)cc2C(=O)c2c1[nH]c1cc(C#N)ccc21]

With the same condition as the method for synthesizing the Compound B3-32, the title compound was synthesized from the Compound F5-15-2 and cyclobutanone.

$^1$H-NMR (400 MHz, DMSO-d$_6$) δ: 8.23 (1H, d, 8 Hz), 7.92 (1H, br.s), 7.59 (1H, s), 7.47 (1H, br.d, 8 Hz), 7.28 (1H, s), 3.12 (4H, br.s), 2.80 (1H, dddd, 8, 8, 8, 8 Hz), 2.20-2.13 (111, m), 2.01 (2H, br.s), 1.86-1.68 (10H, m), 1.05 (2H, d, 8 Hz), 0.76 (2H, d, 4 Hz) LCMS: m/z 465 [M+H]$^+$
HPLC retention time: 2.79 minutes (analysis condition W)
Compound F5-46 Hydrochloride Salt
8-(4-Cyclobutyl-piperazin-1-yl)-9-cyclopropyl-6,6-dimethyl-11-oxo-6,11-dihydro-5H-benzo[b]carbazole-3-carbonitrile was added with 1.05 eq. of 6 N hydrochloric acid and DMSO and dissolved therein. After freeze-drying, the mixture was crystallized from ethanol containing 25% water to give 8-(4-cyclobutyl-piperazin-1-yl)-9-cyclopropyl-6,6-dimethyl-11-oxo-6,11-dihydro-5H-benzo[b]carbazole-3-carbonitrile monohydrochloride salt.

$^1$H-NMR (400 MHz, DMSO-d$_6$) δ: 12.81 (1H, s), 10.64 (1H, br.s), 8.32-8.29 (1H, m), 8.01 (1H, s), 7.67 (1H, s), 7.61-7.60 (1H, m), 7.33 (1H, s), 4.00-3.39 (6H, m), 3.28-3.02 (3H, m), 2.45-2.05 (5H, m), 1.83-1.77 (8H, m), 1.09-1.07 (2H, m), 0.81-0.80 (2H, m)

LCMS: m/z 465 [M+H]$^+$

F5-46 mesylate salt

F5-46 was dissolved in 5 v/w of dimethyl sulfoxide and 1.1 v/w of aqueous solution of mesylic acid (2 N), and then the dissolved solution was subjected to freeze-drying. To the freeze-dried product, 5 v/w of benzyl alcohol was added. The precipitated crystals were filtered and dried to give the F5-46 monomesylate salt.

Production Example 44

Compound A7-24

8-(2-Bromo-ethoxy)-6,6-dimethyl-11-oxo-6,11-dihydro-5H-benzo[b]carbazole-3-carbonitrile

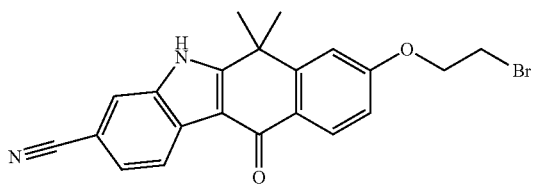 [SMILES: CC1(C)c2cc(OCCBr)ccc2C(=O)c2c1[nH]c1cc(C#N)ccc21]

With the same condition as the Compound A7-1 (8-hydroxy-6,6-dimethyl-11-oxo-6,11-dihydro-5H-benzo[b]carbazole-3-carbonitrile (Compound A6, 30 mg, 0.099 mmol) was dissolved in THF (1 mL), added with 4-hydroxy-piperidine-1-carboxylic acid tert-butyl ester (40 mg, 2 eq.), triphenylphosphine (52 mg, 2 eq.), and diisopropyl azo dicarboxylate (43 µL, 2 eq.) in order, and stirred at room temperature for 4 hours. The reaction solution was poured into water, and then extracted with ethyl acetate. The organic layer was washed with brine and dried over sodium sulfate. The drying agent was removed by filtration and the residues obtained after concentration under reduced pressure were purified by silica gel column chromatography (ethyl acetate/hexane) to obtain the Compound A7-1 (4-(3-cyano-6,6-dimethyl-11-oxo-6,11-dihydro-5H-benzo[b]carbazol-8-yl oxy)-piperidin-1-carboxylic acid tert-butyl ester) (37 mg, 76%)), the title compound was synthesized from the Compound A6 and 2-bromoethanol.

$^1$H-NMR (270 MHz, DMSO-d$_6$) δ: 12.75 (1H, br.s), 8.32 (1H, d, J=8.2 Hz), 8.17 (1H, d, J=8.6 Hz), 8.01 (1H, s), 7.61 (1H, dd, J=8.2, 1.4 Hz), 7.40 (1H, d, J=2.2 Hz), 7.12 (1H, dd, J=8.6, 2.2 Hz), 4.50 (2H, t, J=5.3 Hz), 3.88 (2H, t, J=5.3 Hz), 1.77 (6H, s).

LCMS: m/z 409, 411 [M+H]$^+$

HPLC retention time: 2.48 minutes (analysis condition S)

Production Example 45

Compound A8-10

8-(2-Tert-butylamino-ethoxy)-6,6-dimethyl-11-oxo-6,11-dihydro-5H-benzo[b]carbazole-3-carbonitrile

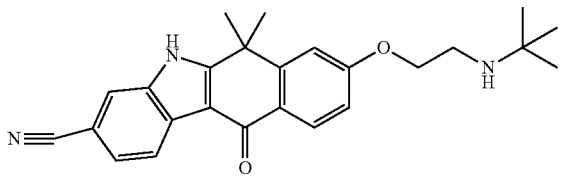 [SMILES: CC(C)(C)NCCOc1ccc2c(c1)C(C)(C)c1[nH]c3cc(C#N)ccc3c1C2=O]

With the same synthesis condition as the Compound A7-17 (8-hydroxy-6,6-dimethyl-11-oxo-6,11-dihydro-5H-benzo[b]carbazole-3-carbonitrile (Compound A6, 25 mg, 0.083 mmol) was dissolved in N,N-dimethylacetamide (1 mL), added with 2-chloroethyldiethylamine (16 mg, 1.1 eq.) and cesium carbonate (54 mg, 2 eq.) in order and stirred at 100° C. for 4 hours. The reaction solution was poured into water and extracted with ethyl acetate. The organic layer was washed with brine and dried over sodium sulfate. The drying agent was removed by filtration and the residues obtained after concentration under reduced pressure were purified by amino silica gel column chromatography (ethyl acetate/hexane) to obtain the Compound A7-17 (8-(2-diethylamino-ethoxy)-6, 6-dimethyl-11-oxo-6,11-dihydro-5H-benzo[b]carbazole-3-carbonitrile) (11 mg, 32%)), the title compound was synthesized from the Compound A7-24 and tert-butyl amine.

$^1$H-NMR (400 MHz, DMSO-d$_6$) δ: 12.71 (1H, s), 8.32 (1H, d, 7.9 Hz), 8.15 (1H, d, 9.1 Hz), 8.07 (1d, 1.8 Hz), 7.60 (1H, dd, 1.8, 7.9 Hz), 7.35 (1H, d, 2.4 Hz), 7.09 (1H, dd, 2.4, 9.1 Hz), 4.16 (2H, t, 6.1 Hz), 2.91 (2H, t, 6.1 Hz), 1.77 (6H, s), 1.08 (9H, s)

LCMS: nth 402 [M+H]$^+$

HPLC retention time: 2.55 minutes (analysis condition W)

Production Example 46

Compound F3-3

9-Bromo-8-(4-methanesulfonyl-piperazin-1-yl)-6,6-dimethyl-11-oxo-6,11-dihydro-5H-benzo[b]carbazole-3-carbonitrile

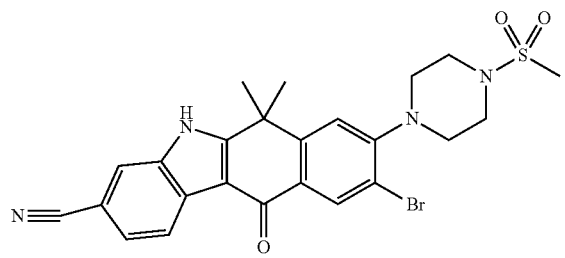 [SMILES: CC1(C)c2cc(N3CCN(S(C)(=O)=O)CC3)c(Br)cc2C(=O)c2c1[nH]c1cc(C#N)ccc21]

With the same condition as the method for synthesizing the Compound B2-1, the title compound was synthesized from the Compound F2 and 1-methanesulfonyl piperazine.

LCMS: m/z 527, 529 [M+H]$^+$

HPLC retention time: 2.48 minutes (analysis condition S)

Production Example 47

Compound F5-1

9-Ethynyl-8-(4-methanesulfonyl-piperazin-1-yl)-6,6-dimethyl-11-oxo-6,11-dihydro-5H-benzo[b]carbazole-3-carbonitrile

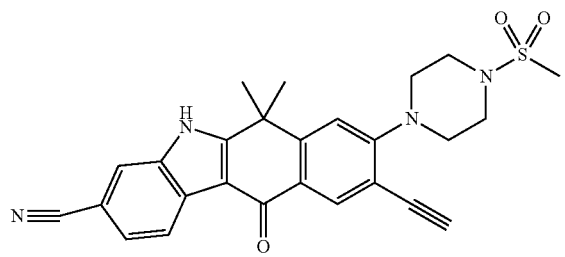 [SMILES: C#Cc1cc2c(cc1N1CCN(S(C)(=O)=O)CC1)C(C)(C)c1[nH]c3cc(C#N)ccc3c1C2=O]

With the same condition as the method for synthesizing the Compound F5-43, the title compound was synthesized from the Compound F3-3.

$^1$H-NMR (270 MHz, DMSO-D$_6$) δ: 12.78 (1H, s), 8.31 (1H, dd, J=8.1, 0.7 Hz), 8.19 (1H, s), 8.02 (1H, dd, J=1.4, 0.7 Hz), 7.61 (1H, dd, J=8.2, 1.4 Hz), 7.33 (1H, 4.55 (1H, s), 3.43 (4H, br), 2.98 (3H, s), 1.79 (6H, s).

LCMS: m/z 473 [M+H]$^+$

HPLC retention time: 2.27 minutes (analysis condition S)

Production Example 48

Compound F4-10

9-Bromo-8-(4-cyclobutyl-piperazin-1-yl)-6,6-dimethyl-11-oxo-6,11-dihydro-5H-benzo[b]carbazole-3-carbonitrile

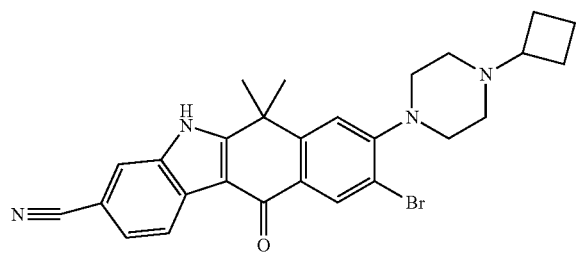 [SMILES: CC1(C)c2cc(N3CCN(C4CCC4)CC3)c(Br)cc2C(=O)c2c1[nH]c1cc(C#N)ccc21]

With the same condition as the method for synthesizing the Compound B3-32, the title compound was synthesized from the Compound F3-9 and cyclobutanone.

$^1$H-NMR (400 MHz, DMSO-d$_6$) δ: 8.23-8.29 (2H, m), 8.00 (1H, s), 7.55 (1H, d, 7.9 Hz), 7.45 (1H, s), 4.04-4.15 (1H, m), 3.10-3.20 (4H, m), 2.39-2.48 (4H, m), 1.97-2.06 (2H, m), 1.78-1.88 (2H, m), 1.77 (6H, s), 1.61-1.72 (2H, m) LCMS: m/z 503, 505 [M+H]$^+$

HPLC retention time: 2.78 minutes (analysis condition W)

Production Example 49

Compound F6-8

6,6-Dimethyl-8-(4-oxetan-3-yl-piperazin-1-yl)-11-oxo-9-propyl-6,11-dihydro-5,1-benzo[b]carbazole-3-carbonitrile

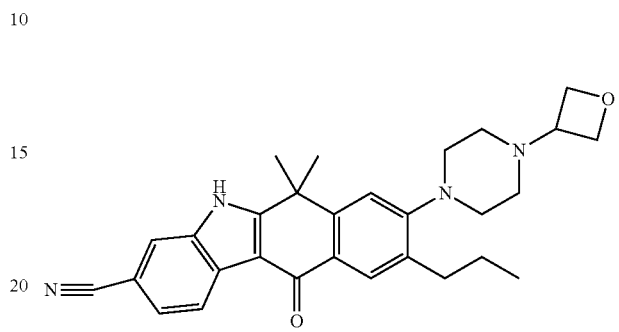

With the same condition as the method for synthesizing the Compound B3-13-1, the title compound was synthesized from the Compound F5-22.

$^1$H-NMR (270 mHz DMSO-D$_6$) δ: 12.75 (1H, s), 8.30 (1H, d, J=8.2 Hz), 8.01-7.97 (2H, m), 7.59 (1H, d, J=7.1 Hz), 7.38 (1H, s), 4.51 (4H, dt, J=27.7, 6.3 Hz), 3.55-3.49 (1H, m), 3.02-2.96 (4H, m), 2.63 (2H, t, J=7.3 Hz), 2.47-2.41 (4H, m), 1.73 (6H, s), 1.70-1.61 (2H, m), 0.94 (3H, t, J=7.4 Hz).

LCMS: m/z 469 [M+H]$^+$

HPLC retention time: 1.57 minutes (analysis condition S)

Production Example 50

Compound F3-4

9-Bromo-6,6-dimethyl-8-morpholin-4-yl-11-oxo-6,11-dihydro-5H-benzo[b]carbazole-3-carbonitrile

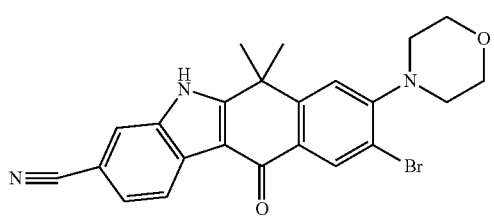 [SMILES: CC1(C)c2cc(N3CCOCC3)c(Br)cc2C(=O)c2c1[nH]c1cc(C#N)ccc21]

With the same condition as the method for synthesizing the Compound B2-1, the title compound was synthesized from the Compound F2 and morpholine.

LCMS: m/z 450, 452 [M+H]$^+$

HPLC retention time: 2.65 minutes (analysis condition S)

Production Example 51

Compound F5-5

9-Ethynyl-6,6-dimethyl-8-morpholin-4-yl-1 oxo-6,11-dihydro-5H-benzo[b]carbazole-3-carbonitrile

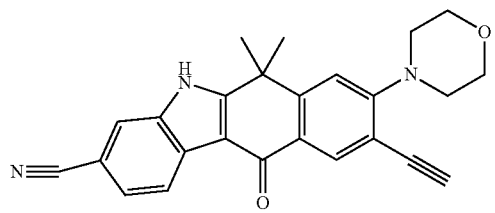 [SMILES: C#Cc1cc2c(cc1N1CCOCC1)C(C)(C)c1[nH]c3cc(C#N)ccc3c1C2=O]

With the same condition as the method for synthesizing the Compound E4-2-1 and the Compound E4-2-2, the title compound was synthesized from the Compound F3-4.

$^1$H-NMR (400 MHz, DMSO-$d_6$) δ: 12.82 (1H, s), 8.31 (1H, d, J=7.9 Hz), 8.18 (1H, s), 8.02 (1H, s), 7.61 (1H, d, J=7.9 Hz), 7.28 (1H, s), 4.53 (1H, s), 3.80 (4H, s), 3.36 (4H, s), 1.79 (6H, s).

LCMS: m/z 396 [M+H]$^+$

HPLC retention time: 2.32 minutes (analysis condition S)

Examples 1 to 269

Ultramicro Scale Dissolution Test

Materials

Materials for the Compound F6-20 (free form) were produced according to the method described in the Production example 30 and used. Additives shown in Table 2 were used as additives for the formulation.

(Preparation of Composition)

For the Examples 1 to 269, the Compound F6-20 was dissolved in DMSO to the concentration of 0.5 mg/mL and added with hydrochloric acid in the same molar equivalent of the Compound F6-20. Then, various dissolution aids which have been dissolved or dispersed in the solvent shown in Table 2 were added to the Compound F6-20 to have 100% weight ratio. The resultant was freeze-dried to obtain a mixture of the Compound F6-20 and various dissolution aids.

TABLE 2

Dissolution aids and solvents for dissolving them

| Example | Dissolution aid | Manufacturer | Solvent |
|---|---|---|---|
| 1 | D-Sorbitol | B Food Science | DMSO |
| 2 | D-Mannitol | Towa Chemical Co. Ltd | DMSO |
| 3 | Pregelatinized starch | Nippon Starch Chemical Co., Ltd. | DMSO |
| 4 | Ethylcellulose | Colorcon | DMSO |
| 5 | Sodium carboxymethyl starch | DMV | water |
| 6 | Citric acid | Showa Kako Corporation | DMSO |
| 7 | Sodium citrate | Showa Kako Corporation | water |
| 8 | Crosscarmellose sodium | Asahi Kasei Chemicals Corporation | DMSO |
| 9 | Microcrystalline cellulose | Asahi Kasei Chemicals Corporation | water |
| 10 | Titanium oxide | Freund Industrial Co., Ltd. | DMSO |
| 11 | Stearic acid | NOF Corporation | DMSO |
| 12 | Magnesium stearate | Merck & Co., Inc. | DMSO |
| 13 | Sucrose | Ensuiko Sugar Refining | DMSO |
| 14 | Tocopherol | Eisai Co., Ltd. | DMSO |
| 15 | Lactose | DMV | DMSO |
| 16 | Hydroxypropyl cellulose | Nippon Soda Co., Ltd. | DMSO |
| 17 | Hydroxypropylmethyl cellulose 2910 | Shin-Etsu Chemical Co., Ltd. | DMSO |
| 18 | Sodium stearyl fumarate | Kimura Sangyo Co., Ltd. | DMSO |
| 19 | Propylene glycol | Kanto Chemical Co., Inc. | DMSO |
| 20 | Povidone | BASF | DMSO |
| 21 | Polysorbate 80 | Nihon Surfactant Kogyo K.K. | DMSO |
| 22 | Methacrylic acid copolymer LD | Rohm GmbH | DMSO |
| 23 | Methyl cellulose | Shin-Etsu Chemical Co., Ltd. | DMSO |
| 24 | Sodium lauryl sulfate | Nikko Chemicals Co., Ltd. | DMSO |
| 25 | Ascorbic acid | Wako Pure Chemical Industries Ltd. | DMSO |
| 26 | Sodium alginate | Wako Pure Chemical Industries Ltd. | water |
| 27 | Disodium edetate | Wako Pure Chemical Industries Ltd. | water |
| 28 | Caramel | Semba Tohka Industries | DMSO |

TABLE 2-continued

Dissolution aids and solvents for dissolving them

| Example | Dissolution aid | Manufacturer | Solvent |
|---|---|---|---|
| 29 | Carmellose calcium | Nichirin Chemical Industries, Ltd. | water |
| 30 | Dried aluminum hydroxide gel | Kyowa Chemical Industry Co., Ltd. | water |
| 31 | Calcium citrate | Kanto Chemical Co., Inc. | DMSO |
| 32 | Triethyl citrate | Wako Pure Chemical Industries Ltd. | DMSO |
| 33 | Cholesterol | Wako Pure Chemical Industries Ltd. | DMSO |
| 34 | Magnesium oxide | Kyowa Chemical Industry Co., Ltd. | DMSO |
| 35 | Dibutylhydroxy toluene | Kanto Chemical Co., Inc. | DMSO |
| 36 | Sodium hydroxide | Wako Pure Chemical Industries Ltd. | water |
| 37 | Stearyl alcohol | NOF Corporation | DMSO |
| 38 | Polyoxyl 40 stearate | Nikko Chemicals Co., Ltd. | DMSO |
| 39 | Purified shellac | The Japan Shellac Industries, Ltd. | DMSO |
| 40 | Cetostearyl alcohol | NOF Corporation | DMSO |
| 41 | Soy bean oil | Kaneda | DMSO |
| 42 | Sodium hydrogencarbonate | Wako Pure Chemical Industries Ltd. | water |
| 43 | Magnesium carbonate | Kyowa Chemical Industry Co., Ltd. | DMSO |
| 44 | Sodium dehydroacetate | Wako Pure Chemical Industries Ltd. | DMSO |
| 45 | Triacetin | Yuki Gosei Kogyo Co., Ltd. | DMSO |
| 46 | Fumaric acid | Kanto Chemical Co., Inc. | DMSO |
| 47 | Macrogol 1500 | NOF Corporation | DMSO |
| 48 | Macrogol 400 | Wako Pure Chemical Industries Ltd. | DMSO |
| 49 | Macrogol 6000 | Sanyo Chemical Industries, Ltd. | water |
| 50 | Sorbitan monolaurate | Kao Corporation | DMSO |
| 51 | Magnesium sulfate | Wako Pure Chemical Industries Ltd. | water |
| 52 | Sodium dihydrogen phosphate | Nacalai Tesque | water |
| 53 | 1,3-Butylene glycol | Daicel Chemical Industries Ltd. | DMSO |
| 54 | 2-Mercaptobenzimidazole | Kawaguchi Chemical Industry Co., Ltd. | DMSO |
| 55 | β-Cyclodextrin | Funakoshi Co., Ltd. | DMSO |
| 56 | Tocopherol | Tama Biochemical Co., Ltd. | DMSO |
| 57 | DL-Malic acid | Wako Pure Chemical Industries Ltd. | DMSO |
| 58 | Stearic L-ascorbate ester | Tokyo Chemical Industry Co., Ltd. | DMSO |
| 59 | L-Aspartic acid | Kanto Chemical Co., Inc. | DMSO |
| 60 | L-Glutamine | Wako Pure Chemical Industries Ltd. | water |
| 61 | Sodium L-tartrate | Wako Pure Chemical Industries Ltd. | water |
| 62 | L-Phenylalanine | Kanto Chemical Co., Inc. | DMSO |
| 63 | N-Cocoyl-L-arginineethylester DL-pyrrolidonecarboxylate | Ajinomoto Co., Inc. | DMSO |
| 64 | Ethyl actylrate•methyl methacrylate copolymer dispersion | EVONIK | DMSO |
| 65 | Starch grafted acrylate 1000 | Sanyo Chemical Industries, Ltd. | water |
| 66 | Adipic acid | Kanto Chemical Co., Inc. | DMSO |
| 67 | Aminoalkyl methacrylate copolymer E | Rohm GmbH | DMSO |
| 68 | Taurine | Wako Pure Chemical Industries Ltd. | DMSO |

TABLE 2-continued

Dissolution aids and solvents for dissolving them

| Example | Dissolution aid | Manufacturer | Solvent |
|---|---|---|---|
| 69 | Powdered *acacia* | San-Ei Yakuhin Boeki Co., Ltd. | water |
| 70 | Sodium bisulfite | Junsei Chemical Co., Ltd. | DMSO |
| 71 | Sodium sulfite | Kanto Chemical Co., Inc. | water |
| 72 | Alginic acid | Wako Pure Chemical Industries Ltd. | DMSO/water |
| 73 | Propylene glycol alginate | Wako Pure Chemical Industries Ltd. | water |
| 74 | Alpha thioglycerol | Wako Pure Chemical Industries Ltd. | DMSO |
| 75 | Ammonia water | Wako Pure Chemical Industries Ltd. | DMSO |
| 76 | Inositol | Wako Pure Chemical Industries Ltd. | DMSO |
| 77 | Erythorbic acid | Wako Pure Chemical Industries Ltd. | DMSO |
| 78 | Hydrochloric acid | Junsei Chemical Co., Ltd. | DMSO |
| 79 | Cysteine hydrochloride | Sigma | DMSO |
| 80 | Olive oil | Nikko Chemicals Co., Ltd. | DMSO |
| 81 | Casein | Wako Pure Chemical Industries Ltd. | DMSO |
| 82 | Sodium caseinate | Wako Pure Chemical Industries Ltd. | water |
| 83 | Fructose | Wako Pure Chemical Industries Ltd. | DMSO |
| 84 | Carnauba wax | Freund Corporation | DMSO |
| 85 | Carboxy vinyl polymer | Lubrizol | DMSO |
| 86 | Carboxymethyl ethyl cellulose | Sanyo Chemical Industries, Ltd. | DMSO |
| 87 | Carmellose | Nichirin Chemical Industries Ltd. | DMSO/water |
| 88 | Powdered agar | Ina Food Industry Co., Ltd. | DMSO |
| 89 | Xylitol | Mitsubishi Shoji Foodtech Co., Ltd. | DMSO |
| 90 | Guar gum | San-Ei Yakuhin Boeki Co., Ltd. | DMSO |
| 91 | Monobasic sodium citrate | Kanto Chemical Co., Inc. | DMSO |
| 92 | Dibasic sodium citrate | Kanto Chemical Co., Inc. | water |
| 93 | Glycine | Wako Pure Chemical Industries Ltd. | water |
| 94 | Glycerol esters of fatty acids | Sasol Germany | DMSO |
| 95 | Calcium glycerophosphate | Kanto Chemical Co., Inc. | water |
| 96 | Glucono-δ-lactone | Wako Pure Chemical Industries Ltd. | DMSO |
| 97 | Gluconic acid | Kanto Chemical Co., Inc. | DMSO |
| 98 | Calcium gluconate | Wako Pure Chemical Industries Ltd. | water |
| 99 | Sodium gluconate | Wako Pure Chemical Industries Ltd. | water |
| 100 | Magnesium aluminosilicate | Fuji Chemical Industry Co., Ltd. | DMSO |
| 101 | Calcium silicate | Tomita Pharmaceutical Co., Ltd. | DMSO |
| 102 | Magnesium silicate | Kyowa Chemical Industry Co., Ltd. | DMSO |
| 103 | Synthetic aluminum silicate | Kyowa Chemical Industry Co., Ltd. | DMSO |
| 104 | Concentrated glycerin | NOF Corporation | DMSO |
| 105 | Powdered hydrogenated maltose starch syrup | Mitsubishi Shoji Foodtech Co., Ltd. | DMSO |
| 106 | Succinic acid | Wako Pure Chemical Industries Ltd. | DMSO |
| 107 | Copolyvidone | BASF | DMSO |
| 108 | Sesame oil | Kaneda | DMSO |
| 109 | Acetic acid | Kanto Chemical Co., Inc. | DMSO |
| 110 | Calcium acetate | Nacalai Tesque | water |

TABLE 2-continued

Dissolution aids and solvents for dissolving them

| Example | Dissolution aid | Manufacturer | Solvent |
|---|---|---|---|
| 111 | Tocopherol acetate | Eisai Co., Ltd. | DMSO |
| 112 | Cellulose acetate phthalate | Sigma | DMSO |
| 113 | Tartaric acid | Wako Pure Chemical Industries Ltd. | DMSO |
| 114 | Potassium bitartrate | Wako Pure Chemical Industries Ltd. | water |
| 115 | Safflower oil | Nikko Chemicals Co., Ltd. | DMSO |
| 116 | Diisopropanolamine | Wako Pure Chemical Industries Ltd. | DMSO |
| 117 | Dioctyl sodium sulfosuccinate | Sanyo Chemical Industries, Ltd. | DMSO |
| 118 | Dihydroxy aluminum aminoacetate | Kyowa Chemical Industry Co., Ltd. | DMSO |
| 119 | Dimethyl polysiloxane | Sigma | DMSO/water |
| 120 | Potassium sodium tartrate | Wako Pure Chemical Industries Ltd. | water |
| 121 | Sucrose esters of fatty acids | Dai-ichi Kogyo Seiyaku Co., Ltd. | DMSO |
| 122 | Potassium hydroxide | Junsei Chemical Co., Ltd. | water |
| 123 | Calcium hydroxide | Junsei Chemical Co., Ltd. | DMSO/water |
| 124 | Magnesium hydroxide | Kyowa Chemical Industry Co., Ltd. | DMSO |
| 125 | Squalane | Mitsuba Trading Co., Ltd. | DMSO |
| 126 | Aluminum stearate | Wako Pure Chemical Industries Ltd. | DMSO |
| 127 | Purified gelatin | Nippi Inc. | DMSO |
| 128 | Zein | Wako Pure Chemical Industries Ltd. | DMSO |
| 129 | Sorbitan sesquioleate | Nihon Surfactant Kogyo K.K. | DMSO |
| 130 | Cetanol | Nikko Chemicals Co., Ltd. | DMSO |
| 131 | Cetomacrogol 1000 | Nihon Surfactant Kogyo K.K. | DMSO |
| 132 | Diethyl sebacate | Nihon Surfactant Kogyo K.K. | DMSO |
| 133 | Sorbitan esters of fatty acids | Lion Corporation | DMSO |
| 134 | Tribasic calcium phosphate | Kanto Chemical Co., Inc. | DMSO |
| 135 | Soybean lecithin | Tsuji Oil Mill Co., Ltd. | water |
| 136 | Skimmed milk powder | Wako Pure Chemical Industries Ltd. | DMSO/water |
| 137 | Ammonium carbonate | Wako Pure Chemical Industries Ltd. | DMSO |
| 138 | Calcium carbonate | Kanto Chemical Co., Inc. | DMSO |
| 139 | Sodium carbonate | Wako Pure Chemical Industries Ltd. | water |
| 140 | Sodium thioglycolate | Wako Pure Chemical Industries Ltd. | water |
| 141 | Dextran 40 | Wako Pure Chemical Industries Ltd. | water |
| 142 | Dextrin | Nippon Starch Chemical Co., Ltd. | DMSO |
| 143 | Starch | Wako Pure Chemical Industries | DMSO |
| 144 | Tragacanth | Suzu Pharmaceutical Co., Ltd. | DMSO |
| 145 | Triisopropanolamine | Wako Pure Chemical Industries Ltd. | DMSO |
| 146 | Triethanolamine | Wako Pure Chemical Industries Ltd. | DMSO |
| 147 | Sorbitan trioleate | Nihon Surfactant Kogyo K.K. | DMSO |
| 148 | Lactic acid | Acros | DMSO |
| 149 | Aluminum lactate | Wako Pure Chemical Industries Ltd. | DMSO |
| 150 | Calcium lactate | Wako Pure Chemical Industries Ltd. | DMSO |
| 151 | Sodium lactate solution | Wako Pure Chemical Industries Ltd. | DMSO |

TABLE 2-continued

Dissolution aids and solvents for dissolving them

| Example | Dissolution aid | Manufacturer | Solvent |
|---|---|---|---|
| 152 | Ascorbic acid palmitate | Wako Pure Chemical Industries Ltd. | DMSO |
| 153 | Hydroxyethyl cellulose | Wako Pure Chemical Industries Ltd. | DMSO |
| 154 | Hydroxyethyl methyl cellulose | Tokyo Chemical Co., Ltd. | DMSO |
| 155 | Hydroxypropyl starch | Freund Industrial Co., Ltd. | DMSO |
| 156 | Hydroxypropylmethyl cellulose acetate succinate | Shin-Etsu Chemical Co., Ltd. | DMSO |
| 157 | Hydroxypropylmethyl cellulose phthalate | Shin-Etsu Chemical Co., Ltd. | DMSO |
| 158 | Piperonyl butoxide | Wako Pure Chemical Industries Ltd. | DMSO |
| 159 | Castor oil | Itoh Oil Chemicals Co., Ltd. | DMSO |
| 160 | Sunflower oil | Nikko Chemicals Co., Ltd. | DMSO |
| 161 | Sodium pyrosulfite | Wako Pure Chemical Industries Ltd. | DMSO |
| 162 | Phytic acid | Wako Pure Chemical Industries Ltd. | DMSO |
| 163 | Diethyl phthalate | Wako Pure Chemical Industries Ltd. | DMSO |
| 164 | Dibutyl phthalate | Wako Pure Chemical Industries Ltd. | DMSO |
| 165 | Butylhydroxy anisole | Wako Pure Chemical Industries Ltd. | DMSO |
| 166 | Butyl phthalyl butyl glycolate | Wako Pure Chemical Industries Ltd. | DMSO |
| 167 | Glucose | Kanto Chemical Co., Inc. | DMSO |
| 168 | Mono sodium fumarate | Wako Pure Chemical Industries Ltd. | water |
| 169 | Pullulan | Hayashibara Co., Ltd. | DMSO |
| 170 | Sodium propionate | Wako Pure Chemical Industries Ltd. | DMSO |
| 171 | Pectin | Wako Pure Chemical Industries Ltd. | water |
| 172 | Benzotriazole | Wako Pure Chemical Industries Ltd. | DMSO |
| 173 | Boric acid | Junsei Chemical Co., Ltd. | DMSO |
| 174 | Borax | Wako Pure Chemical Industries Ltd. | DMSO |
| 175 | Sodium polyacrylate | Wako Pure Chemical Industries Ltd. | water |
| 176 | Polyoxyethylene (105) polyoxypropylene (5) glycol | Freund Industrial Co., Ltd. | DMSO |
| 177 | Polyoxyethylene (160) polyoxypropylene (30) glycol | ADEKA | DMSO |
| 178 | Polyoxyethylene (20) polyoxypropylene (20) glycol | ADEKA | DMSO |
| 179 | Polyoxyethylene alkyl ether | Dai-ichi Kogyo Seiyaku Co., Ltd. | DMSO |
| 180 | Polyoxyethylene octyl phenyl ether | Wako Pure Chemical Industries Ltd. | DMSO |
| 181 | Polyoxyethylene hydrogenated castor oil 20 | NOF Corporation | DMSO |
| 182 | Polyoxyethylene hydrogenated castor oil 60 | Nikko Chemicals Co., Ltd. | DMSO |
| 183 | Polyoxyethylene stearyl ether | Nihon Surfactant Kogyo K.K. | DMSO |
| 184 | Polyoxyethylene cetyl ether | Nihon Surfactant Kogyo K.K. | DMSO |
| 185 | Polyoxyl 35 castor oil | Sigma | DMSO |
| 186 | Poly(sodium 4-styrene sulfonate) | Sigma | water |
| 187 | Polysorbate 20 | Nacalai Tesque | DMSO |
| 188 | Polysorbate 40 | Nihon Surfactant Kogyo K.K. | DMSO |
| 189 | Polysorbate 60 | Nihon Surfactant Kogyo K.K. | DMSO |
| 190 | Polyvinyl acetal diethyl amino acetate | Mitsubishi-Kagaku Foods Corporation | DMSO |

TABLE 2-continued

Dissolution aids and solvents for dissolving them

| Example | Dissolution aid | Manufacturer | Solvent |
| --- | --- | --- | --- |
| 191 | Polyvinyl alcohol | Japan Vam & Poval Co., Ltd. | DMSO |
| 192 | Polybutene | NOF Corporation | water |
| 193 | Sodium polyphosphate | Wako Pure Chemical Industries Ltd. | water |
| 194 | Macrogol 1540 | NOF Corporation | DMSO |
| 195 | Macrogol 20000 | Sanyo Chemical Industries, Ltd. | water |
| 196 | Macrogol 4000 | NOF Corporation | DMSO |
| 197 | Macrogol 600 | NOF Corporation | DMSO |
| 198 | Maltitol | Mitsubishi Shoji Foodtech Co., Ltd. | DMSO |
| 199 | Maltose | Hayashibara Shoji Inc. | DMSO |
| 200 | Maleic acid | Wako Pure Chemical Industries Ltd. | DMSO |
| 201 | Strach syrup | Hayashibara Shoji Inc. | DMSO |
| 202 | Isopropyl myristate | Nihon Surfactant Kogyo K.K. | DMSO |
| 203 | Anhydrous sodium sulfate | Wako Pure Chemical Industries Ltd. | water |
| 204 | Meglumine | Tokyo Chemical Industry Co., Ltd. | DMSO |
| 205 | Methacrylic acid copolymer L | Rohm GmbH | DMSO |
| 206 | Methacrylic acid copolymer S | Rohm GmbH | DMSO |
| 207 | Magnesium aluminometasilicate | Fuji Chemical Industry Co., Ltd. | DMSO/water |
| 208 | Sodium metaphosphate | Kanto Chemical Co., Inc. | DMSO |
| 209 | Methane sulfonic acid | Wako Pure Chemical Industries Ltd. | DMSO |
| 210 | Cotton seed oil | Okamura Oil Mill Ltd. | DMSO |
| 211 | Monoethanolamine | Wako Pure Chemical Industries Ltd. | DMSO |
| 212 | Sorbitan monooleate | Nihon Surfactant Kogyo K.K. | DMSO |
| 213 | Sorbitan monostearate | Nihon Surfactant Kogyo K.K. | DMSO |
| 214 | Lauryl dimethylamine oxide solution | Sigma | DMSO |
| 215 | Lauric acid diethanolamide | Kao Corporation | DMSO |
| 216 | Lauromacrogol | NOF Corporation | DMSO |
| 217 | Peanut oil | Kaneda | DMSO |
| 218 | Isopropyl linolate | Nihon Surfactant Kogyo K.K. | DMSO |
| 219 | Sulfuric acid | Junsei Chemical Co., Ltd. | DMSO |
| 220 | Aluminum sulfate | Wako Pure Chemical Industries Ltd. | water |
| 221 | Aluminum potassium sulfate | Wako Pure Chemical Industries Ltd. | DMSO |
| 222 | Calcium sulfate | Wako Pure Chemical Industries Ltd. | water |
| 223 | Phosphoric acid | Kanto Chemical Co., Inc. | DMSO |
| 224 | Calcium monohydrogen phosphate | Wako Pure Chemical Industries Ltd. | DMSO/water |
| 225 | Trisodium phosphate | Sigma | DMSO |
| 226 | Dibasic calcium phosphate | Fuji Chemical Industry Co., Ltd. | DMSO/water |
| 227 | Dibasic sodium phosphate hydrate | Wako Pure Chemical Industries Ltd. | water |
| 228 | Dibasic potassium phosphate | Wako Pure Chemical Industries Ltd. | water |
| 229 | Monobasic potassium phosphate | Wako Pure Chemical Industries Ltd. | DMSO |
| 230 | Monobasic calcium phosphate | Wako Pure Chemical Industries Ltd. | water |
| 231 | Powdered hydrolyzed gelatin | Nippi Inc. | DMSO |
| 232 | Hydrated silicon dioxide | Freund Industrial Co., Ltd. | DMSO |
| 233 | Light anhydrous silicic acid | Freund Industrial Co., Ltd. | DMSO/water |
| 234 | Partly pregelatinized starch | Asahi Kasei Chemicals Corporation | DMSO |

TABLE 2-continued

Dissolution aids and solvents for dissolving them

| Example | Dissolution aid | Manufacturer | Solvent |
|---|---|---|---|
| 235 | Propyl gallate | Wako Pure Chemical Industries Ltd. | DMSO |
| 236 | Amylopectin | Nippon Starch Chemical Co., Ltd. | DMSO |
| 237 | Epoxydation soybean oil | Kao Corporation | DMSO |
| 238 | Ammonium acetate | Kanto Chemical Co., Inc. | DMSO |
| 239 | Magnesia alumina hydrate | Kyowa Chemical Industry Co., Ltd. | DMSO |
| 240 | Sodium dodecyl benzene sulfonate | Kao Corporation | DMSO |
| 241 | Vinyl pyrrolidone vinyl acetate copolymer | Sigma | DMSO |
| 242 | Ammonium pentaborate | Kanto Chemical Co., Inc. | DMSO |
| 243 | Polyoxyethylene sorbitan monolaurate | Nihon Surfactant Kogyo K.K. | DMSO |
| 244 | Anhydrous sodium acetate | Wako Pure Chemical Industries Ltd. | DMSO |
| 245 | Sodium lauroyl sarcosinate | Nikko Chemicals Co., Ltd. | DMSO |
| 246 | Sodium polyoxyethylene laurylether phosphate | Nihon Surfactant Kogyo K.K. | DMSO |
| 247 | Amorphous silicon oxide hydrate | DSL. Japan Co., Ltd. | DMSO |
| 248 | DL-Alanine | Showa Chemical Industry Co., Ltd. | water |
| 249 | Sodium L-ascorbate | Wako Pure Chemical Industries Ltd. | DMSO |
| 250 | Sodium L-aspartate | Wako Pure Chemical Industries Ltd. | water |
| 251 | L-Arginine | Kanto Chemical Co., Inc. | water |
| 252 | L-Arginine hydrochloride | Wako Pure Chemical Industries Ltd. | water |
| 253 | Acetyl tryptophan | Wako Pure Chemical Industries Ltd. | DMSO |
| 254 | Acetanilide | Wako Pure Chemical Industries Ltd. | DMSO |
| 255 | Benzoic acid | Junsei Chemical Co., Ltd. | DMSO |
| 256 | Sodium benzoate | Wako Pure Chemical Industries Ltd. | DMSO |
| 257 | Hydroxypropyl cyclodextrin | Nihon Shokuhin Kako Co., Ltd. | DMSO |
| 258 | Sodium β-cyclodextrin sulfobutyl ether | CYDEX | DMSO |
| 259 | Polyoxyethylene (54) polyoxypropylene (39) glycol | ADEKA | DMSO |
| 260 | Sodium methyl sulfate | Tokyo Chemical Industry Co., Ltd. | DMSO |
| 261 | Sodium ethyl sulfate | Tokyo Chemical Industry Co., Ltd. | DMSO |
| 262 | Sodium butyl sulfate | Sigma | DMSO |
| 263 | Sodium octyl sulfate | Sigma | DMSO |
| 264 | Sodium decyl sulfate | Kanto Chemical Co., Inc. | DMSO |
| 265 | Sodium tetradecyl sulfate | Wako Pure Chemical Industries Ltd. | DMSO |
| 266 | Sodium hexadecylsulfate | Wako Pure Chemical Industries Ltd. | DMSO |
| 267 | Sodium octadecyl sulfate | Wako Pure Chemical Industries Ltd. | DMSO |
| 268 | Sodium chondroitin sulfate | Wako Pure Chemical Industries Ltd. | water |
| 269 | Dodecane | Wako Pure Chemical Industries Ltd. | DMSO |

Comparative Example 1

For Comparative example 1, the Compound F6-20 was dissolved in DMSO to the concentration of 0.5 mg/mL, added with hydrochloric acid in the same molar equivalent of the Compound F6-20, and freeze-dried.

Test Example 1

To Nos. 1 to 269 and Comparative example 1, FaSSIF (Fasted state simulated intestinal fluid, E. Galia et al. Pharm. Res. 15: 698Y705 (1998)), which is simulating fasted human intestinal fluids, was added and stirred with a shaker (trade name: Bio Shaker, manufactured by TAITEC) at stirring rate of 200 rpm. After stirring for 10 minutes and 240 minutes, respectively, the concentration was measured with high performance liquid chromatography (trade name; UFLC, manufactured by Shimadzu).

As a result, as shown in Table 3, it was found that solubility of the Compound F6-20 was significantly increased for citric acid (Example 6), hydroxypropyl cellulose (Example 16), hydroxypropylmethyl cellulose (Example 17), sodium stearyl fumarate (Example 18), methacrylate copolymer LD (Example 22), methyl cellulose (Example 23), sodium lauryl sulfate (Example 24), polyoxyl 40 stearate (Example 38), purified shellac (Example 39), sodium dehydroacetate (Example 44), fumaric acid (Example 46), DL-malic acid (Example 57), stearic L-ascorbate ester (Example 58), L-aspartic acid (Example 59), adipic acid (Example 66), amino alkylmethacrylate copolymer E (Example 67), propylene glycol alginate ester (Example 73), casein (Example 81), sodium caseinate (Example 82), a carboxyvinyl polymer (Example 85), carboxymethylethyl cellulose (Example 86), powdered agar (Example 88), guar gum (Example 90), succinic acid (Example 106), copolyvidone (Example 107), cellulose acetate phthalate (Example 112), tartaric acid (Example 113), dioctyl sodium sulfosuccinate (Example 117), zein (Example 128), skimmed milk powder (Example 136), sorbitan trioleate (Example 147), lactic acid (Example 148), aluminum lactate (Example 149), ascorbic acid palmitate (Example 152), hydroxyethylmethyl cellulose (Example 154), hydroxypropylmethyl cellulose acetate succinate (Example 156), polyoxyethylene (105) polyoxypropylene (5) glycol (Example 176), polyoxyethylene hydrogenated castor oil 60 (Example 182), polyoxyl 35 castor oil (Example 185), poly(sodium 4-styrene sulfonate) (Example 186), polyvinylacetal diethylaminoacetate (Example 190), polyvinyl alcohol (Example 191), maleic acid (Example 200), methacrylate copolymer S (Example 206), lauromacrogol (Example 216), sulfuric acid (Example 219), aluminum sulfate (Example 220), phosphoric acid (Example 223), monobasic calcium phosphate (Example 230), sodium dodecylbenzene sulfonate (Example 240), vinyl pyrrolidone vinyl acetate copolymer (Example 241), sodium lauroylsarco sine (Example 245), acetyl tryptophan (Example 253), sodium methyl sulfate (Example 260), sodium ethyl sulfate (Example 261), sodium butyl sulfate (Example 262), sodium octyl sulfate (Example 263), sodium decyl sulfate (Example 264), sodium tetradecyl sulfate (Example 265), sodium hexadecyl sulfate (Example 266), and sodium octadecyl sulfate (Example 267).

Among them, the effect was remarkable for citric acid (Example 6), hydroxypropyl cellulose (Example 16), hydroxypropylmethyl cellulose (Example 17), methacrylate copolymer LD (Example 22), methyl cellulose (Example 23), sodium lauryl sulfate (Example 24), purified shellac (Example 39), sodium dehydroacetate (Example 44), fumaric acid (Example 46), DL-malic acid (Example 57), stearic L-ascorbate ester (Example 58), L-aspartic acid (Example 59), adipic acid (Example 66), propylene glycol alginate ester (Example 73), casein (Example 81), sodium caseinate (Example 82), carboxymethylethyl cellulose (Example 86), succinic acid (Example 106), copolyvidone (Example 107), dioctyl sodium sulfosuccinate (Example 117), lactic acid (Example 148), aluminum lactate (Example 149), ascorbic acid palmitate (Example 152), hydroxyethylmethyl cellulose (Example 154), hydroxypropylmethyl cellulose acetate succinate (Example 156), polyoxyethylene hydrogenated castor oil 60 (Example 182), polyoxyl 35 castor oil (Example 185), poly(sodium 4-styrene sulfonate) (Example 186), polyvinylacetal diethylaminoacetate (Example 190), polyvinyl alcohol (Example 191), methacrylate copolymer S (Example 206), lauromacrogol (Example 216), sulfuric acid (Example 219), aluminum sulfate (Example 220), sodium dodecylbenzene sulfonate (Example 240), vinyl pyrrolidone.vinyl acetate copolymer (Example 241), acetyl tryptophan (Example 253), sodium decyl sulfate (Example 264), sodium tetradecyl sulfate (Example 265), and sodium octadecyl sulfate (Example 267).

Among them, the effect was particularly remarkable for citric acid (Example 6), hydroxypropyl cellulose (Example 16), hydroxypropylmethyl cellulose (Example 17), methacrylate copolymer LD (Example 22), methyl cellulose (Example 23), sodium lauryl sulfate (Example 24), purified shellac (Example 39), sodium dehydroacetate (Example 44), fumaric acid (Example 46), DL-malic acid (Example 57), L-aspartic acid (Example 59), adipic acid (Example 66), propylene glycol alginate ester (Example 73), sodium caseinate (Example 82), carboxymethylethyl cellulose (Example 86), succinic acid (Example 106), copolyvidone (Example 107), dioctyl sodium sulfosuccinate (Example 117), lactic acid (Example 148), aluminum lactate (Example 149), hydroxyethylmethyl cellulose (Example 154), hydroxypropylmethyl cellulose acetate succinate (Example 156), poly(sodium 4-styrene sulfonate) (Example 186), polyvinylacetal diethylaminoacetate (Example 190), methacrylate copolymer S (Example 206), sulfuric acid (Example 219), aluminum sulfate (Example 220), vinyl pyrrolidone.vinyl acetate copolymer (Example 241), and sodium decyl sulfate (Example 264).

TABLE 3

Effect of various dissolution aids on the solubility of Compound F6-20 hydrochloride salt (* $p < 0.05$,  $p < 0.01$, * $p < 0.001$)

| Example | Dissolution aid | Concentration after 10 min (μg/mL) | Concentration after 240 min (μg/mL) |
|---|---|---|---|
| Comparative example 1 | Not added | 5.0 ± 2.4 | 0.8 ± 0.3 |
| 1 | D-Sorbitol | 1.1 ± 0.3 | 0.6 ± 0.1 |
| 2 | D-Mannitol | 1.0 ± 0.1 | 0.5 ± 0.0 |
| 3 | Pregelatinized starch | 2.6 ± 0.5 | 0.5 ± 0.0 |
| 4 | Ethylcellulose | 3.1 ± 0.2 | 0.9 ± 0.1 |
| 5 | Sodium carboxymethyl starch | 2.0 ± 0.7 | 0.4 ± 0.1 |
| 6 | Citric acid | 5.1 ± 1.0 | 3.2 ± 0.1*** |
| 7 | Sodium citrate | 1.0 ± 0.3 | 0.3 ± 0.1 |
| 8 | Crosscarmellose sodium | 4.1 ± 2.6 | 1.2 ± 0.1 |
| 9 | Microcrystalline cellulose | 4.4 ± 0.7 | 0.3 ± 0.1 |
| 10 | Titanium oxide | 2.5 ± 0.3 | 1.1 ± 0.0 |
| 11 | Stearic acid | 1.9 ± 0.8 | 0.4 ± 0.0 |

TABLE 3-continued

Effect of various dissolution aids on the solubility of Compound F6-20 hydrochloride salt ($*$ p < 0.05, $$p < 0.01, $*$p < 0.001)

| Example | Dissolution aid | Concentration after 10 min (μg/mL) | Concentration after 240 min (μg/mL) |
|---|---|---|---|
| 12 | Magnesium stearate | 1.6 ± 0.3 | 0.5 ± 0.1 |
| 13 | Purified sucrose | 1.1 ± 0.2 | 0.5 ± 0.1 |
| 14 | Tocopherol | 1.9 ± 0.4 | 0.8 ± 0.1 |
| 15 | Lactose | 1.3 ± 0.4 | 0.4 ± 0.0 |
| 16 | Hydroxypropyl cellulose | 9.4 ± 2.5** | 2.9 ± 0.6*** |
| 17 | Hydroxypropylmethyl cellulose 2910 | 7.3 ± 2.1 | 2.2 ± 0.3*** |
| 18 | Sodium stearyl fumarate | 3.0 ± 0.3 | 1.3 ± 0.2 * |
| 19 | Propylene glycol | 1.3 ± 0.1 | 0.6 ± 0.2 |
| 20 | Povidone | 5.8 ± 1.3 | 0.6 ± 0.1 |
| 21 | Polysorbate 80 | 2.9 ± 0.8 | 0.5 ± 0.0 |
| 22 | Methacrylic acid copolymer LD | 4.9 ± 0.5 | 6.0 ± 0.5*** |
| 23 | Methyl cellulose | 7.2 ± 4.0 | 2.5 ± 0.0*** |
| 24 | Sodium lauryl sulfate | 19.6 ± 2.2*** | 6.3 ± 1.0*** |
| 25 | Ascorbic acid | 1.9 ± 0.6 | 0.6 ± 0.1 |
| 26 | Sodium alginate | 4.3 ± 0.4 | 0.3 ± 0.1 |
| 27 | Disodium edetate | 4.9 ± 2.1 | 0.3 ± 0.0 |
| 28 | Caramel | 3.0 ± 0.4 | 0.8 ± 0.1 |
| 29 | Carmellose calcium | 7.5 ± 1.7 | 0.7 ± 0.1 |
| 30 | Dried aluminum hydroxide gel | 3.2 ± 0.3 | 0.3 ± 0.1 |
| 31 | Calcium citrate | 0.5 ± 0.1 | 0.3 ± 0.2 |
| 32 | Triethyl citrate | 2.1 ± 0.4 | 0.6 ± 0.0 |
| 33 | Cholesterol | 2.3 ± 0.9 | 0.4 ± 0.1 |
| 34 | Magnesium oxide | 1.1 ± 0.1 | 0.1 ± 0.0 |
| 35 | Dibutylhydroxy toluene | 2.2 ± 0.3 | 0.5 ± 0.1 |
| 36 | Sodium hydroxide | 2.2 ± 0.2 | 0.4 ± 0.3 |
| 37 | Stearyl alcohol | 1.8 ± 0.1 | 0.6 ± 0.0 |
| 38 | Polyoxyl 40 stearate | 2.6 ± 0.4 | 1.4 ± 0.5 * |
| 39 | Purified shellac | 2.7 ± 0.2 | 2.6 ± 0.3*** |
| 40 | Cetostearyl alcohol | 1.9 ± 0.1 | 0.3 ± 0.0 |
| 41 | Soy bean oil | 1.5 ± 0.4 | 0.4 ± 0.0 |
| 42 | Sodium hydrogencarbonate | 1.9 ± 0.7 | 1.1 ± 0.8 |
| 43 | Magnesium carbonate | 1.5 ± 0.0 | 0.5 ± 0.2 |
| 44 | Sodium dehydroacetate | 12.7 ± 1.7*** | 14.8 ± 1.3*** |
| 45 | Triacetin | 2.4 ± 0.2 | 0.4 ± 0.0 |
| 46 | Fumaric acid | 5.5 ± 0.9 | 1.9 ± 0.0*** |
| 47 | Macrogol 1500 | 1.7 ± 0.2 | 0.6 ± 0.1 |
| 48 | Macrogol 400 | 1.7 ± 0.3 | 0.9 ± 0.1 |
| 49 | Macrogol 6000 | 3.8 ± 0.9 | 0.3 ± 0.1 |
| 50 | Sorbitan monolaurate | 0.7 ± 0.1 | 0.4 ± 0.0 |
| 51 | Magnesium sulfate | 2.4 ± 0.2 | 0.2 ± 0.1 |
| 52 | Sodium dihydrogen phosphate | 2.7 ± 0.2 | 0.3 ± 0.1 |
| 53 | 1,3-Butylene glycol | 1.3 ± 0.1 | 0.6 ± 0.0 |
| 54 | 2-Mercaptobenzimidazole | 0.7 ± 0.1 | 0.6 ± 0.1 |
| 55 | β-Cyclodextrin | 1.1 ± 0.3 | 0.6 ± 0.1 |
| 56 | Tocopherol | 1.5 ± 0.0 | 0.9 ± 0.1 |
| 57 | DL-Malic acid | 5.2 ± 0.6 | 2.8 ± 0.4*** |
| 58 | Stearic L-ascorbate ester | 2.6 ± 0.3 | 1.7 ± 0.2** |
| 59 | L-Aspartic acid | 5.2 ± 1.0 | 1.8 ± 0.2*** |
| 60 | L-Glutamine | 1.6 ± 0.4 | 0.2 ± 0.1 |
| 61 | Sodium L-tartrate | 4.8 ± 0.4 | 0.2 ± 0.1 |
| 62 | L-Phenylalanine | 2.7 ± 0.2 | 0.6 ± 0.1 |
| 63 | N-Cocoyl-L-arginineethylester DL-pyrrolidonecarboxylate | 0.3 ± 0.1 | 0.3 ± 0.0 |
| 64 | Ethyl actylrate • methyl methacrylate copolymer dispersion | 1.4 ± 0.0 | 0.7 ± 0.2 |
| 65 | Starch grafted acrylate 1000 | 1.8 ± 0.8 | 0.4 ± 0.2 |
| 66 | Adipic acid | 5.4 ± 0.6 | 1.9 ± 0.2*** |
| 67 | Aminoalkyl methacrylate copolymer E | 2.8 ± 1.0 | 1.3 ± 0.2 * |
| 68 | Taurine | 1.1 ± 0.2 | 0.6 ± 0.1 |
| 69 | Powdered acacia | 7.2 ± 2.3 | 0.6 ± 0.1 |
| 70 | Sodium bisulfite | 3.3 ± 0.3 | 0.9 ± 0.1 |
| 71 | Sodium sulfite | 2.8 ± 1.2 | 0.6 ± 0.1 |
| 72 | Alginic acid | 2.4 ± 1.1 | 1.0 ± 0.4 |
| 73 | Propylene glycol alginate | 15.7 ± 0.5*** | 1.1 ± 0.2 |
| 74 | Alpha thioglycerol | 1.5 ± 0.3 * | 0.7 ± 0.2 |
| 75 | Ammonia water | 1.3 ± 0.2 | 0.4 ± 0.0 |
| 76 | Inositol | 1.2 ± 0.1 | 0.5 ± 0.0 |

TABLE 3-continued

Effect of various dissolution aids on the solubility of Compound F6-20 hydrochloride salt (* $p < 0.05$, $p < 0.01$, *$p < 0.001$)

| Example | Dissolution aid | Concentration after 10 min (μg/mL) | Concentration after 240 min (μg/mL) |
|---|---|---|---|
| 77 | Erythorbic acid | 1.2 ± 0.1 | 0.5 ± 0.0 |
| 78 | Hydrochloric acid | 1.4 ± 0.2 | 0.6 ± 0.1 |
| 79 | Cysteine hydrochloride | 2.3 ± 0.2 | 1.1 ± 0.1 |
| 80 | Olive oil | 1.7 ± 0.5 | 0.8 ± 0.0 |
| 81 | Casein | 14.1 ± 2.5*** | 7.1 ± 0.9** |
| 82 | Sodium caseinate | 17.1 ± 3.0*** | 15.8 ± 4.8*** |
| 83 | Fructose | 0.7 ± 0.1 | 0.7 ± 0.2 |
| 84 | Carnauba wax | 2.8 ± 0.5 | 2.0 ± 2.1 |
| 85 | Carboxy vinyl polymer | 7.4 ± 0.4 * | 1.1 ± 0.2 |
| 86 | Carboxymethyl ethyl cellulose | 8.7 ± 3.1 | 9.5 ± 2.2*** |
| 87 | Carmellose | 1.9 ± 0.3 | 0.9 ± 0.1 |
| 88 | Powdered agar | 3.2 ± 0.1 | 1.3 ± 0.1 * |
| 89 | Xylitol | 1.3 ± 0.1 | 0.5 ± 0.0 |
| 90 | Guar gum | 2.8 ± 0.3 | 1.3 ± 0.1 * |
| 91 | Monobasic sodium citrate | 4.1 ± 0.6 | 0.7 ± 0.1 |
| 92 | Dibasic sodium citrate | 2.2 ± 0.5 | 0.9 ± 0.3 |
| 93 | Glycine | 2.7 ± 1.2 | 0.4 ± 0.0 |
| 94 | Glycerol esters of fatty acids | 1.1 ± 0.1 | 0.5 ± 0.1 |
| 95 | Calcium glycerophosphate | 0.9 ± 0.1 | 0.3 ± 0.0 |
| 96 | Glucono-δ-lactone | 1.6 ± 0.5 | 0.7 ± 0.0 |
| 97 | Gluconic acid | 1.0 ± 0.1 | 3.3 ± 2.0 |
| 98 | Calcium gluconate | 2.3 ± 0.9 | 0.3 ± 0.1 |
| 99 | Sodium gluconate | 5.7 ± 0.6 | 0.5 ± 0.2 |
| 100 | Magnesium aluminosilicate | 2.2 ± 0.1 | 0.5 ± 0.1 |
| 101 | Calcium silicate | 3.1 ± 1.2 | 0.5 ± 0.2 |
| 102 | Magnesium silicate | 2.8 ± 0.9 | 0.7 ± 0.2 |
| 103 | Synthetic aluminum silicate | 2.2 ± 0.5 | 0.5 ± 0.1 |
| 104 | Concentrated glycerin | 0.9 ± 0.0 | 1.9 ± 1.3 |
| 105 | Powdered hydrogenated maltose starch syrup | 0.8 ± 0.1 | 0.6 ± 0.1 |
| 106 | Succinic acid | 5.6 ± 0.5 | 3.8 ± 0.2*** |
| 107 | Copolyvidone | 14.1 ± 2.7*** | 2.0 ± 0.1*** |
| 108 | Sesame oil | 0.8 ± 0.1 | 1.0 ± 0.1 |
| 109 | Acetic acid | 1.0 ± 0.1 | 0.8 ± 0.0 |
| 110 | Calcium acetate | 2.5 ± 1.1 | 0.5 ± 0.1 |
| 111 | Tocopherol acetate | 1.1 ± 0.1 | 1.1 ± 0.1 |
| 112 | Cellulose acetate phthalate | 5.4 ± 0.6 | 19.0 ± 5.1 * |
| 113 | Tartaric acid | 3.3 ± 0.5 | 1.4 ± 0.2 * |
| 114 | Potassium bitartrate | 5.1 ± 0.8 | 0.4 ± 0.2 |
| 115 | Safflower oil | 0.8 ± 0.1 | 1.0 ± 0.1 |
| 116 | Diisopropanolamine | 0.3 ± 0.1 | 0.6 ± 0.1 |
| 117 | Dioctyl sodium sulfosuccinate | 4.9 ± 1.7 | 2.3 ± 0.1*** |
| 118 | Dihydroxy aluminum aminoacetate | 1.8 ± 0.2 | 0.4 ± 0.1 |
| 119 | Dimethyl polysiloxane | 1.6 ± 0.3 | 0.8 ± 0.1 |
| 120 | Potassium sodium tartrate | 4.6 ± 0.1 | 0.3 ± 0.1 |
| 121 | Sucrose esters of fatty acids | 2.4 ± 0.2 | 0.8 ± 0.1 |
| 122 | Potassium hydroxide | 3.4 ± 0.5 | 0.2 ± 0.1 |
| 123 | Calcium hydroxide | 0.7 ± 0.1 | 0.9 ± 0.1 |
| 124 | Magnesium hydroxide | 1.4 ± 0.1 | 0.5 ± 0.1 |
| 125 | Squalane | 1.2 ± 0.1 | 0.7 ± 0.3 |
| 126 | Aluminum stearate | 2.3 ± 0.5 | 0.6 ± 0.0 |
| 127 | Purified gelatin | 1.7 ± 0.2 | 0.7 ± 0.3 |
| 128 | Zein | 1.2 ± 0.1 | 1.4 ± 0.3 * |
| 129 | Sorbitan sesquioleate | 0.9 ± 0.2 | 0.7 ± 0.2 |
| 130 | Cetanol | 1.7 ± 0.1 | 0.3 ± 0.1 |
| 131 | Cetomacrogol 1000 | 4.5 ± 0.5 | 0.7 ± 0.1 |
| 132 | Diethyl sebacate | 1.0 ± 0.1 | 0.9 ± 0.0 |
| 133 | Sorbitan esters of fatty acids | 0.6 ± 0.1 | 0.7 ± 0.0 |
| 134 | Tribasic calcium phosphate | 5.0 ± 1.8 | 0.6 ± 0.1 |
| 135 | Soybean lecithin | 7.0 ± 1.4 | 0.4 ± 0.2 |
| 136 | Skimmed milk powder | 7.3 ± 3.3 | 10.0 ± 2.0 * |
| 137 | Ammonium carbonate | 1.1 ± 0.3 | 0.9 ± 0.1 |
| 138 | Calcium carbonate | 2.1 ± 0.4 | 0.5 ± 0.1 |
| 139 | Sodium carbonate | 2.5 ± 1.0 | 0.8 ± 0.2 |
| 140 | Sodium thioglycolate | 3.5 ± 0.2 | 0.3 ± 0.0 |
| 141 | Dextran 40 | 3.9 ± 1.0 | 0.4 ± 0.0 |
| 142 | Dextrin | 2.2 ± 0.1 | 0.9 ± 0.1 |
| 143 | Starch | 2.6 ± 0.3 | 1.0 ± 0.1 |
| 144 | Tragacanth | 6.7 ± 6.0 | 0.5 ± 0.1 |
| 145 | Triisopropanolamine | 0.2 ± 0.0 | 0.5 ± 0.1 |
| 146 | Triethanolamine | 1.2 ± 0.1 | 1.1 ± 0.0 |

TABLE 3-continued

Effect of various dissolution aids on the solubility of Compound F6-20 hydrochloride salt (* p < 0.05, p < 0.01, *p < 0.001)

| Example | Dissolution aid | Concentration after 10 min (μg/mL) | Concentration after 240 min (μg/mL) |
|---|---|---|---|
| 147 | Sorbitan trioleate | 1.0 ± 0.2 | 1.4 ± 0.1 * |
| 148 | Lactic acid | 2.7 ± 0.2 | 1.8 ± 0.2*** |
| 149 | Aluminum lactate | 3.5 ± 0.7 | 2.5 ± 0.3*** |
| 150 | Calcium lactate | 1.9 ± 0.2 | 0.5 ± 0.1 |
| 151 | Sodium lactate solution | 1.4 ± 0.2 | 0.5 ± 0.1 |
| 152 | Ascorbic acid palmitate | 3.6 ± 0.2 | 1.8 ± 0.2** |
| 153 | Hydroxyethyl cellulose | 1.8 ± 0.2 | 0.6 ± 0.1 |
| 154 | Methyl hydroxyethyl-cellulose | 4.3 ± 1.2 | 4.3 ± 0.7*** |
| 155 | Hydroxypropyl starch | 1.5 ± 0.2 | 0.6 ± 0.1 |
| 156 | Hydroxypropylmethyl cellulose acetate succinate | 6.1 ± 1.3 | 16.0 ± 3.5*** |
| 157 | Hydroxypropylmethyl cellulose phthalate | 7.6 ± 3.2 | 2.8 ± 1.4 |
| 158 | Piperonyl butoxide | 1.7 ± 0.3 | 0.6 ± 0.0 |
| 159 | Castor oil | 1.4 ± 0.3 | 0.4 ± 0.1 |
| 160 | Sunflower oil | 1.8 ± 0.2 | 0.4 ± 0.1 |
| 161 | Sodium pyrosulfite | 3.4 ± 0.2 | 0.8 ± 0.0 |
| 162 | Phytic acid | 4.9 ± 0.2 | 1.2 ± 0.1 |
| 163 | Diethyl phthalate | 0.9 ± 0.0 | 0.5 ± 0.0 |
| 164 | Dibutyl phthalate | 0.9 ± 0.1 | 0.4 ± 0.1 |
| 165 | Butylhydroxy anisole | 1.3 ± 0.1 | 0.5 ± 0.1 |
| 166 | Butyl phthalyl butyl glycolate | 0.7 ± 0.0 | 0.5 ± 0.1 |
| 167 | Glucose | 0.8 ± 0.1 | 0.5 ± 0.0 |
| 168 | Monosodium fumarate | 6.8 ± 1.6 | 0.5 ± 0.0 |
| 169 | Pullulan | 1.5 ± 0.3 | 0.5 ± 0.0 |
| 170 | Sodium propionate | 0.7 ± 0.1 | 0.4 ± 0.1 |
| 171 | Pectin | 2.5 ± 1.7 | 0.5 ± 0.2 |
| 172 | Benzotriazole | 1.0 ± 0.3 | 0.7 ± 0.0 |
| 173 | Boric acid | 0.7 ± 0.1 | 0.4 ± 0.0 |
| 174 | Borax | 1.0 ± 0.1 | 0.5 ± 0.1 |
| 175 | Sodium polyacrylate | 2.4 ± 0.5 | 0.5 ± 0.2 |
| 176 | Polyoxyethylene (105) polyoxypropylene (5) glycol | 1.7 ± 0.1 | 4.9 ± 1.7 * |
| 177 | Polyoxyethylene (160) polyoxypropylene (30) glycol | 0.7 ± 0.1 | 0.5 ± 0.1 |
| 178 | Polyoxyethylene (20) polyoxypropylene (20) glycol | 2.2 ± 0.1 | 0.7 ± 0.1 |
| 179 | Polyoxyethylene alkyl ether | 1.5 ± 0.1 | 0.6 ± 0.1 |
| 180 | Polyoxyethylene octyl phenyl ether | 1.0 ± 0.3 | 0.6 ± 0.0 |
| 181 | Polyoxyethylene hydrogenated castor oil 20 | 1.8 ± 0.2 | 1.4 ± 0.9 |
| 182 | Polyoxyethylene hydrogenated castor oil 60 | 3.3 ± 0.5 | 1.8 ± 0.3** |
| 183 | Polyoxyethylene stearyl ether | 1.1 ± 0.2 | 0.3 ± 0.0 |
| 184 | Polyoxyethylene cetyl ether | 1.8 ± 0.3 | 0.4 ± 0.0 |
| 185 | Polyoxyl 35 castor oil | 4.5 ± 0.5 | 2.2 ± 0.6** |
| 186 | Poly(sodium 4-styrene sulfonate) | 11.2 ± 2.3*** | 63.7 ± 14.6*** |
| 187 | Polysorbate 20 | 2.4 ± 0.5 | 0.5 ± 0.1 |
| 188 | Polysorbate 40 | 3.1 ± 0.2 | 0.8 ± 0.1 |
| 189 | Polysorbate 60 | 2.5 ± 0.1 | 0.7 ± 0.1 |
| 190 | Polyvinyl acetal diethyl aminoacetate | 8.4 ± 1.1 * | 11.2 ± 0.3*** |
| 191 | Polyvinyl alcohol | 1.7 ± 0.6 | 1.5 ± 0.2** |
| 192 | Polybutene | 4.4 ± 1.8 | 0.5 ± 0.0 |
| 193 | Sodium polyphosphate | 1.5 ± 0.5 | 0.7 ± 0.4 |
| 194 | Macrogol 1540 | 2.1 ± 0.1 | 0.5 ± 0.1 |
| 195 | Macrogol 20000 | 2.6 ± 0.3 | 0.5 ± 0.1 |
| 196 | Macrogol 4000 | 2.0 ± 0.2 | 0.4 ± 0.1 |
| 197 | Macrogol 600 | 1.7 ± 0.1 | 0.6 ± 0.1 |
| 198 | Maltitol | 0.8 ± 0.0 | 0.5 ± 0.0 |
| 199 | Maltose | 0.9 ± 0.1 | 0.5 ± 0.1 |
| 200 | Maleic acid | 1.4 ± 0.3 | 1.3 ± 0.1 * |
| 201 | Starch syrup | 1.3 ± 0.1 | 0.4 ± 0.0 |
| 202 | Isopropyl myristate | 1.3 ± 0.0 | 0.4 ± 0.1 |
| 203 | Anhydrous sodium sulfate | 1.6 ± 0.8 | 0.4 ± 0.1 |
| 204 | Meglumine | 1.0 ± 0.1 | 0.4 ± 0.0 |
| 205 | Methacrylic acid copolymer L | 5.1 ± 0.1 | 0.9 ± 0.1 |

TABLE 3-continued

Effect of various dissolution aids on the solubility of Compound F6-20 hydrochloride salt (* $p < 0.05$,  $p < 0.01$, * $p < 0.001$)

| Example | Dissolution aid | Concentration after 10 min (μg/mL) | Concentration after 240 min (μg/mL) |
|---|---|---|---|
| 206 | Methacrylic acid copolymer S | 2.3 ± 0.6 | 6.6 ± 0.4*** |
| 207 | Magnesium aluminometasilicate | 2.9 ± 0.7 | 0.7 ± 0.1 |
| 208 | Sodium metaphosphate | 1.2 ± 0.1 | 0.5 ± 0.0 |
| 209 | Methane sulfonic acid | 4.9 ± 0.9 | 1.1 ± 0.5 |
| 210 | Cotton seed oil | 0.5 ± 0.1 | 0.5 ± 0.0 |
| 211 | Monoethanolamine | 1.1 ± 0.0 | 0.4 ± 0.0 |
| 212 | Sorbitan monooleate | 1.0 ± 0.3 | 0.5 ± 0.1 |
| 213 | Sorbitan monostearate | 1.5 ± 0.2 | 0.4 ± 0.0 |
| 214 | Lauryl dimethylamine oxide solution | 0.3 ± 0.1 | 0.4 ± 0.0 |
| 215 | Lauric acid diethanolamide | 0.3 ± 0.1 | 0.3 ± 0.1 |
| 216 | Lauromacrogol | 10.1 ± 2.3** | 0.8 ± 0.0 |
| 217 | Peanut oil | 0.8 ± 0.0 | 0.4 ± 0.1 |
| 218 | Isopropyl linolate | 0.9 ± 0.1 | 0.5 ± 0.1 |
| 219 | Sulfuric acid | 12.5 ± 2.2*** | 3.0 ± 0.0*** |
| 220 | Aluminum sulfate | 5.7 ± 0.5 | 3.5 ± 0.6*** |
| 221 | Aluminum potassium sulfate | 2.0 ± 0.5 | 0.8 ± 0.0 |
| 222 | Calcium sulfate | 5.3 ± 0.4 | 0.7 ± 0.4 |
| 223 | Phosphoric acid | 3.8 ± 1.1 | 1.3 ± 0.2 * |
| 224 | Potassium monohydrogen phosphate | 1.8 ± 0.3 | 0.6 ± 0.1 |
| 225 | Trisodium phosphate | 1.5 ± 0.3 | 0.5 ± 0.1 |
| 226 | Dibasic calcium phosphate | 1.6 ± 0.3 | 0.6 ± 0.0 |
| 227 | Dibasic sodium phosphate hydrate | 1.2 ± 0.0 | 1.2 ± 0.8 |
| 228 | Dibasic potassium phosphate | 1.1 ± 0.3 | 0.7 ± 0.1 |
| 229 | Monobasic potassium phosphate | 1.4 ± 0.1 | 0.6 ± 0.2 |
| 230 | Monobasic calcium phosphate | 4.5 ± 0.0 | 1.5 ± 0.6 * |
| 231 | Powdered hydrolyzed gelatin | 3.3 ± 0.1 | 0.6 ± 0.1 |
| 232 | Hydrated silicon dioxide | 1.1 ± 0.1 | 0.6 ± 0.1 |
| 233 | Light anhydrous silicic acid | 1.8 ± 0.3 | 0.7 ± 0.4 |
| 234 | Partly pregelatinized starch | 1.3 ± 0.0 | 0.5 ± 0.1 |
| 235 | Propyl gallate | 4.9 ± 0.7 | 0.7 ± 0.1 |
| 236 | Amylopectin | 1.2 ± 0.1 | 5.5 ± 2.9 |
| 237 | Epoxydation soybean oil | 0.5 ± 0.0 | 0.7 ± 0.1 |
| 238 | Ammonium acetate | 0.8 ± 0.1 | 0.4 ± 0.1 |
| 239 | Magnesia alumina hydrate | 3.9 ± 1.5 | 0.4 ± 0.0 |
| 240 | Sodium dodecyl benzene sulfonate | 4.5 ± 1.1 | 2.1 ± 0.4** |
| 241 | Vinyl pyrrolidone • vinyl acetate copolymer | 14.7 ± 4.1*** | 2.0 ± 0.8 |
| 242 | Ammonium pentaborate | 0.6 ± 0.0 | 5.5 ± 3.1 |
| 243 | Polyoxyethylene sorbitan monolaurate | 1.6 ± 0.2 | 0.5 ± 0.1 |
| 244 | Anhydrous sodium acetate | 1.5 ± 0.2 | 0.2 ± 0.1 |
| 245 | Sodium N-lauroyl sarcosinate | 5.4 ± 0.5 | 1.3 ± 0.1 * |
| 246 | Sodium polyoxyethylene laurylether phosphate | 3.6 ± 1.0 | 0.7 ± 0.0 |
| 247 | Amorphous silicon oxide hydrate | 2.5 ± 0.7 | 0.5 ± 0.0 |
| 248 | DL-Alanine | 3.6 ± 1.7 | 0.7 ± 0.4 |
| 249 | Sodium L-ascorbate | 1.1 ± 0.1 | 1.7 ± 1.2 |
| 250 | Sodium L-aspartate | 1.3 ± 0.3 | 0.4 ± 0.2 |
| 251 | L-Arginine | 1.5 ± 0.6 | 0.4 ± 0.1 |
| 252 | L-Arginine hydrochloride | 1.1 ± 0.2 | 1.0 ± 0.4 |
| 253 | Acetyl tryptophan | 3.9 ± 0.7 | 1.5 ± 0.1** |
| 254 | Acetanilide | 0.6 ± 0.0 | 1.1 ± 0.1 |
| 255 | Benzoic acid | 2.8 ± 0.2 | 1.3 ± 0.5 |
| 256 | Sodium benzoate | 1.1 ± 0.4 | 0.4 ± 0.2 |
| 257 | Hydroxypropyl cyclodextrin | 2.1 ± 0.2 | 0.4 ± 0.1 |
| 258 | Sodium β-cyclodextrin sulfobutyl ether | 2.4 ± 0.4 | 0.6 ± 0.3 |
| 259 | Polyoxyethylene (54) polyoxypropylene (39) glycol | 3.7 ± 0.8 | 0.8 ± 0.1 |
| 260 | Methyl sodium sulfate | 1.0 ± 0.1 | 1.5 ± 0.3 * |
| 261 | Ethyl sodium sulfate | 0.9 ± 0.0 | 1.3 ± 0.2 * |
| 262 | Butyl sodium sulfate | 2.4 ± 0.5 | 1.3 ± 0.3 * |
| 263 | Octyl sodium sulfate | 4.2 ± 0.4 | 1.3 ± 0.1 * |
| 264 | Decyl sodium sulfate | 18.8 ± 2.0*** | 3.4 ± 0.4*** |

TABLE 3-continued

Effect of various dissolution aids on the solubility of Compound F6-20 hydrochloride salt (* p < 0.05, p < 0.01, *p < 0.001)

| Example | Dissolution aid | Concentration after 10 min (μg/mL) | Concentration after 240 min (μg/mL) |
|---|---|---|---|
| 265 | Tetradecyl sodium sulfate | 46.5 ± 17.9** | 19.8 ± 9.0** |
| 266 | Hexadecyl sodium sulfate | 32.1 ± 18.3 * | 13.2 ± 8.3 * |
| 267 | Octadecyl sodium sulfate | 20.9 ± 7.1** | 8.1 ± 2.8** |
| 268 | Sodium chondroitin sulfate | 3.0 ± 1.0 | 0.5 ± 0.1 |
| 269 | Dodecane | 2.3 ± 0.3 | 0.8 ± 0.1 |

Examples 270 to 281

Materials

Hydrochloride salt crystal of the Compound F6-20 was obtained according a method generally known in the art (for example, the method described in the Production example 30). For the Examples 270 to 281, hydrochloride salt crystal of the Compound F6-20 was prepared according to dry blending method using agate mortar and pestle with the formula shown in Tables 4 to 8. Sodium lauryl sulfate passed with 100 mesh was used. For the Comparative example 2, hydrochloride salt crystal of the Compound F6-20 and lactose were mixed with each other at weight ratio of 1:9.

Test Example 2

Small Scale Dissolution Test

For the small dissolution scale test (R. Takano et al, Pharm. Res. 23: 1144-1156 (2006)), a small scale dissolution tester (Vankel Technologies, Inc.) was used and the solubilities in FaSSIF were determined at 37° C. with paddle stirred rate of 50 rpm. For each test sample, after 5, 10, 15, 20, 25, 30, 45, 60, 120, and 240 minutes lapse, concentration of the Compound F6-20 in FaSSIF was measured by high performance liquid chromatography.

Examples 270 to 272

Using the Examples 270 to 272 shown in Table 4 and the above Comparative Example 2, the effect of the additive amount of SLS on solubility of the Compound F6-20 hydrochloride salt crystal was determined. As a result, it was found that the solubility of the Compound F6-20 is improved in accordance with the additive amount of sodium lauryl sulfate as shown in FIG. 1.

TABLE 4

|  | Example 270 | Example 271 | Example 272 |
|---|---|---|---|
| Compound F6-20 hydrochloride salt | 20.0% | 20.0% | 20.0% |
| Lactose hydrate | 60.0% | 75.0% | 79.0% |
| Sodium lauryl sulfate | 20.0% | 5.0% | 1.0% |

Examples 273 to 275

Figure 2:
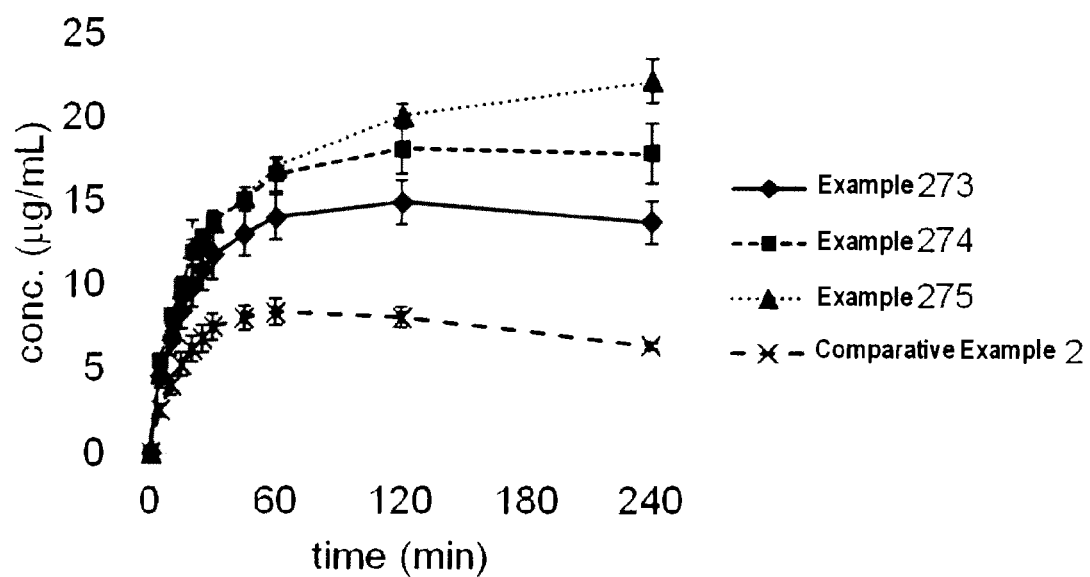
FIG. 2 It is a graph to illustrate the effect of various cellulose polymers on the solubility of the Compound F6-20 hydrochloride salt.

Using the Examples 273 to 275 shown in Table 5 and the above Comparative Example 2, the effect of various cellulose polymers on solubility of the Compound F6-20 hydrochloride salt crystal was determined. As a result, it was found that, among the various cellulose polymers, HPC exhibits the most excellent effect of improving the solubility of the Compound F6-20 as shown in FIG. 2, even though it is slightly.

TABLE 5

|  | Example 273 | Example 274 | Example 275 |
|---|---|---|---|
| Compound F6-20 hydrochloride salt | 21.5% | 21.5% | 21.5% |
| Lactose hydrate | 67.5% | 67.5% | 67.5% |
| Sodium lauryl sulfate | 1.0% | 1.0% | 1.0% |
| Low substituted hydroxypropyl cellulose | 5.0% | 5.0% | 5.0% |
| Methyl cellulose | 5.0% | 0.0% | 0.0% |
| Hydroxypropylmethyl cellulose | 0.0% | 5.0% | 0.0% |
| Hydroxypropyl cellulose | 0.0% | 0.0% | 5.0% |

Examples 276 to 278

Figure 3:
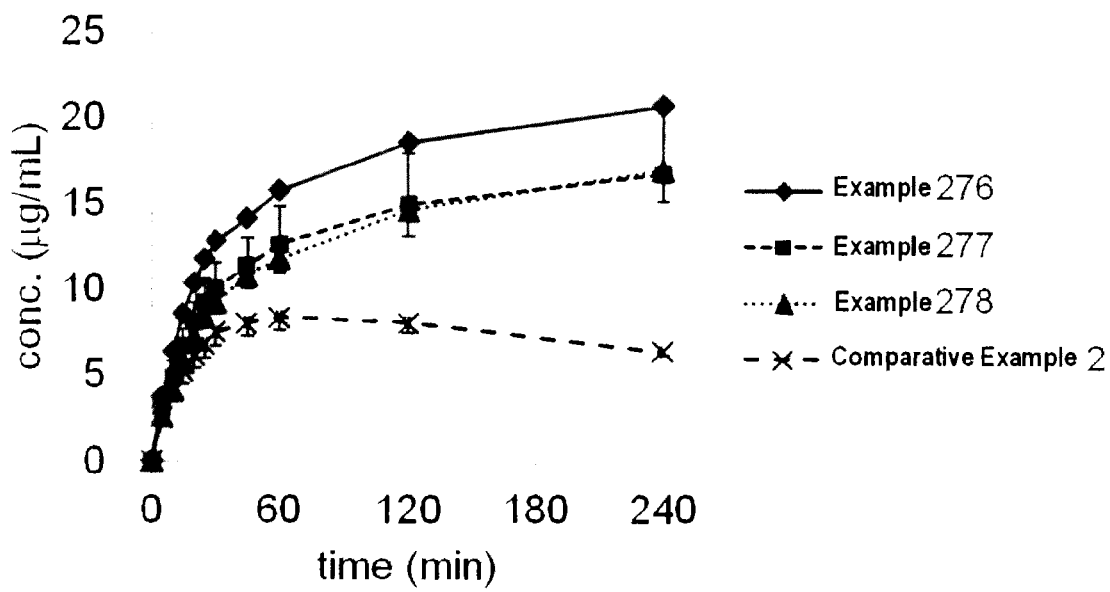
FIG. 3 It is a graph to illustrate the effect of the additive amount of hydroxypropyl cellulose on the solubility of the Compound F6-20 hydrochloride salt.

Using the Examples 276 to 278 shown in Table 6 and the above Comparative Example 2, the effect of additive amount of HPC on solubility of the Compound F6-20 hydrochloride salt crystal was determined. As a result, it was found that the Examples 276 to 278 have higher solubility than Comparative example 2 as shown in FIG. 3. Thus, at least by adding the HPC in an amount of 25 to 100% by weight compared to the Compound F6-20, the solubility improving effect can be obtained.

TABLE 6

|  | Example 276 | Example 277 | Example 278 |
|---|---|---|---|
| Compound F6-20 hydrochloride salt | 21.5% | 21.5% | 21.5% |
| Lactose hydrate | 68.5% | 63.5% | 53.5% |
| Low substituted hydroxypropyl cellulose | 5.0% | 5.0% | 5.0% |
| Hydroxypropyl cellulose | 5.0% | 10.0% | 20.0% |

Example 279

Figure 4:
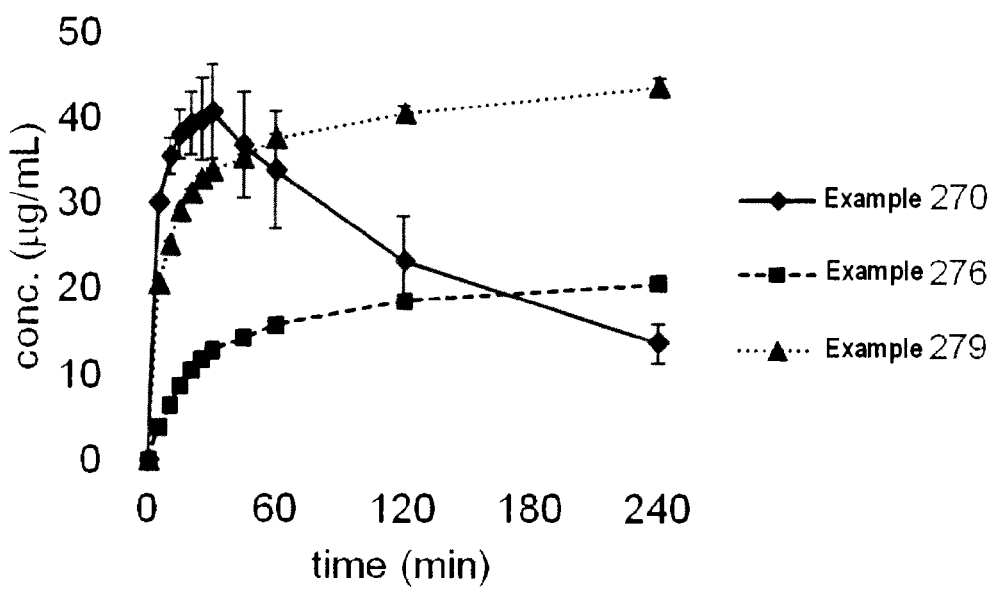

Using the Example 279 shown in Table 7, the solubility of the Compound F6-20 hydrochloride salt crystal when SLS and HPC were added thereto was determined. As a result, as illustrated in FIG. 4, it was found that the solubility was higher than the Example 276 in which only HPC was added, and the higher solubility was maintained compared to the Example 270 in which only SLS was added.

TABLE 7

|  | Example 279 |
|---|---|
| Compound F6-20 hydrochloride salt | 21.5% |
| Lactose hydrate | 48.5% |

TABLE 7-continued

|  | Example 279 |
|---|---|
| Sodium lauryl sulfate | 20.0% |
| Low substituted hydroxypropyl cellulose | 5.0% |
| Hydroxypropyl cellulose | 5.0% |

Examples 280 to 281

Figure 5:
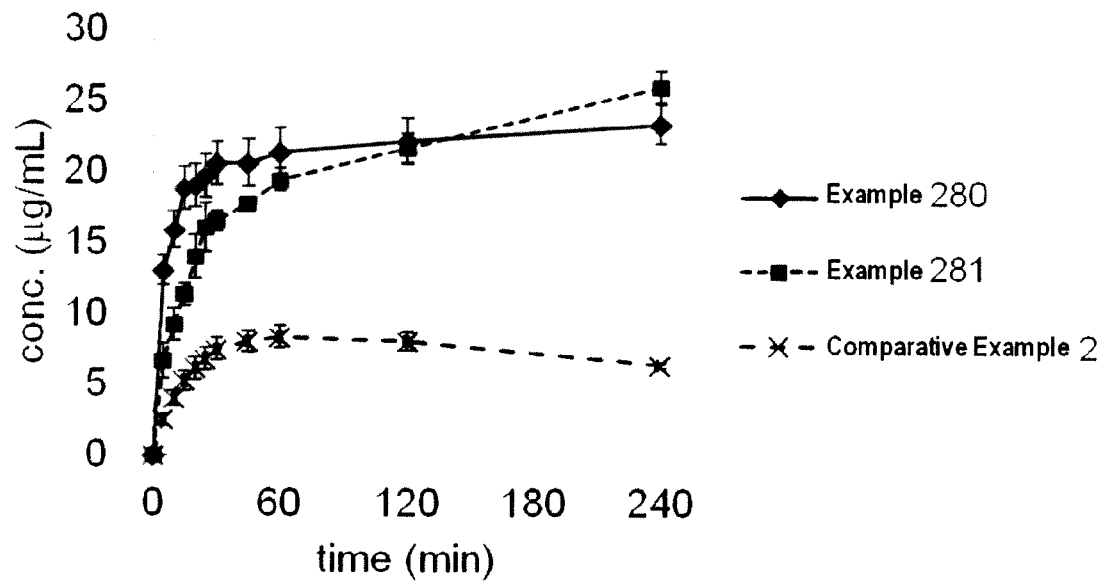
FIG. 5 It is a graph to compare the effect of the manufacturing method on the solubility of the Compound F6-20 hydrochloride salt.

Using the Examples 280 to 281 shown in Table 8 and the above Comparative Example 2, effect of the difference in manufacturing method on the solubility of the Compound F6-20 hydrochloride salt crystal was determined. For the dry blending method, Compound F6-20 hydrochloride salt crystal and each formula ingredient were mixed by using agate mortar and pestle. For the wet granulation method, the dissolution aids other than magnesium stearate and the Compound F6-20 were mixed using agate mortar and pestle. After adding water dropwise, the wet powder was subjected to granulating using a mesh with sieve opening of 850 μm. After drying at 60° C. for 3 hours, particle size regulating was carried out by using an 850 μm mesh again. As a result, it was found that there is no significant difference in the solubility of the Compound F6-20 hydrochloride salt crystal between different production methods, as shown in FIG. 5. Thus, it was shown that the effect of improving the solubility by SLS and the polymer does not depend on production method.

TABLE 8

|  | Example 280 | Example 281 |
|---|---|---|
| Compound F6-20 hydrochloride salt | 20.0% | 20.0% |
| Lactose hydrate | 41.5% | 41.5% |
| Microcrystalline cellulose | 20.0% | 20.0% |
| Crosscarmellose sodium | 3.0% | 3.0% |
| Hydroxypropyl cellulose | 5.0% | 5.0% |
| Sodium lauryl sulfate | 10.0% | 10.0% |
| Magnesium stearate | 0.5% | 0.5% |
| Production method | Dry blending | Wet granulation |

Examples 282 to 284

For the Examples 282 to 284 and Comparative example 3, mesylate salt crystal of the Compound F6-20 was used in preparing the Compound according to dry production method using agate mortar and pestle with the formula shown in Table 9. For the Comparative example 3, mesylate salt crystal of the Compound F6-20 and lactose were mixed with each other at weight ratio of 1:9.

Figure 6:
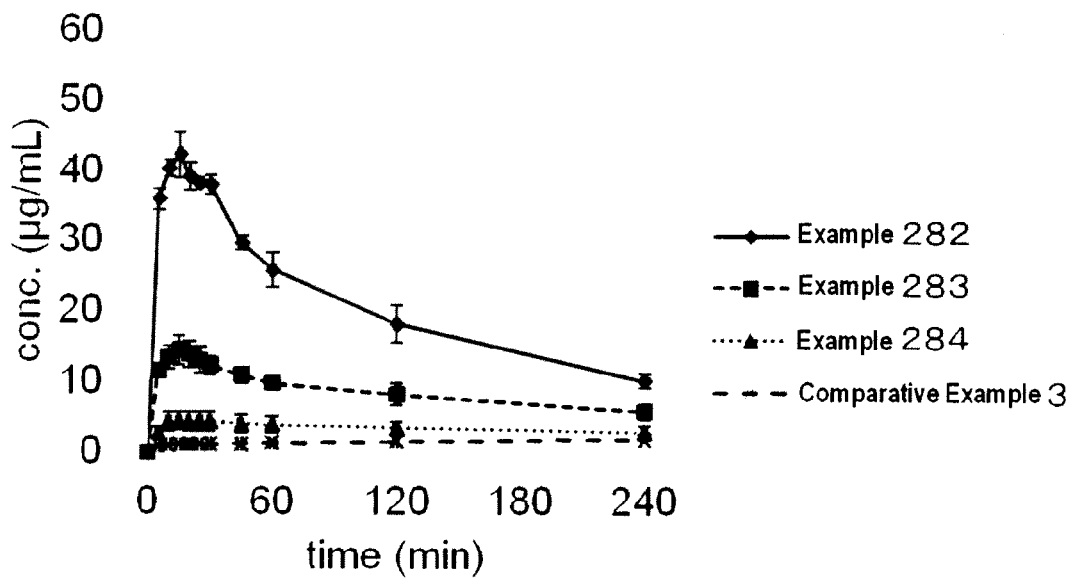
FIG. 6 It is a graph to illustrate the effect of the additive amount of sodium lauryl sulfate on the solubility of the Compound F6-20 mesylate salt.

The effect of the additive amount of SLS on solubility of the Compound F6-20 mesylate salt crystal was determined. As a result, it was found that the solubility of the Compound F6-20 mesylate salt is improved in accordance with the additive amount of sodium lauryl sulfate as shown in FIG. 6.

TABLE 9

|  | Example 282 | Example 283 | Example 284 |
|---|---|---|---|
| Compound F6-20 mesylate salt | 20.0% | 20.0% | 20.0% |
| Lactose hydrate | 60.0% | 75.0% | 79.0% |
| Sodium lauryl sulfate | 20.0% | 5.0% | 1.0% |

Example 285

Figure 7:
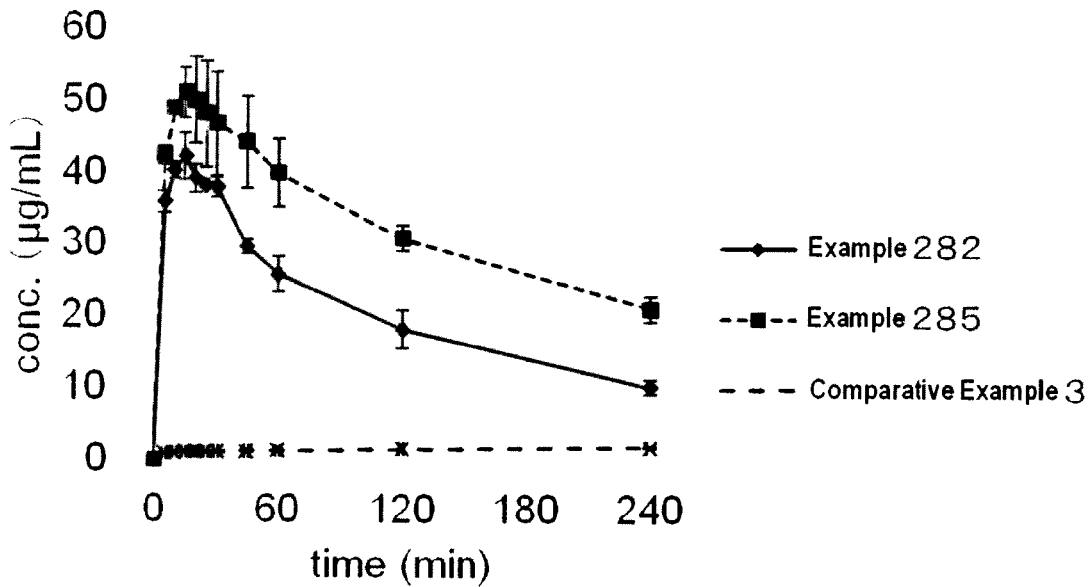

Solubility of the Compound F6-20 mesylate salt crystal in the case when SLS and HPC were added using the Example 285 shown in Table 10 and the above Comparative Example 3 was determined. As a result, it was found that high solubility was obtained by adding SLS and HPC, as shown in FIG. 7.

TABLE 10

|  | Example 285 |
|---|---|
| Compound F6-20 mesylate salt | 24.0% |
| Lactose hydrate | 46.0% |
| Sodium lauryl sulfate | 20.0% |
| Low substituted hydroxypropyl cellulose | 5.0% |
| Hydroxypropyl cellulose | 5.0% |

Examples 286 to 298

For the Comparative example 4 and the Examples 286 to 298, the effect of various dissolution aids on the solubility of the Compound B4-8 (Production example 12) was determined in the same manner as the Examples 1 to 269. The results are shown in Table 11.

TABLE 11

Effect of various dissolution aids on the solubility of Compound B4-8 hydrochloride salt

| Example | Dissolution aid | Dissolved concentration after 10 min (μg/mL) | Dissolved concentration after 240 min (μg/mL) |
|---|---|---|---|
| Comparative example 4 | Not added | 8.3 ± 1.5 | 3.8 ± 2.6 |
| 286 | Methyl cellulose | 5.8 ± 1.3 | 1.9 ± 0.6 |
| 287 | Hydroxypropyl-methyl cellulose | 6.8 ± 0.9 | 1.4 ± 0.1 |
| 288 | Hydroxypropyl cellulose | 14.2 ± 3.2 * | 3.2 ± 2.7 |
| 289 | Povidone | 4.8 ± 0.4 | 1.1 ± 0.3 |
| 290 | Macrogol 6000 | 3.8 ± 0.2 | 0.9 ± 0.1 |
| 291 | Glycerin monostearate | 4.8 ± 0.8 | 1.5 ± 0.1 |
| 292 | Sodium lauryl sulfate | 31.7 ± 7.3** | 7.2 ± 1.0 |
| 293 | Sucrose esters of fatty acids | 6.8 ± 2.7 | 3.5 ± 2.0 |
| 294 | Polyoxyl 40 stearate | 5.6 ± 1.2 | 2.3 ± 0.2 |
| 295 | Sorbitan esters of fatty acids | 4.6 ± 0.3 | 1.6 ± 0.1 |
| 296 | Polyoxyethylene hydrogenated castor oil 60 | 3.3 ± 0.1 | 2.7 ± 0.5 |
| 297 | Polyoxyethylene (105) polyoxypropylene (5) glycol | 4.1 ± 0.4 | 3.5 ± 0.6 |
| 298 | Polyoxyethylene (160) polyoxypropylene (30) glycol | 3.2 ± 0.2 | 1.9 ± 0.1 |

Examples 299 to 311

For the Comparative example 5 and the Examples 299 to 311, the effect of various dissolution aids on the solubility of the Compound F4-3 (Production example 19) was determined in the same manner as the Examples 1 to 269. The results are shown in Table 12.

TABLE 12

Effect of various dissolution aids on the solubility of Compound F4-3 hydrochloride salt

| Example | Dissolution aid | Dissolved concentration after 10 min (μg/mL) | Dissolved concentration after 240 min (μg/mL) |
|---|---|---|---|
| Comparative example 5 | Not added | 4.4 ± 0.4 | 4.8 ± 0.3 |
| 299 | Methyl cellulose | 17.8 ± 3.7 * | 13.9 ± 5.8 |
| 300 | Hydroxypropyl-methyl cellulose | 16.9 ± 11.1 | 23.7 ± 6.1 * |
| 301 | Hydroxypropyl cellulose | 13.7 ± 4.0 | 8.8 ± 7.8 |
| 302 | Povidone | 48.1 ± 19.7 | 22.5 ± 3.8 * |
| 303 | Macrogol 6000 | 4.6 ± 0.5 | 4.6 ± 0.8 |
| 304 | Glycerin monostearate | 3.8 ± 0.4 | 3.0 ± 0.6 |
| 305 | Sodium lauryl sulfate | 8.1 ± 0.2 *** | 6.8 ± 1.3 |
| 306 | Sucrose esters of fatty acids | 4.9 ± 0.7 | 5.2 ± 0.5 |
| 307 | Polyoxyl 40 stearate | 11.6 ± 1.5 ** | 20.3 ± 1.4 *** |
| 308 | Sorbitan esters of fatty acids | 2.2 ± 0.7 | 3.1 ± 0.3 |
| 309 | Polyoxyethylene hydrogenated castor oil 60 | 10.4 ± 2.5 * | 21.0 ± 8.4 |
| 310 | Polyoxyethylene (105) polyoxypropylene (5) glycol | 90.0 ± 5.1 ** | 43.2 ± 8.5 * |
| 311 | Polyoxyethylene (160) polyoxypropylene (30) glycol | 54.9 ± 18.9 * | 6.7 ± 1.4 |

Examples 312 to 324

For the Comparative example 6 and the Examples 312 to 324, the effect of various dissolution aids on the solubility of the Compound F4-9 (Production example 20) was determined in the same manner as the Examples 1 to 269. The results are shown in Table 13.

TABLE 13

Effect of various dissolution aids on the solubility of Compound F4-9 hydrochloride salt

| Example | Dissolution aid | Dissolved concentration after 10 min (μg/mL) | Dissolved concentration after 240 min (μg/mL) |
|---|---|---|---|
| Comparative example 6 | Not added | 18.2 ± 0.1 | 3.7 ± 0.5 |
| 312 | Methyl cellulose | 21.0 ± 4.6 | 6.4 ± 0.5 ** |
| 313 | Hydroxypropyl-methyl cellulose | 26.1 ± 3.7 | 9.9 ± 1.0 *** |
| 314 | Hydroxypropyl cellulose | 28.8 ± 3.4 * | 7.4 ± 6.4 |
| 315 | Povidone | 82.6 ± 10.4 *** | 40.0 ± 15.8 |
| 316 | Macrogol 6000 | 18.8 ± 0.6 | 9.8 ± 0.8 *** |
| 317 | Glycerin monostearate | 8.7 ± 0.4 | 7.2 ± 1.3 * |
| 318 | Sodium lauryl sulfate | 72.7 ± 2.0 *** | 37.6 ± 3.1 ** |
| 319 | Sucrose esters of fatty acids | 31.9 ± 7.5 | 9.1 ± 0.7 *** |
| 320 | Polyoxyl 40 stearate | 24.9 ± 14.8 | 55.4 ± 21.0 |
| 321 | Sorbitan esters of fatty acids | 6.3 ± 2.3 | 4.6 ± 0.6 |
| 322 | Polyoxyethylene hydrogenated castor oil 60 | 62.2 ± 58.9 | 77.6 ± 68.1 |
| 323 | Polyoxyethylene (105) polyoxypropylene (5) glycol | 50.4 ± 13.1 | 14.3 ± 4.0 * |
| 324 | Polyoxyethylene (160) polyoxypropylene (30) glycol | 60.1 ± 18.1 | 31.1 ± 14.5 |

Examples 325 to 337

For the Comparative example 7 and the Examples 325 to 337, the effect of various dissolution aids on the solubility of the Compound F6-4 (Production example 28) was determined in the same manner as the Examples 1 to 269. The results are shown in Table 14.

TABLE 14

Effect of various dissolution aids on the solubility of Compound F6-4 hydrochloride salt

| Example | Dissolution aid | Dissolved concentration after 10 min (μg/mL) | Dissolved concentration after 240 min (μg/mL) |
|---|---|---|---|
| Comparative example 7 | Not added | 0.4 ± 0.2 | 0.4 ± 0.4 |
| 325 | Methyl cellulose | 10.8 ± 2.9 * | 8.3 ± 4.0 |
| 326 | Hydroxypropyl-methyl cellulose | 16.8 ± 12.7 | 18.4 ± 7.7 |
| 327 | Hydroxypropyl cellulose | 3.6 ± 0.4 *** | 2.6 ± 0.5 ** |
| 328 | Povidone | 12.9 ± 3.8 * | 24.5 ± 5.0 |
| 329 | Macrogol 6000 | 0.7 ± 0.5 | 0.4 ± 0.1 |
| 330 | Glycerin monostearate | 0.3 ± 0.1 | 0.7 ± 0.2 |
| 331 | Sodium lauryl sulfate | 1.8 ± 0.3 ** | 37 ± 0.9 ** |
| 332 | Sucrose esters of fatty acids | 1.2 ± 0.9 | 1.6 ± 0.7 |
| 333 | Polyoxyl 40 stearate | 36.0 ± 6.5 * | 43.9 ± 6.8 ** |
| 334 | Sorbitan esters of fatty acids | 0.3 ± 0.2 | 0.1 ± 0.0 |
| 335 | Polyoxyethylene hydrogenated castor oil 60 | 16.3 ± 2.2 ** | 27.1 ± 4.5 ** |
| 336 | Polyoxyethylene (105) polyoxypropylene (5) glycol | 50.1 ± 8.3 ** | 52.6 ± 8.9 ** |
| 337 | Polyoxyethylene (160) polyoxypropylene (30) glycol | 19.3 ± 2.3 ** | 15.4 ± 4.0 * |

Examples 338 to 350

For the Comparative example 8 and the Examples 338 to 350, the effect of various dissolution aids on the solubility of the Compound F5-43 (Production example 36) was determined in the same manner as the Examples 1 to 269. The results are shown in Table 15.

TABLE 15

Effect of various dissolution aids on the solubility of Compound F5-43 hydrochloride salt

| Example | Dissolution aid | Dissolved concentration after 10 min (µg/mL) | Dissolved concentration after 240 min (µg/mL) |
|---|---|---|---|
| Comparative example 8 | Not added | 12.7 ± 1.8 | 5.5 ± 0.6 |
| 338 | Methyl cellulose | 32.5 ± 3.8 ** | 5.8 ± 1.3 |
| 339 | Hydroxypropyl-methyl cellulose | 35.4 ± 5.8 ** | 7.9 ± 0.7 * |
| 340 | Hydroxypropyl cellulose | 17.6 ± 4.2 | 6.8 ± 0.5 * |
| 341 | Povidone | 40.9 ± 0.6 *** | 5.0 ± 0.7 |
| 342 | Macrogol 6000 | 37.4 ± 1.1 *** | 3.4 ± 0.3 |
| 343 | Glycerin monostearate | 9.9 ± 2.0 | 2.5 ± 0.4 |
| 344 | Sodium lauryl sulfate | 35.8 ± 5.5 ** | 39.5 ± 1.4 *** |
| 345 | Sucrose esters of fatty acids | 24.1 ± 1.8 ** | 2.6 ± 0.1 |
| 346 | Polyoxyl 40 stearate | 23.6 ± 2.4 ** | 3.5 ± 0.1 |
| 347 | Sorbitan esters of fatty acids | 8.6 ± 2.0 | 2.3 ± 0.6 |
| 348 | Polyoxyethylene hydrogenated castor oil 60 | 15.1 ± 2.1 | 3.2 ± 0.1 |
| 349 | Polyoxyethylene (105) polyoxypropylene (5) glycol | 38.9 ± 4.4 *** | 3.4 ± 0.6 |
| 350 | Polyoxyethylene (160) polyoxypropylene (30) glycol | 37.8 ± 1.5 *** | 4.4 ± 0.9 |

Examples 351 to 363

For the Comparative example 9 and the Examples 351 to 363, the effect of various dissolution aids on the solubility of the Compound F6-17 (Production example 32) was determined in the same manner as the Examples 1 to 269. The results are shown in Table 16.

TABLE 16

Effect of various dissolution aids on the solubility of Compound F6-17 hydrochloride salt

| Example | Dissolution aid | Dissolved concentration after 10 min (µg/mL) | Dissolved concentration after 240 min (µg/mL) |
|---|---|---|---|
| Comparative example 9 | Not added | 9.2 ± 1.3 | 5.2 ± 0.5 |
| 351 | Methyl cellulose | 16.9 ± 3.2 | 8.7 ± 2.4 |
| 352 | Hydroxypropyl-methyl cellulose | 20.6 ± 4.9 | 10.6 ± 1.5 ** |
| 353 | Hydroxypropyl cellulose | 8.8 ± 3.3 | 7.7 ± 0.6 ** |
| 354 | Povidone | 20.8 ± 1.4 * | 5.2 ± 0.6 |
| 355 | Macrogol 6000 | 23.2 ± 2.2 ** | 3.3 ± 0.2 |
| 356 | Glycerin monostearate | 8.7 ± 0.7 | 2.4 ± 0.5 |
| 357 | Sodium lauryl sulfate | 36.6 ± 5.4 ** | 40.5 ± 4.4 ** |
| 358 | Sucrose esters of fatty acids | 13.6 ± 1.4 * | 5.3 ± 0.5 |
| 359 | Polyoxyl 40 stearate | 22.6 ± 1.4 ** | 8.7 ± 8.0 |
| 360 | Sorbitan esters of fatty acids | 5.3 ± 0.3 | 4.2 ± 1.1 |
| 361 | Polyoxyethylene hydrogenated castor oil 60 | 18.1 ± 1.6 ** | 8.0 ± 1.2 * |
| 362 | Polyoxyethylene (105) polyoxypropylene (5) glycol | 23.6 ± 3.7 * | 9.1 ± 0.6 *** |
| 363 | Polyoxyethylene (160) polyoxypropylene (30) glycol | 30.0 ± 3.9 ** | 4.6 ± 0.6 |

Examples 64 to 376

For the Comparative example 10 and the Examples 364 to 376, the effect of various dissolution aids on the solubility of the Compound F5-46 (Production example 43) was determined in the same manner as the Examples 1 to 269. The results are shown in Table 17.

TABLE 17

Effect of various dissolution aids on the solubility of Compound F5-46 hydrochloride salt

| Example | Dissolution aid | Dissolved concentration after 10 min (µg/mL) | Dissolved concentration after 240 min (µg/mL) |
|---|---|---|---|
| Comparative example 10 | Not added | 7.5 ± 0.6 | 5.6 ± 0.8 |
| 364 | Methyl cellulose | 13.1 ± 1.1 ** | 4.0 ± 0.9 |
| 365 | Hydroxypropyl-methyl cellulose | 12.3 ± 0.7 *** | 5.2 ± 0.4 |
| 366 | Hydroxypropyl cellulose | 10.0 ± 1.3 * | 5.5 ± 1.2 |
| 367 | Povidone | 14.5 ± 1.8 ** | 4.3 ± 1.3 |
| 368 | Macrogol 6000 | 25.7 ± 3.4 *** | 5.8 ± 0.8 |
| 369 | Glycerin monostearate | 8.5 ± 1.0 | 2.3 ± 0.4 |
| 370 | Sodium lauryl sulfate | 33.4 ± 4.1 ** | 23.1 ± 1.1 *** |
| 371 | Sucrose esters of fatty acids | 10.8 ± 0.3 *** | 3.0 ± 0.7 |
| 372 | Polyoxyl 40 stearate | 9.8 ± 1.6 | 4.1 ± 0.3 |
| 373 | Sorbitan esters of fatty acids | 1.8 ± 0.8 | 1.5 ± 0.9 |
| 374 | Polyoxyethylene hydrogenated castor oil 60 | 9.3 ± 3.0 | 3.4 ± 0.4 |
| 375 | Polyoxyethylene (105) polyoxypropylene (5) glycol | 18.3 ± 7.6 | 11.7 ± 6.6 |
| 376 | Polyoxyethylene (160) polyoxypropylene (30) glycol | 12.6 ± 0.9 *** | 3.0 ± 0.2 |

Examples 377 to 389

For the Comparative example 11 and the Examples 377 to 389, the effect of various dissolution aids on the solubility of the Compound F6-18 (Production example 37) was determined in the same manner as the Examples 1 to 269. The results are shown in Table 18.

TABLE 18

Effect of various dissolution aids on the solubility of Compound F6-18 hydrochloride salt

| Example | Dissolution aid | Dissolved concentration after 10 min (μg/mL) | Dissolved concentration after 240 min (μg/mL) |
|---|---|---|---|
| Comparative example 11 | Not added | 10.0 ± 2.0 | 1.8 ± 0.2 |
| 377 | Methyl cellulose | 6.3 ± 0.3 | 2.9 ± 0.2 ** |
| 378 | Hydroxypropyl-methyl cellulose | 6.0 ± 5.2 | 3.5 ± 0.9 * |
| 379 | Hydroxypropyl cellulose | 7.8 ± 1.7 | 5.1 ± 0.6 *** |
| 380 | Povidone | 8.2 ± 0.1 | 1.9 ± 1.7 |
| 381 | Macrogol 6000 | 7.1 ± 1.4 | 1.3 ± 0.1 |
| 382 | Glycerin monostearate | 1.8 ± 0.4 | 0.7 ± 0.1 |
| 383 | Sodium lauryl sulfate | 19.0 ± 0.8 ** | 23.4 ± 3.3 ** |
| 384 | Sucrose esters of fatty acids | 9.2 ± 7.1 | 3.7 ± 0.3 *** |
| 385 | Polyoxyl 40 stearate | 5.4 ± 0.2 | 3.9 ± 0.4 *** |
| 386 | Sorbitan esters of fatty acids | 1.0 ± 0.1 | 1.4 ± 0.2 |
| 387 | Polyoxyethylene hydrogenated castor oil 60 | 6.3 ± 1.6 | 3.1 ± 0.8 |
| 388 | Polyoxyethylene (105) polyoxypropylene (5) glycol | 9.8 ± 4.0 | 1.4 ± 2.4 |
| 389 | Polyoxyethylene (160) polyoxypropylene (30) glycol | 3.7 ± 0.4 | 1.5 ± 0.8 |

Examples 390 to 402

For the Comparative example 12 and the Examples 390 to 402, the effect of various dissolution aids on the solubility of the Compound F5-51 (Production example 27) was determined in the same manner as the Examples 1 to 269. The results are shown in Table 19.

TABLE 19

Effect of various dissolution aids on the solubility of Compound F5-51 hydrochloride salt

| Example | Dissolution aid | Dissolved concentration after 10 min (μg/mL) | Dissolved concentration after 240 min (μg/mL) |
|---|---|---|---|
| Comparative example 12 | Not added | 7.1 ± 0.9 | 0.0 ± 0.1 |
| 390 | Methyl cellulose | 8.5 ± 0.4 | 0.5 ± 0.8 |
| 391 | Hydroxypropyl-methyl cellulose | 10.8 ± 1.5 * | 0.5 ± 0.2 * |
| 392 | Hydroxypropyl cellulose | 11.2 ± 0.3 ** | 0.5 ± 0.2 * |
| 393 | Povidone | 10.8 ± 1.5 * | 0.0 ± 0.1 |
| 394 | Macrogol 6000 | 4.6 ± 0.7 | 0.0 ± 0.1 |
| 395 | Glycerin monostearate | 2.4 ± 0.2 | 0.1 ± 0.1 |
| 396 | Sodium lauryl sulfate | 20.2 ± 1.3 *** | 15.7 ± 0.8 *** |
| 397 | Sucrose esters of fatty acids | 6.8 ± 1.5 | 0.1 ± 0.1 |
| 398 | Polyoxyl 40 stearate | 1.2 ± 0.4 | 0.4 ± 0.3 |
| 399 | Sorbitan esters of fatty acids | 0.5 ± 0.3 | 0.8 ± 0.3 ** |
| 400 | Polyoxyethylene hydrogenated castor oil 60 | 7.0 ± 0.5 | 0.8 ± 1.0 |
| 401 | Polyoxyethylene (105) polyoxypropylene (5) glycol | 2.7 ± 1.0 | 0.1 ± 0.2 |
| 402 | Polyoxyethylene (160) polyoxypropylene (30) glycol | 3.9 ± 0.4 | 0.0 ± 0.1 |

Examples 403 to 415

For the Comparative example 13 and the Examples 403 to 415, the effect of various dissolution aids on the solubility of the Compound I6-4 (Production example 24) was determined in the same manner as the Examples 1 to 269. The results are shown in Table 20.

TABLE 20

Effect of various dissolution aids on the solubility of Compound I6-4 hydrochloride salt

| Example | Dissolution aid | Dissolved concentration after 10 min (μg/mL) | Dissolved concentration after 240 min (μg/mL) |
|---|---|---|---|
| Comparative example 13 | Not added | 9.3 ± 3.4 | 0.0 ± 0.1 |
| 403 | Methyl cellulose | 1.6 ± 0.3 | 0.0 ± 0.1 |
| 404 | Hydroxypropyl-methyl cellulose | 2.9 ± 1.7 | 0.0 ± 0.1 |
| 405 | Hydroxypropyl cellulose | 8.9 ± 1.3 | 0.7 ± 0.3 * |
| 406 | Povidone | 9.9 ± 3.1 | 0.0 ± 0.1 |
| 407 | Macrogol 6000 | 3.4 ± 0.2 | 0.0 ± 0.1 |
| 408 | Glycerin monostearate | 1.3 ± 0.1 | 0.0 ± 0.1 |
| 409 | Sodium lauryl sulfate | 35.0 ± 5.9 ** | 30.0 ± 2.7 ** |
| 410 | Sucrose esters of fatty acids | 0.6 ± 0.3 | 0.0 ± 0.1 |
| 411 | Polyoxyl 40 stearate | 0.3 ± 0.3 | 0.3 ± 0.2 * |
| 412 | Sorbitan esters of fatty acids | 1.9 ± 0.3 | 0.1 ± 0.1 |
| 413 | Polyoxyethylene hydrogenated castor oil 60 | 0.4 ± 0.2 | 0.3 ± 0.2 |
| 414 | Polyoxyethylene (105) polyoxypropylene (5) glycol | 2.5 ± 2.6 | 0.0 ± 0.1 |
| 415 | Polyoxyethylene (160) | 1.9 ± 0.9 | 0.2 ± 0.2 |

TABLE 20-continued

Effect of various dissolution aids on the solubility of Compound I6-4 hydrochloride salt

| Example | Dissolution aid | Dissolved concentration after 10 min (µg/mL) | Dissolved concentration after 240 min (µg/mL) |
|---|---|---|---|
| | polyoxypropylene (30) glycol | | |

Examples 416 to 418

Figure 8:
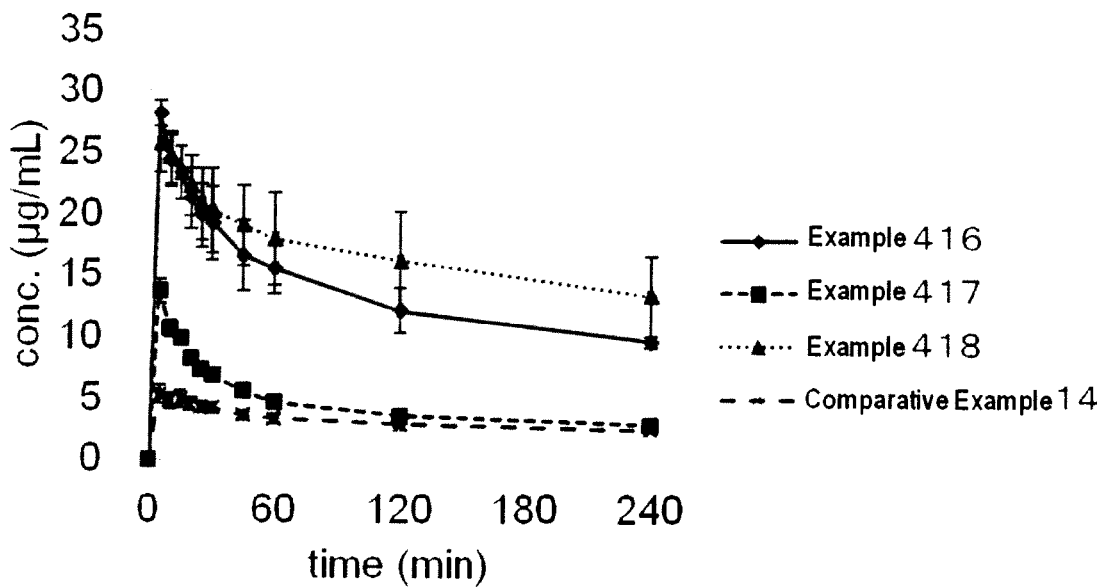
FIG. 8 It is a graph to illustrate the effect of SLS and polyvinyl pyrrolidone on the solubility of the Compound B4-8 hydrochloride salt crystal.

With the Examples 416 to 418 shown in Table 21, the effect of SLS and polyvinyl pyrrolidone on solubility of the Compound B4-8 hydrochloride salt crystal was determined based on a small scale dissolution test. For the Comparative example 14, the Compound B4-8 hydrochloride salt crystal and lactose were mixed at weight ratio of 1:9. The results are shown in FIG. 8.

TABLE 21

| | Example 416 | Example 417 | Example 418 |
|---|---|---|---|
| Compound B4-8 hydrochloride salt | 10.0% | 10.0% | 10.0% |
| Lactose hydrate | 80.0% | 80.0% | 70.0% |
| Polyvinyl pyrrolidone | 0.0% | 10.0% | 10.0% |
| Sodium lauryl sulfate | 10.0% | 0.0% | 10.0% |

Examples 419 to 421

Figure 9:
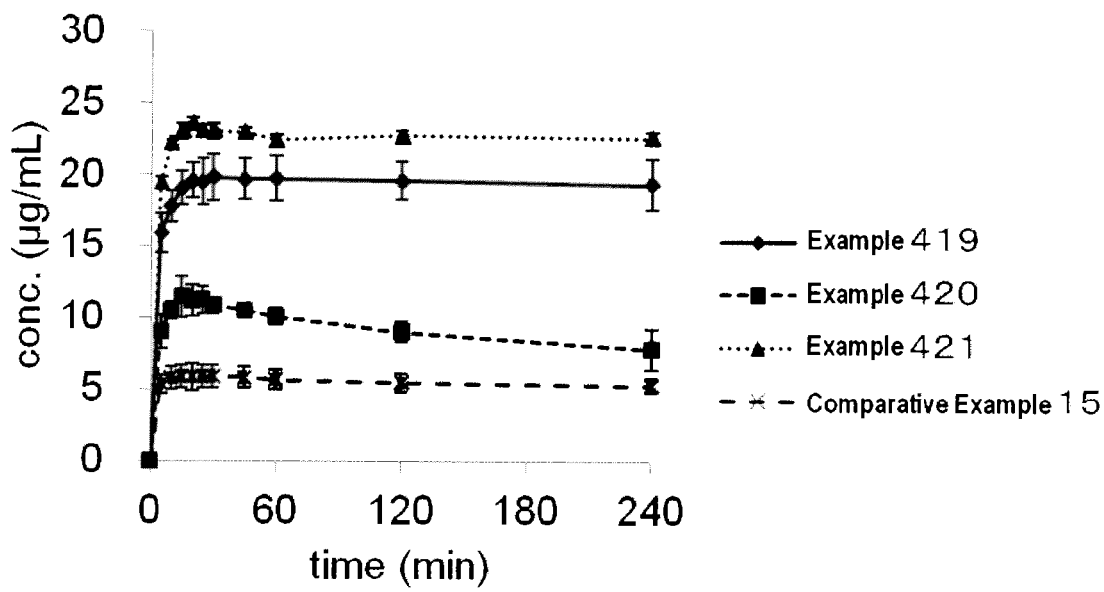
FIG. 9 It is a graph to illustrate the effect of SLS and polyvinyl pyrrolidone on the solubility of the Compound B4-8 mesylate salt crystal.

With the Examples 419 to 421 shown in Table 22, the effect of SLS and polyvinyl pyrrolidone on solubility of the Compound B4-8 mesylate salt crystal was determined based on a small scale dissolution test. For the Comparative example 15, the Compound B4-8 mesylate salt crystal and lactose were mixed at weight ratio of 1:9.
The results are shown in FIG. 9.

TABLE 22

| | Example 419 | Example 420 | Example 421 |
|---|---|---|---|
| Compound B4-8 mesylate salt | 10.0% | 10.0% | 10.0% |
| Lactose hydrate | 80.0% | 80.0% | 70.0% |
| Polyvinyl pyrrolidone | 0.0% | 10.0% | 10.0% |
| Sodium lauryl sulfate | 10.0% | 0.0% | 10.0% |

Examples 422 to 424

Figure 10:
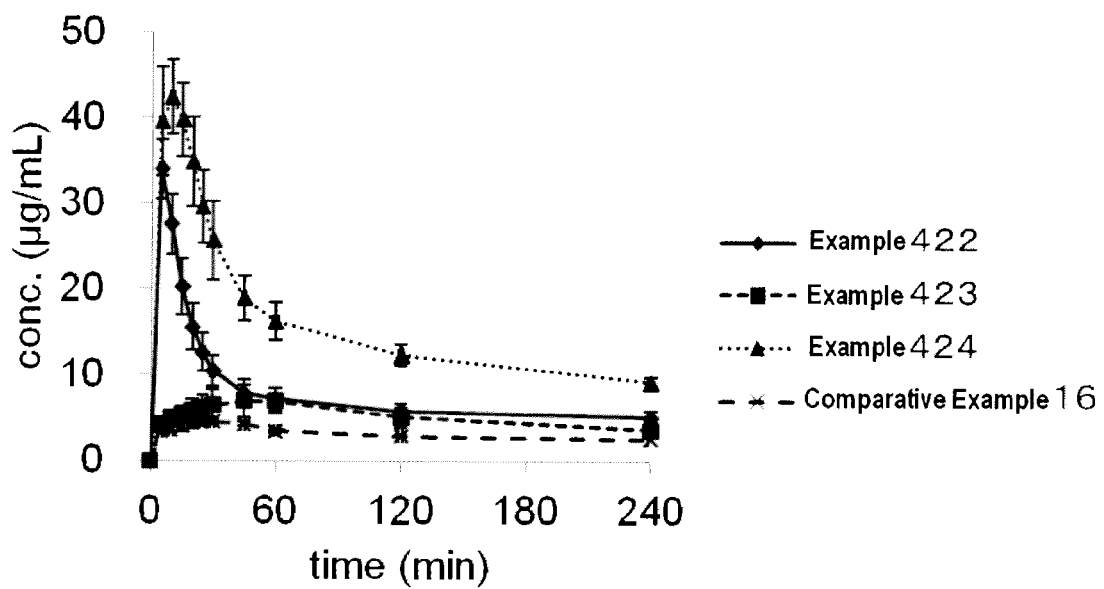
FIG. 10 It is a graph to illustrate the effect of SLS and HPC on the solubility of the Compound B4-8 sulfate salt crystal.

With the Examples 422 to 424 shown in Table 23, the effect of SLS and HPC on solubility of the Compound B4-8 sulfate salt crystal was determined based on a small scale dissolution test. For the Comparative example 16, the Compound B4-8 sulfate salt crystal and lactose were mixed at weight ratio of 1:9. The results are shown in FIG. 10.

TABLE 23

| | Example 422 | Example 423 | Example 424 |
|---|---|---|---|
| Compound B4-8 sulfate salt | 24.6% | 24.6% | 24.6% |
| Lactose hydrate | 55.4% | 70.4% | 50.4% |

TABLE 23-continued

| | Example 422 | Example 423 | Example 424 |
|---|---|---|---|
| Sodium lauryl sulfate | 20.0% | 0.0% | 20.0% |
| Hydroxypropyl cellulose | 0.0% | 5.0% | 5.0% |

Examples 425 to 427

Figure 11:
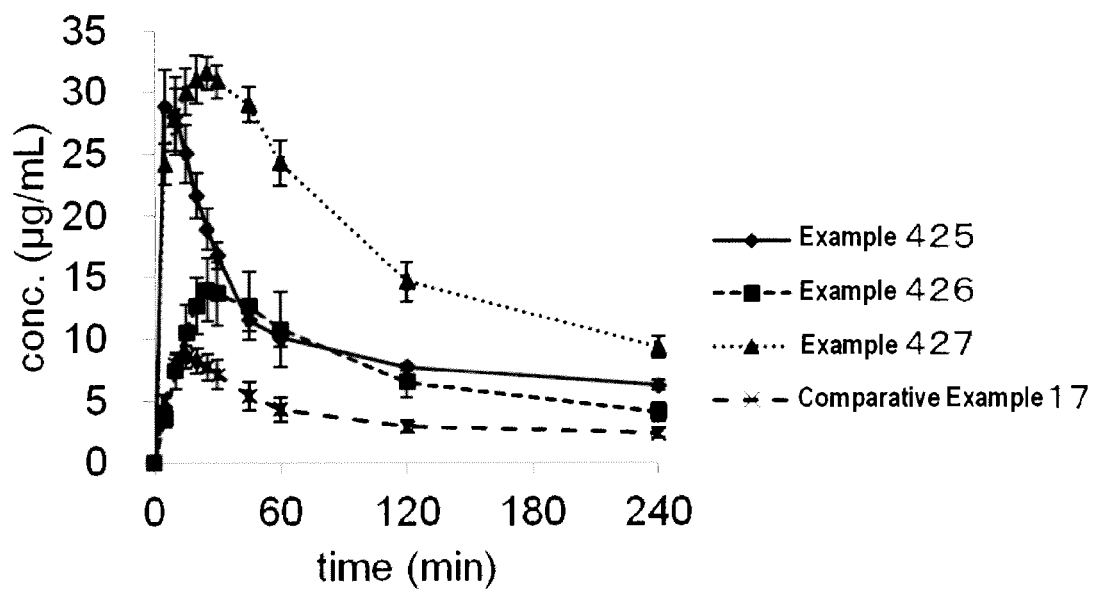
FIG. 11 It is a graph to illustrate the effect of SLS and HPC on the solubility of the Compound B4-8 L-tartrate salt crystal.

With the Examples 425 to 427 shown in Table 24, the effect of SLS and HPC on solubility of the Compound B4-8 L-tartrate salt crystal was determined based on a small scale dissolution test. For the Comparative example 17, the Compound B4-8 L-tartrate salt crystal and lactose were mixed at weight ratio of 1:9. The results are shown in FIG. 11.

TABLE 24

| | Example 425 | Example 426 | Example 427 |
|---|---|---|---|
| Compound B4-8 L-tartrate salt | 24.4% | 24.4% | 24.4% |
| Lactose hydrate | 55.6% | 70.6% | 50.6% |
| Sodium lauryl sulfate | 20.0% | 0.0% | 20.0% |
| Hydroxypropyl cellulose | 0.0% | 5.0% | 5.0% |

Examples 428 to 429

Figure 12:
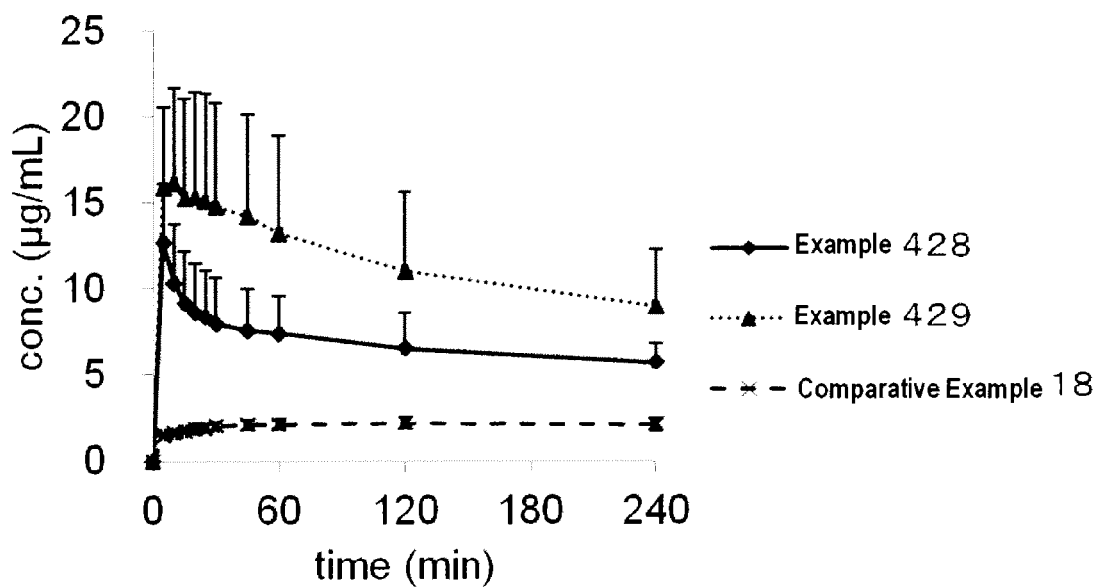
FIG. 12 It is a graph to illustrate the effect of SLS and HPC on the solubility of the Compound B4-8 phosphate salt crystal.

With the Examples 428 to 429 shown in Table 25, the effect of SLS and HPC on solubility of the Compound B4-8L-phosphate salt crystal was determined based on a small scale dissolution test. For the Comparative example 18, the Compound B4-8 phosphate salt crystal and lactose were mixed at weight ratio of 1:9. The results are shown in FIG. 12.

TABLE 25

| | Example 428 | Example 429 |
|---|---|---|
| Compound B4-8 phosphate salt | 26.3% | 26.3% |
| Lactose hydrate | 53.7% | 48.7% |
| Sodium lauryl sulfate | 20.0% | 20.0% |
| Hydroxypropyl cellulose | 0.0% | 5.0% |

Example 430

Figure 13:
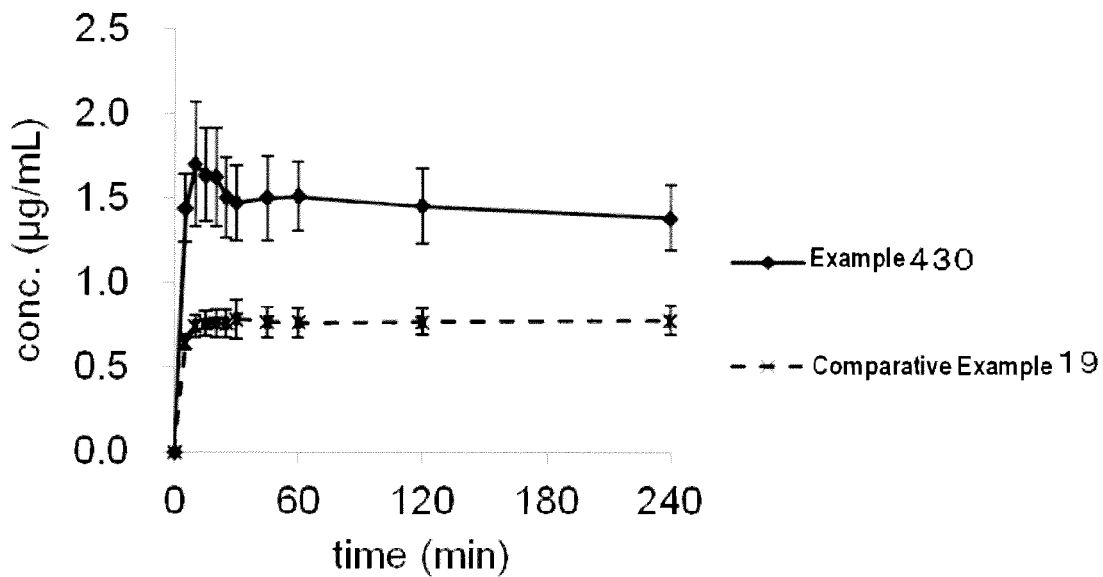
FIG. 13 It is a graph to illustrate the effect of polyoxyethylene (105) polyoxypropylene (5) glycol on the solubility of the Compound F6-4 hydrochloride salt crystal.

With the Example 430 shown in Table 26, the effect of polyoxyethylene (105) polyoxypropylene (5) glycol on solubility of the Compound F6-4 hydrochloride salt crystal was determined based on a small scale dissolution test. For the Comparative example 19, the Compound F6-4 hydrochloride salt crystal and lactose were mixed at weight ratio of 1:9. The results are shown in FIG. 13.

TABLE 26

| | Example 430 |
|---|---|
| Compound F6-4 hydrochloride salt | 8.3% |
| Lactose hydrate | 83.3% |
| Polyoxyethylene (105) polyoxypropylene (5) glycol | 8.3% |

Example 431

Figure 14:
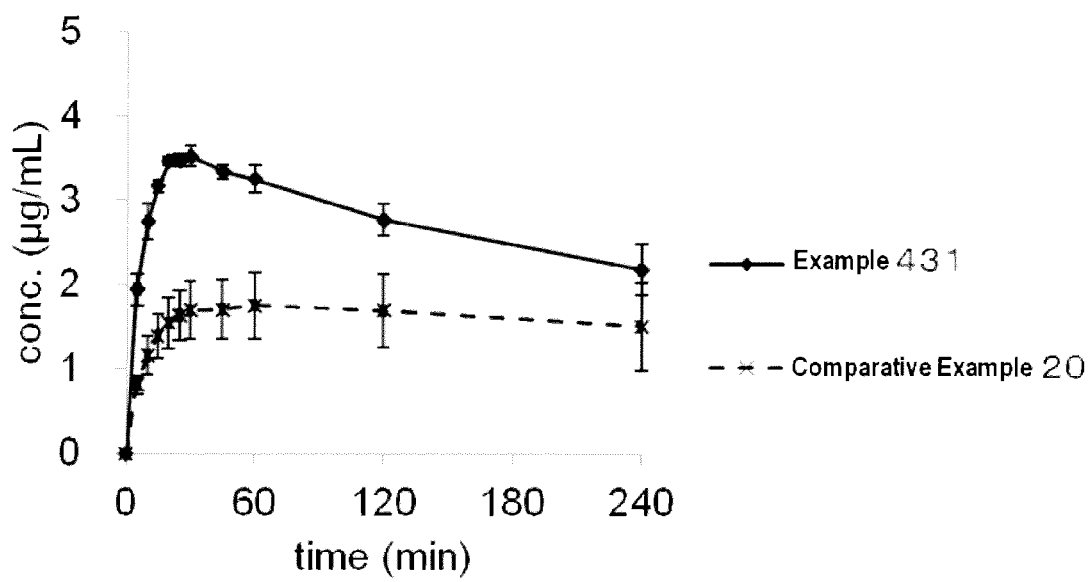
FIG. 14 It is a graph to illustrate the effect of polyoxyethylene (105) polyoxypropylene (5) glycol on the solubility of the Compound F6-4 mesylate salt crystal.

With the Example 431 shown in Table 27, the effect of polyoxyethylene (105) polyoxypropylene (5) glycol on solubility of the Compound F6-4 mesylate salt crystal was determined based on a small scale dissolution test. For the Comparative example 20, the Compound F6-4 mesylate salt crystal and lactose were mixed at weight ratio of 1:9. The results are shown in FIG. 14.

TABLE 27

|  | Example 431 |
| --- | --- |
| Compound F6-4 mesylate salt | 8.3% |
| Lactose hydrate | 83.3% |
| Polyoxyethylene (105) polyoxypropylene (5) glycol | 8.3% |

Example 432

Figure 15:
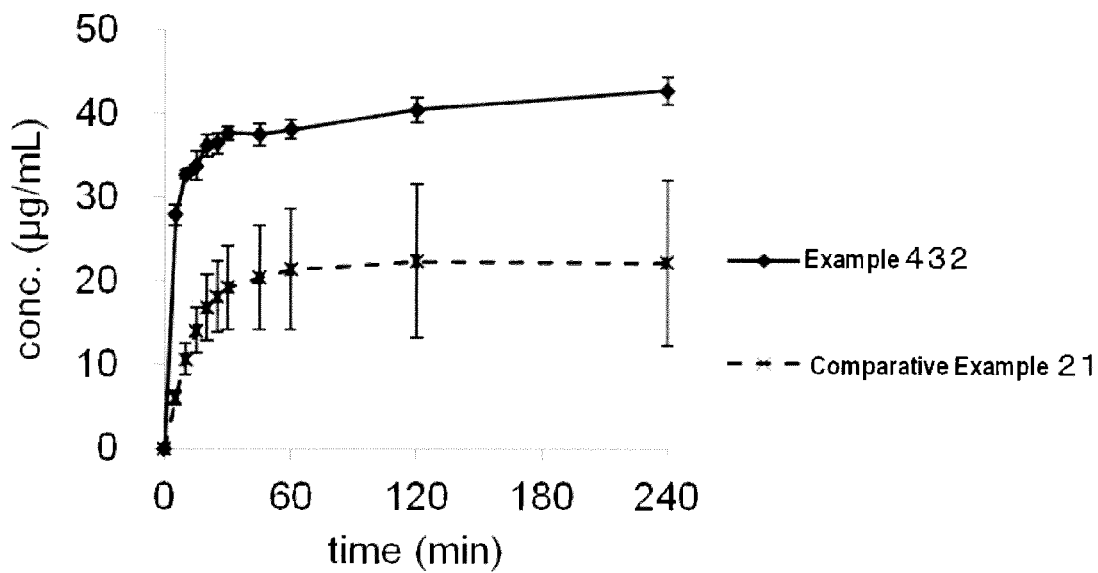
FIG. 15 It is a graph to illustrate the effect of SLS on the solubility of the Compound F6-17 hydrochloride salt crystal.

With the Example 432 shown in Table 28, the effect of SLS on solubility of the Compound F6-17 hydrochloride salt crystal was determined based on a small scale dissolution test. For the Comparative example 21, the Compound F6-17 hydrochloride salt crystal and lactose were mixed at weight ratio of 1:9. The results are shown in FIG. 15.

TABLE 28

|  | Example 432 |
| --- | --- |
| Compound F6-17 hydrochloride salt | 8.3% |
| Lactose hydrate | 83.3% |
| Sodium lauryl sulfate | 8.3% |

Examples 433 to 435

Figure 16:
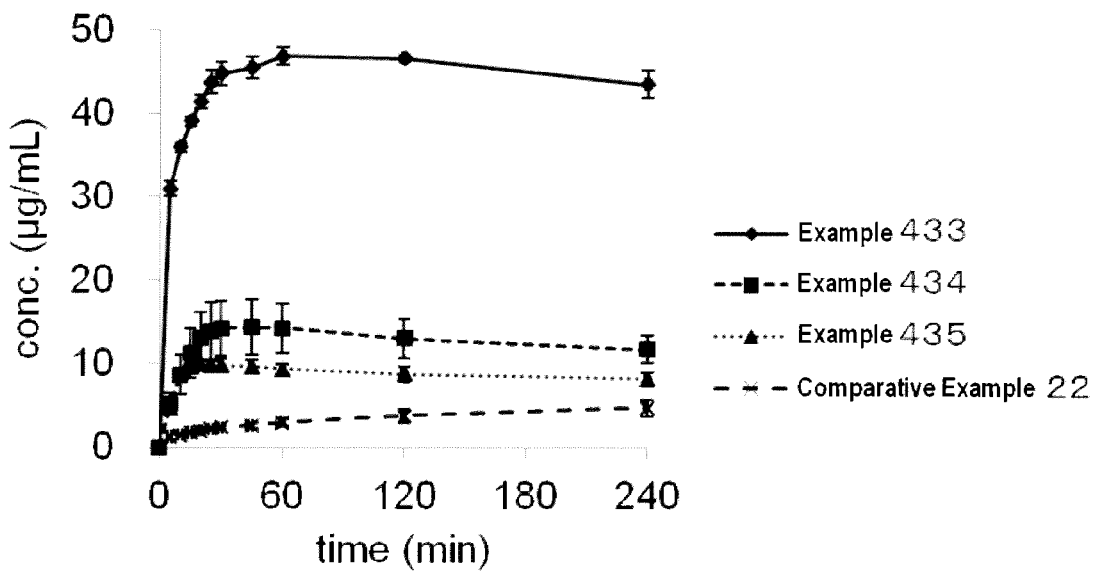
FIG. 16 It is a graph to illustrate the effect of SLS on the solubility of the Compound F6-17 mesylate salt crystal.

With the Examples 433 to 435 shown in Table 29, the effect of SLS on solubility of the Compound F6-17 mesylate salt crystal was determined based on a small scale dissolution test. For the Comparative example 22, the Compound F6-17 mesylate salt crystal and lactose were mixed at weight ratio of 1:9. The results are shown in FIG. 16.

TABLE 29

|  | Example 433 | Example 434 | Example 435 |
| --- | --- | --- | --- |
| Compound F6-17 mesylate salt | 20.0% | 20.0% | 20.0% |
| Lactose hydrate | 60.0% | 75.0% | 79.0% |
| Sodium lauryl sulfate | 20.0% | 5.0% | 1.0% |

Examples 436 to 437

Figure 17:
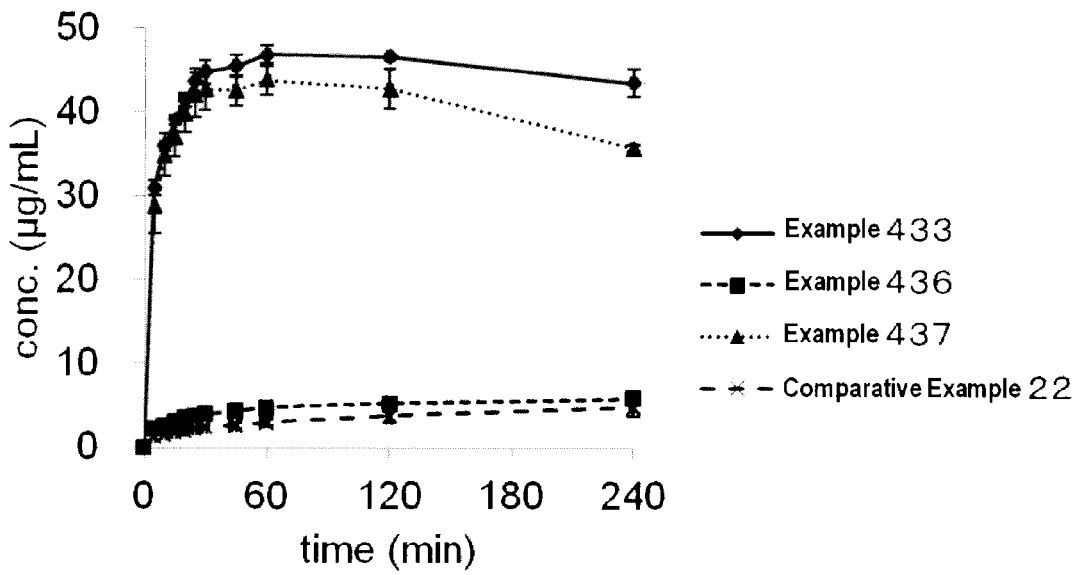
FIG. 17 It is a graph to illustrate the effect of SLS and polyvinyl pyrrolidone on the solubility of the Compound F6-17 mesylate salt crystal.

With the Examples 436 to 437 shown in Table 30 and the above Comparative Example 22, the effect of SLS and polyvinyl pyrrolidone on solubility of the Compound F6-17 mesylate salt crystal was determined based on a small scale dissolution test. The results are shown in FIG. 17.

TABLE 30

|  | Example 436 | Example 437 |
| --- | --- | --- |
| Compound F6-17 mesylate salt | 24.2% | 24.2% |
| Lactose hydrate | 70.8% | 50.8% |
| Sodium lauryl sulfate | 0.0% | 20.0% |
| Polyvinyl pyrrolidone | 5.0% | 5.0% |

Example 438

Figure 18:
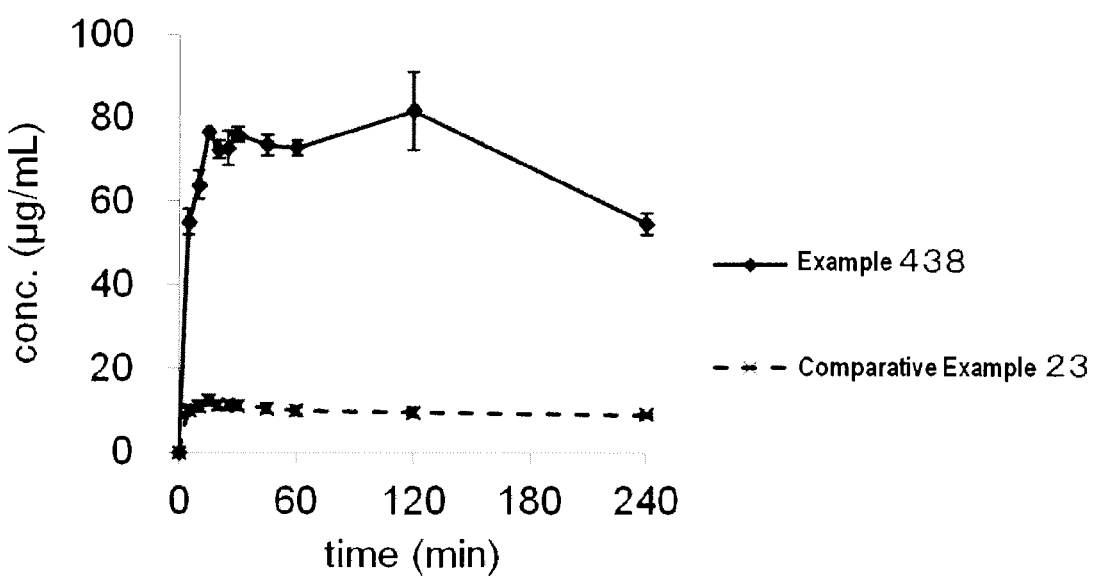
FIG. 18 It is a graph to illustrate the effect of SLS on the solubility of the Compound F6-17 maleate salt crystal.

With the Example 438 shown in Table 31, the effect of SLS on solubility of the Compound F6-17 maleate salt crystal was determined based on a small scale dissolution test. For the Comparative example 23, the Compound F6-17 maleate salt crystal and lactose were mixed at weight ratio of 1:9. The results are shown in FIG. 18.

TABLE 31

|  | Example 438 |
| --- | --- |
| Compound F6-17 maleate salt | 8.3% |
| Lactose hydrate | 83.3% |
| Sodium lauryl sulfate | 8.3% |

Examples 439 to 440

Figure 19:
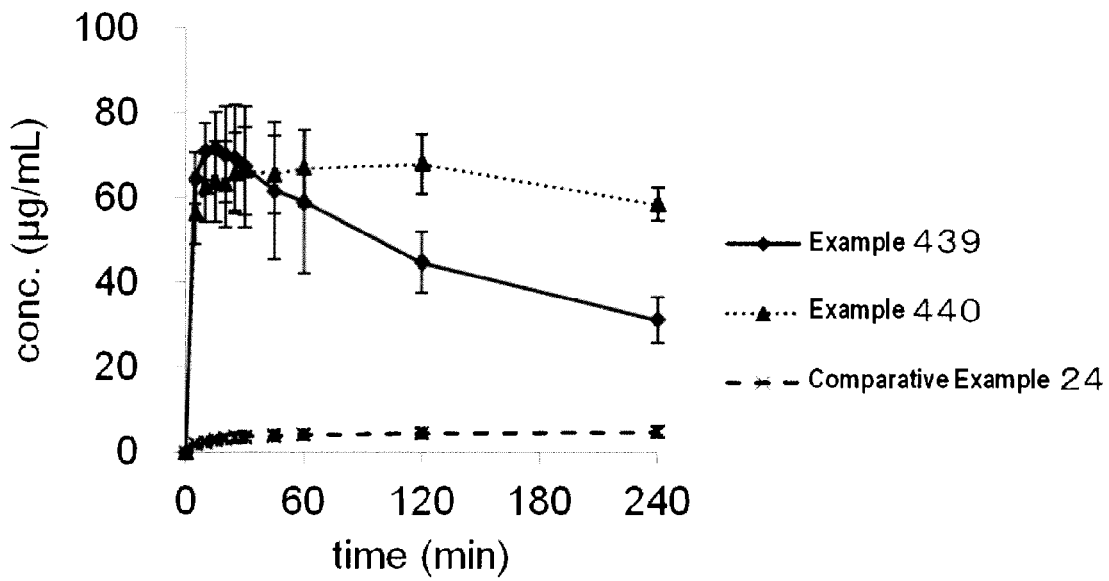
FIG. 19 It is a graph to illustrate the effect of SLS and polyvinyl pyrrolidone on the solubility of the Compound F6-17 L-tartrate salt crystal.

With the Examples 439 to 440 shown in Table 32, the effect of SLS and polyvinyl pyrrolidone on solubility of the Compound F6-17 L-tartrate salt crystal was determined based on small scale dissolution test. For the Comparative example 24, the Compound F6-17 L-tartrate salt crystal and lactose were mixed at weight ratio of 1:9. The results are shown in FIG. 19.

TABLE 32

|  | Example 439 | Example 440 |
| --- | --- | --- |
| Compound F6-17 L-tartrate salt | 26.6% | 26.6% |
| Lactose hydrate | 53.4% | 48.4% |
| Sodium lauryl sulfate | 20.0% | 20.0% |
| Polyvinyl pyrrolidone | 0.0% | 5.0% |

Examples 441 to 443

Figure 20:
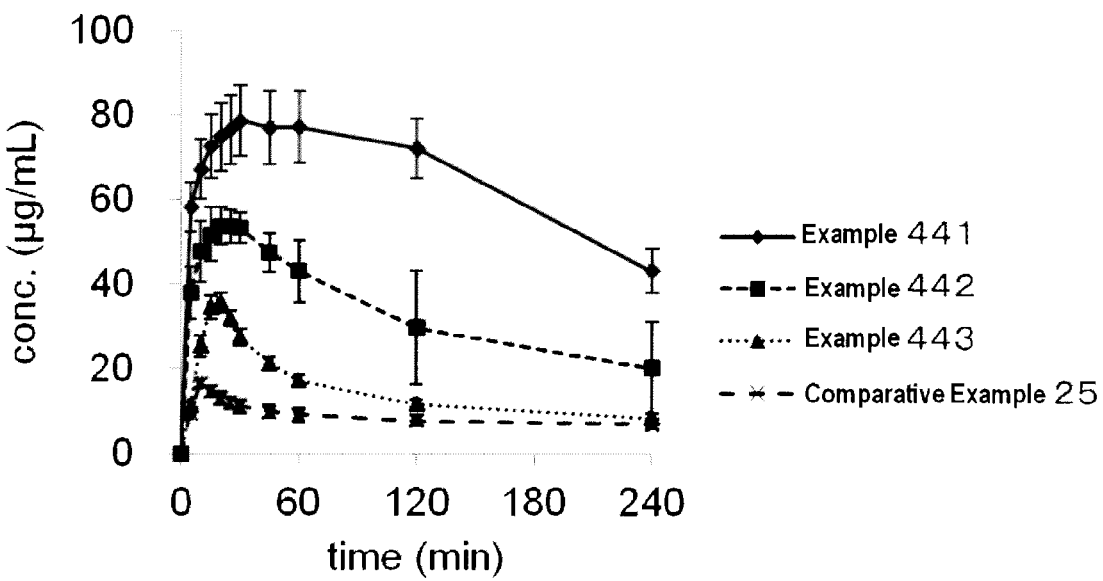
FIG. 20 It is a graph to illustrate the effect of SLS on the solubility of the Compound F6-17 citrate salt crystal.

With the Examples 441 to 443 shown in Table 33, the effect of SLS on solubility of the Compound F6-17 citrate salt crystal was determined based on a small scale dissolution test. For the Comparative example 25, the Compound F6-17 citrate salt crystal and lactose were mixed at weight ratio of 1:9. The results are shown in FIG. 20.

TABLE 33

|  | Example 441 | Example 442 | Example 443 |
| --- | --- | --- | --- |
| Compound F6-17 citrate salt | 24.1% | 24.1% | 24.1% |
| Lactose hydrate | 55.9% | 70.9% | 74.9% |
| Sodium lauryl sulfate | 20.0% | 5.0% | 1.0% |

Examples 444 to 446

Figure 21:
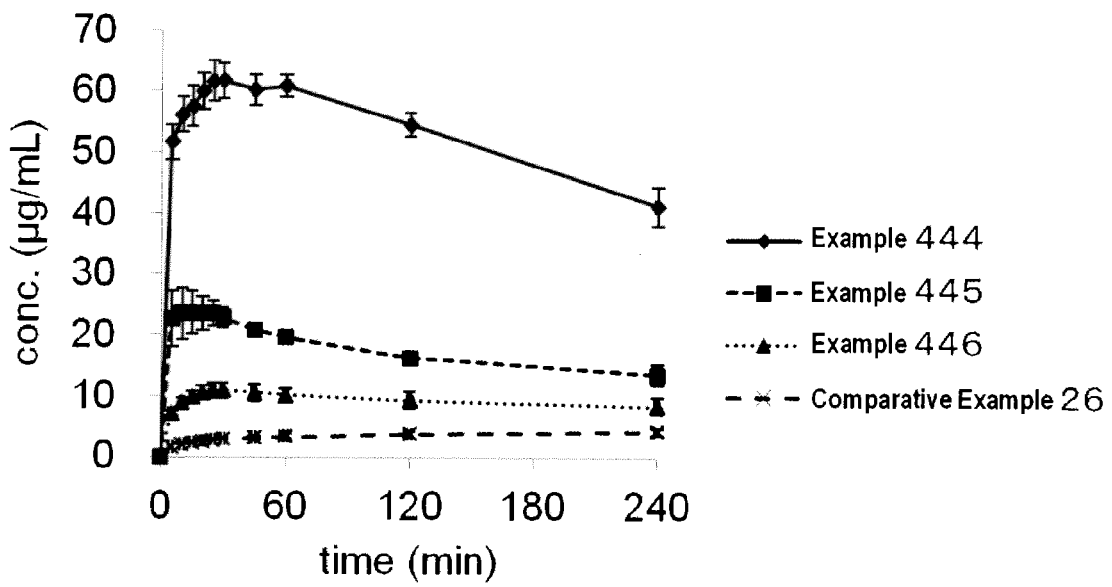
FIG. 21 It is a graph to illustrate the effect of SLS on the solubility of the Compound F6-17 malate salt crystal.

With the Examples 444 to 446 shown in Table 34, the effect of SLS on solubility of the Compound F6-17 malate salt crystal was determined based on a small scale dissolution test. For the Comparative example 26, the Compound F6-17 malate salt crystal and lactose were mixed at weight ratio of 1:9. The results are shown in FIG. 21.

TABLE 34

|  | Example 444 | Example 445 | Example 446 |
|---|---|---|---|
| Compound F6-17 malate salt | 25.9% | 25.9% | 25.9% |
| Lactose hydrate | 54.1% | 69.1% | 73.1% |
| Sodium lauryl sulfate | 20.0% | 5.0% | 1.0% |

Example 447

Figure 22:
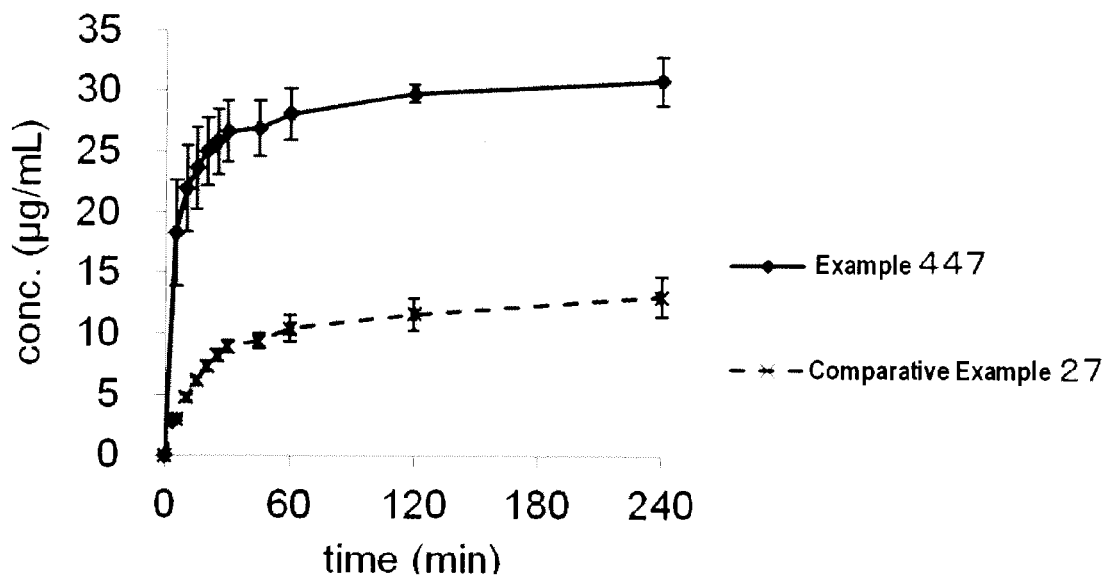
FIG. 22 It is a graph to illustrate the effect of SLS on the solubility of the Compound F5-46 hydrochloride salt crystal.

With the Example 447 shown in Table 35, the effect of SLS on solubility of the Compound F5-46 hydrochloride salt crystal was determined based on a small scale dissolution test. For the Comparative example 27, the Compound F5-46 hydrochloride salt crystal and lactose were mixed at weight ratio of 1:9. The results are shown in FIG. 22.

TABLE 35

|  | Example 447 |
|---|---|
| Compound F5-46 hydrochloride salt | 8.3% |
| Lactose hydrate | 83.3% |
| Sodium lauryl sulfate | 8.3% |

Example 448

Figure 23:
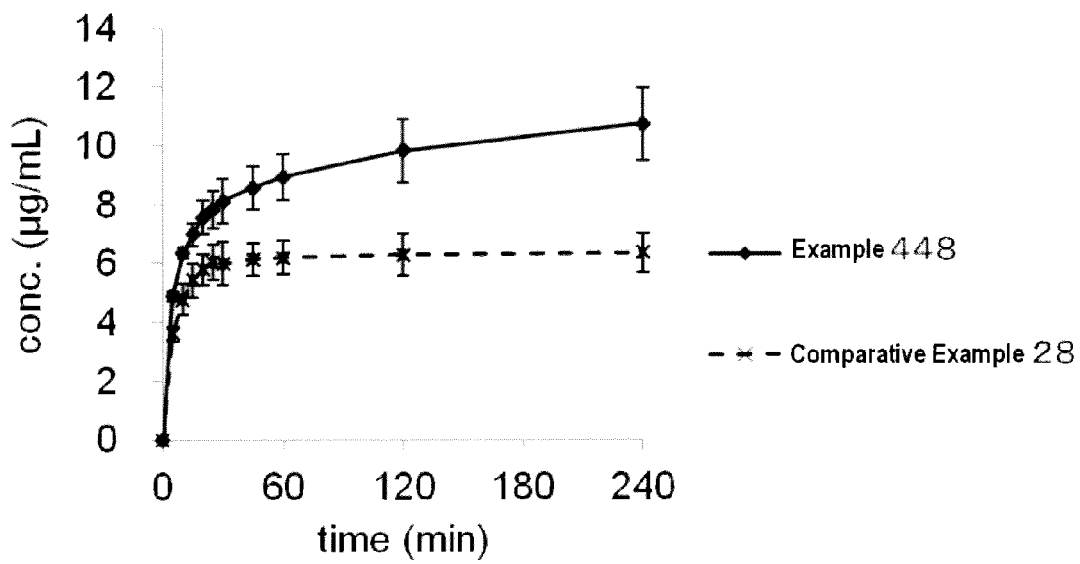
FIG. 23 It is a graph to illustrate the effect of SLS on the solubility of the Compound F5-46 mesylate salt crystal.

With the Example 448 shown in Table 36, the effect of SLS on solubility of the Compound F5-46 mesylate salt crystal was determined based on small scale dissolution test. For the Comparative example 28, the Compound F5-46 mesylate salt crystal and lactose were mixed at weight ratio of 1:9. The results are shown in FIG. 23.

TABLE 36

|  | Example 448 |
|---|---|
| Compound F5-46 mesylate salt | 8.3% |
| Lactose hydrate | 83.3% |
| Sodium lauryl sulfate | 8.3% |

Example 449

Figure 24:
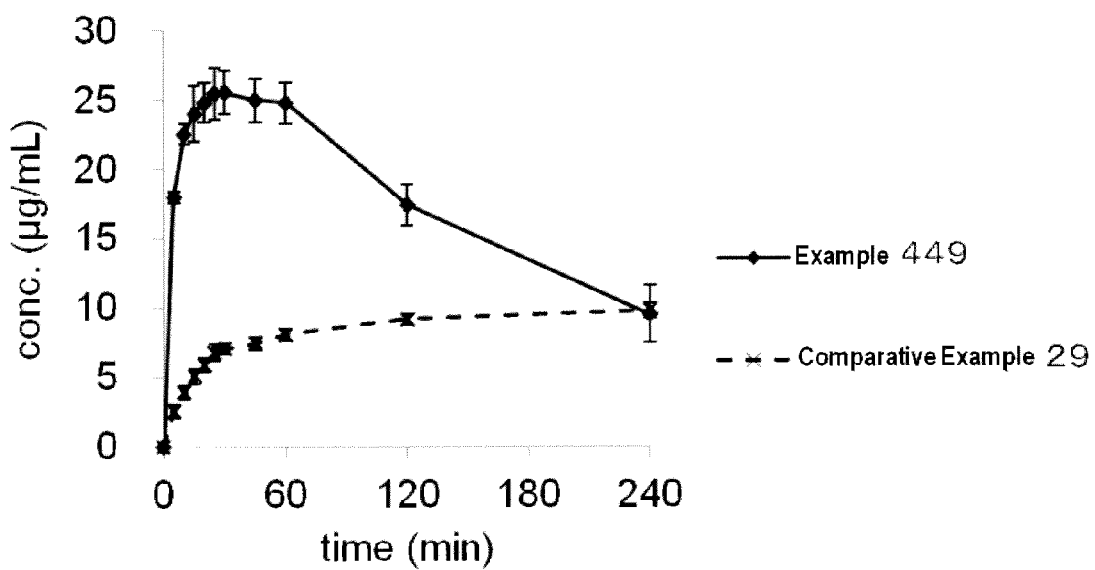
FIG. 24 It is a graph to illustrate the effect of SLS on the solubility of the Compound F5-51 hydrochloride salt crystal.

With the Example 449 shown in Table 37, the effect of SLS on solubility of the Compound F5-51 hydrochloride salt crystal was determined based on a small scale dissolution test. For the Comparative example 29, the Compound F5-51 hydrochloride salt crystal and lactose were mixed at weight ratio of 1:9. The results are shown in FIG. 24.

TABLE 37

|  | Example 449 |
|---|---|
| Compound F5-51 hydrochloride salt | 8.3% |
| Lactose hydrate | 83.3% |
| Sodium lauryl sulfate | 8.3% |

Example 450

Figure 25:
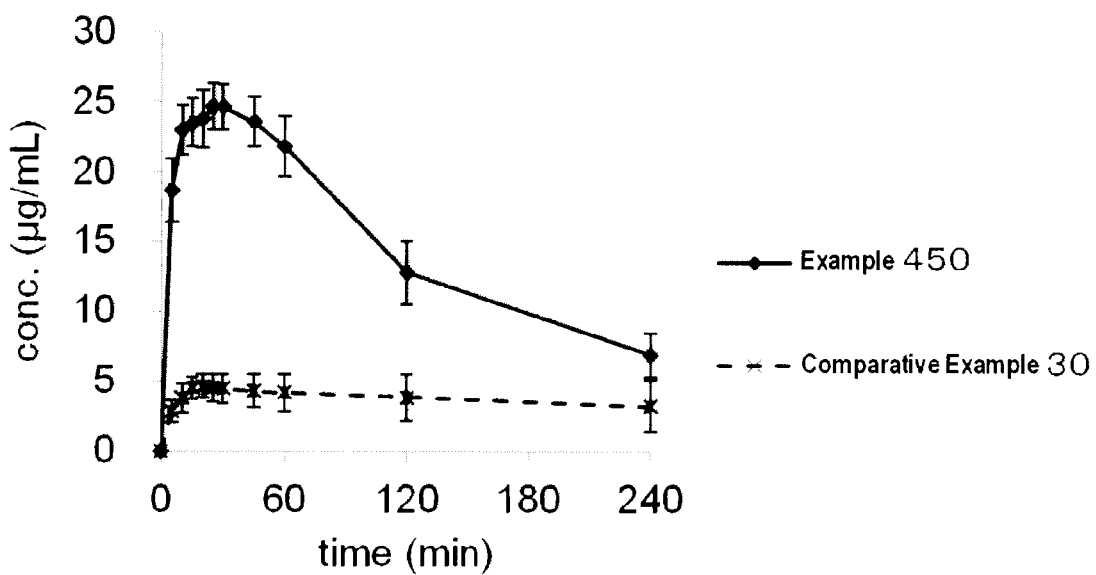
FIG. 25 It is a graph to illustrate the effect of SLS on the solubility of the Compound F5-51 mesylate salt crystal.

With the Example 450 shown in Table 38, the effect of SLS on solubility of the Compound F5-51 mesylate salt crystal was determined based on a small scale dissolution test. For the Comparative example 30, the Compound F5-51 mesylate salt crystal and lactose were mixed at weight ratio of 1:9. The results are shown in FIG. 25.

TABLE 38

|  | Example 450 |
|---|---|
| Compound F5-51 mesylate salt | 8.3% |
| Lactose hydrate | 83.3% |
| Sodium lauryl sulfate | 8.3% |

(Example for Producing a Formulation)

Each component described in Tables 39 to 41 (except the lubricating agent) was added to a high speed mixing granulator for pre-mixing. The resulting mixture was sprayed with purified water and granulated under stirring. After drying under vacuum, dried powder was obtained. The dried powder was then granulated using a granulator. The granule powder obtained and the lubricating agent were admixed with each other with a V-type mixer to obtain powder blend, which was then filled in a capsule to produce a capsule formulation which contains 20 mg of active ingredient per capsule.

TABLE 39

| | Mixing ratio (%) | | | | | | | |
|---|---|---|---|---|---|---|---|---|
| Component name | F1 | F2 | F3 | F4 | F5 | F6 | F7 | F8 |
| Compound F6-20 hydrochloride salt | 20 | 20 | 20 | 20 | 20 | 20 | 20 | 20 |
| Lactose hydrate | 46.5 | 46.5 | 46.5 | 46.5 | 46.5 | 46.5 | 46.5 | 46.5 |
| Microcrystalline cellulose | 15 | 15 | 15 | 15 | 15 | 15 | 15 | 15 |
| Crosscarmellose sodium | 3 | 3 | 3 | 3 | | | | |
| Crospovidone | | | | | 3 | 3 | 3 | 3 |
| Hydroxypropyl cellulose | 5 | | | | 5 | | | |
| Hydroxypropylmethyl cellulose | | 5 | | | | 5 | | |
| Methyl cellulose | | | 5 | | | | 5 | |
| Sodium caseinate | | | | 5 | | | | 5 |
| Sodium lauryl sulfate | 10 | 10 | 10 | 10 | 10 | 10 | 10 | 10 |
| Magnesium stearate | 0.5 | 0.5 | 0.5 | 0.5 | 0.5 | 0.5 | 0.5 | 0.5 |
| Total | 100 | 100 | 100 | 100 | 100 | 100 | 100 | 100 |

TABLE 40

| Component name | Mixing ratio (%) | | | | | | | |
|---|---|---|---|---|---|---|---|---|
| | F9 | F10 | F11 | F12 | F13 | F14 | F15 | F16 |
| Compound F6-20 mesylate salt | 20 | 20 | 20 | 20 | 20 | 20 | 20 | 20 |
| Lactose hydrate | 46.5 | 46.5 | 46.5 | 46.5 | 46.5 | 46.5 | 46.5 | 46.5 |
| Microcrystalline cellulose | 15 | 15 | 15 | 15 | 15 | 15 | 15 | 15 |
| Sodium glycolate starch | 3 | 3 | 3 | 3 | 3 | 3 | 3 | 3 |
| Hydroxypropyl cellulose | 5 | | | | | | | |
| Hydroxypropylmethyl cellulose | | 5 | | | | | | |
| Methyl cellulose | | | 5 | | | | | |
| Sodium caseinate | | | | 5 | | | | |
| Aminoalkyl methacrylate copolymer E | | | | | 5 | | | |
| Polyvinyl acetal diethyl aminoacetate | | | | | | 5 | | |
| Methacrylic acid copolymer S | | | | | | | 5 | |
| Hydroxypropylmethyl cellulose acetate succinate | | | | | | | | 5 |
| Sodium lauryl sulfate | 10 | 10 | 10 | 10 | 10 | 10 | 10 | 10 |
| Magnesium stearate | 0.5 | 0.5 | 0.5 | 0.5 | 0.5 | 0.5 | 0.5 | 0.5 |
| Total | 100 | 100 | 100 | 100 | 100 | 100 | 100 | 100 |

TABLE 41

| Component name | Mixing ratio (%) | | | | | | | |
|---|---|---|---|---|---|---|---|---|
| | F17 | F18 | F19 | F20 | F21 | F22 | F23 | F24 |
| Compound B4-8 L-tartrate salt | 20 | 20 | 20 | 20 | | | | |
| Compound F6-17 citrate salt | | | | | 20 | 20 | 20 | 20 |
| Lactose hydrate | 46.5 | 46.5 | 46.5 | 46.5 | 46.5 | 46.5 | 46.5 | 46.5 |
| Microcrystalline cellulose | 15 | 15 | 15 | 15 | 15 | 15 | 15 | 15 |
| Sodium glycolate starch | 3 | 3 | 3 | 3 | 3 | 3 | 3 | 3 |
| Hydroxypropyl cellulose | 5 | | | | 5 | | | |
| Hydroxypropylmethyl cellulose | | 5 | | | | 5 | | |
| Methyl cellulose | | | 5 | | | | 5 | |
| Sodium caseinate | | | | 5 | | | | 5 |
| Sodium lauryl sulfate | 10 | 10 | 10 | 10 | 10 | 10 | 10 | 10 |
| Magnesium stearate | 0.5 | 0.5 | 0.5 | 0.5 | 0.5 | 0.5 | 0.5 | 0.5 |
| Total | 100 | 100 | 100 | 100 | 100 | 100 | 100 | 100 |

Examples 451 to 453

For the Examples 451 to 453, preparation was carried out by using hydrochloride salt crystal of the Compound F6-20 according to dry production method using agate mortar and pestle with the formula shown in Table 42. The Comparative example 31 was prepared by mixing hydrochloride salt crystal of the Compound F6-20 with lactose.

Figure 26:
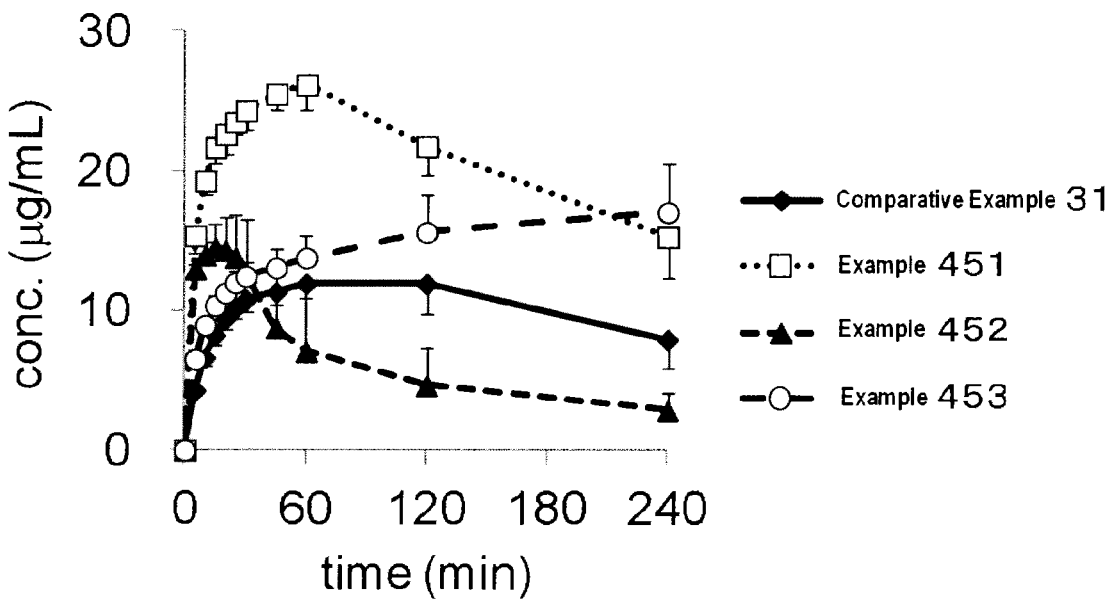
FIG. 26 It is a graph to illustrate the effect of SLS, polyoxyethylene (105) polyoxypropylene (5) glycol, and poly (sodium 4-styrene sulfonate) on the solubility of the Compound F6-20 hydrochloride salt crystal.

Effect of SLS, polyoxyethylene (105) polyoxypropylene (5) glycol, and poly(sodium 4-styrene sulfonate) on the solubility of the Compound F6-20 hydrochloride salt crystal was determined. As a result, as it is shown in FIG. 26, it was evident that the solubility of the Compound F6-20 hydrochloride salt crystal is improved by addition of SLS and poly (sodium 4-styrene sulfonate). It was also evident that the initial solubility of the Compound F6-20 hydrochloride salt crystal is improved by addition of polyoxyethylene (105) polyoxypropylene (5) glycol.

As for the poly(sodium 4-styrene sulfonate), the compound from Sigma Chemical Company was used (i.e., product number 243051).

TABLE 42

| | Example 451 | Example 452 | Example 453 |
|---|---|---|---|
| Compound F6-20 hydrochloride salt crystal | 10.8% | 10.8% | 10.8% |
| Lactose hydrate | 79.2% | 79.2% | 79.2% |
| Sodium lauryl sulfate | 10.0% | 0.0% | 0.0% |
| Polyoxyethylene (105) polyoxypropylene (5) glycol | 0.0% | 10.0% | 0.0% |
| Poly(sodium 4-styrene sulfonate) | 0.0% | 0.0% | 10.0% |
| Total | 100.0% | 100.0% | 100.0% |

Examples 454 to 457

Figure 27:
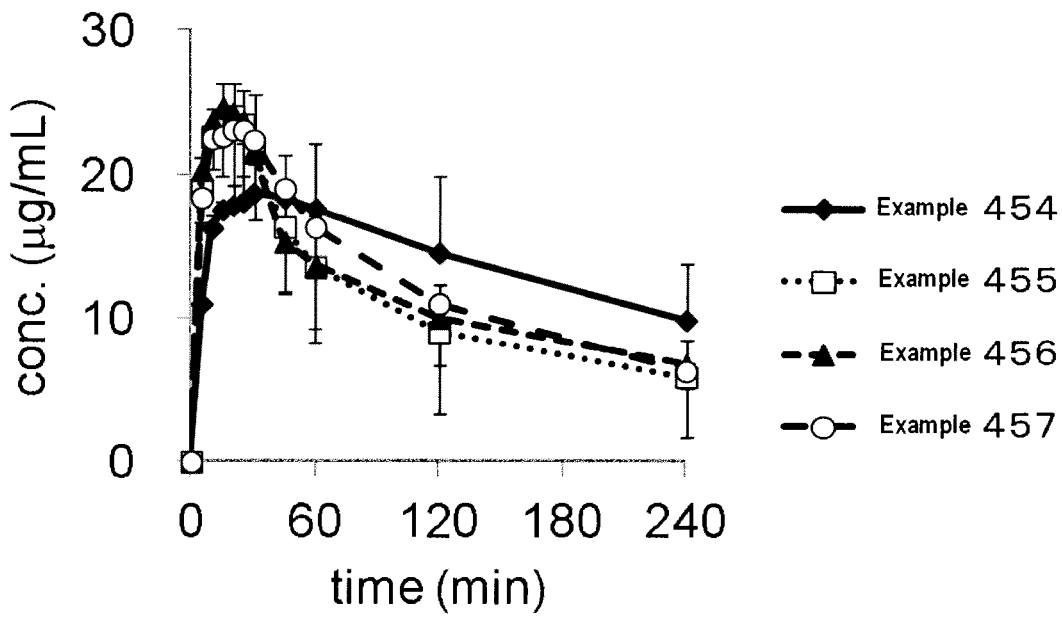
FIG. 27 It is a graph to illustrate the effect of a combination of SLS and polyoxyethylene (105) polyoxypropylene (5) glycol on the solubility of the Compound F6-20 hydrochloride salt crystal.

With the Examples 454 to 457 shown in Table 43, the effect of a combination of SLS and polyoxyethylene (105) polyoxypropylene (5) glycol on the solubility of the Compound F6-20 hydrochloride salt crystal was determined. As a result, as it is shown in FIG. 27, it was evident that the solubility of the Compound F6-20 hydrochloride salt crystal improved by SLS is further enhanced by adding at least 1% of polyoxyethylene (105) polyoxypropylene (5) glycol to the formulation, especially in the early phase.

TABLE 43

| | Example 454 | Example 455 | Example 456 | Example 457 |
|---|---|---|---|---|
| Compound F6-20 hydrochloride salt crystal | 10.8% | 10.8% | 10.8% | 10.8% |
| Lactose hydrate | 84.2% | 83.2% | 81.7% | 74.2% |
| Sodium lauryl sulfate | 5.0% | 5.0% | 5.0% | 5.0% |
| Polyoxyethylene (105) polyoxypropylene (5) glycol | 0.0% | 1.0% | 2.5% | 10.0% |
| Total | 100.0% | 100.0% | 100.0% | 100.0% |

Examples 458 to 460

Figure 28:
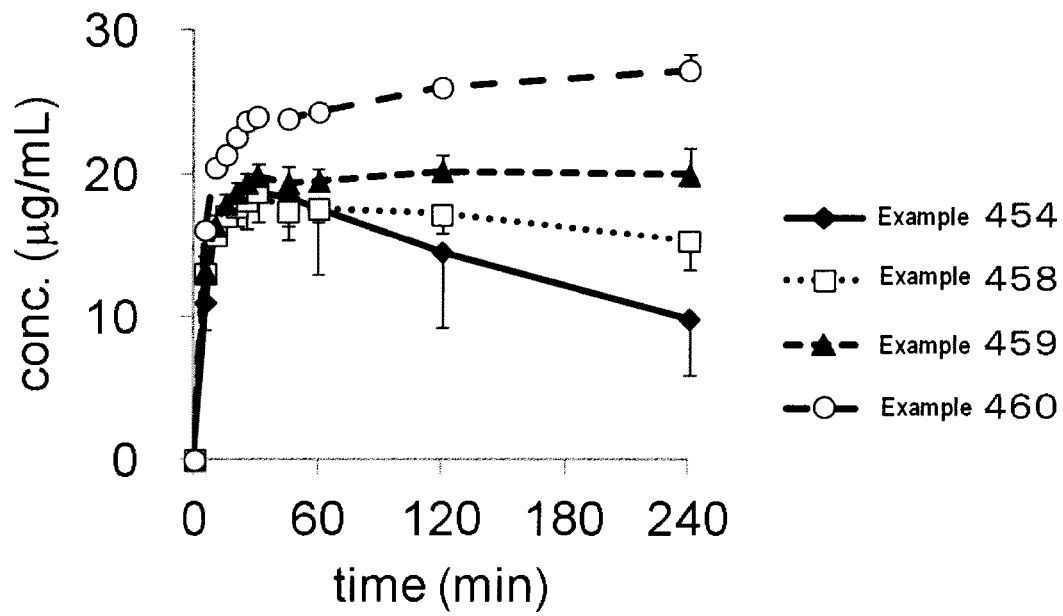
FIG. 28 It is a graph to illustrate the effect of a combination of SLS and poly(sodium 4-styrene sulfonate) on the solubility of the Compound F6-20 hydrochloride salt crystal.

With the Examples 458 to 460 shown in Table 44, the effect of a combination of SLS and poly(sodium 4-styrene sulfonate) on the solubility of the Compound F6-20 hydrochloride salt crystal was determined. As a result, as it is shown in FIG. 28, it was evident that the effect of improving the solubility of the Compound F6-20 hydrochloride salt crystal by SLS is further enhanced depending on the additive amount of poly(sodium 4-styrene sulfonate).

As for the poly(sodium 4-styrene sulfonate), the compound from Sigma Chemical Company was used (i.e., product number 243051).

TABLE 44

| | Example 458 | Example 459 | Example 460 |
|---|---|---|---|
| Compound F6-20 hydrochloride salt crystal | 10.8% | 10.8% | 10.8% |
| Lactose hydrate | 83.2% | 81.7% | 74.2% |
| Sodium lauryl sulfate | 5.0% | 5.0% | 5.0% |
| Poly(sodium 4-styrene sulfonate) | 1.0% | 2.5% | 10.0% |
| Total | 100.0% | 100.0% | 100.0% |

Examples 461 to 465

Figure 29:
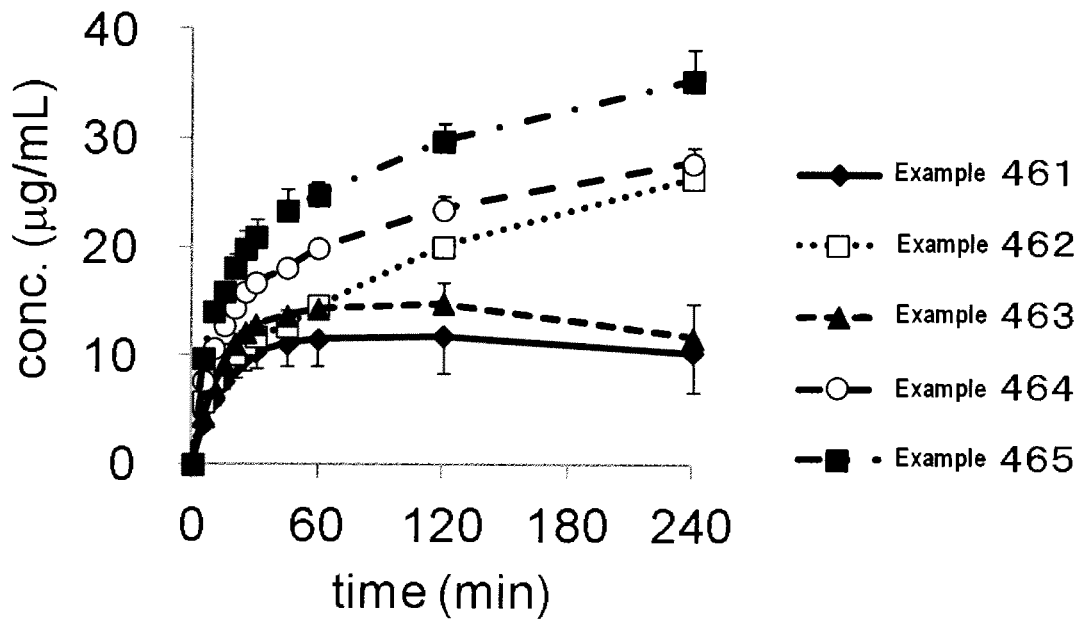
FIG. 29 It is a graph to illustrate the effect of a combination of SLS, polyoxyethylene (105) polyoxypropylene (5) glycol, and poly(sodium 4-styrene sulfonate) on the solubility of the Compound F6-20 hydrochloride salt crystal.

With the Examples 461 to 465 shown in Table 45, the effect of a combination of SLS, polyoxyethylene (105) polyoxypropylene (5) glycol, and poly(sodium 4-styrene sulfonate) on the solubility of the Compound F6-20 hydrochloride salt crystal was determined. As a result, as it is shown in FIG. 29, it was evident that the solubility of the Compound F6-20 hydrochloride salt crystal is improved by the combination of SLS, polyoxyethylene (105) polyoxypropylene (5) glycol, and poly(sodium 4-styrene sulfonate).

As for the poly(sodium 4-styrene sulfonate), the compound from Sigma Chemical Company was used (i.e., product number 243051).

TABLE 45

| | Example 461 | Example 462 | Example 463 | Example 464 | Example 465 |
|---|---|---|---|---|---|
| Compound F6-20 hydrochloride salt crystal | 16.5% | 16.5% | 16.5% | 16.5% | 16.5% |
| Lactose hydrate | 52.0% | 44.3% | 40.5% | 21.2% | 2.0% |
| Microcrystalline cellulose | 20.0% | 20.0% | 20.0% | 20.0% | 20.0% |
| Sodium glycolate starch | 6.0% | 6.0% | 6.0% | 6.0% | 6.0% |
| Hydroxy propyl cellulose | 5.0% | 5.0% | 5.0% | 5.0% | 5.0% |
| Sodium lauryl sulfate | 0.0% | 7.7% | 0.0% | 0.0% | 7.7% |
| Polyoxyethylene (105) polyoxypropylene (5) glycol | 0.0% | 0.0% | 11.5% | 0.0% | 11.5% |
| Poly(sodium 4-styrene sulfonate) | 0.0% | 0.0% | 0.0% | 30.8% | 30.8% |
| Magnesium stearate | 0.5% | 0.5% | 0.5% | 0.5% | 0.5% |
| Total | 100.0% | 100.0% | 100.0% | 100.0% | 100.0% |

Examples 466 and 467

Figure 30:
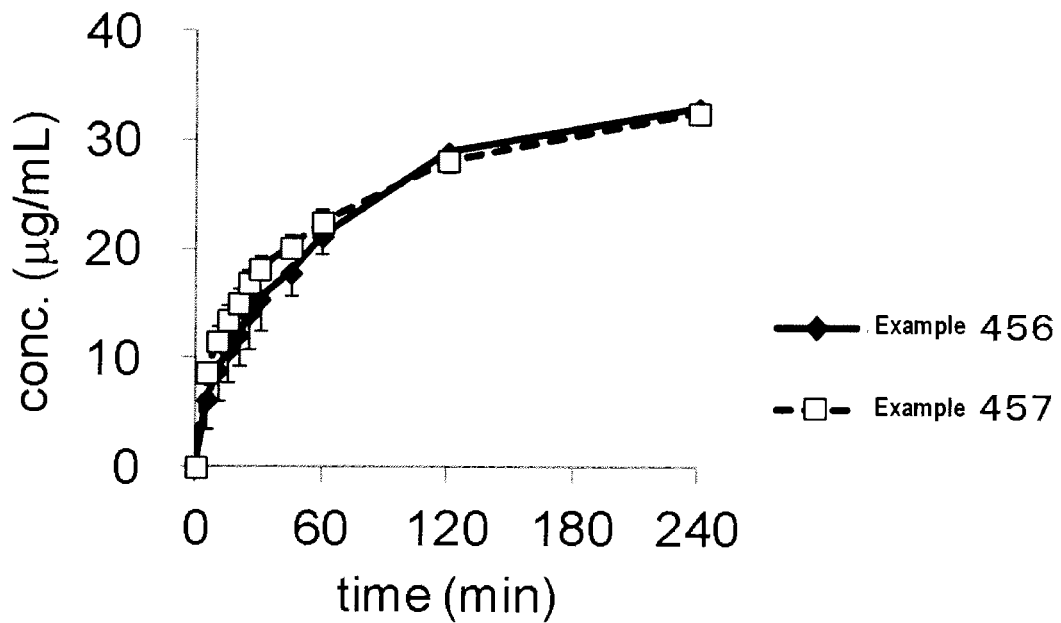
FIG. 30 It is a graph to illustrate the effect of amount of SLS on the solubility of the formulation of the Compound F6-20 hydrochloride salt crystal containing polyoxyethylene (105) polyoxypropylene (5) glycol and poly(sodium 4-styrene sulfonate).

With the Examples 466 and 467 shown in Table 46, the effect of the amount of SLS on the solubility of the formulation of the Compound F6-20 hydrochloride salt crystal containing polyoxyethylene (105) polyoxypropylene (5) glycol and poly(sodium 4-styrene sulfonate) was determined. As a result, as it is shown in FIG. 30, it was evident that the solubility of the formulation of the Compound F6-20 hydrochloride salt crystal containing polyoxyethylene (105) polyoxypropylene (5) glycol and poly(sodium 4-styrene sulfonate) remained the same even when the amount of SLS was cut to half.

As for the poly(sodium 4-styrene sulfonate), the compound from Sigma Chemical Company was used (i.e., product number 243051).

TABLE 46

| | Example 466 | Example 467 |
|---|---|---|
| Compound F6-20 hydrochloride salt crystal | 16.5% | 16.5% |
| Lactose hydrate | 27.3% | 31.2% |
| Microcrystalline cellulose | 20.0% | 20.0% |
| Sodium glycolate starch | 6.0% | 6.0% |
| Hydroxy propyl cellulose | 5.0% | 5.0% |
| Sodium lauryl sulfate | 7.7% | 3.8% |
| Polyoxyethylene (105) polyoxypropylene (5) glycol | 1.5% | 1.5% |
| Poly(sodium 4-styrene sulfonate) | 15.4% | 15.4% |
| Magnesium stearate | 0.5% | 0.5% |
| Total | 100.0% | 100.0% |

The invention claimed is:

1. A composition comprising a substance which is 9-Ethyl-6,6-dimethyl-8-(4-morpholin-4-yl-piperidin-1-yl)-11-oxo-6,11-dihydro-5H-benzo[b]carbazole-3-carbonitrile or a salt thereof, a pharmaceutically acceptable carrier, and a dissolution aid, wherein the dissolution aid is sodium lauryl sulfate.

2. An orally administrable formulation comprising the composition described in claim 1.

3. The composition according to claim 1, wherein the composition further comprises an organic polymer which is selected the group consisting of hydroxypropyl cellulose, hydroxypropylmethyl cellulose, methyl cellulose, propylene glycol alginate ester, powdered agar, guar gum, zein, hydroxyethylmethyl cellulose, a carboxyvinyl polymer, polyvinyl alcohol, a vinyl acetate resin, sodium polystyrene sulfonate, casein, sodium caseinate, a carboxyvinyl polymer, copolyvidone, amino alkylmethacrylate copolymer E, polyvinylacetal diethylaminoacetate, methacrylic acid copolymer LD, methacrylic acid copolymer S, purified shellac, carboxymethylethyl cellulose, cellulose acetate phthalate, hydroxypropylmethyl cellulose acetate succinate, and a mixture thereof.

4. The composition according to claim 1, wherein said water solubility of the substance is less than 100 μg/mL at 25° C.

* * * * *